(12) United States Patent
Alper et al.

(10) Patent No.: US 8,153,635 B2
(45) Date of Patent: Apr. 10, 2012

(54) COMPOUNDS AND COMPOSITIONS AS MODULATORS OF GPR119 ACTIVITY

(75) Inventors: Phillip B. Alper, San Diego, CA (US);
Mihai Azimioara, La Jolla, CA (US);
Christopher Cow, San Diego, CA (US);
Robert Epple, San Diego, CA (US);
Songchun Jiang, San Diego, CA (US);
Gerald Lelais, San Diego, CA (US);
Pierre-Yves Michellys, San Marcos, CA (US); Daniel Mutnick, San Diego, CA (US); Victor Nikulin, Carlsbad, CA (US)

(73) Assignee: IRM LLC, Hamilton (BM)

( * ) Notice: Subject to any disclaimer, the term of this patent is extended or adjusted under 35 U.S.C. 154(b) by 116 days.

(21) Appl. No.: 12/204,600

(22) Filed: Sep. 4, 2008

(65) Prior Publication Data

US 2009/0270409 A1  Oct. 29, 2009

Related U.S. Application Data

(60) Provisional application No. 60/974,064, filed on Sep. 20, 2007, provisional application No. 61/045,263, filed on Apr. 15, 2008.

(51) Int. Cl.
*A61K 31/496* (2006.01)
(52) U.S. Cl. .............. 514/252.11; 514/253.01; 544/357; 544/360; 544/405
(58) Field of Classification Search .................... 544/357
See application file for complete search history.

(56) References Cited

U.S. PATENT DOCUMENTS

| | | | |
|---|---|---|---|
| 3,975,384 A | 8/1976 | Narr et al. |
| 3,983,140 A | 9/1976 | Endo et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,686,237 A | 8/1987 | Anderson |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,691,322 A | 11/1997 | Robl |
| 5,753,675 A | 5/1998 | Wattanasin |
| 5,770,615 A | 6/1998 | Cheng et al. |
| 5,776,983 A | 7/1998 | Washburn et al. |
| 6,221,660 B1 | 4/2001 | Bonini et al. |
| 6,468,756 B1 | 10/2002 | Bonini et al. |
| 6,653,102 B2 | 11/2003 | Roch et al. |
| 6,989,402 B1 | 1/2006 | Hangeland et al. |
| 7,083,933 B1 | 8/2006 | Griffin |
| 7,335,658 B2 | 2/2008 | Chakka et al. |
| 7,416,848 B2 | 8/2008 | Bonini et al. |
| 7,456,180 B2 | 11/2008 | Sviridov et al. |
| 2003/0082534 A1 | 5/2003 | Lind et al. |
| 2003/0143590 A1 | 7/2003 | Ramakrishnan |
| 2004/0067499 A1 | 4/2004 | Haga et al. |
| 2006/0154866 A1 | 7/2006 | Chu et al. |
| 2007/0087363 A1 | 4/2007 | Bartel et al. |
| 2009/0170861 A1* | 7/2009 | Ting et al. ................ 514/252.02 |

FOREIGN PATENT DOCUMENTS

| | | |
|---|---|---|
| AR | 072725 | 9/2010 |
| DE | 2341925 | 3/1975 |
| EP | 0142146 | 5/1985 |
| EP | 0221025 | 5/1987 |
| EP | 1133559 | 9/2001 |
| EP | 1287133 | 3/2003 |
| EP | 1606282 | 12/2005 |
| EP | 1644357 | 4/2006 |
| EP | 1756084 | 2/2007 |
| EP | 1931654 | 6/2008 |
| EP | 1939188 | 7/2008 |
| EP | 2108960 | 10/2009 |
| FR | 2596393 | 10/1987 |
| GB | 2205837 | 12/1988 |
| JP | 2010189298 | 9/2010 |
| WO | WO 86/03488 | 6/1986 |
| WO | WO 86/07054 | 12/1986 |
| WO | WO 97/21993 | 6/1997 |

(Continued)

OTHER PUBLICATIONS

Fredriksson, et al., "Seven evolutionarily conserved human rhodopsin G protein-coupled receptors lacking close relatives", FEBS Letters, 2003, pp. 381-388, vol. 554, Elsevier B.V.

Takeda, et al., "Identification of G protein-coupled receptor genes from the human genome sequence", FEBS Letters, 2002, pp. 97-101, vol. 520, Elsevier Science B.V.

Wu, et al., "2,5-disubstituted pyridines as potent GPR119 agonists", Bioorganic and Medicinal Chemistry Letters, 2010, pp. 2577-2581, vol. 20, Elsevier Ltd.

*Primary Examiner* — James O Wilson
*Assistant Examiner* — Brian McDowell
(74) *Attorney, Agent, or Firm* — Genomics Institute of the Novartis Research Foundation; Chihang Amy Smith

(57) ABSTRACT

The invention provides compounds of Formula I:

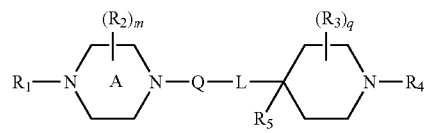

wherein A, L, m, q, Q, $R_1$, $R_2$, $R_3$, $R_4$ and $R_5$ are defined in the Summary of the Invention. The invention further provides for pharmaceutical compositions comprising such compounds and methods of using such compounds to treat or prevent diseases or disorders associated with the activity of GPR119.

17 Claims, No Drawings

FOREIGN PATENT DOCUMENTS

| | | |
|---|---|---|
| WO | WO 99/00353 | 1/1999 |
| WO | WO 00/01389 | 1/2000 |
| WO | WO0114333 | 3/2001 |
| WO | WO 01/32864 | 5/2001 |
| WO | WO 01/62954 | 8/2001 |
| WO | WO 01/96327 | 12/2001 |
| WO | WO 02/10154 | 2/2002 |
| WO | WO 02/16548 | 2/2002 |
| WO | WO 03/043985 | 5/2003 |
| WO | WO 03/075929 | 9/2003 |
| WO | WO 03/091247 | 11/2003 |
| WO | WO 2004/035556 | 4/2004 |
| WO | WO 2004/047755 | 6/2004 |
| WO | WO2004054973 | 7/2004 |
| WO | WO2004056823 | 7/2004 |
| WO | WO 2004/065380 | 8/2004 |
| WO | WO 2004/094618 | 11/2004 |
| WO | WO 2004/007658 | 1/2005 |
| WO | WO2005007647 | 1/2005 |
| WO | WO 2005/011655 | 2/2005 |
| WO | WO 2005/013907 | 2/2005 |
| WO | WO2005011657 | 2/2005 |
| WO | WO 2005/044250 | 5/2005 |
| WO | WO2005044797 | 5/2005 |
| WO | WO2005061489 | 7/2005 |
| WO | WO 2006/047516 | 5/2006 |
| WO | WO 2006/070208 | 7/2006 |
| WO | WO 2006/076231 | 7/2006 |
| WO | WO2006086445 | 8/2006 |
| WO | WO2006123257 | 11/2006 |
| WO | WO 2007/003961 | 1/2007 |
| WO | WO 2008/005569 | 1/2007 |
| WO | WO2007003960 | 1/2007 |
| WO | WO2007003962 | 1/2007 |
| WO | WO2007003964 | 1/2007 |
| WO | WO2007092435 | 8/2007 |
| WO | WO 2007/116229 | 10/2007 |
| WO | WO2007/116230 | 10/2007 |
| WO | WO 2007/120689 | 10/2007 |
| WO | WO 2007/120702 | 10/2007 |
| WO | WO 2007/138362 | 12/2007 |
| WO | WO 2008/005576 | 1/2008 |
| WO | WO 2008/008887 | 1/2008 |
| WO | WO 2008/008895 | 1/2008 |
| WO | WO 2008/025798 | 3/2008 |
| WO | WO 2008/025799 | 3/2008 |
| WO | WO 2008/025800 | 3/2008 |
| WO | WO 2008/033460 | 3/2008 |
| WO | WO 2008/033465 | 3/2008 |
| WO | WO 2008/046216 | 4/2008 |
| WO | WO 2008/070692 | 6/2008 |
| WO | WO 2008/076243 | 6/2008 |
| WO | WO 2008/081204 | 7/2008 |
| WO | WO 2008/081205 | 7/2008 |
| WO | WO 2008/081206 | 7/2008 |
| WO | WO 2008/081207 | 7/2008 |
| WO | WO 2008/081208 | 7/2008 |
| WO | WO 2008/083238 | 7/2008 |
| WO | WO 2008/085316 | 7/2008 |
| WO | WO2008097428 | 8/2008 |
| WO | WO2008109702 | 9/2008 |
| WO | WO2008110611 | 9/2008 |
| WO | WO 2008/130581 | 10/2008 |
| WO | WO 2008/130584 | 10/2008 |
| WO | WO 2008/130615 | 10/2008 |
| WO | WO 2008/137435 | 11/2008 |
| WO | WO 2008/137436 | 11/2008 |
| WO | WO 2009/012275 | 1/2009 |
| WO | WO 2009/012277 | 1/2009 |
| WO | WO 2009/014910 | 1/2009 |
| WO | WO 2009/034388 | 3/2009 |
| WO | WO2009038974 | 3/2009 |
| WO | WO 2009/040410 | 4/2009 |
| WO | WO 2009/050522 | 4/2009 |
| WO | WO 2009/050523 | 4/2009 |
| WO | WO 2009/055331 | 4/2009 |
| WO | WO 2009/105715 | 8/2009 |
| WO | WO 2009/105717 | 8/2009 |
| WO | WO 2009/105722 | 8/2009 |
| WO | WO 2009/106561 | 9/2009 |
| WO | WO 2009/106565 | 9/2009 |
| WO | WO 2009/117421 | 9/2009 |
| WO | WO 2009/123992 | 10/2009 |
| WO | WO 2009/125434 | 10/2009 |
| WO | WO 2009/126245 | 10/2009 |
| WO | WO 2009/126535 | 10/2009 |
| WO | WO 2009/129036 | 10/2009 |
| WO | WO 2009/141238 | 11/2009 |
| WO | WO 2009/143049 | 11/2009 |
| WO | WO 2009/150144 | 12/2009 |
| WO | WO 2010/001166 | 1/2010 |
| WO | WO 2010/004343 | 1/2010 |
| WO | WO 2010/004344 | 1/2010 |
| WO | WO2010/004345 | 1/2010 |
| WO | WO 2010/004346 | 1/2010 |
| WO | WO 2010/004347 | 1/2010 |
| WO | WO 2010/004348 | 1/2010 |
| WO | WO 2010/006191 | 1/2010 |
| WO | WO 2010/008739 | 1/2010 |
| WO | WO 2010/009183 | 1/2010 |
| WO | WO 2010/009195 | 1/2010 |
| WO | WO 2010/009208 | 1/2010 |
| WO | WO 2010/013849 | 2/2010 |
| WO | WO 2010/014593 | 2/2010 |
| WO | WO 2010/029089 | 3/2010 |
| WO | WO 2010/048149 | 4/2010 |
| WO | WO 2010/074271 | 7/2010 |
| WO | WO 2010/075269 | 7/2010 |
| WO | WO 2010/075271 | 7/2010 |
| WO | WO 2010/075273 | 7/2010 |
| WO | WO 2010/084512 | 7/2010 |
| WO | WO 2010/084944 | 7/2010 |
| WO | WO2010/088518 | 8/2010 |
| WO | WO 2010/095663 | 8/2010 |
| WO | WO 2010/103333 | 9/2010 |
| WO | WO 2010/103334 | 9/2010 |
| WO | WO 2010/103335 | 9/2010 |
| WO | WO 2010/106457 | 9/2010 |
| WO | WO 2010/114957 | 10/2010 |
| WO | WO 2010/120578 | 10/2010 |
| WO | WO 2010/123018 | 10/2010 |
| WO | WO 2010/128414 | 11/2010 |

* cited by examiner

COMPOUNDS AND COMPOSITIONS AS MODULATORS OF GPR119 ACTIVITY

CROSS-REFERENCE TO RELATED APPLICATIONS

This application claims the benefit of priority to U.S. Provisional Patent Application No. 60/974,064, filed 20 Sep. 2007 and U.S. Provisional Patent Application No. 61/045,263, filed 15 Apr. 2008. The full disclosures of these applications are incorporated herein by reference in their entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of GPR119.

2. Background

GPR119 is a G-protein coupled receptor (GPCR) that is mainly expressed in the pancreas, small intestine, colon and adipose tissue. The expression profile of the human GPR119 receptor indicates its potential utility as a target for the treatment of obesity and diabetes. The novel compounds of this invention modulate the activity of GPR119 and are, therefore, expected to be useful in the treatment of GPR119-associated diseases or disorders such as, but not limited to, diabetes, obesity and associated metabolic disorders.

SUMMARY OF THE INVENTION

In one aspect, the present invention provides a compound of Formula I:

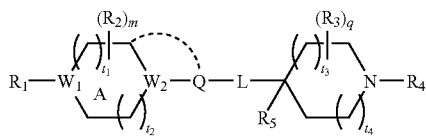

in which:

Q is a divalent or trivalent radical selected from $C_{6-10}$aryl, $C_{1-10}$heteroaryl, $C_{3-8}$cycloalkyl and $C_{3-8}$heterocycloalkyl; wherein said aryl, heteroaryl, cycloalkyl or heterocycloalkyl of Q is optionally substituted with up to 3 radicals independently selected from halo, $C_{1-6}$alkyl, halo-substituted-$C_{1-6}$alkyl, $C_{1-6}$alkoxy, halo-substituted-$C_{1-6}$alkoxy, —C(O)$R_{20}$ and —C(O)O$R_{20}$; wherein $R_{20}$ is selected from hydrogen and $C_{1-6}$alkyl; and optionally connecting a carbon adjacent to $W_2$ through a $CR_{31}$, O, S or $NR_{31}$ with a carbon of Q (indicated by the dotted line) to form a 5-membered ring fused to rings A and Q (such as the fused rings in examples V1-V5, infra); wherein $R_{31}$ is selected from hydrogen and $C_{1-6}$alkyl;

$W_1$ and $W_2$ are independently selected from $CR_{21}$ and N; wherein $R_{21}$ is selected from hydrogen, cyano, $C_{1-6}$alkyl and —C(O)O$R_{25}$; wherein $R_{25}$ is selected from hydrogen and $C_{1-6}$alkyl; ring A can have up to 2 ring carbons substituted with a group selected from —C(O)—, —C(S)— and —C(=N$OR_{30}$)— and can be partially unsaturated with up to 2 double bonds; wherein $R_{30}$ is selected from hydrogen and $C_{1-6}$alkyl;

L is selected from $C_{1-6}$alkylene, $C_{2-6}$alkenylene, —(CH$_2$)$_n$O—, —OC(O)(CH$_2$)$_n$—, —C(O)O(CH$_2$)$_n$—, —NR$_{26}$(CH$_2$)$_n$— and —O(CH$_2$)$_n$—; wherein $R_{26}$ is selected from hydrogen and $C_{1-6}$alkyl; and n is selected from 0, 1, 2, 3, 4 and 5; wherein any alkyl of L can be optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —C(O)$R_{22}$ and —C(O)O$R_{22}$; wherein $R_{22}$ is selected from hydrogen and $C_{1-6}$alkyl;

m is selected from 0, 1, 2, 3 and 4;

q is selected from 0, 1, 2, 3 and 4;

$t_1, t_2, t_3$ and $t_4$ are each independently selected from 0, 1 and 2;

$R_1$ is selected from —$X_1$S(O)$_{0-2}X_2R_{6a}$, —$X_1$S(O)$_{0-2}X_2OR_{6a}$, —$X_1$S(O)$_{0-2}X_2C(O)R_{6a}$, —$X_1$S(O)$_{0-2}X_2C(O)OR_{6a}$, —$X_1$S(O)$_{0-2}X_2OC(O)R_{6a}$ and —$X_1$S(O)$_{0-2}NR_{6a}R_{6b}$; wherein $X_1$ is selected from a bond, O, $NR_{7a}R_{7b}$ and $C_{1-4}$alkylene; $X_2$ is selected from a bond and $C_{1-4}$alkylene; $R_{6a}$ is selected from hydrogen, halo, $C_{1-6}$alkyl, $C_{2-6}$alkenyl, $C_{6-10}$aryl, $C_{1-10}$heteroaryl, $C_{3-8}$heterocycloalkyl and $C_{3-8}$cycloalkyl; wherein said aryl, heteroaryl, cycloalkyl and heterocycloalkyl of $R_{6a}$ is optionally substituted with 1 to 3 radicals independently selected from hydroxy, halo, $C_{1-6}$alkyl, halo-substituted-$C_{1-6}$alkyl, hydroxy-substituted-$C_{1-6}$alkyl, cyano-substituted-$C_{1-6}$alkyl, $C_{1-6}$alkoxy, halo-substituted-$C_{1-6}$alkoxy and $C_{6-10}$aryl-$C_{1-4}$alkoxy; $R_{6b}$ is selected from hydrogen and $C_{1-6}$alkyl; and $R_{7a}$ and $R_{7b}$ are independently selected from hydrogen and $C_{1-6}$alkyl;

$R_2$ and $R_3$ are independently selected from hydrogen, halo, hydroxy, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —C(O)$R_{23}$, and —C(O)O$R_{23}$; wherein $R_{23}$ is selected from hydrogen and $C_{1-6}$alkyl;

$R_4$ is selected from $R_8$ and —C(O)O$R_8$; wherein $R_8$ is selected from $C_{1-6}$alkyl, $C_{6-10}$aryl, $C_{1-10}$heteroaryl, $C_{3-8}$cycloalkyl and $C_{3-8}$heterocycloalkyl; wherein said aryl, heteroaryl, cycloalkyl or heterocycloalkyl of $R_8$ is optionally substituted with 1 to 3 radicals independently selected from halo, $C_{1-6}$alkyl, $C_{3-12}$cycloalkyl, $C_{3-8}$heterocycloalkyl, halo-substituted-$C_{1-6}$alkyl, hydroxy-substituted-$C_{1-6}$alkyl, $C_{1-6}$alkoxy and halo-substituted-$C_{1-6}$alkoxy;

$R_5$ is selected from hydrogen, $C_{1-6}$alkyl, halo-substituted-$C_{1-6}$alkyl, hydroxy-substituted-$C_{1-6}$alkyl, $C_{1-6}$alkoxy and halo-substituted-$C_{1-6}$alkoxy.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of GPR119 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which GPR119 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be straight-chained, branched, cyclic or spiro. $C_{1-6}$alkoxy includes methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example, $C_{1-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, 1H-pyridin-2-onyl, 6-oxo-1,6-dihydro-pyridin-3-yl, etc. "$C_{6-10}$aryl$C_{0-4}$alkyl" means an aryl as described above connected via a alkylene grouping. For example, $C_{6-10}$aryl$C_{0-4}$alkyl includes phenethyl, benzyl, etc. Heteroaryl also includes the N-oxide derivatives, for example, pyridine N-oxide derivatives with the following structure:

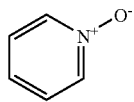

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, 2-oxo-pyrrolidin-1-yl, 2-oxo-piperidin-1-yl, etc.

GPR119 means G protein-coupled receptor 119 (GenBank® Accession No. AAP72125) is also referred to in the literature as RUP3 and GPR116. The term GPR119 as used herein includes the human sequences found in GeneBank accession number AY288416, naturally-occurring allelic variants, mammalian orthologs, and recombinant mutants thereof.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of GPR119 activity can prevent, inhibit or ameliorate the pathology and/or symptomology of the diseases, which method comprises administering to the animal a therapeutically effective amount of a compound of Formula I.

In one embodiment, with reference to compounds of Formula I, are compounds of Formula Ia:

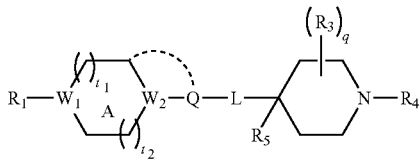

in which:

Q is a divalent or trivalent radical selected from $C_{6-10}$aryl, $C_{1-10}$heteroaryl, $C_{3-8}$cycloalkyl and $C_{3-8}$heterocycloalkyl; wherein said aryl, heteroaryl, cycloalkyl or heterocycloalkyl of Q is optionally substituted with up to 3 radicals independently selected from halo, $C_{1-6}$alkyl, halo-substituted-$C_{1-6}$alkyl, $C_{1-6}$alkoxy, halo-substituted-$C_{1-6}$alkoxy, —C(O)$R_{20}$ and —C(O)O$R_{20}$; wherein $R_{20}$ is selected from hydrogen and $C_{1-6}$alkyl; and optionally connecting a carbon adjacent to $W_2$ through a $CR_{31}$ or O with a carbon of Q (indicated by the dotted line in Formula Ia) to form a 5-membered ring fused to rings A and Q (such as the fused rings in examples V1-V5, infra); wherein $R_{31}$ is selected from hydrogen and $C_{1-6}$alkyl; $W_1$ and $W_2$ are independently selected from $CR_{21}$ and N; wherein $R_{21}$ is selected from hydrogen, cyano, $C_{1-6}$alkyl and —C(O)O$R_{25}$; wherein $R_{25}$ is selected from hydrogen and $C_{1-6}$alkyl; ring A can have up to 2 ring carbons substituted with a group selected from —C(O)—, —C(S)— and —C(═NO$R_{30}$)— and can be partially unsaturated with up to 2 double bonds; wherein $R_{30}$ is selected from hydrogen and $C_{1-6}$alkyl;

L is selected from $C_{1-6}$alkylene, $C_{2-6}$alkenylene, —(CH$_2$)$_n$O—, —NR$_{26}$CH$_2$)$_n$—, —OC(O)(CH$_2$)$_n$—, —C(O)O(CH$_2$)$_n$— and —O(CH$_2$)$_n$—; wherein $R_{26}$ is selected from hydrogen and $C_{1-6}$alkyl; wherein n is selected from 0, 1, 2, 3, 4 and 5; wherein any alkyl of L can be optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —C(O)$R_{22}$ and —C(O)O$R_{22}$; wherein $R_{22}$ is selected from hydrogen and $C_{1-6}$alkyl;

$t_1$ and $t_2$ are each independently selected from 0, 1 and 2;

q is selected from 0, 1, 2, 3 and 4;

$R_1$ is selected from —$X_1$S(O)$_{0-2}X_2R_{6a}$, —$X_1$S(O)$_{0-2}X_2$O$R_{6a}$, —$X_1$S(O)$_{0-2}X_2$C(O)$R_{6a}$, —$X_1$S(O)$_{0-2}X_2$C(O)O$R_{6a}$, —$X_1$S(O)$_{0-2}X_2$OC(O)$R_{6a}$ and —$X_1$S(O)$_{0-2}$NR$_{6a}R_{6b}$; wherein $X_1$ is selected from a bond, O, NR$_{7a}R_{7b}$ and $C_{1-4}$alkylene; $X_2$ is selected from a bond and $C_{1-4}$alkylene; $R_{6a}$ is selected from hydrogen, halo, $C_{1-6}$alkyl, $C_{2-6}$alkenyl, $C_{6-10}$aryl, $C_{1-10}$heteroaryl, $C_{3-8}$heterocycloalkyl and $C_{3-8}$cycloalkyl; wherein said aryl, heteroaryl, cycloalkyl and heterocycloalkyl of $R_{6a}$ is optionally substituted with 1 to 3 radicals independently selected from hydroxy, halo, $C_{1-6}$alkyl, halo-substituted-$C_{1-6}$alkyl, hydroxy-substituted-$C_{1-6}$alkyl, cyano-substituted-$C_{1-6}$alkyl, $C_{1-6}$alkoxy, halo-substituted-$C_{1-6}$alkoxy and $C_{6-10}$aryl-$C_{1-4}$alkoxy; $R_{6b}$ is selected from hydrogen and $C_{1-6}$alkyl; and $R_{7a}$ and $R_{7b}$ are independently selected from hydrogen and $C_{1-6}$alkyl;

$R_3$ is selected from hydrogen, halo, hydroxy, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, —C(O)$R_{23}$, and —C(O)O$R_{23}$; wherein $R_{23}$ is selected from hydrogen and $C_{1-6}$alkyl;

$R_4$ is selected from $R_8$ and —C(O)O$R_8$; wherein $R_8$ is selected from $C_{1-6}$alkyl, $C_{6-10}$aryl, $C_{1-10}$heteroaryl, $C_{3-8}$cycloalkyl and $C_{3-8}$heterocycloalkyl; wherein said aryl, heteroaryl, cycloalkyl or heterocycloalkyl of $R_8$ is optionally substituted with 1 to 3 radicals independently selected from halo, $C_{1-6}$alkyl, $C_{3-12}$cycloalkyl, $C_{3-8}$heterocycloalkyl, halo-substituted-$C_{1-6}$alkyl, hydroxy-substituted-$C_{1-6}$alkyl, $C_{1-6}$alkoxy and halo-substituted-$C_{1-6}$alkoxy;

$R_5$ is selected from hydrogen, $C_{1-6}$alkyl, halo-substituted-$C_{1-6}$alkyl, hydroxy-substituted-$C_{1-6}$alkyl, $C_{1-6}$alkoxy and halo-substituted-$C_{1-6}$alkoxy.

In a further embodiment, Q is a divalent or trivalent radical selected from phenyl, pyridinyl, pyrazinyl, pyridazinyl, pyrimidinyl, 1,2,4-oxadiazolyl, and thiazolyl; wherein said phenyl, pyridinyl, pyrazinyl, pyridazinyl, pyrimidinyl and thiazolyl of Q is optionally substituted with up to 3 radicals independently selected from halo, $C_{1-6}$alkyl, $C_{1-6}$alkoxy, halo-substituted-$C_{1-6}$alkyl, —C(O)O$R_{20}$ and —C(O)$R_{20}$; wherein $R_{20}$ is selected from hydrogen and $C_{1-6}$alkyl; and optionally connecting a carbon adjacent to $W_2$ through a C$R_{31}$ or O with a carbon of Q to form a 5-membered ring fused to rings A and Q; wherein $R_{31}$ is selected from hydrogen and $C_{1-6}$alkyl.

In a further embodiment, $W_1$ and $W_2$ are independently selected from C$R_{21}$ and N; wherein $R_{21}$ is selected from hydrogen, cyano, $C_{1-6}$alkyl and —C(O)O$R_{25}$; wherein $R_{25}$ is selected from hydrogen and $C_{1-6}$alkyl; ring A can have a ring carbon substituted with a group selected from —C(O)—, —C(S)— and —C(=NO$R_{30}$)— and can be partially unsaturated with a double bond; wherein $R_{30}$ is selected from hydrogen and $C_{1-6}$alkyl; and L is selected from —O(CH$_2$)$_{0-4}$—, —(CH=CH)—, —OC(O)—, —NH(CH$_2$)$_{0-4}$—, —NCH$_3$(CH$_2$)$_{0-4}$— and —(CH$_2$)$_{1-4}$—.

In another embodiment, $R_1$ is selected from —$X_1$S(O)$_{0-2}X_2R_{6a}$, —$X_1$S(O)$_{0-2}X_2$O$R_{6a}$, —$X_1$S(O)$_{0-2}X_2$C(O)O$R_{6a}$, —$X_1$S(O)$_{0-2}X_2$OC(O)$R_{6a}$ and —$X_1$S(O)$_{0-2}$N$R_{6a}R_{6b}$; wherein $X_1$ is selected from a bond and O; $X_2$ is selected from a bond and $C_{1-4}$alkylene; $R_{6a}$ is selected from hydrogen, halo, cyano, methyl, ethyl, propyl, isopropyl, ethenyl, pyridinyl, pyrrolidinyl, piperidinyl, morpholino, isoxazolyl, tetrazolyl, phenyl and imidazolyl; wherein said piperidinyl, pyridinyl, pyrrolidinyl, morpholino, isoxazolyl, tetrazolyl, phenyl or imidazolyl of $R_{6a}$ is optionally substituted with 1 to 3 radicals independently selected from hydroxy, halo, $C_{1-6}$alkyl and benzoxy; and $R_{6b}$ is selected from hydrogen, methyl and ethyl.

In another embodiment, $R_4$ is selected from $R_8$ and —C(O)O$R_8$; wherein $R_8$ is selected from isopropyl, cyclopropyl, t-butyl, 1,2,4-oxadiazolyl, pyrimidinyl, pyridinyl, pyridazinyl, tetrahydro-2H-pyranyl, tetrahydrofuranyl, oxetanyl, 2H-tetrazolyl and thiazolyl; wherein said cyclopropyl, 1,2,4-oxadiazolyl, pyrimidinyl, pyridinyl, pyridazinyl, tetrahydro-2H-pyranyl, tetrahydrofuranyl, oxetanyl, 2H-tetrazolyl or thiazolyl of $R_8$ is optionally substituted with 1 to 3 radicals independently selected from halo, trifluoromethyl, isopropyl, t-butyl, methyl, ethyl and cyclopropyl optionally substituted with methyl; and $R_5$ is selected from hydrogen and methoxy.

In another embodiment are compounds selected from: isopropyl 4-((4-((4-methanesulfonylpiperazin)-1-yl)phenoxy)methyl)piperidine-1-carboxylate, isopropyl 4-(2-(4-(4-(methylsulfonyl)piperazin-1-yl)phenoxy)ethyl)piperidine-1-carboxylate, isopropyl 4-(3-(4-(4-(methylsulfonyl)piperazin-1-yl)phenoxy)propyl)piperidine-1-carboxylate, isopropyl 4-(4-(4-(4-(methylsulfonyl)piperazin-1-yl)phenoxy)butyl)piperidine-1-carboxylate, Isopropyl 4-((6-(4-(methylsulfonyl)piperazin-1-yl)pyridin-3-yloxy)methyl)piperidine-1-carboxylate, tert-Butyl 4-((6-(4-(methylsulfonyl)piperazin-1-yl)pyridin-3-yloxy)methyl)piperidine-1-carboxylate, Isopropyl 4-((5-(4-(methylsulfonyl)piperazin-1-yl)pyrazin-2-yloxy)methyl)piperidine-1-carboxylate, tert-Butyl 4-((5-(4-(methylsulfonyl)piperazin-1-yl)pyrazin-2-yloxy)methyl)piperidine-1-carboxylate, 3-Cyclopropyl-5-(4-((5-(4-(methylsulfonyl)piperazin-1-yl)pyrazin-2-yloxy)methyl)piperidin-1-yl)-1,2,4-oxadiazole, 5-Cyclopropyl-3-(4-((5-(4-(methylsulfonyl)piperazin-1-yl)pyrazin-2-yloxy)methyl)piperidin-1-yl)-1,2,4-oxadiazole, 2-(4-(Methylsulfonyl)piperazin-1-yl)-5-((1-(5-(trifluoromethyl)pyridin-2-yl)piperidin-4-yl)methoxy)pyrazine, 5-Isopropyl-3-(4-((5-(4-(methylsulfonyl)piperazin-1-yl)pyrazin-2-yloxy)methyl)piperidin-1-yl)-1,2,4-oxadiazole, Tetrahydro-2H-pyran-4-yl 4-((5-(4-(methylsulfonyl)piperazin-1-yl)pyrazin-2-yloxy)methyl)piperidine-1-carboxylate, (S)-Tetrahydrofuran-3-yl 4-((5-(4-(methylsulfonyl)piperazin-1-yl)pyrazin-2-yloxy)methyl)piperidine-1-carboxylate, (R)-Tetrahydrofuran-3-yl 4-((5-(4-(methylsulfonyl)piperazin-1-yl)pyrazin-2-yloxy)methyl)piperidine-1-carboxylate, 2-Isopropyl-5-(4-((5-(4-(methylsulfonyl)piperazin-1-yl)pyrazin-2-yloxy)methyl)piperidin-1-yl)thiazole, 2-((1-(2-methyl-2H-tetrazol-5-yl)piperidin-4-yl)methoxy)-5-(4-(methylsulfonyl)piperazin-1-yl)pyrazine, Oxetan-3-yl 4-((5-(4-(methylsulfonyl)piperazin-1-yl)pyrazin-2-yloxy)methyl)piperidine-1-carboxylate, Isopropyl 4-((5-(4-(methylsulfonyl)piperazin-1-yl)pyridin-2-yloxy)methyl)piperidine-1-carboxylate, Isopropyl 4-((6-(4-(methylsulfonyl)piperazin-1-yl)pyridazin-3-yloxy)methyl)piperidine-1-carboxylate, Isopropyl 4-((5-(4-(methylsulfonyl)piperazin-1-yl)pyrimidin-2-yloxy)methyl)piperidine-1-carboxylate, (E)-isopropyl 4-(2-(6-(4-(methylsulfonyl)piperazin-1-yl)pyridin-3-yl)vinyl)piperidine-1-carboxylate, Isopropyl 4-(2-(6-(4-(methylsulfonyl)piperazin-1-yl)pyridin-3-yl)ethyl)piperidine-1-carboxylate, (E)-Isopropyl 4-(2-(2-(4-(methylsulfonyl)piperazin-1-yl)pyrimidin-5-yl)vinyl)piperidine-1-carboxylate, 5-Ethyl-2-(4-((6-(4-(methylsulfonyl)piperazin-1-yl)pyridin-3-yloxy)methyl)piperidin-1-yl)pyrimidine, 1-(Methylsulfonyl)-4-(5-((1-(5-(trifluoromethyl)pyridin-2-yl)piperidin-4-yl)methoxy)pyridin-2-yl)piperazine, 1-Methylcyclopropyl 4-((5-(4-(methylsulfonyl)piperazin-1-yl)pyrazin-2-yloxy)methyl)piperidine-1-carboxylate, 5-Ethyl-2-(4-((5-(4-(methylsulfonyl)piperazin-1-yl)pyrazin-2-yloxy)methyl)piperidin-1-yl)pyrimidine, 2-((1-(5-Methylpyridin-2-yl)piperidin-4-yl)methoxy)-5-(4-(methylsulfonyl)piperazin-1-yl)pyrazine, 1-Methylcyclopropyl 4-((5-(4-(methylsulfonyl)piperazin-1-yl)pyridin-2-yloxy)methyl)piperidine-1-carboxylate, 5-Ethyl-2-(4-((5-(4-(methylsulfonyl)piperazin-1-yl)pyridin-2-yloxy)methyl)piperidin-1-yl)pyrimidine, 3-Isopropyl-5-(4-((5-(4-(methylsulfonyl)piperazin-1-yl)pyrazin-2-yloxy)methyl)piperidin-1-yl)-1,2,4-oxadiazole, 3-Isopropyl-5-(4-((5-(4-(methylsulfonyl)piperazin-1-yl)pyridin-2-yloxy)methyl)piperidin-1-yl)-1,2,4-oxadiazole, 1-Methylcyclopropyl 4-((6-(4-(methylsulfonyl)piperazin-1-yl)pyridin-3-yloxy)methyl)piperidine-1-carboxylate, 5-Isopropyl-3-(4-((6-(4-(methylsulfonyl)piperazin-1-yl)pyridin-3-yloxy)methyl)piperidin-1-yl)-1,2,4-oxadiazole, 2-((1-(5-Fluoropyridin-2-yl)piperidin-4-yl)methoxy)-5-(4-(methylsulfonyl)piperazin-1-yl)pyrazine, 3-Isopropyl-5-(4-((6-(4-(methylsulfonyl)piperazin-1-yl)pyridin-3-yloxy)methyl)piperidin-1-yl)-1,2,4-oxadiazole, tert-Butyl 4-((5-(4-(methylsulfonyl)-1,4-diazepan-1-yl)pyrazin-2-yloxy)methyl)piperidine-1-carboxylate, tert-Butyl 4-(5-(4-(methylsulfonyl)-1,4-diazepan-1-yl)pyrazin-2-yloxy)methyl)piperidine-1-carboxylate, tert-butyl 4-((5-(4-(methylsulfonyl)piperidin-1-yl)pyrazin-2-yloxy)methyl)piperidine-1-carboxylate, 1-Methylcyclopropyl 4-((5-(4-

(methylsulfonyl)piperidin-1-yl)pyrazin-2-yloxy)methyl)piperidine-1-carboxylate, tert-Butyl 4-(2-(3-(4-(methylsulfonyl)piperazin-1-yl)-1,2,4-oxadiazol-5-yl)ethyl)piperidine-1-carboxylate, tert-Butyl 4-(3-(3-(4-(methylsulfonyl)piperazin-1-yl)-1,2,4-oxadiazol-5-yl)propyl)piperidine-1-carboxylate, 5-(3-(1-(5-ethylpyrimidin-2-yl)piperidin-4-yl)propyl)-3-(4-(methylsulfonyl)piperazin-1-yl)-1,2,4-oxadiazole, Isopropyl 4-(3-(3-(4-(methylsulfonyl)piperazin-1-yl)-1,2,4-oxadiazol-5-yl)propyl)piperidine-1-carboxylate, 3-Isopropyl-5-(4-(2-(5-(4-(methylsulfonyl)piperazin-1-yl)thiazol-2-yl)ethyl)piperidin-1-yl)-1,2,4-oxadiazole, Isopropyl 4-((4-(1-methanesulfonyl-1,2,3,6-tetrahydropyridin-4-yl)phenoxy)methyl)piperidine-1-carboxylate, isopropyl 4-(4-(1-(methylsulfonyl)-1,2,3,6-tetrahydropyridin-4-yl)phenoxy)piperidine-1-carboxylate, isopropyl 4-(2-(4-(1-(methylsulfonyl)-1,2,3,6-tetrahydropyridin-4-yl)phenoxy)ethyl)piperidine-1-carboxylate, isopropyl 4-(3-(4-(1-(methylsulfonyl)-1,2,3,6-tetrahydropyridin-4-yl)phenoxy)propyl)piperidine-1-carboxylate, isopropyl 4-(4-(4-(1-(methylsulfonyl)-1,2,3,6-tetrahydropyridin-4-yl)phenoxy)butyl)piperidine-1-carboxylate, 1-methylcyclopropyl 4-((4-(1-(methylsulfonyl)-1,2,3,6-tetrahydropyridin-4-yl)phenoxy)methyl)piperidine-1-carboxylate, 5-isopropyl-3-(4-((4-(1-(methylsulfonyl)-1,2,3,6-tetrahydropyridin-4-yl)phenoxy)methyl)piperidin-1-yl)-1,2,4-oxadiazole, Isopropyl 4-((4-(1-methanesulfonylpiperidin-4-yl)phenoxy)methyl)piperidine-1-carboxylate, isopropyl 4-(4-(1-(methylsulfonyl)piperidin-4-yl)phenoxy)piperidine-1-carboxylate, isopropyl 4-(2-(4-(1-(methylsulfonyl)piperidin-4-yl)phenoxy)ethyl)piperidine-1-carboxylate, isopropyl 4-(3-(4-(1-(methylsulfonyl)piperidin-4-yl)phenoxy)propyl)piperidine-1-carboxylate, isopropyl 4-(4-(4-(1-(methylsulfonyl)piperidin-4-yl)phenoxy)butyl)piperidine-1-carboxylate, 1-Methylcyclopropyl 4-((4-(1-(methylsulfonyl)piperidin-4-yl)phenoxy)methyl)piperidine-1-carboxylate, 2-(4-((4-(1-(methylsulfonyl)piperidin-4-yl)phenoxy)methyl)piperidin-1-yl)-5-(trifluoromethyl)pyridine, 5-isopropyl-3-(4-((4-(1-(methylsulfonyl)piperidin-4-yl)phenoxy)methyl)piperidin-1-yl)-1,2,4-oxadiazole, 3-chloro-2-(4-((4-(1-(methylsulfonyl)piperidin-4-yl)phenoxy)methyl)piperidin-1-yl)-5-(trifluoromethyl)pyridine, 5-chloro-2-(4-((4-(1-(methylsulfonyl)piperidin-4-yl)phenoxy)methyl)piperidin-1-yl)pyridine, 3-chloro-6-(4-((4-(1-(methylsulfonyl)piperidin-4-yl)phenoxy)methyl)piperidin-1-yl)pyridazine, 5-bromo-2-(4-((4-(1-(methylsulfonyl)piperidin-4-yl)phenoxy)methyl)piperidin-1-yl)pyrimidine, 5-ethyl-2-(4-((4-(1-(methylsulfonyl)piperidin-4-yl)phenoxy)methyl)piperidin-1-yl)pyrimidine, 5-fluoro-2-(4-((4-(1-(methylsulfonyl)piperidin-4-yl)phenoxy)methyl)piperidin-1-yl)pyridine, 3-isopropyl-5-(4-((4-(1-(methylsulfonyl)piperidin-4-yl)phenoxy)methyl)piperidin-1-yl)-1,2,4-oxadiazole, 3-tert-butyl-6-(4-((4-(1-(methylsulfonyl)piperidin-4-yl)phenoxy)methyl)piperidin-1-yl)pyridazine, 5-fluoro-2-(4-((4-(1-(methylsulfonyl)piperidin-4-yl)phenoxy)methyl)piperidin-1-yl)pyrimidine, Isopropyl 4-(2-(3-(1-methanesulfonyl-1,2,3,6-tetrahydropyridin-4-yl)phenoxy)ethyl)piperidine-1-carboxylate, 1-Methylcyclopropyl 4-methoxy-4-(5-(4-(methylsulfonyl)piperazin-1-yl)pyrazin-2-yloxy)methyl)piperidine-1-carboxylate, 1-methylcyclopropyl 4-((6-formyl-5-(4-(methylsulfonyl)piperazin-1-yl)pyrazin-2-yloxy)methyl)piperidine-1-carboxylate, 1-Methylcyclopropyl 4-((6-chloro-5-(4-(methylsulfonyl)piperazin-1-yl)pyrazin-2-yloxy)methyl)piperidine-1-carboxylate, 1-Methylcyclopropyl 4-((5-(4-(3-methoxy-3-oxopropylsulfonyl)piperazin-1-yl)pyrazin-2-yloxy)methyl)piperidine-1-carboxylate, 3-(4-(5-((1-((1-methylcyclopropoxy)carbonyl)-piperidin-4-yl)methoxy)pyrazin-2-yl)piperazin-1-ylsulfonyl)propanoic acid, 3-(4-(5-((1-((1-methylcyclopropoxy)carbonyl)piperidin-4-yl)methoxy)pyrazin-2-yl)piperazin-1-ylsulfonyl)propanoic acid, 3-(4-(5-((1-((1-methylcyclopropoxy)carbonyl)piperidin-4-yl)methoxy)pyrazin-2-yl)piperazin-1-ylsulfonyl)propanoic acid, 3-(4-(5-((1-((1-methylcyclopropoxy)carbonyl)piperidin-4-yl)methoxy)pyrazin-2-yl)piperazin-1-ylsulfonyl)propanoic acid, 3-(4-(5-((1-((1-methylcyclopropoxy)carbonyl)piperidin-4-yl)methoxy)pyrazin-2-yl)piperazin-1-ylsulfonyl)propanoic acid, 3-(4-(5-((1-((1-methylcyclopropoxy)carbonyl)piperidin-4-yl)methoxy)pyrazin-2-yl)piperazin-1-ylsulfonyl)propanoic acid; 1-methylcyclopropyl 4-((5-(4-(3-cyanopropylsulfonyl)piperazin-1-yl)pyrazin-2-yloxy)methyl)piperidine-1-carboxylate; 1-methylcyclopropyl 4-((5-(4-(3-(1H-tetrazol-5-yl)propylsulfonyl)piperazin-1-yl)pyrazin-2-yloxy)methyl)piperidine-1-carboxylate; 1-methylcyclopropyl 4-((5-(4-(vinylsulfonyl)piperazin-1-yl)pyrazin-2-yloxy)methyl)piperidine-1-carboxylate; 1-methylcyclopropyl 4-((5-(4-(2-(piperidin-1-yl)ethylsulfonyl)piperazin-1-yl)pyrazin-2-yloxy)methyl)piperidine-1-carboxylate; 1-methylcyclopropyl 4-((5-(4-(2-morpholinoethylsulfonyl)piperazin-1-yl)pyrazin-2-yloxy)methyl)piperidine-1-carboxylate; 1-methylcyclopropyl 4-((5-(4-(2-(dimethylamino)ethylsulfonyl)piperazin-1-yl)pyrazin-2-yloxy)methyl)piperidine-1-carboxylate; tert-butyl 4-((5-(4-(3-chloropropylsulfonyl)piperazin-1-yl)pyrazin-2-yloxy)methyl)piperidine-1-carboxylate; tert-butyl 4-((5-(4-(3-acetoxypropylsulfonyl)piperazin-1-yl)pyrazin-2-yloxy)methyl)piperidine-1-carboxylate; 1-methylcyclopropyl 4-((5-(4-(3-aminopropylsulfonyl)piperazin-1-yl)pyrazin-2-yloxy)methyl)piperidine-1-carboxylate; 1-methylcyclopropyl 4-((5-(4-(2-ethoxyethylsulfonyl)piperazin-1-yl)pyrazin-2-yloxy)methyl)piperidine-1-carboxylate; 1-methylcyclopropyl 4-((5-(4-(3-(pyrrolidin-1-yl)propylsulfonyl)piperazin-1-yl)pyrazin-2-yloxy)methyl)piperidine-1-carboxylate; 1-methylcyclopropyl 4-((5-(4-(3-(2-methyl-1H-imidazol-1-yl)propylsulfonyl)piperazin-1-yl)pyrazin-2-yloxy)methyl)piperidine-1-carboxylate; 1-methylcyclopropyl 4-((5-(4-(3-(dimethylamino)propylsulfonyl)piperazin-1-yl)pyrazin-2-yloxy)methyl)piperidine-1-carboxylate; 1-methylcyclopropyl 4-((5-(4-(propylsulfonyl)piperazin-1-yl)pyrazin-2-yloxy)methyl)piperidine-1-carboxylate; 1-methylcyclopropyl 4-((5-(4-(ethylsulfonyl)piperazin-1-yl)pyrazin-2-yloxy)methyl)piperidine-1-carboxylate; 1-methylcyclopropyl 4-((5-(4-(isopropylsulfonyl)piperazin-1-yl)pyrazin-2-yloxy)methyl)piperidine-1-carboxylate; 1-methylcyclopropyl 4-((5-(4-(isobutylsulfonyl)piperazin-1-yl)pyrazin-2-yloxy)methyl)piperidine-1-carboxylate; 1-methylcyclopropyl 4-((5-(4-(sec-butylsulfonyl)piperazin-1-yl)pyrazin-2-yloxy)methyl)piperidine-1-carboxylate; 1-methylcyclopropyl 4-((5-(4-(3-acetoxy-2,2-dimethylpropylsulfonyl)piperazin-1-yl)pyrazin-2-yloxy)methyl)piperidine-1-carboxylate; 1-methylcyclopropyl 4-((5-(4-(3-hydroxy-2,2-dimethylpropylsulfonyl)piperazin-1-yl)pyrazin-2-yloxy)methyl)piperidine-1-carboxylate; 1-Methylcyclopropyl 4-((5-(4-(2-(pyridin-3-yl)ethylsulfonyl)piperazin-1-yl)pyrazin-2-yloxy)methyl)piperidine-1-carboxylate; 1-Methylcyclopropyl 4-((5-(4-(2-(pyridin-4-yl)ethylsulfonyl)piperazin-1-yl)pyrazin-2-yloxy)methyl)piperidine-1-carboxylate; 1-Methylcyclopropyl 4-((5-(4-sulfamoylpiperazin-1-yl)pyrazin-2-yloxy)methyl)piperidine-1-carboxylate; tert-Butyl 4-((5-(4-(morpholinosulfonyl)piperazin-1-yl)pyrazin-2-yloxy)methyl)piperidine-1-carboxylate; 1-methylcyclopropyl 4-((6-(4-(ethylsulfonyl)piperazin-1-yl)pyridin-3-yloxy)methyl)piperidine-1-carboxylate; 1-methylcyclopropyl 4-((6-(4-(ethylsulfonyl)piperazin-1-yl)pyridin-3-yloxy)methyl)piperidine-1-carboxylate; 1-methylcyclopropyl 4-((6-(4-(ethylsulfonyl)piperazin-1-yl)pyridin-3-yloxy)methyl)piperidine-1-carboxylate; 1-methylcyclopropyl 4-((6-(4-(ethylsulfonyl)piperazin-1-yl)pyridin-3-yloxy)methyl)piperidine-1-carboxylate; 1-methylcyclopropyl 4-((6-(4-

(ethylsulfonyl)piperazin-1-yl)pyridin-3-yloxy)methyl)piperidine-1-carboxylate; 1-Methylcyclopropyl 4-((5-fluoro-6-(4-(methylsulfonyl)piperazin-1-yl)pyridin-3-yloxy)methyl) piperidine-1-carboxylate; tert-Butyl 4-((5-(4-(methylsulfonyl)-2-oxopiperazin-1-yl)pyrazin-2-yloxy) methyl)piperidine-1-carboxylate; 1-Methylcyclopropyl 4-((5-(4-(methylsulfonyl)-2-oxopiperazin-1-yl)pyrazin-2-yloxy)methyl)piperidine-1-carboxylate; 1-Methylcyclopropyl 4-((5-(2-oxo-4-(propylsulfonyl)piperazin-1-yl)pyrazin-2-yloxy)methyl)piperidine-1-carboxylate; 1-Methylcyclopropyl 4-((5-(4-(isopropylsulfonyl)-2-oxopiperazin-1-yl)pyrazin-2-yloxy)methyl)piperidine-1-carboxylate; 1-Methylcyclopropyl 4-((5-(4-(isopropylsulfonyl)-2-oxopiperazin-1-yl)pyrazin-2-yloxy)methyl) piperidine-1-carboxylate; 1-methylcyclopropyl 4-((6-(2-oxo-4-(propylsulfonyl)piperazin-1-yl)pyridin-3-yloxy) methyl)piperidine-1-carboxylate; 1-methylcyclopropyl 4-((6-(4-(isopropylsulfonyl)-2-oxopiperazin-1-yl)pyridin-3-yloxy)methyl)piperidine-1-carboxylate; 1-(5-((1-(5-Ethylpyrimidin-2-yl)piperidin-4-yl)methoxy)pyrazin-2-yl)-4-(methylsulfonyl)piperazin-2-one; 1-(5-((1-(5-Ethylpyrimidin-2-yl)piperidin-4-yl)methoxy)pyridin-2-yl)-4-(methylsulfonyl)piperazin-2-one; tert-Butyl 4-((2,6-difluoro-4-(1-(methylsulfonyl)piperidin-4-yl)phenoxy) methyl)piperidine-1-carboxylate; tert-butyl 4-((2-methyl-4-(1-(methylsulfonyl)piperidin-4-yl)phenoxy)methyl) piperidine-1-carboxylate; tert-butyl 4-((3-methoxy-4-(1-(methylsulfonyl)piperidin-4-yl)phenoxy)methyl)piperidine-1-carboxylate; tert-butyl 4-((2,6-dimethyl-4-(1-(methylsulfonyl)piperidin-4-yl)phenoxy)methyl)piperidine-1-carboxylate; tert-butyl 4-((2,5-dimethyl-4-(1-(methylsulfonyl)piperidin-4-yl)phenoxy)methyl)piperidine-1-carboxylate; tert-butyl 4-((2-(methoxycarbonyl)-4-(1-(methylsulfonyl)piperidin-4-yl)phenoxy)methyl)piperidine-1-carboxylate; tert-butyl 4-((2-chloro-4-(1-(methylsulfonyl) piperidin-4-yl)phenoxy)methyl)piperidine-1-carboxylate; tert-butyl 4-((3-methyl-4-(1-(methylsulfonyl)piperidin-4-yl) phenoxy)methyl)piperidine-1-carboxylate; tert-butyl 4-((2,3-dimethyl-4-(1-(methylsulfonyl)piperidin-4-yl)phenoxy) methyl)piperidine-1-carboxylate; tert-butyl 4-((2-fluoro-4-(1-(methylsulfonyl)piperidin-4-yl)phenoxy)methyl) piperidine-1-carboxylate; tert-butyl 4-((4-(1-(methylsulfonyl)piperidin-4-yl)-2-(trifluoromethyl) phenoxy)methyl)piperidine-1-carboxylate; 2-(4-((2,6-Difluoro-4-(1-(methylsulfonyl)piperidin-4-yl)phenoxy) methyl)piperidin-1-yl)-5-ethylpyrimidine; 1-Methylcyclopropyl 4-((2,6-difluoro-4-(1-(methylsulfonyl) piperidin-4-yl)phenoxy)methyl)piperidine-1-carboxylate; 3-(4-(4-((1-(5-Ethylpyrimidin-2-yl)piperidin-4-yl)methoxy)-3,5-difluorophenyl)piperidin-1-ylsulfonyl)propyl acetate; 1-Methylcyclopropyl 4-((4-(1-(3-acetoxypropylsulfonyl)piperidin-4-yl)-2,6-difluorophenoxy)methyl)piperidine-1-carboxylate; 3-(4-(4-((1-(5-Ethylpyrimidin-2-yl)piperidin-4-yl)methoxy)-3,5-difluorophenyl)piperidin-1-ylsulfonyl)propan-1-ol; 1-Methylcyclopropyl 4-((2,6-difluoro-4-(1-(3-hydroxypropylsulfonyl)piperidin-4-yl) phenoxy)methyl)piperidine-1-carboxylate; Isopropyl 4-((5-(1,2,3,6-tetrahydro-1-methanesulfonylpyridin-4-yl)pyrazin-2-yloxy)methyl)piperidine-1-carboxylate; 1-Methylcyclopropyl 4-((6-(1,2,3,6-tetrahydro-1-methanesulfonylpyridin-4-yl)pyridin-3-yloxy)methyl)piperidine-1-carboxylate; Isopropyl 4-(2-(6-(1,2,3,6-tetrahydro-1-methanesulfonylpyridin-4-yl)pyridin-3-yloxy)ethyl)piperidine-1-carboxylate; 2-(4-((5-(1,2,3,6-Tetrahydro-1-methanesulfonylpyridin-4-yl)pyrazin-2-yloxy)methyl) piperidin-1-yl)-5-ethylpyrimidine; 2-(4-((6-(1,2,3,6-Tetrahydro-1-methanesulfonylpyridin-4-yl)pyridin-3-yloxy) methyl)piperidin-1-yl)-5-ethylpyrimidine; 2-((1-(5-Ethylpyrimidin-2-yl)piperidin-4-yl)methoxy)-5-(1-methanesulfonylpiperidin-4-yl)pyrazine; 2-(4-((6-(1-Methanesulfonylpiperidin-4-yl)pyridin-3-yloxy)methyl) piperidin-1-yl)-5-ethylpyrimidine; 3-((1-(5-Ethylpyrimidin-2-yl)piperidin-4-yl)methoxy)-6-(1-methanesulfonylpiperidin-4-yl)pyridazine; 2-(4-((5-(1-Methanesulfonylpiperidin-4-yl)pyridin-2-yloxy)methyl) piperidin-1-yl)-5-ethylpyrimidine; 1-tert-Butyl 4-(4-(1-(methylsulfonyl)piperidin-4-yl)phenyl)piperazine-1,4-dicarboxylate; N-((1-(5-Ethylpyrimidin-2-yl)piperidin-4-yl) methyl)-4-(1-(methylsulfonyl)piperidin-4-yl)aniline; N-((1-(5-Ethylpyrimidin-2-yl)piperidin-4-yl)methyl)-N-methyl-4-(1-(methylsulfonyl)piperidin-4-yl)aniline; 4-(4-((1-(5-fluoropyrimidin-2-yl)piperidin-4-yl)methoxy)phenyl)-1-(methylsulfonyl)piperidine-4-carboxylic acid; 2-[(2-{4-[5-({1-[(1-methylcyclopropoxy)carbonyl]piperidin-4-yl}methoxy)pyrazin-2-yl]-3-oxopiperazine-1-sulfonyl}ethyl)amino]acetic acid; 1-methylcyclopropyl 4-{[(5-{4-[(2-carbamimidamidoethane)sulfonyl]-2-oxopiperazin-1-yl}pyrazin-2-yl)oxy]methyl}piperidine-1-carboxylate; 1-methylcyclopropyl 4-{[(5-{4-[(3-methyl-3-nitrobutane)sulfonyl]-2-oxopiperazin-1-yl}pyrazin-2-yl)oxy] methyl}piperidine-1-carboxylate; 1-methylcyclopropyl 4-[({5-[4-(1-benzylpyrrolidine-3-sulfonyl)-2-oxopiperazin-1-yl]pyrazin-2-yl}oxy)methyl]piperidine-1-carboxylate; 1-methylcyclopropyl 4-{[(5-{4-[(carbamoylmethane)sulfonyl]-2-oxopiperazin-1-yl}pyrazin-2-yl)oxy] methyl}piperidine-1-carboxylate; 1-methylcyclopropyl 4-{[(5-{4-[(1-carbamoyl-1-methylethane)sulfonyl]-2-oxopiperazin-1-yl}pyrazin-2-yl)oxy]methyl}piperidine-1-carboxylate; 1-methylcyclopropyl 4-({[5-(2-oxo-4-{[2-(pyrrolidin-1-yl)ethane]sulfonyl}piperazin-1-yl)pyrazin-2-yl] oxy}methyl)piperidine-1-carboxylate; 1-methylcyclopropyl 4-({[5-(4-{[2-(morpholin-4-yl)ethane]sulfonyl}-2-oxopiperazin-1-yl)pyrazin-2-yl]oxy}methyl)piperidine-1-carboxylate; 1-methylcyclopropyl 4-({[5-(4-{[3-(dimethylamino) propane]sulfonyl}-2-oxopiperazin-1-yl)pyrazin-2-yl] oxy}methyl)piperidine-1-carboxylate; 1-methylcyclopropyl 4-({[5-(4-{[2-(1,3-dioxo-2,3-dihydro-1H-isoindol-2-yl) ethane]sulfonyl}-2-oxopiperazin-1-yl)pyrazin-2-yl] oxy}methyl)piperidine-1-carboxylate; 1-methylcyclopropyl 4-({[5-(4-{[(dimethylcarbamoyl)methane]sulfonyl}-2-oxopiperazin-1-yl)pyrazin-2-yl]oxy}methyl)piperidine-1-carboxylate; 1-methylcyclopropyl 4-{[(5-{4-[1-(2-methylpropyl)pyrrolidine-3-sulfonyl]-2-oxopiperazin-1-yl}pyrazin-2-yl)oxy]methyl}piperidine-1-carboxylate; 1-methylcyclopropyl 4-({[5-(2-oxo-4-{[3-(1H-pyrazol-1-yl) propane]sulfonyl}piperazin-1-yl)pyrazin-2-yl]oxy}methyl) piperidine-1-carboxylate; 1-methylcyclopropyl 4-[({5-[2-oxo-4-(pyrrolidine-3-sulfonyl)piperazin-1-yl]pyrazin-2-yl}oxy)methyl]piperidine-1-carboxylate; 1-methylcyclopropyl 4-{[(5-{4-[(2-amino-2-methylpropane)sulfonyl]-2-oxopiperazin-1-yl}pyrazin-2-yl)oxy] methyl}piperidine-1-carboxylate; 1-methylcyclopropyl 4-({[5-(4-{[(1-methylpyrrolidin-3-yl)methane]sulfonyl}-2-oxopiperazin-1-yl)pyrazin-2-yl]oxy}methyl)piperidine-1-carboxylate; 1-methylcyclopropyl 4-({[5-(4-{[2-(azetidin-1-yl)ethane]sulfonyl}-2-oxopiperazin-1-yl)pyrazin-2-yl] oxy}methyl)piperidine-1-carboxylate; 1-methylcyclopropyl 4-({[5-(2-oxo-4-{[2-(1H-pyrazol-1-yl)ethane] sulfonyl}piperazin-1-yl)pyrazin-2-yl]oxy}methyl)piperidine-1-carboxylate; 1-methylcyclopropyl 4-[({5-[4-(1-methylpyrrolidine-3-sulfonyl)-2-oxopiperazin-1-yl]pyrazin-2-yl}oxy)methyl]piperidine-1-carboxylate; 1-methylcyclopropyl 4-({[5-(4-{[1-(dimethylcarbamoyl)-1-methylethane]sulfonyl}-2-oxopiperazin-1-yl)pyrazin-2-yl] oxy}methyl)piperidine-1-carboxylate; 1-methylcyclopropyl 4-({[5-(4-{[2-(3,3-difluoroazetidin-1-yl)ethane]sulfonyl}-2-oxopiperazin-1-yl)pyrazin-2-yl]oxy}methyl)piperidine-1-carboxylate; 1-methylcyclopropyl 4-({[5-(4-{[3-(dimethylamino)-3-methylbutane]sulfonyl}-2-oxopiperazin-1-yl) pyrazin-2-yl]oxy}methyl)piperidine-1-carboxylate; 1-methylcyclopropyl 4-{[(5-{4-[(2-{[2-(tert-butoxy)-2-oxoethyl]amino}ethane)sulfonyl]-2-oxopiperazin-1-yl}pyrazin-2-yl)oxy]methyl}piperidine-1-carboxylate; 1-methylcyclopropyl 4-[({5-[4-(azetidine-3-sulfonyl)-2-oxopiperazin-1- yl]pyrazin-2-yl}oxy)methyl]piperidine-1-carboxylate; 1-methylcyclopropyl 4-({[5-(4-{[3-(3,3-difluoroazetidin-1-yl)propane]sulfonyl}-2-oxopiperazin-1-yl)pyrazin-2-yl]oxy}methyl)piperidine-1-carboxylate; 1-methylcyclopropyl 4-({[5-(4-{[3-(azetidin-1-yl)propane]sulfonyl}-2-oxopiperazin-1-yl)pyrazin-2-yl]oxy}methyl)piperidine-1-carboxylate; 1-methylcyclopropyl 4-{[(5-{2-oxo-4-[(3S)-pyrrolidine-3-sulfonyl]piperazin-1-yl}pyrazin-2-yl)oxy]methyl}piperidine-1-carboxylate; 1-methylcyclopropyl 4-{[(5-{4-[(3S)-1-methylpyrrolidine-3-sulfonyl]piperazin-1-yl}pyrazin-2-yl)oxy]methyl}piperidine-1-carboxylate; 1-methylcyclopropyl 4-{[(5-{4-[(3R)-1-methylpyrrolidine-3-sulfonyl]piperazin-1-yl}pyrazin-2-yl)oxy]methyl}piperidine-1-carboxylate; 1-methylcyclopropyl 4-{[(5-{4-[(3S)-pyrrolidine-3-sulfonyl]piperazin-1-yl}pyrazin-2-yl)oxy]methyl}piperidine-1-carboxylate; 1-methylcyclopropyl 4-{[(5-{4-[(3R)-pyrrolidine-3-sulfonyl]piperazin-1-yl}pyrazin-2-yl)oxy]methyl}piperidine-1-carboxylate; 1-methylcyclopropyl 4-[({5-[4-(azetidine-3-sulfonyl)piperazin-1-yl]pyrazin-2-yl}oxy)methyl]piperidine-1-carboxylate; 1-methylcyclopropyl 4-{[(5-{2-oxo-4-[(pyrrolidin-3-ylmethane)sulfonyl]piperazin-1-yl}pyrazin-2-yl)oxy]methyl}piperidine-1-carboxylate; 1-methylcyclopropyl 4-[({5-[4-(1-hydroxy-2-methylpropane-2-sulfonyl)piperazin-1-yl]pyrazin-2-yl}oxy)methyl]piperidine-1-carboxylate; 1-methylcyclopropyl 4-{[(5-{4-[(2-hydroxyethane)sulfonyl]piperazin-1-yl}pyrazin-2-yl)oxy]methyl}piperidine-1-carboxylate; 1-methylcyclopropyl 4-{[(5-{4-[(azetidin-3-ylmethane)sulfonyl]piperazin-1-yl}pyrazin-2-yl)oxy]methyl}piperidine-1-carboxylate; 1-methylcyclopropyl 4-({[5-(4-{[(1-methylpyrrolidin-2-yl)methane]sulfonyl}-2-oxopiperazin-1-yl)pyrazin-2-yl]oxy}methyl)piperidine-1-carboxylate; 1-methylcyclopropyl 4-{[(5-{2-oxo-4-[(3R)-pyrrolidine-3-sulfonyl]piperazin-1-yl}pyrazin-2-yl)oxy]methyl}piperidine-1-carboxylate; 1-methylcyclopropyl 4-[({5-[4-(1-methylazetidine-3-sulfonyl)piperazin-1-yl]pyrazin-2-yl}oxy)methyl]piperidine-1-carboxylate; 1-methylcyclopropyl 4-[({5-[4-(1-methylazetidine-3-sulfonyl)-2-oxopiperazin-1-yl]pyrazin-2-yl}oxy)methyl]piperidine-1-carboxylate; 1-methylcyclopropyl 4-({[5-(4-{[(1-methylazetidin-3-yl)methane]sulfonyl}-2-oxopiperazin-1-yl)pyrazin-2-yl]oxy}methyl)piperidine-1-carboxylate; 1-methylcyclopropyl 4-({[5-(4-{[(1-methylazetidin-3-yl)methane]sulfonyl}piperazin-1-yl)pyrazin-2-yl]oxy}methyl)piperidine-1-carboxylate; 1-methylcyclopropyl 4-[({5-[4-({3-[(3S,4S)-3,4-dihydroxypyrrolidin-1-yl]propane}sulfonyl)-2-oxopiperazin-1-yl]pyrazin-2-yl}oxy)methyl]piperidine-1-carboxylate; 1-methylcyclopropyl 4-[({5-[4-({2-[(3S,4S)-3,4-dihydroxypyrrolidin-1-yl]ethane}sulfonyl)-2-oxopiperazin-1-yl]pyrazin-2-yl}oxy)methyl]piperidine-1-carboxylate; 1-methylcyclopropyl 4-{[(5-{4-[(azetidin-3-ylmethane)sulfonyl]-2-oxopiperazin-1-yl}pyrazin-2-yl)oxy]methyl}piperidine-1-carboxylate; 1-methylcyclopropyl 4-{[(5-{2-oxo-4-[(pyrrolidin-2-ylmethane)sulfonyl]piperazin-1-yl}pyrazin-2-yl)oxy]methyl}piperidine-1-carboxylate; 1-methylcyclopropyl 4-{[(5-{4-[(3-aminopropane)sulfonyl]-2-oxopiperazin-1-yl}pyrazin-2-yl)oxy]methyl}piperidine-1-carboxylate; 1-methylcyclopropyl 4-{[(5-{4-[(2-aminoethane)sulfonyl]-2-oxopiperazin-1-yl}pyrazin-2-yl)oxy]methyl}piperidine-1-carboxylate; 1-methylcyclopropyl 4-({[5-(3-methanesulfonamidoazetidin-1-yl)pyrazin-2-yl]oxy}methyl)piperidine-1-carboxylate; 1-methylcyclopropyl 4-({[5-(4-{[2-(dimethylamino)ethane]sulfonyl}-2-oxopiperazin-1-yl)pyrazin-2-yl]oxy}methyl)piperidine-1-carboxylate; 1-methylcyclopropyl 4-({[5-(2-oxo-4-{[3-(pyrrolidin-1-yl)propane]sulfonyl}piperazin-1-yl)pyrazin-2-yl]oxy}methyl)piperidine-1-carboxylate; 1-methylcyclopropyl 4-({[5-(4-{[3-(morpholin-4-yl)propane]sulfonyl}-2-oxopiperazin-1-yl)pyrazin-2-yl]oxy}methyl)piperidine-1-carboxylate; 1-methylcyclopropyl 4-({[5-(4-{[(3-methyloxetan-3-yl)methane]sulfonyl}piperazin-1-yl)pyrazin-2-yl]oxy}methyl)piperidine-1-carboxylate; 1-methylcyclopropyl 4-({[5-(4-{[3-(acetyloxy)propane]sulfonyl}-2-oxopiperazin-1-yl)pyrazin-2-yl]oxy}methyl)piperidine-1-carboxylate; 1-methylcyclopropyl 4-{[(5-{4-[(3,3,3-trifluoropropane)sulfonyl]piperazin-1-yl}pyrazin-2-yl)oxy]methyl}piperidine-1-carboxylate; 1-methylcyclopropyl 4-[({5-[(2E)-2-(hydroxyimino)-4-methanesulfonylpiperazin-1-yl]pyrazin-2-yl}oxy)methyl]piperidine-1-carboxylate; 1-methylcyclopropyl 4-{[(5-{4-[(3-chloropropane)sulfonyl]-2-oxopiperazin-1-yl}pyrazin-2-yl)oxy]methyl}piperidine-1-carboxylate; 1-methylcyclopropyl 4-{[(5-{4-[(3-hydroxypropane)sulfonyl]-2-oxopiperazin-1-yl}pyrazin-2-yl)oxy]methyl}piperidine-1-carboxylate; 1-methylcyclopropyl 4-[({5-[4-({[1-(dimethylamino)cyclopropyl]methane}sulfonyl)-2-oxopiperazin-1-yl]pyrazin-2-yl}oxy)methyl]piperidine-1-carboxylate; 1-methylcyclopropyl 4-[({5-[4-({[1-(dimethylamino)cyclopropyl]methane}sulfonyl)piperazin-1-yl]pyrazin-2-yl}oxy)methyl]piperidine-1-carboxylate; 1-methylcyclopropyl 4-{[(5-{4-[(3-hydroxy-3-methylbutane)sulfonyl]piperazin-1-yl}pyrazin-2-yl)oxy]methyl}piperidine-1-carboxylate; 1-methylcyclopropyl 4-{[(5-{2-oxo-4-[(3R)-oxolane-3-sulfonyl]piperazin-1-yl}pyrazin-2-yl)oxy]methyl}piperidine-1-carboxylate; 1-methylcyclopropyl 4-{[(5-{2-oxo-4-[(3S)-oxolane-3-sulfonyl]piperazin-1-yl}pyrazin-2-yl)oxy]methyl}piperidine-1-carboxylate; 1-methylcyclopropyl 4-({[5-(4-{[3-(acetyloxy)-3-methylbutane]sulfonyl}piperazin-1-yl)pyrazin-2-yl]oxy}methyl)piperidine-1-carboxylate; 1-methylcyclopropyl 4-[({6-[4-({[1-(azetidin-1-yl)cyclopropyl]methane}sulfonyl)piperazin-1-yl]pyridin-3-yl}oxy)methyl]piperidine-1-carboxylate; 1-methylcyclopropyl 4-[({5-[4-({[1-(benzylamino)cyclopropyl]methane}sulfonyl)piperazin-1-yl]pyrazin-2-yl}oxy)methyl]piperidine-1-carboxylate; 1-methylcyclopropyl 4-[({5-[4-({[1-(azetidin-1-yl)cyclopropyl]methane}sulfonyl)piperazin-1-yl]pyrazin-2-yl}oxy)methyl]piperidine-1-carboxylate; 1-methylcyclopropyl 4-({[5-(4-{[(1-hydroxycyclopropyl)methane]sulfonyl}piperazin-1-yl)pyrazin-2-yl]oxy}methyl)piperidine-1-carboxylate; 1-methylcyclopropyl 4-({[5-(4-{[2-(1-hydroxycyclopropyl)ethane]sulfonyl}piperazin-1-yl)pyrazin-2-yl]oxy}methyl)piperidine-1-carboxylate; 1-methylcyclopropyl 4-[({5-[4-({2-[1-(acetyloxy)cyclopropyl]ethane}sulfonyl)piperazin-1-yl]pyrazin-2-yl}oxy)methyl]piperidine-1-carboxylate; 1-methylcyclopropyl 4-[({5-[4-({[1-(benzyloxy)cyclopropyl]methane}sulfonyl)piperazin-1-yl]pyrazin-2-yl}oxy)methyl]piperidine-1-carboxylate; 1-methylcyclopropyl 4-({[5-(4-{[(1-aminocyclopropyl)methane]sulfonyl}piperazin-1-yl)pyrazin-2-yl]oxy}methyl)piperidine-1-carboxylate; 1-methylcyclopropyl 4-({[5-(4-{[2-(1-hydroxycyclopropyl)ethane]sulfonyl}-2-oxopiperazin-1-yl)pyrazin-2-yl]oxy}methyl)piperidine-1-carboxylate; 1-methylcyclopropyl 4-{2,6-difluoro-4-[3-(N-methylmethanesulfonamido)azetidin-1-yl]phenoxymethyl}piperidine-1-carboxylate; 1-methylcyclopropyl 4-[2,6-difluoro-4-(3-methanesulfonamidoazetidin-1-yl)phenoxymethyl]piperidine-1-carboxylate; 1-methylcyclopropyl 4-{2,6-difluoro-4-[3-(2-methylpropane-1-sulfonamido)azetidin-1-yl]phenoxymethyl}piperidine-1-carboxylate; 1-methylcyclopropyl 4-{4-[3-(N,2-dimethylpropane-1-sulfonamido)azetidin-1-yl]-2,6-difluorophenoxymethyl}piperidine-1-carboxylate; 5-ethyl-2-{4-[({2-methanesulfonyl-1H,2H,3H,4H-pyrazino[1,2-a]indol-8-yl}oxy)methyl]piperidin-1-yl}pyrimidine; 11-{[1-(5-ethylpyrimidin-2-yl)piperidin-4-yl]oxy}-5-methanesulfonyl-8-oxa-5-azatricyclo[7.4.0.0{2,7}]trideca-1(13),2(7),9,11-tetraene; 11-{[1-(5-ethylpyrimidin-2-yl)piperidin-4-yl]methoxy}-5-methanesulfonyl-8-oxa-5-azatricyclo[7.4.0.0{2,7}]trideca-1(13),2(7),9,11-tetraene; tert-butyl 4-[({2-methanesulfonyl-1H,2H,3H,4H-pyrazino[1,2-a]indol-8-yl}oxy)methyl]piperidine-1-carboxylate; 1-methylcyclopropyl 4-[({2- methanesulfonyl-1H,2H,3H,4H-pyrazino[1,2-a]indol-8-yl}oxy)methyl]piperidine-1-carboxylate; propan-2-yl 4-{3-[3-(1-methanesulfonylpiperidin-4-yl)phenoxy]propyl}piperidine-1-carboxylate; propan-2-yl 4-{2-[3-(1-methanesulfonylpiperidin-4-yl)phenoxy]ethyl}piperidine-1-carboxylate; propan-2-yl 4-[3-(1-methanesulfonylpiperidin-4-yl)phenoxymethyl]piperidine-1-carboxylate; propan-2-yl 4-{3-[3-(1-methanesulfonyl-1,2,3,6-tetrahydropyridin-4-yl)phenoxy]propyl}piperidine-1-carboxylate; 1-methylcyclopropyl 4-({[5-(4-methanesulfonyl-2-sulfanylidenepiperazin-1-yl)pyrazin-2-yl]oxy}methyl)piperidine-1-carboxylate; 1-methylcyclopropyl (3S,4S)-3-hydroxy-4-{[(6-{4-[(2-methylpropane)sulfonyl]piperazin-1-yl}pyridin-3-yl)oxy]methyl}piperidine-1-carboxylate; 1-methylcyclopropyl (3R,4S)-3-hydroxy-4-{[(6-{4-[(2-methylpropane)sulfonyl]piperazin-1-yl}pyridin-3-yl)oxy]methyl}piperidine-1-carboxylate; 1-methylcyclopropyl 4-hydroxy-4-{[(6-{4-[(2-methylpropane)sulfonyl]piperazin-1-yl}pyridin-3-yl)oxy]methyl}piperidine-1-carboxylate; 1-methylcyclopropyl 4-{[(6-{4-[(2-hydroxy-2-methylpropane)sulfonyl]piperazin-1-yl}pyridin-3-yl)oxy]methyl}piperidine-1-carboxylate; 1-methylcyclopropyl (3S,4R)-3-methoxy-4-{[(6-{4-[(2-methylpropane)sulfonyl]piperazin-1-yl}pyridin-3-yl)oxy]methyl}piperidine-1-carboxylate; 1-methylcyclopropyl 4-({[5-(4-{[3-(3,3-difluoroazetidin-1-yl)propane]sulfonyl}piperazin-1-yl)pyrazin-2-yl]oxy}methyl)piperidine-1-carboxylate; 1-methylcyclopropyl 4-({[5-(4-{[3-(azetidin-1-yl)propane]sulfonyl}piperazin-1-yl)pyrazin-2-yl]oxy}methyl)piperidine-1-carboxylate; 1-methylcyclopropyl 4-{[(5-{4-[(3-methoxypropane)sulfonyl]piperazin-1-yl}pyrazin-2-yl)oxy]methyl}piperidine-1-carboxylate; 1-methylcyclopropyl 4-{[(6-{4-[(3-chloropropane)sulfonyl]-2-oxopiperazin-1-yl}pyridin-3-yl)oxy]methyl}piperidine-1-carboxylate; 1-methylcyclopropyl 4-({[5-(4-{[2-(azetidin-1-yl)ethane]sulfonyl}piperazin-1-yl)pyrazin-2-yl]oxy}methyl)piperidine-1-carboxylate; 1-methylcyclopropyl 4-({[6-(4-{[3-(azetidin-1-yl)propane]sulfonyl}piperazin-1-yl)pyridin-3-yl]oxy}methyl)piperidine-1-carboxylate; 1-methylcyclopropyl 4-[({5-[4-(pyrrolidine-3-sulfonyl)piperazin-1-yl]pyrazin-2-yl}oxy)methyl]piperidine-1-carboxylate; 1-methylcyclopropyl 4-({[5-(4-{[2-(3,3-difluoroazetidin-1-yl)ethane]sulfonyl}piperazin-1-yl)pyrazin-2-yl]oxy}methyl)piperidine-1-carboxylate; 1-methylcyclopropyl 4-{[(6-{4-[(3-hydroxypropane)sulfonyl]-2-oxopiperazin-1-yl}pyridin-3-yl)oxy]methyl}piperidine-1-carboxylate; 1-methylcyclopropyl 4-({[6-(4-{[3-(azetidin-1-yl)propane]sulfonyl}-2-oxopiperazin-1-yl)pyridin-3-yl]oxy}methyl)piperidine-1-carboxylate; 1-methylcyclopropyl 4-[2,6-difluoro-4-(4-methanesulfonyl-2-oxopiperazin-1-yl)phenoxymethyl]piperidine-1-carboxylate; and 1-methylcyclopropyl 4-[({5-[4-(oxetane-3-sulfonyl)-2-oxopiperazin-1-yl]pyrazin-2-yl}oxy)methyl]piperidine-1-carboxylate.

Further compounds of the invention are detailed in the Examples and Tables, infra.

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature. Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmacology and Utility

Compounds of the invention modulate the activity of GPR119 and, as such, are useful for treating diseases or disorders in which the activity of GPR119 contributes to the pathology and/or symptomology of the disease. This invention further provides compounds of this invention for use in the preparation of medicaments for the treatment of diseases or disorders in which GPR119 activity contributes to the pathology and/or symptomology of the disease.

The resultant pathologies of Type II diabetes are impaired insulin signaling at its target tissues and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling. Physiological signaling systems which function in this manner are well-characterized and include the gut peptides GLP-1, GIP and PACAP. These hormones act via their cognate G-protein coupled receptor to stimulate the production of cAMP in pancreatic β-cells. The increased cAMP does not appear to result in stimulation of insulin release during the fasting or pre-prandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including GPR119, would also stimulate the release of endogenous insulin and consequently promote normoglycemia in Type II diabetes. It is also established that increased cAMP, for example as a result of GLP-1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

Some β-cell GPCRs, including GPR119, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In an embodiment of the invention is a method for treatment of a metabolic disease and/or a metabolic-related disorder in an individual comprising administering to the individual in need of such treatment a therapeutically effective amount of a compound of the invention or a pharmaceutical composition thereof. The metabolic diseases and metabolic-related disorders are selected from, but not limited to, hyperlipidemia, type 1 diabetes, type 2 diabetes mellitus, idiopathic type 1 diabetes (Type Ib), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

In an embodiment of the invention are therapeutic benefits of GPR119 activity modulators derived from increasing levels of GIP and PPY. For example, neuroprotection, learning and memory, seizures and peripheral neuropathy.

GLP-1 and GLP-1 receptor agonists have been shown to be effective for treatment of neurodegenerative diseases and other neurological disorders. GLP-1 and exendin-4 have been shown to stimulate neurite outgrowth and enhance cell survival after growth factor withdrawal in PC12 cells. In a rodent model of neurodegeneration, GLP-1 and exendin-4 restore cholinergic marker activity in the basal forebrain. Central infusion of GLP-1 and exendin-4 also reduce the levels of amyloid-β peptide in mice and decrease amyloid precursor protein amount in cultured PC12 cells. GLP-1 receptor agonists have been shown to enhance learning in rats and the GLP-1 receptor knockout mice show deficiencies in learning behavior. The knockout mice also exhibit increased susceptibility to kainate-induced seizures which can be prevented by administration of GLP-1 receptor agonists. GLP-1 and exendin-4 has also been shown to be effective in treating pyridoxine-induced peripheral nerve degeneration, an experimental model of peripheral sensory neuropathy.

Glucose-dependent insulinotropic polypeptide (GIP) has also been shown to have effects on proliferation of hippocampal progenitor cells and in enhancing sensorimotor coordination and memory recognition.

In an embodiment of the invention are therapeutic benefits of GPR119 activity modulators. For example, GLP-2 and short bowel syndrome (SBS). Several studies in animals and from clinical trials have shown that GLP-2 is a trophic hormone that plays an important role in intestinal adaptation. Its role in regulation of cell proliferation, apoptosis, and nutrient absorption has been well documented. Short bowel syndrome is characterized by malabsorption of nutrients, water and vitamins as a result of disease or surgical removal of parts of the small intestine (eg. Crohn's disease). Therapies that improve intestinal adaptation are thought to be beneficial in treatment of this disease. In fact, phase II studies in SBS patients have shown that teduglutide, a GLP-2 analog, modestly increased fluid and nutrient absorption.

In an embodiment of the invention are therapeutic benefits of GPR19 activity modulators derived from increasing levels of GIP and PPY. For example, GLP-1, GIP and osteoporosis. GLP-1 has been shown to increase calcitonin and calcitonin related gene peptide (CGRP) secretion and expression in a murine C-cell line (CA-77). Calcitonin inhibits bone resorption by osteoclasts and promotes mineralization of skeletal bone. Osteoporosis is a disease that is characterized by reduced bone mineral density and thus GLP-1 induced increase in calcitonin might be therapeutically beneficial.

GIP has been reported to be involved in upregulation of markers of new bone formation in osetoblasts including collagen type I mRNA and in increasing bone mineral density. Like GLP-1, GIP has also been shown to inhibit bone resorption.

In an embodiment of the invention are therapeutic benefits of GPR119 activity modulators derived from increasing levels of GIP and PPY. For example, PPY and gastric emptying. GPR119 located on the pancreatic polypeptide (PP) cells of the islets has been implicated in the secretion of PPY. PPY has been reported to have profound effects on various physiological processes including modulation of gastric emptying and gastrointestinal motility. These effects slow down the digestive process and nutrient uptake and thereby prevent the post-prandial elevation of blood glucose. PPY can suppress food intake by changing the expression of hypothalamic feeding-regulatory peptides. PP-overexpressing mice exhibited the thin phenotype with decreased food intake and gastric emptying rate.

In accordance with the foregoing, the present invention further provides a method for preventing or ameliorating the symptamology of any of the diseases or disorders described above in a subject in need thereof, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations).

For example, synergistic effects can occur with other anti-obesity agents, anorectic agents, appetite suppressant and related agents. Diet and/or exercise can also have synergistic effects. Anti-obesity agents include, but are not limited to, apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, compounds described in WO2006/047516), melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Where compounds of the invention are administered in conjunction with other therapies, dosages of the co-administered compounds will of course vary depending on the type of co-drug employed, on the specific drug employed, on the condition being treated and so forthours.

A combined preparation or pharmaceutical composition can comprise a compound of the invention as defined above or a pharmaceutical acceptable salt thereof and at least one active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448, 784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as a CB 1 activity modulator, melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta δ agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389.

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-HT$_3$ receptor and/or an agent interacting with 5-HT$_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfuram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

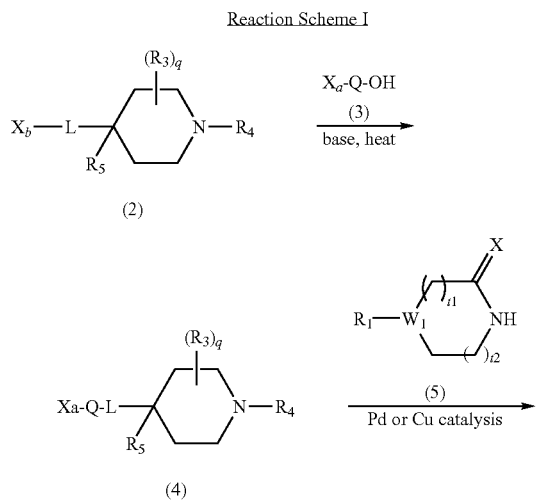

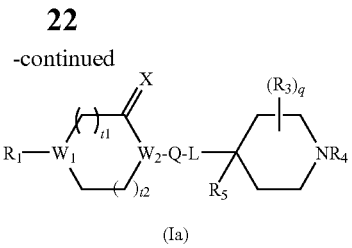

A compound of Formula Ia, where $W_2$ is nitrogen, can be prepared as in reaction scheme I by reacting a compound of formula 3 (where $X_a$ refers to a chloride, bromide, iodide, triflate, nonaflate, or the like) with a compound of the formula 2 (where $X_b$ refers to a leaving group such as an aryl- or alkylsulfonate ester, halide, epoxide where $R_5$ is the oxygen of the epoxide, or other appropriate group familiar to one skilled in the art) in a suitable solvent such as N,N-dimethylformamide, tetrahydrofuran and the like in the presence of a suitable base such as $Cs_2CO_3$, NaH or the like at an elevated temperature of up to about 80° C. to generate an intermediate of the formula 4. A compound of the formula 5 (where C=X can be a C=O or $CH_2$) can be coupled with a compound of the formula 4 using the Pd or Cu methodology known in the art (for example, Shafir, A, Buchwald, S. F.; *J. Am. Chem. Soc.* 2006, 128, 8742 and references cited therein and Hartwig, J. F. *Handbook of Organopalladium Chemistry for Organic Synthesis*, Negishi, E., Ed., Wiley-Interscience: Weinheim, 2002). In this scheme, it is understood that the groups may be protected versions of the radicals defined in the Summary of the Invention which may be deprotected and manipulated to a final compound of the invention after completion of this scheme or in the middle of the scheme.

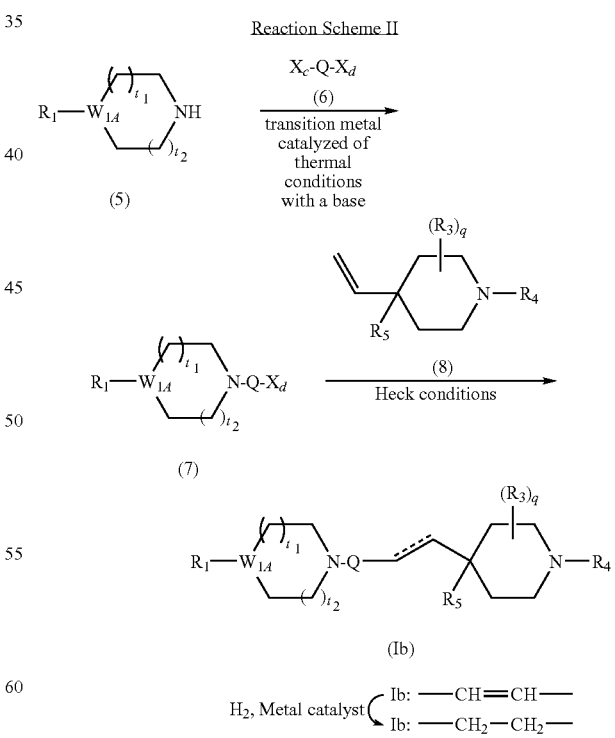

A compound of the Formula Ib, wherein $W_2$ is N and L can be —CH=CH— or —$CH_2$—$CH_2$—, can be prepared as in reaction scheme II. A compound of the formula 5 can be reacted with a compound of the formula 6 (where $X_c$ and $X_d$ both independently represent leaving groups such as F, Cl, Br, OTf, etc. with $X_c$ being the more reactive group) using either the transition metal catalysis mentioned in scheme 1 or using a stoichiometric base such as $K_2CO_3$, triethylamine and the like in a suitable solvent such as N,N-dimethylformamide and the like at an elevated temperature to generate an intermediate of the formula 7. Intermediate 7 can then be reacted with an olefin of the formula 8 using heck reaction conditions (for example, Littke, A. F.; Fu, G. C, *J. Am. Chem. Soc.* 2001, 123, 6989) to generate compounds where L is —(CH=CH)— which can subsequently be reduced using hydrogen and a catalytic amount of a transition metal such as Pd/C and the like to compounds where L is —$(CH_2)_2$—. In this scheme, it is understood that the groups can be protected versions of the radicals defined in the Summary of the Invention which can be deprotected and manipulated to the final compound after completion of this scheme or in the middle of the scheme.

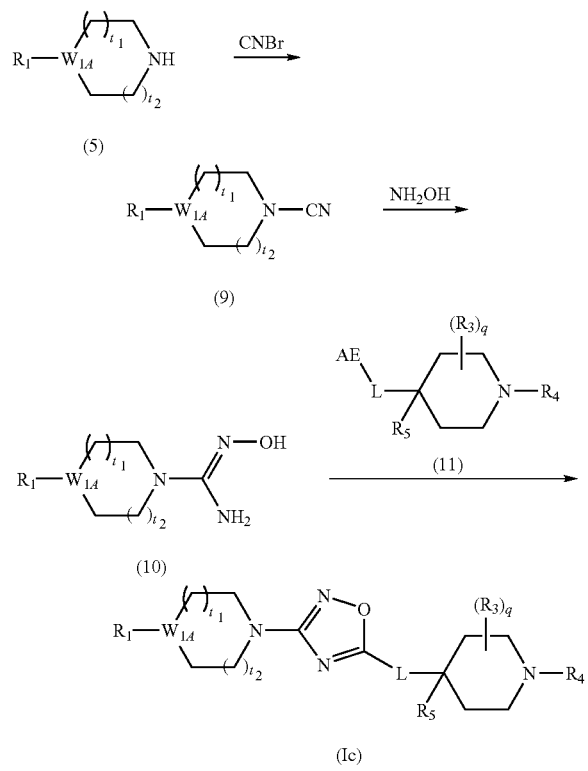

A compound of the Formula Ic, in which Q is a heteroaryl group such as 1,2,4-oxadiazolyl (as shown) and $W_2$ is N, can be prepared as in reaction scheme III by reacting a compound of the formula 5 with cyanogen bromide in a suitable solvent system such as aqueous $Na_2CO_3$ and dichloromethane and the to generate a compound of the formula 9. This intermediate can then be reacted with hydroxylamine in an appropriate solvent such as ethanol and the like at an elevated temperature such as 60° C. to furnish a compound of the formula 10. Intermediate 10 can then be reacted with a compound of the formula 11 (where AE stands for an acid equivalent such as a carboxylic acid, alkyl ester or activated ester such as an NHS ester and the like) using any of the protocols known in the literature (such as *Science of Synthesis* 2004, 13, 127, *Tetrahedron Lett.* 2006, 47, 3629 and *J. Med. Chem.* 2004, 47, 5821) to afford the desired compounds of the formula Ic. In this scheme, it is understood that the groups designated can be protected versions of the radicals defined in the Summary of the Invention which can be deprotected and manipulated to the final compound after completion of this scheme or in the middle of the scheme.

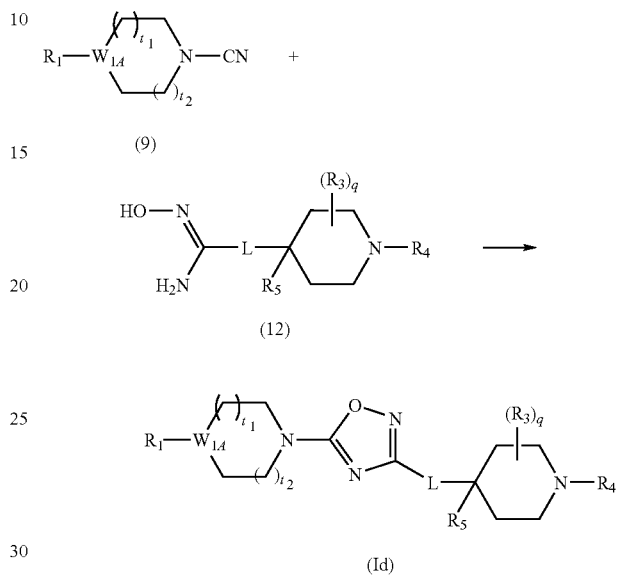

A compound of the Formula Id can be prepared as in reaction scheme IV by reacting a compound of the formula 9 with a compound of the formula 12 in a solvent such as tetrahydrofuran or the like in the presence of a Lewis acid such as $ZnCl_2$ and the like at an elevated temperature. In this scheme, it is understood that the groups designated can be protected versions of the radicals defined in the Summary of the Invention which can be deprotected and manipulated to the final compound after completion of this scheme or in the middle of the scheme.

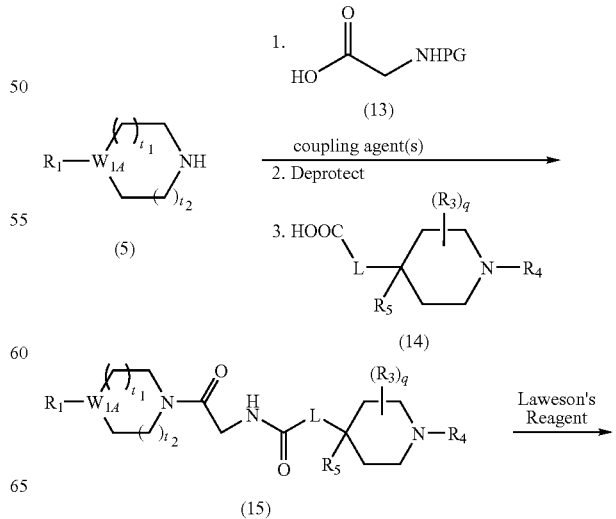

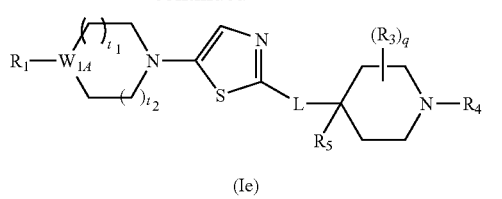

(Ie)

A compound of the Formula Ie, in which Q is thiazolyl (as sown above) and $W_2$ is N, can be prepared as in reaction scheme V by reacting a compound of the formula 5 with a protected glycine derivative of the formula 13 using appropriate coupling reagents followed by deprotection and coupling with a carboxylate of the formula 14 to generate an intermediate of the formula 15. This intermediate can then be cyclized using Lawesson's reagent or other thiotransfer/dehydrating agent in an appropriate solvent such as xylene at an elevated temperature such as 130° C. to generate the desired compound of the formula Ie. In this scheme, it is understood that the groups designated can be protected versions of the radicals defined in the Summary of the Invention which can be deprotected and manipulated to the final compound after completion of this scheme or in the middle of the scheme.

Reaction Scheme VI

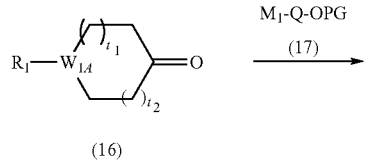

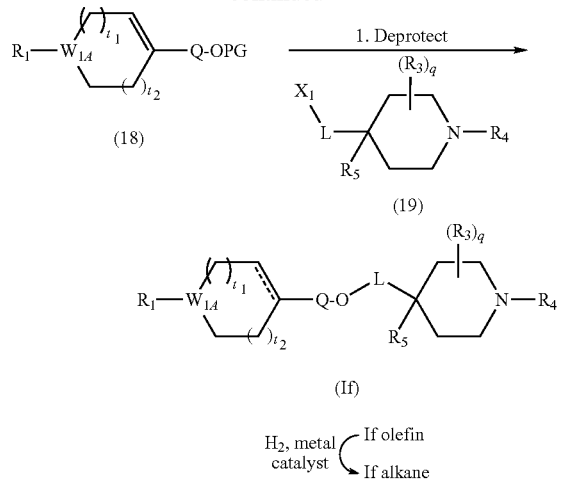

A compound of the Formula If, can be prepared as in reaction scheme VI. A ketone derivative of formula 16 can be reacted with an organometal reagent of formula 17 such as a Grignard reagent or the like to furnish after dehydration with an acid such as TFA and the like, an olefin of the formula 18. This material can be deprotected with the appropriate reagents followed by reaction with an electophile of the formula 19 where $X_1$ can be a leaving group such as mesylate, halide or the like in an appropriate solvent such as N,N-dimethylformamide or the like using a base such as $Cs_2CO_3$ or the like to afford If as the olefin. The olefin can then be reduced with a metal catalyst such as Pd/C or the like with hydrogen gas or the appropriate hydrogen transfer reagent to afford If as an alkane. In this scheme, it is understood that the groups designated can be protected versions of the radicals defined in the Summary of the Invention which can be deprotected and manipulated to the final compound after completion of this scheme or in the middle of the scheme.

Reaction Scheme VII

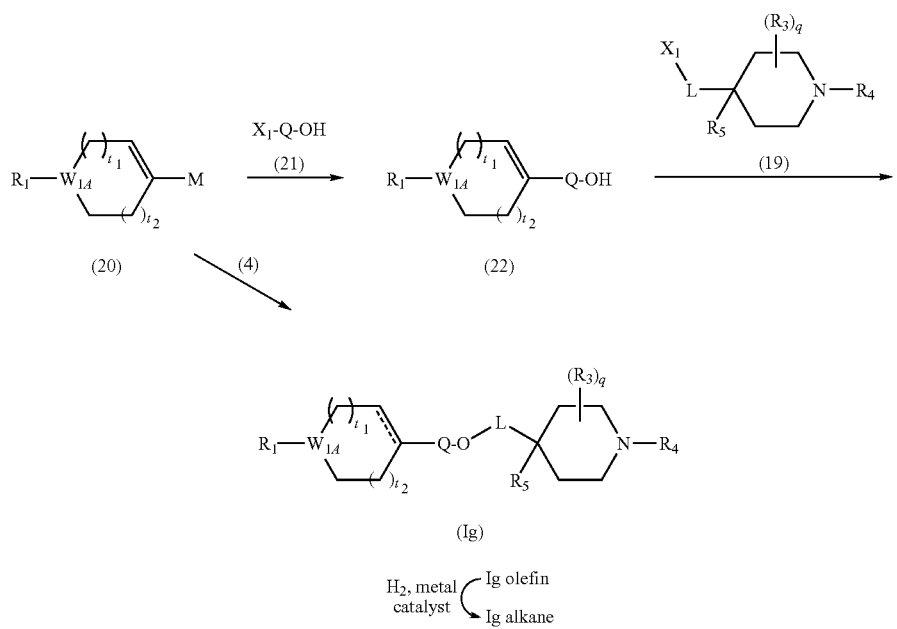

A compound of the Formula Ig, can be prepared as in reaction scheme VII. A vinyl metal derivative of formula 19 (where M is B, Sn, Si, Mg, Zn or other metals known to participate in metal catalyzed coupling reactions) can be reacted with a halide of formula 21 (where $X_f$ refers to a chloride, bromide, iodide, triflate, nonaflate, or the like) using an appropriate metal catalyst such as Pd with an appropriate ligand system such as familiar to those skilled in the art to generate an intermediate of formula 22. This intermediate can then be alkylated with an intermediate of formula 18 as outlined in scheme VI to afford Ig as an olefin. The olefin can then be reduced with a metal catalyst such as Pd/C or the like with hydrogen gas or the appropriate hydrogen transfer reagent to afford Ig as an alkane. Alternatively, Ig can be prepared by carrying out a metal mediated coupling on a compound of formula 20 with a compound of formula 4 and manipulating as before to get to the alkane. In this scheme, it is understood that the groups designated can be protected versions of the radicals defined in the Summary of the Invention which can be deprotected and manipulated to the final compound after completion of this scheme or in the middle of the scheme.

Reaction Scheme VIII

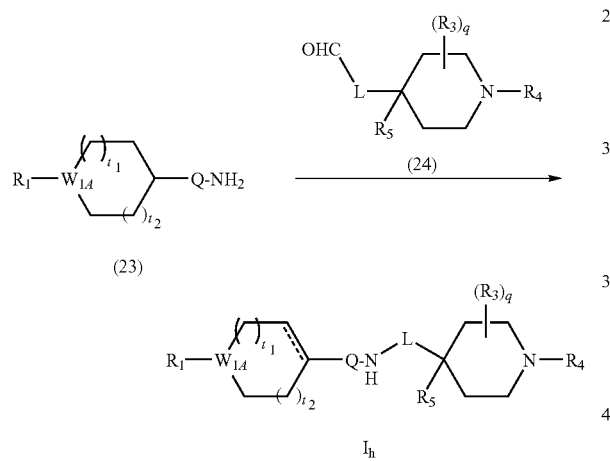

A compound of the Formula Ih, can be prepared as in reaction scheme VIII. A compound of formula 23 can be reductively aminated with a compound of formula 24 using the appropriate reductant such as $NaHB(OAc)_3$, $NaCNBH_3$ and the like in an appropriate solvent such as dichloromethane, methanol, ethanol and the like to afford $I_h$. The amine in $I_h$ can then be further manipulated. In this scheme, it is understood that the groups designated can be protected versions of the radicals defined in the Summary of the Invention which can be deprotected and manipulated to the final compound after completion of this scheme or in the middle of the scheme.

Reaction Scheme IX

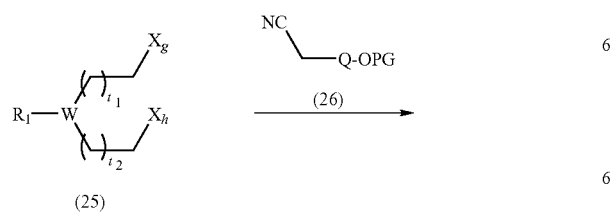

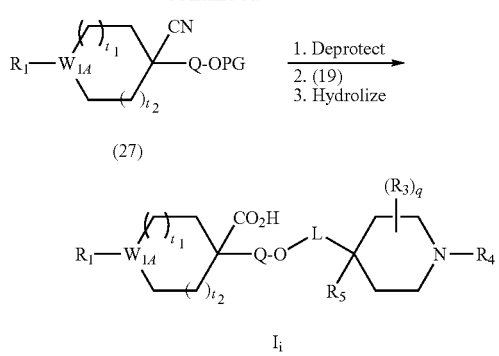

A compound of the Formula Ii, can be prepared as in reaction scheme IX. A compound of formula 25 (Where $X_g$ and $X_h$ can be chosen from chloro, bromo, iodo, mesylate, tosylate and the like) can be reacted with a compound of formula 26 using an appropriate base such as sodium hydride, LDA and the like in an appropriate solvent such as N,N-dimethylformamide, N-methylpyrrolidinone, DMSO, tetrahydrofuran and the like at an elevated temperature such as 75° C. or similar to afford an intermediate of formula 27. This material can then be manipulated in a similar fashion to intermediate 18 in scheme VI to arrive at $I_i$. In this scheme, it is understood that the groups designated can be protected versions of the radicals defined in the Summary of the Invention which can be deprotected and manipulated to the final compound after completion of this scheme or in the middle of the scheme.

Reaction Scheme X

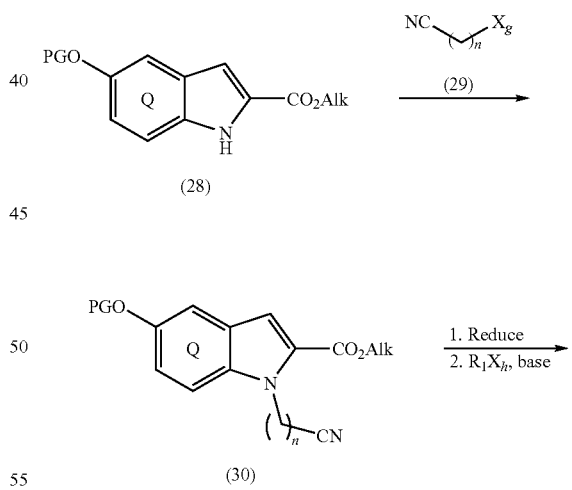

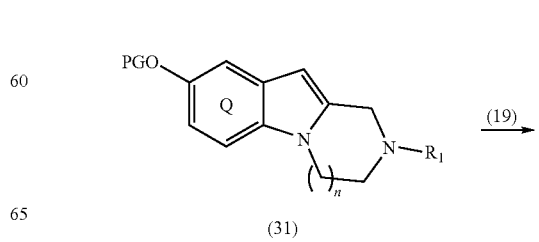

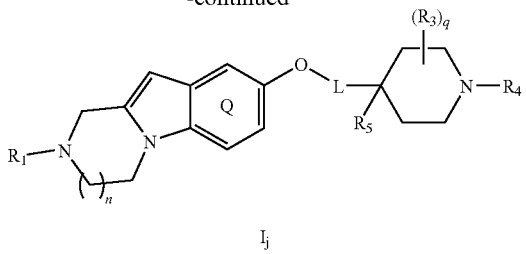

I$_j$

A compound of the Formula Ij, can be prepared as in reaction scheme X. A compound of formula 28 can be reacted with a compound of formula 29 (where $X_g$ can be chosen from chloro, bromo, iodo, mesylate, tosylate and the like) using an appropriate base such as cesium carbonate, sodium hydride, LDA and the like in an appropriate solvent such as N,N-dimethylformamide, N-methylpyrrolidinone, DMSO, tetrahydrofuran and the like to afford an intermediate of formula 30. This material can then be reduced using an appropriate metal hydride such as LAH or $BH_3$ and then functionalized with the appropriate electrophile $R_iX_h$ (where $X_h$ can be chosen from chloro, bromo, succinate, p-nitrophenyl and the like) to afford an intermediate of the formula 31. This material can then be manipulated in a similar fashion to intermediate 18 in scheme VI to arrive at $I_j$. In this scheme, it is understood that the groups designated can be protected versions of the radicals defined in the Summary of the Invention which can be deprotected and manipulated to the final compound after completion of this scheme or in the middle of the scheme.

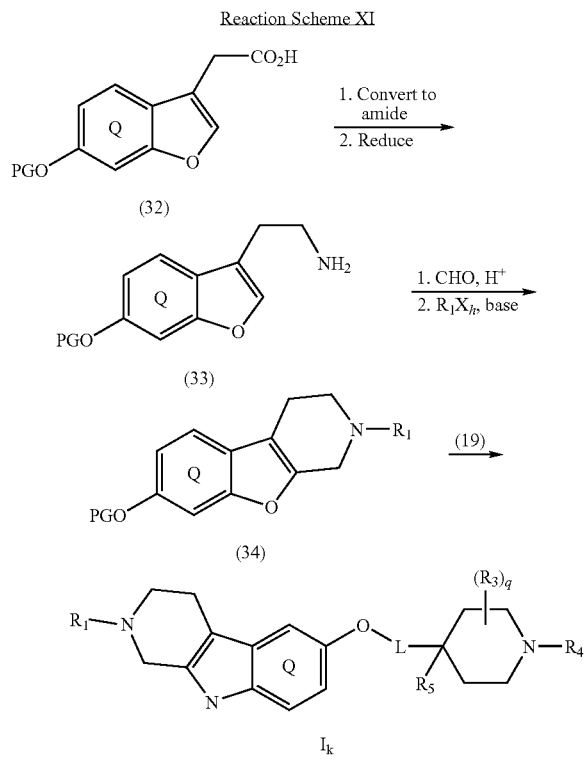

A compound of the Formula Ik, can be prepared as in reaction scheme XI. A compound of formula 32 can be converted to an amide by reacting with an activating agent such as oxlyl chloride or the like in an appropriate solvent such as dichloromethane or the like followed by reaction with ammonia or an equivalent followed by reduction with an appropriate reagent such as LAH or $BH_3$ to afford an intermediate of the formula 33. This material can then be cyclized with formaldehyde and acid such as acetic acid or the like followed by functionalization with an appropriate $R_iX_h$ (where $X_h$ can be chosen from chloro, bromo, succinate, p-nitrophenyl and the like) to afford an intermediate of the formula 34. This material can then be manipulated in a similar fashion to intermediate 18 in scheme VI to arrive at $I_k$. In this scheme, it is understood that the groups designated can be protected versions of the radicals defined in the Summary of the Invention which can be deprotected and manipulated to the final compound after completion of this scheme or in the middle of the scheme.

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I to XI; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following Examples that illustrate the preparation of compounds of the invention.

Example A1

Isopropyl 4-((4-((4-methanesulfonylpiperazin)-1-yl)phenoxy)methyl)piperidine-1-carboxylate

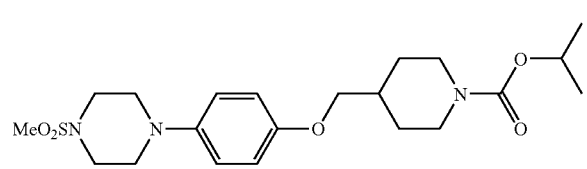

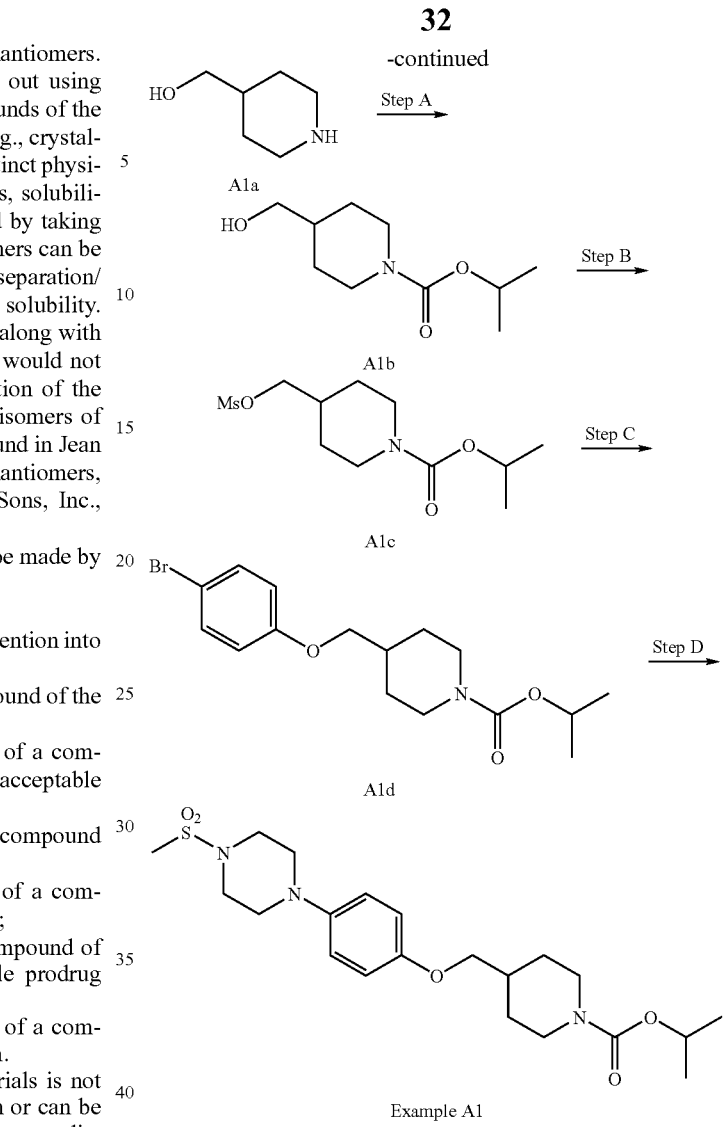

Example A1

Step A: To a solution of A1a (5.26 g, 45.7 mmol) in dry dimethoxyethane (30 mL) is added triethylamine (8.0 g, 56.9 mmol). To the resulting mixture, a 1.0-M solution of isopropyl chloroformate in toluene (50 mL) is added dropwise, with vigorous stirring, over 10 min. A white precipitate forms. The suspension is stirred at room temperature for 4 hours; the white precipitate is filtered off, washed with more dimethoxyethane, and discarded. The resulting solution is concentrated to dryness to yield A1b; $^1$H NMR (DMSO-$d_6$, 400.13 MHz): δ 4.75 (septet, J=6.2 Hz, 1H), 4.49 (t, J=5.3 Hz, 1H), 3.95 (dd, J=5.6, 5.6 Hz, 2H), 3.24 (br, 2H), 1.63 (dd, J=2.0, 12.9 Hz, 2H), 1.51 (m, 1H), 1.17 (d, J=6.2 Hz, 6H), 0.98 (m, 2H); no mass spectrum could be obtained.

Step B: To a solution of A1b (4.25 g, 21.1 mmol) in dichloromethane (30 mL) is added triethylamine (4.5 g, 32.0 mmol) in one portion. The resulting mixture is cooled in an ice/water bath and methanesulfonyl chloride (1.8 mL, 23.2 mmol) is added dropwise, with stirring, over 5 min. The bath is removed and the resulting solution is stirred at room temperature for 30 min. The reaction mixture is added to water (40 mL) and extracted with dichloromethane (2×40 mL). The combined organic extracts are washed with saturated ammonium chloride aqueous solution, dried over MgSO$_4$, and concentrated to yield A1c; $^1$H NMR (CDCl$_3$, 400.13 MHz): δ 4.74 (septet, J=6.2 Hz, 1H), 4.07 (d, J=6.4 Hz, 2H), 3.99 (d, J=11.0 Hz, 2H), 3.17 (s, 3H), 2.51 (br, 2H), 1.88 (dd, J=1.6, 14.6 Hz, 2H), 1.68 (m, 1H), 1.18 (d, J=6.2 Hz, 6H), 1.17 (m, 2H); ESIMS calcd. for $C_{11}H_{22}NO_5S$ (M+H$^+$) 280.11. found 280.2.

Step C: A solution of A1c (0.42 g, 1.50 mmol) and 4-bromophenol (0.26 g, 1.50 mmol) in acetonitrile (5.0 mL) is treated with powdered cesium carbonate (0.60 g, 1.84 mmol) and the mixture is stirred at 65° C. for 16 hours. Cooling to room temperature, filtration and concentration yields A1d; $^1$H NMR (CDCl$_3$, 400.13 MHz): δ 7.36 (d, J=9.0 Hz, 2H), 6.76 (d, J=9.0 Hz, 2H), 4.91 (septet, J=6.2 Hz, 1H), 4.19 (br, 2H), 3.76 (d, J=6.4 Hz, 2H), 3.26 (br, 2H), 2.78 (m, 2H), 1.96 (m, 1H), 1.82 (dd, J=1.6, 14.6 Hz, 2H), 1.30 (m, 2H), 1.28 (d, J=6.2 Hz, 6H); ESIMS calcd. for $C_{16}H_{23}BrNO_3$ (M+H$^+$) 356.1. found 356.0.

Step D: A solution of A1d (0.55 g, 1.50 mmol), 4-methanesulfonyl-piperazine (0.25 g, 1.52 mmol), and tri-t-butylphosphonium tetrafluoroborate (92.2 mg, 0.32 mmol) in dry dioxane (6 mL) is treated with powdered cesium carbonate (1.03 g, 3.16 mmol) and the mixture is degassed using argon. Tris(dibenzylidene acetone)dipalladium(0) (0.15 g, 0.16 mmol) is added and the mixture is degassed again with argon. The suspension is stirred vigorously under argon at 110° C. for 18 hours. Cooling, filtration and purification using mass-triggered reverse phase HPLC yields A1; $^1$H NMR (CDCl$_3$, 400.13 MHz): δ 6.90 (d, J=8.9 Hz, 2H), 6.84 (d, J=8.9 Hz, 2H), 4.92 (septet, J=6.2 Hz, 1H), 4.19 (br, 2H), 3.76 (d, J=6.4 Hz, 2H), 3.39 (t, J=3.9 Hz, 4H), 3.17 (t, J=3.9 Hz, 4H), 2.83 (s, 1H), 2.77 (t, J=11.2 Hz, 2H), 1.96 (m, 1H), 1.83 (dd, J=1.4, 14.2 Hz, 2H), 1.27 (m, 2H), 1.24 (d, J=6.2 Hz, 6H); ESIMS calcd. for $C_{21}H_{34}N_3O_5S$ (M+H$^+$) 440.2. found 440.2.

By following a similar procedure as the one used for preparing A1 from A1a except substituting the appropriate alcohol for A1a, the following examples are obtained:

Example B1

Isopropyl 4-((6-(4-(methylsulfonyl)piperazin-1-yl)pyridin-3-yloxy)methyl)piperidine-1-carboxylate

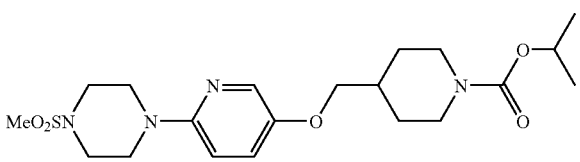

By following a similar procedure as the one used for preparing A1 from A1a except substituting 2-chloro-5-hydroxypyridine for 4-bromophenol and performing step D as follows, B1 is prepared;

A flask is charged with Pd$_2$dba$_3$ (6 mg, 0.006 mmol), xantphos (11 mg, 0.019 mmol), 1-(methylsulfonyl)piperazine (63 mg, 384 mmol), sodium tert-butoxide (46 mg, 0.48 mmol), and a solution of isopropyl 4-((6-chloropyridin-3-yloxy)methyl)piperidine-1-carboxylate (100 mg, 0.32 mmol) in toluene (1 mL). The reaction is purged by bubbling nitrogen through the solution for 5 minutes and then sealed. The reaction is then dipped into a pre-heated 100° C. bath and stirred at this temperature for 3 hours. After cooling to room temperature, the reaction is treated with ethyl acetate and water and the aqueous phase is isolated, washed with ethyl acetate once more and discarded. The combined organics are

| Example | Structure | Analytical data |
|---|---|---|
| A2 | 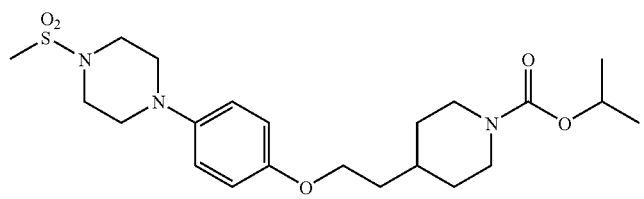 | ESIMS calcd. for $C_{22}H_{36}N_3O_5S$ (M + H$^+$) 454.2, found 454.2. |
| A3 | 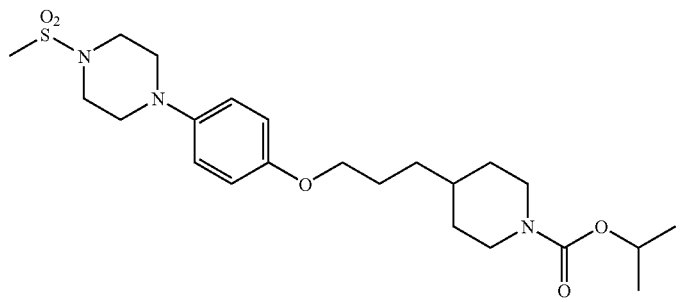 | ESIMS calcd. for $C_{23}H_{38}N_3O_5S$ (M + H$^+$) 468.2, found 468.2. |
| A4 | 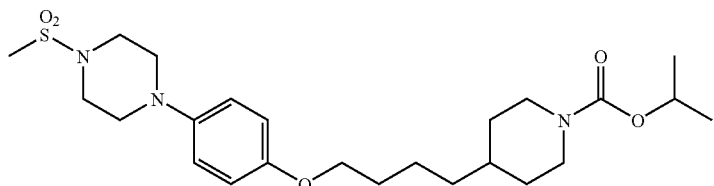 | ESIMS calcd. for $C_{24}H_{40}N_3O_5S$ (M + H$^+$) 482.2, found 482.2. | dried over MgSO₄ and the solvent is removed. The residue is purified on a silica gel column using a linear gradient of 0-100% ethyl acetate in hexane as eluent to afford B1; ¹H NMR (CDCl₃, 400 MHz): δ 7.92 (d, J=3.0, 1H), 7.18 (dd, J=3.0, 9.1, 1H), 6.67 (d, J=9.1, 1H), 4.91 (m, 1H), 4.20 (m, 2H), 3.78 (d, J=6.4, 2H), 3.56 (m, 4H), 3.34 (m, 4H), 2.81 (s, 3H), 2.76 (m, 2H), 1.94 (m, 1H), 1.81 (m, 2H), 1.29 (m, 2H), 1.24, d, J=6.2, 6H); ESIMS m/z for (M+H)⁺ C₂₀H₃₃N₄O₅S calcd.: 441.2. found: 441.3.

Example B2 tert-Butyl 4-((6-(4-(methylsulfonyl)piperazin-1-yl)pyridin-3-yloxy)methyl)piperidine-1-carboxylate

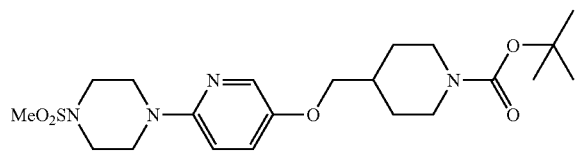

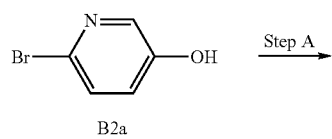

B2a

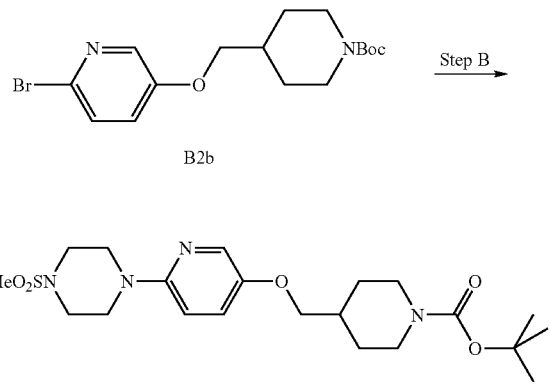

Step A: A solution of B2a (4.00 g, 23 mmol) and tert-butyl 4-((methylsulfonyloxy)methyl)piperidine-1-carboxylate (7.08 g, 24 mmol) in N-methylpyrrolidinone (50 mL) is treated with Cs₂CO₃ (9.74 g, 30 mmol) and heated to 100° C. overnight. The reaction is then diluted with ethyl acetate, extracted with water 3 times, dried over MgSO₄, filtered, evaporated and crystallized from toluene/hexane to afford B2b; ESIMS m/z for (M-tBu+H)⁺ C₁₂H₁₆BrN₂O₃ calcd.: 315.0. found: 315.0.

Step B: Following the procedure for the palladium coupling outlined for B1 above, substituting B2b for isopropyl 4-((6-chloropyridin-3-yloxy)methyl)piperidine-1-carboxylate, B2 is prepared; ¹H NMR (CDCl₃, 400 MHz): δ 7.91 (d, J=2.9, 1H), 7.15 (dd, J=9.1, 3.1, 1H), 6.65 (d, J=9.0, 1H), 4.15 (m, 2H), 3.78 (d, J=6.4, 2H), 3.54 (m, 4H), 3.33 (m, 4H), 2.81 (s, 3H), 2.72 (m, 2H), 1.93 (m, 1H), 1.80 (m, 2H), 1.46 (s, 9H), 1.25 (m, 2H); ESIMS m/z for (M+H)⁺ C₂₁H₃₅N₄O₅S calcd.: 455.2. found: 455.2.

Example B3

Isopropyl 4-((5-(4-(methylsulfonyl)piperazin-1-yl)pyrazin-2-yloxy)methyl)piperidine-1-carboxylate

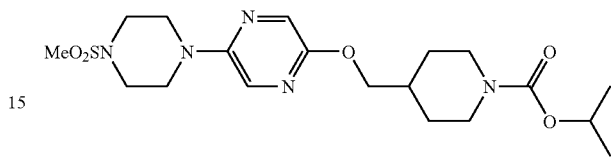

By following a similar procedure as the one used for preparing B1 except using 2-bromo-5-hydroxypyrazine as the heterocycle, B3 is prepared; ¹H NMR (CDCl₃, 400 MHz): δ 7.87 (d, J=1.4, 1H), 7.62 (d, J=1.5, 1H), 4.92 (m, 1H), 4.18 (m, 2H), 4.08 (d, J=6.5, 2H), 3.52 (m, 4H), 3.37 (m, 4H), 2.82 (s, 3H), 2.76 (m, 2H), 1.96 (m, 1H), 1.79 (m, 2H), 1.29 (m, 2H), 1.24, (d, J=6.2, 6H); ESIMS m/z for (M+H)⁺ C₁₉H₃₂N₅O₅S calcd.: 442.2. found: 442.3.

Example B4 tert-Butyl 4-((5-(4-(methylsulfonyl)piperazin-1-yl)pyrazin-2-yloxy)methyl)piperidine-1-carboxylate

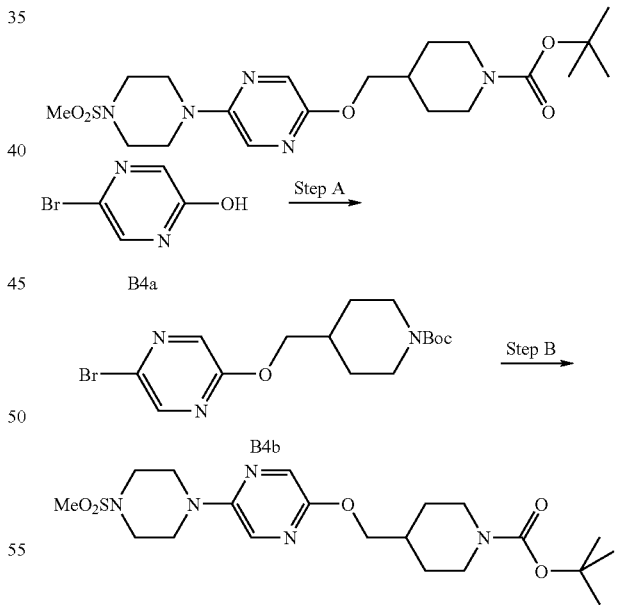

Step A: By following a similar procedure as the one used for preparing B2b from B2a except substituting B4a for B2a, B4b is prepared; ESIMS m/z for (M-tBu+H)⁺ C₁₁H₁₅BrN₃O₃ calcd.: 316.0. found: 316.0.

Step B: By following the procedure for the palladium coupling outlined for the preparation of B1 except substituting B4b for isopropyl 4-((6-chloropyridin-3-yloxy)methyl)piperidine-1-carboxylate, B4 is prepared; $^1$H NMR (CDCl$_3$, 400 MHz): δ 7.87 (d, J=1.2, 1H), 7.62 (d, J=1.2, 1H), 4.13 (m, 2H), 4.08 (d, J=6.8, 2H), 3.52 (m, 4H), 3.37 (m, 4H), 2.82 (s, 3H), 2.72 (m, 2H), 1.93 (m, 1H), 1.46 (s, 9H), 1.26 (m, 2H); ESIMS m/z for (M+H)$^+$ C$_{20}$H$_{34}$N$_5$O$_5$S calcd.: 456.2. found: 456.2.

Example B5

3-Cyclopropyl-5-(4-((5-(4-(methylsulfonyl)piper-azin-1-yl)pyrazin-2-yloxy)methyl)piperidin-1-yl)-1,2,4-oxadiazole

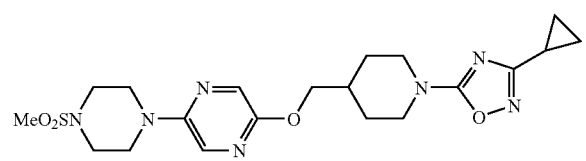

By following a similar procedure as the one used for preparing B3 from B2a except substituting B5c (see scheme below) for B2a, B5 is prepared; $^1$H NMR (CDCl$_3$, 400 MHz): δ 7.88 (d, J=1.3, 1H), 7.62 (d, J=1.4, 1H), 4.16 (m, 2H), 4.10 (d, J=6.8, 2H), 3.53 (m, 4H), 3.37 (m, 4H), 3.05 (ddd, J=12.9, 12.9, 2.8, 2H), 2.82 (s, 3H), 2.02 (m, 1H), 1.88 (m, 4H), 1.41 (m, 2H), 0.94 (m, 4H); ESIMS m/z for (M+H)$^+$ C$_{20}$H$_{30}$N$_7$O$_4$S calcd.: 464.2. found: 464.3.

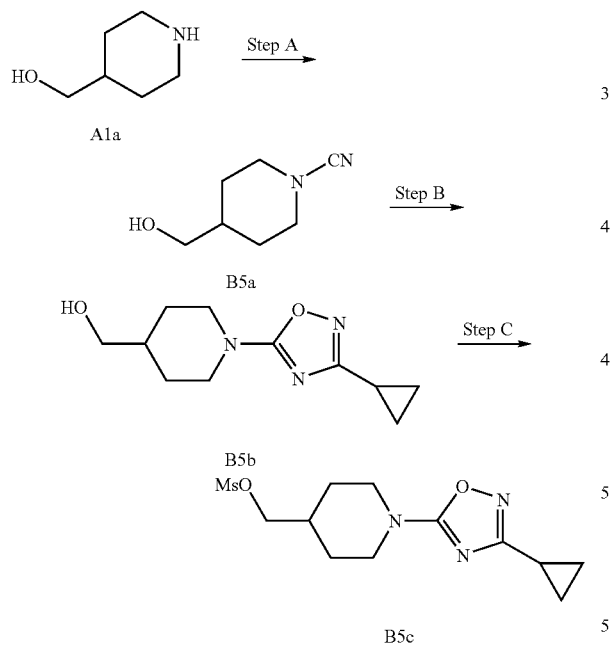

Step A: A sample of A1a (10.19 g, 84.9 mmol) is treated with a solution of K$_2$CO$_3$ (24.5 g, 177 mmol) in water (100 mL). The reaction is cooled in an ice/water bath and treated with a solution of cyanogen bromide (10.31 g, 97.3 mmol) in dichloromethane (100 mL) dropwise. After stirring for an hour, the organic layer is isolated and the aqueous layer is extracted once more with dichloromethane. The combined organic extracts are dried over MgSO$_4$, filtered and evaporated to afford B5a; ESIMS m/z for (M+H)$^+$ C$_7$H$_{13}$N$_2$O calcd.: 141.1. found: 141.1.

Step B: A solution of B5a (993 mg, 7.1 mmol), N'-hydroxy-cyclopropane carboximidamide (1.064 g, 10.6 mmol) and ZnCl$_2$ (1.448 g, 10.6 mmol) in dioxane (25 mL) is heated to 100° C. overnight. The reaction is then evaporated to dryness and partitioned between ethyl acetate and 1 M HCl. The organics are isolated, extracted with 1 M HCl once more, dried over MgSO$_4$, filtered, evaporated and purified by silica gel to afford B5b; ESIMS m/z for (M+H)$^+$ C$_{11}$H$_{18}$N$_3$O$_2$ calcd.: 224.1. found: 224.1.

Step C: A solution of B5b (278.4 mg, 1.25 mmol) and triethylamine (131 mg, 130 mmol) in dichloromethane (1 mL) is cooled in an ice/water bath, treated with methanesulfonyl chloride (149 mg, 1.3 mmol) and stirred overnight. The reaction is diluted with water and extracted with dichloromethane. The organics are dried over MgSO$_4$, filtered, evaporated and purified on silica gel using a linear gradient of 0 to 100% ethyl acetate in hexane to afford E5c; ESIMS m/z for (M+H)$^+$ C$_{12}$H$_{20}$N$_3$O$_4$S calcd.: 302.1. found: 302.1.

Example B6

5-Cyclopropyl-3-(4-((5-(4-(methylsulfonyl)piper-azin-1-yl)pyrazin-2-yloxy)methyl)piperidin-1-yl)-1,2,4-oxadiazole

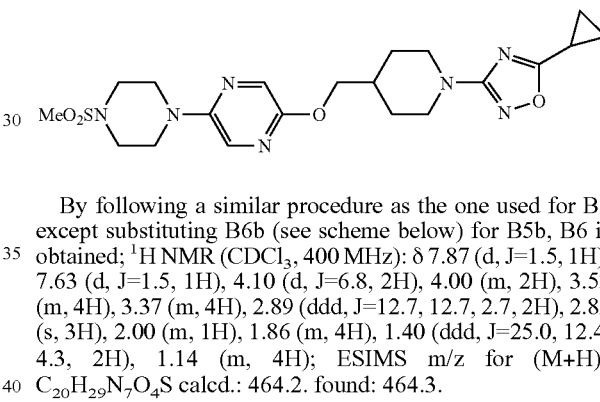

By following a similar procedure as the one used for B5 except substituting B6b (see scheme below) for B5b, B6 is obtained; $^1$H NMR (CDCl$_3$, 400 MHz): δ 7.87 (d, J=1.5, 1H), 7.63 (d, J=1.5, 1H), 4.10 (d, J=6.8, 2H), 4.00 (m, 2H), 3.53 (m, 4H), 3.37 (m, 4H), 2.89 (ddd, J=12.7, 12.7, 2.7, 2H), 2.82 (s, 3H), 2.00 (m, 1H), 1.86 (m, 4H), 1.40 (ddd, J=25.0, 12.4, 4.3, 2H), 1.14 (m, 4H); ESIMS m/z for (M+H)$^+$ C$_{20}$H$_{29}$N$_7$O$_4$S calcd.: 464.2. found: 464.3.

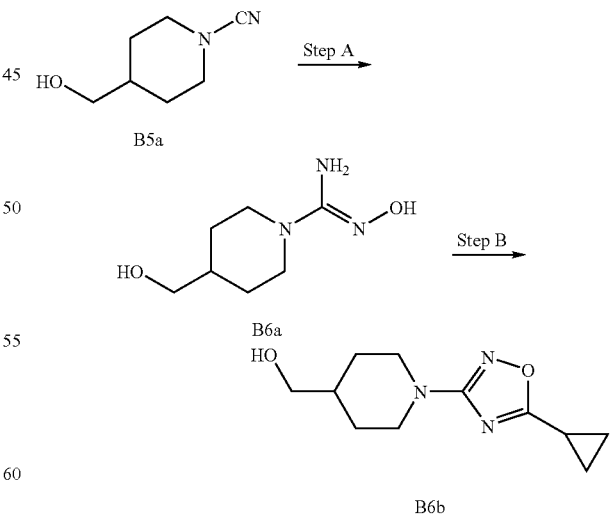

Step A: A solution of B5a (4.01 g, 28.6 mmol) and hydroxylamine (3.51 mL of a 50% by weight aqueous solution, 57.2 mmol) in ethanol (50 mL) is sealed and heated to 60° C. overnight. The solvent is then removed to B6a; ESIMS m/z for (M+H)$^+$ C$_7$H$_{16}$N$_3$O$_2$ calcd.: 174.1. found: 174.1.

Step B: A solution of B6a (905 mg, 5.2 mmol) and 2,5-dioxopyrrolidin-1-yl cyclopropanecarboxylate (957 mg, 5.2 mmol) in dioxane (50 mL) is heated to 80° C. for 3 hours and then 70° C. overnight. The reaction is then cooled to room temperature, concentrated and purified on silica gel using a linear gradient of 0-80% ethyl acetate in hexane to afford B6b; ESIMS m/z for (M+H)⁺ $C_{11}H_{18}N_3O_2$ calcd.: 224.1. found: 224.1.

Example B7

2-(4-(Methylsulfonyl)piperazin-1-yl)-5-((1-(5-(trifluoromethyl)pyridin-2-yl)piperidin-4-yl)methoxy)pyrazine

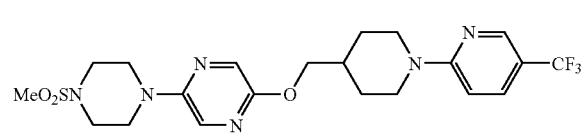

By following a similar procedure as the one used for preparing B3 from B2a except substituting B7a (see scheme below) for A1b, B7 is prepared; ¹H NMR (CDCl₃, 400 MHz): δ 8.37 (m, 1H), 7.88 (d, J=1.4, 1H), 7.63 (d, J=1.4, 1H), 7.60 (dd, J=9.1, 2.5, 1H), 6.65 (d, J=9.1, 1H), 4.45 (m, 2H), 4.11 (d, J=6.5, 1H), 3.53 (m, 4H), 3.37 (m, 4H), 2.95 (m, 2H), 2.82 (s, 3H), 2.11 (m, 1H), 1.93 (m, 2H), 1.37 (ddd, J=24.9, 12.5, 4.1, 2H); ESIMS m/z for (M+H)⁺ $C_{21}H_{28}F_3N_6O_3S$ calcd.: 501.2. found: 501.3.

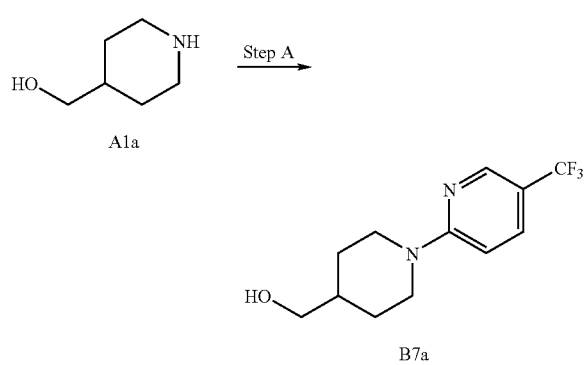

Step A: A mixture of A1a (522.5 mg, 4.5 mmol), 2-chloro-5-trifluoromethylpyridine (1.19 g, 6.5 mmol) and K₂CO₃ (941 mg, 6.8 mmol) in N,N-dimethylformamide (8 mL) is heated to 160° C. for 10 minutes, cooled to room temperature and diluted with ethyl acetate and water. The organics are extracted with water, dried over MgSO4, filtered, evaporated and purified on silica gel using a linear gradient of 0 to 100% ethyl acetate in hexane to afford B1a; ESIMS m/z for (M+H)⁺ $C_{12}H_{16}F_3N_2O$ calcd.: 261.1. found: 261.1.

Example B8

5-Isopropyl-3-(4-((5-(4-(methylsulfonyl)piperazin-1-yl)pyrazin-2-yloxy)methyl)piperidin-1-yl)-1,2,4-oxadiazole

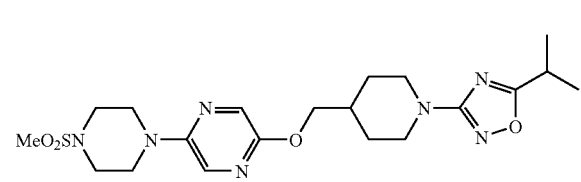

By following a similar procedure as the one used for preparing B6 from B6b except substituting B8a (see scheme below) for B6b, B8 is prepared; ¹H NMR (CDCl₃, 400 MHz): δ 7.88 (d, J=1.5, 1H), 7.63 (d, J=1.5, 1H), 7.60 (dd, J=9.1, 2.5, 1H), 4.11 (d, J=6.6, 1H), 3.53 (m, 4H), 3.37 (m, 4H), 3.07 (m, 1H), 2.92 (ddd, J=12.7, 12.7, 2.7, 2H), 2.82 (s, 3H), 2.01 (m, 1H), 1.88 (m, 2H), 1.42 (m, 2H), 1.35 (d, J=7.0, 6H); ESIMS m/z for (M+H)⁺ $C_{20}H_{32}N_7O_4S$ calcd.: 466.2. found: 466.2.

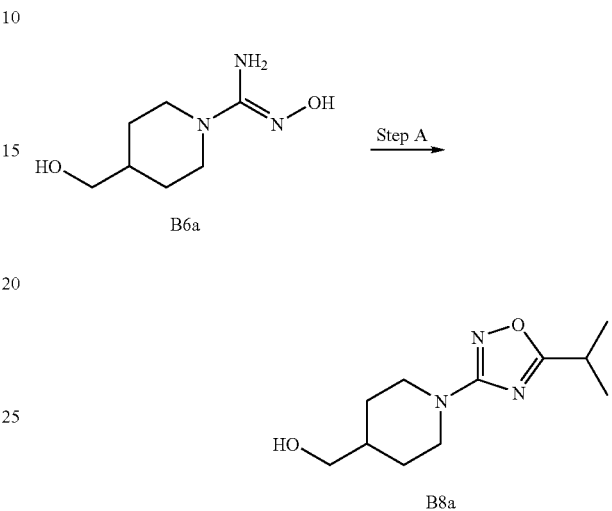

Step A: A solution of B6a (460.3 mg, 2.7 mmol) and isobutyric anhydride (420 mg, 2.7 mmol) in dioxane (3 mL) is heated to 150° C. for 5 minutes. The reaction is cooled to room temperature and diluted with ethyl acetate and water. The organics are isolated and washed once with water, dried over MgSO₄, filtered, evaporated and purified on silica using a linear gradient of ethyl acetate in hexane to afford B8a. A satisfactory mass spectral analysis could not be obtained.

Example B9

Tetrahydro-2H-pyran-4-yl 4-((5-(4-(methylsulfonyl)piperazin-1-yl)pyrazin-2-yloxy)methyl)piperidine-1-carboxylate

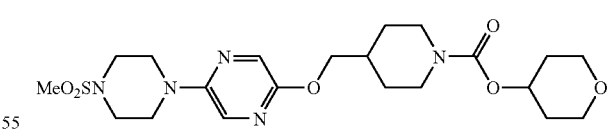

By following a similar procedure as the one used for preparing B3 from A1a except substituting 4-nitrophenyl tetrahydro-2H-pyran-4-yl carbonate for isopropyl chloroformate in the first step, B9 is prepared; ¹H NMR (CDCl₃, 400 MHz): δ 7.87 (d, J=1.5, 1H), 7.62 (d, J=1.5, 1H), 4.87 (m, 1H), 4.20 (m, 2H), 4.09 (d, J=6.5, 1H), 3.89 (m, 2H), 3.57 (m, 2H), 3.54 (m, 4H), 3.46 (m, 4H), 2.82 (s, 3H), 2.80 (m, 2H), 1.95 (m, 3H), 1.82 (m, 2H), 1.67 (m, 3H), 1.28 (m, 2H); ESIMS m/z for (M+H)⁺ $C_{21}H_{34}N_5O_6S$ calcd.: 484.2. found: 484.2.

Example B10

(S)-Tetrahydrofuran-3-yl 4-((5-(4-(methylsulfonyl)piperazin-1-yl)pyrazin-2-yloxy)methyl)piperidine-1-carboxylate

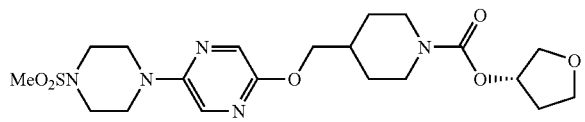

By following a similar procedure as the one used for preparing B3 from A1a except substituting (S)-4-nitrophenyl tetrahydrofuran-3-yl carbonate for isopropyl chloroformate in the first step, B10 is prepared; $^1$H NMR (CDCl$_3$, 400 MHz): δ 7.87 (d, J=1.5, 1H), 7.62 (d, J=1.5, 1H), 5.26 (m, 1H), 4.18 (m, 2H), 4.08 (d, J=6.5, 1H), 3.89 (m, 4H), 3.53 (m, 4H), 3.47 (m, 4H), 2.82 (s, 3H), 2.80 (m, 2H), 2.17 (m, 1H), 2.00 (m, 2H), 1.82 (m, 2H), 1.27 (m, 2H); ESIMS m/z for (M+H)$^+$ C$_{20}$H$_{31}$N$_5$O$_6$S calcd.: 470.2. found: 470.2.

Example B11

(R)-Tetrahydrofuran-3-yl 4-((5-(4-(methylsulfonyl)piperazin-1-yl)pyrazin-2-yloxy)methyl)piperidine-1-carboxylate

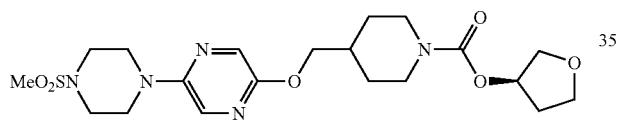

By following a similar procedure as the one used for preparing B3 from A1a except substituting (R)-4-nitrophenyl tetrahydrofuran-3-yl carbonate for isopropyl chloroformate in the first step, B11 is prepared with data identical to B10.

Example B12

2-Isopropyl-5-(4-((5-(4-(methylsulfonyl)piperazin-1-yl)pyrazin-2-yloxy)methyl)piperidin-1-yl)thiazole

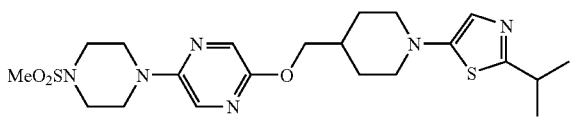

By following a similar procedure as the one used for preparing B3 from A1d except substituting B12d (see scheme below) for A1d, B12 is prepared; $^1$H NMR (CDCl$_3$, 400 MHz): δ 7.88 (d, J=1.5, 1H), 7.63 (d, J=1.5, 1H), 7.60 (dd, J=9.1, 2.5, 1H), 6.79 (s, 1H), 4.13 (d, J=6.2, 1H), 3.53 (m, 4H), 3.46 (m, 2H), 3.37 (m, 4H), 3.14 (m, 1H), 2.82 (s, 3H), 2.79 (m, 2H), 1.91 (m, 3H), 1.53 (m, 2H), 1.34 (d, J=6.9, 6H); ESIMS m/z for (M+H)$^+$ C$_{21}$H$_{33}$N$_6$O$_3$S$_2$ calcd.: 481.2. found: 481.2.

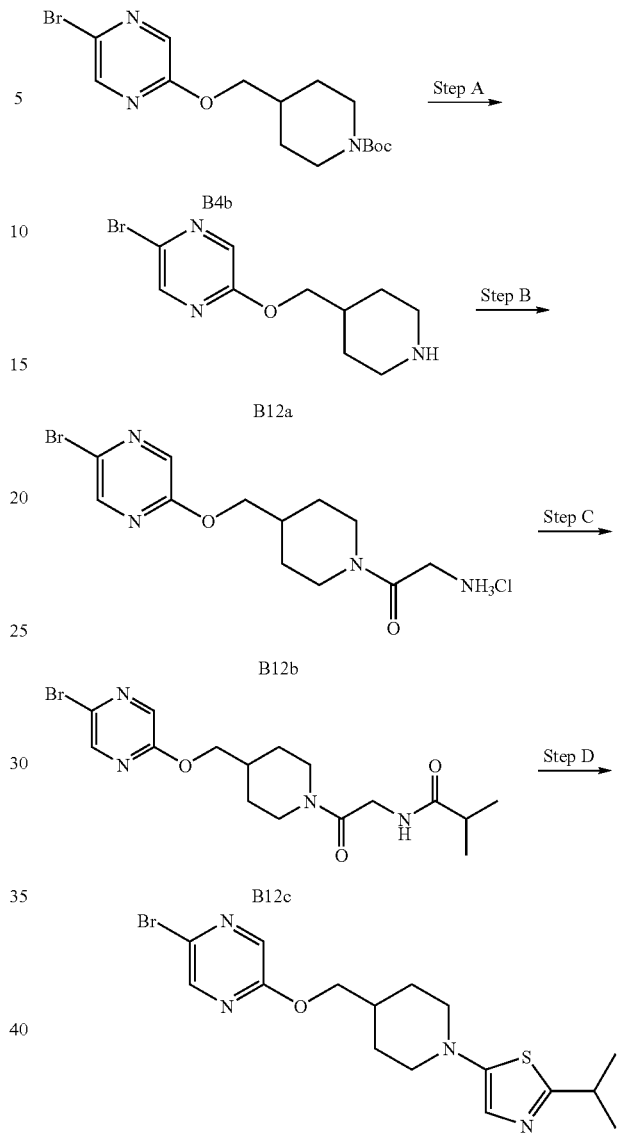

Step A: A sample of B4b (5.55 g, 14.9 mmol) is treated with 4 M HCl in dioxane (20 ml) and aged for 1 hour. The reaction is treated with water and the solvent is removed in vacuo. The residue is partitioned between ethyl acetate and 1 M NaOHOURS. The aqueous phase is isolated, extracted once more with ethyl acetate and discarded. The combined organics are dried over MgSO$_4$, filtered and evaporated to afford B12a which is used without further purification; ESIMS m/z for (M+H)$^+$ C$_{10}$H$_{15}$BrN$_3$O calcd.: 272.0. found: 272.0.

Step B: A solution of B12a (1 g, 3.7 mmol), Boc-gly (966 mg, 5.5 mmol) and HOBt (596 mg, 4.4 mmol) in N-methylpyrrolidinone (5 mL) is treated with EDC (845 mg, 845 mg, 4.4 mmol) and stirred for 1 hour. The reaction is then diluted with ethyl acetate and extracted with water and saturated aqueous sodium hydrogencarbonate twice. The organics are dried over MgSO$_4$, filtered and evaporated. The residue is treated with excess 4 M HCl in dioxane and aged for 1 hour. The mixture is slurried with ether and the solid is collected to afford B12b; ESIMS m/z for (M+H)$^+$ C$_{12}$H$_{18}$BrN$_4$O$_2$ calcd.: 329.1. found: 329.1.

Step C: A suspension of B12b (400 mg, 1.1 mmol) in acetonitrile (8 mL) is treated with isobutyric anhydride (208 mg, 1.3 mmol) followed by triethylamine (360 mg, 3.6 mmol) and stirred for 1 hour. The solvent is removed and the residue is partitioned between ethyl acetate and saturated aqueous sodium hydrogencarbonate. The aqueous phase is isolated, extracted once more with ethyl acetate and discarded. The combined organics are dried over MgSO$_4$, filtered and evaporated to afford B12c which is used without further purification; ESIMS m/z for (M+H)$^+$ C$_{16}$H$_{24}$BrN$_4$O$_3$ calcd.: 399.1. found: 399.1.

Step D: A solution of B12c (440 mg, 1.1 mmol) in m-xylene (2 mL) is treated with Laewesson's reagent (446 mmol, 1.1 mmol) and heated to 140° C. for 5 minutes and then purified on silica gel using a linear gradient of 0-100% ethyl acetate in hexane. The resulting material is further purified on preparative HPLC to afford B12d; ESIMS m/z for (M+H)$^+$ C$_{16}$H$_{22}$BrN$_4$OS calcd.: 397.1. found: 397.1.

Example B13

2-((1-(2-methyl-2H-tetrazol-5-yl)piperidin-4-yl)methoxy)-5-(4-(methylsulfonyl)piperazin-1-yl)pyrazine

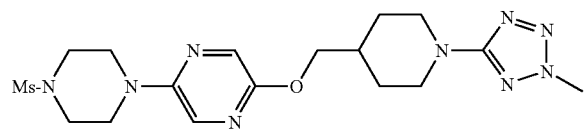

By following a similar procedure as the one used for preparing B3 from A1d except substituting B13c (see scheme below) for A1d, B13 is prepared; $^1$H NMR (400 MHz, CD$_3$CN) δ 7.84 (d, J=0.9 Hz, 1H), 7.72 (d, J=1.2 Hz, 1H), 4.10 (s, 3H), 4.10 (d, J=4.8 Hz, 2H), 4.02 (m, 2H), 3.51 (t, J=3.9 Hz, 4H), 3.27 (t, J=3.9 Hz, 4H), 2.91 (dt, J=2.1, 9.6 Hz, 2H), 2.79 (s, 3H), 1.39 (ddd, J=3.3, 9.3, 16.8 Hz, 4H), 2.20 (t, J=5.4 Hz, 2H), 0.88 (m, 2H); ESIMS (M+H)$^+$ C$_{17}$H$_{28}$N$_9$O$_3$S cacld.: 438.2. found 438.2 (M+1).

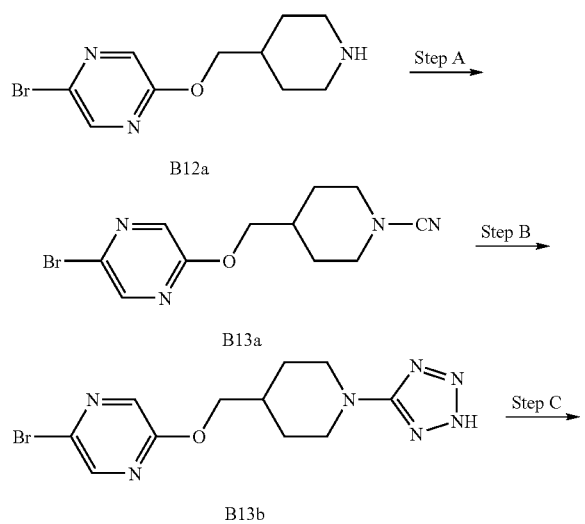

Step A: To a stirred suspension of B12a (200 mg, 0.74 mmol) and sodiumhydrogencarbonate (0.15 g, 1.78 mmol) in a mixed solvent of water (0.1 mL) and dichloromethane (1 mL) at 0° C. is added cyanogen bromide (93 mg, 0.89 mmol) in one portion. The reaction is then stirred at room temperature for 4 h and additional cyanogen bromide (93 mg, 0.89 mmol) is added. After stirring overnight, the reaction is diluted with dichloromethane (30 mL), dried over MgSO$_4$, and evaporated to give B13a; ESIMS (M+H)$^+$ C$_{11}$H$_{14}$BrN$_4$O calcd.: 297.0. found 297.0.

Step B: The above crude B13a is stirred with sodium azide (143 mg, 2.2 mmol) and ammonium chloride (117 mg, 0.22 mmol) in anhydrous N,N-dimethylformamide (2 mL) at 110° C. for 2 hours. Additional sodium azide (143 mg, 2.2 mmol) and ammonium chloride (117 mg, 0.22) are added. After stirring overnight, water is added slowly to precipitate the product. The off white solid is collected by filtration, washed with water (10 mL) and dried in vacuo to afford B13b; $^1$H NMR (400 MHz, DMSO-d$_6$) δ 8.41 (d, J=1.2 Hz, 1H), 8.20 (d, J=0.9 Hz, 1H), 4.18 (d, J=5.1 Hz, 2H), 3.86 (m, 2H), 3.02 (dt, J=2.1, 9.6 Hz, 2H), 2.03 (m, 1H), 1.81 (m, 2H), 1.34 (ddd, J=3.3, 9.6, 18.9 Hz, 2H); ESIMS (M+H)$^+$ C$_{11}$H$_{15}$BrN$_7$O calcd.: 340.0. found: 340.0.

Step C: A mixture of B13b (50 mg, 0.15 mmol), iodomethane (14 uL, 0.22 mmol) and K$_2$CO$_3$ (28 mg, 0.25 mmol) in anhydrous N,N-dimethylformamide (1 mL) is stirred at room temperature for 3 hours. The solvent is evaporated in vacuo and the crude B13c is used without purification: ESIMS (M+H)$^+$ C$_{12}$H$_{17}$BrN$_7$O calcd.: 354.1. found 354.0 (M+1).

Example B14

Oxetan-3-yl 4-((5-(4-(methylsulfonyl)piperazin-1-yl)pyrazin-2-yloxy)methyl)piperidine-1-carboxylate

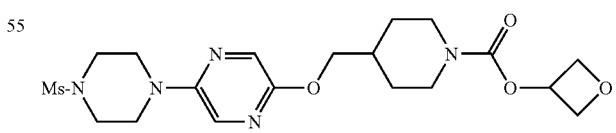

By following a similar procedure as the one used for preparing B3 from A1a except substituting 4-nitrophenyl oxetan-3-yl carbonate for isopropyl chloroformate in the first step, B14 is prepared; ESIMS m/z for (M+H)$^+$ C$_{19}$H$_{30}$N$_5$O$_6$S calcd: 456.2. found: 456.0.

Example C1

Isopropyl 4-((5-(4-(methylsulfonyl)piperazin-1-yl)pyridin-2-yloxy)methyl)piperidine-1-carboxylate

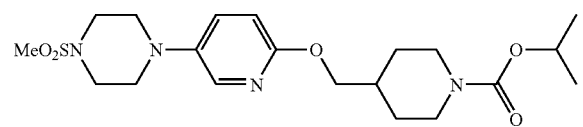

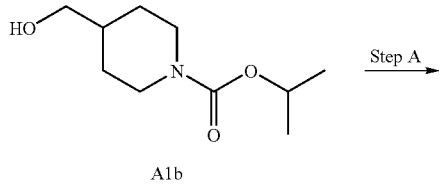

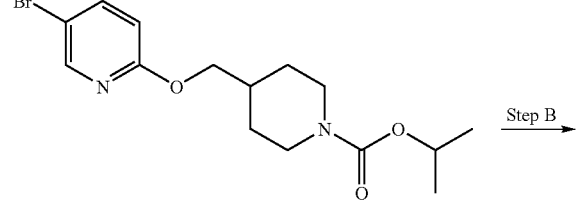

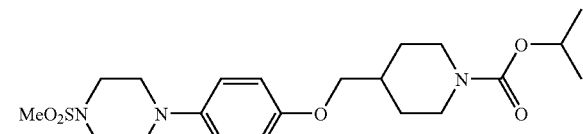

Step A: A solution of 2-chloro-5-bromopyridine (344 mg, 1.8 mmol) and A1b (300 mg, 1.5 mmol) in dimethylformamide (3 mL) is treated with NaH (43 mg, 1.8 mmol) and the reaction is allowed to stir overnight. After quenching by addition of water, the reaction is diluted with ethyl acetate. The organics are isolated and extracted with water once more, dried over MgSO$_4$, filtered and evaporated. The residue is purified on a silica gel column using a linear gradient of 0-50% ethyl acetate in hexane to afford C1b; ESIMS m/z for (M+H)$^+$ C$_{15}$H$_{22}$ClN$_2$O$_3$ calcd.: 313.1. found: 313.1.

Step B: By following a similar Pd coupling procedure described for preparing B1 except substituting C1a as the bromide coupling partner, B14 is prepared; $^1$H NMR (CDCl$_3$, 400 MHz): δ 7.78 (d, J=2.9, 1H), 7.18 (dd, J=3.0, 8.9, 1H), 6.69 (d, J=8.9, 1H), 4.91 (m, 1H), 4.18 (m, 2H), 4.09 (d, J=6.4, 2H), 3.38 (m, 4H), 3.17 (m, 4H), 2.84 (s, 3H), 2.77 (m, 2H), 1.96 (m, 1H), 1.81 (m, 2H), 1.29 (m, 2H), 1.24, d, J=6.3, 6H); ESIMS m/z for (M+H)$^+$ C$_{20}$H$_{33}$N$_4$O$_5$S calcd.: 441.2. found: 441.2.

Example C2

Isopropyl 4-((6-(4-(methylsulfonyl)piperazin-1-yl)pyridazin-3-yloxy)methyl)piperidine-1-carboxylate

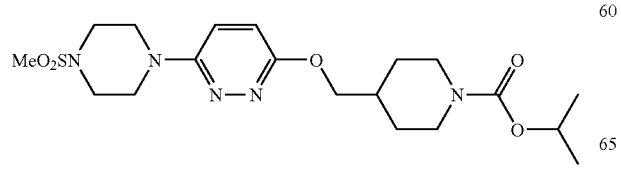

By following a similar procedure as the one used for preparing C1 from A1b except substituting 2,5-dichloropyridazine for 2-chloro-5-bromopyridine in the first step, C2 is prepared; $^1$H NMR (CDCl$_3$, 400 MHz): δ 7.04 (d, J=9.6, 1H), 6.88 (d, J=9.6, 1H), 4.91 (m, 1H), 4.29 (m, 2H), 4.18 (m, 2H), 3.64 (m, 4H), 3.35 (m, 4H), 2.81 (s, 3H), 2.77 (m, 2H), 2.03 (m, 1H), 1.80 (m, 2H), 1.29 (m, 2H), 1.24, d, J=6.4, 6H); ESIMS m/z for (M+H)$^+$ C$_{19}$H$_{32}$N$_5$O$_5$S calcd.: 442.2. found: 442.3.

Example C3

Isopropyl 4-((5-(4-(methylsulfonyl)piperazin-1-yl)pyrimidin-2-yloxy)methyl)piperidine-1-carboxylate

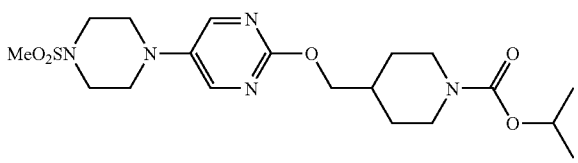

By following a similar procedure as the one used for preparing C1 from A1b except substituting 2-chloro-5-bromopyrimidine for 2-chloro-5-bromopyridine in the first step, C3 is prepared; $^1$H NMR (CDCl$_3$, 400 MHz): δ 8.38 (s, 2H), 4.91 (sept., J=6.3 Hz, 1H), 4.23 (m, 5H), 3.50 (m, 4H), 3.29 (m, 4H), 2.87 (s, 3H), 2.76 (m, 2H), 2.04 (m, 1H), 1.84 (m, 2H), 1.27 (m, 1H), 1.24 (d, J=6.3 Hz, 6H); ESIMS m/z for (M+H)$^+$ C$_{19}$H$_{32}$N$_5$O$_5$S calcd.: 442.2. found: 442.3.

Example D1

(E)-isopropyl 4-(2-(6-(4-(methylsulfonyl)piperazin-1-yl)pyridin-3-yl)vinyl)piperidine-1-carboxylate

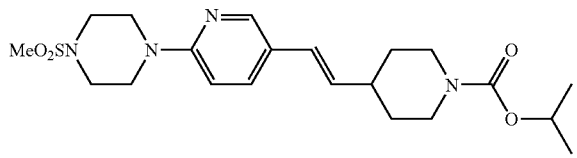

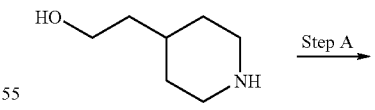

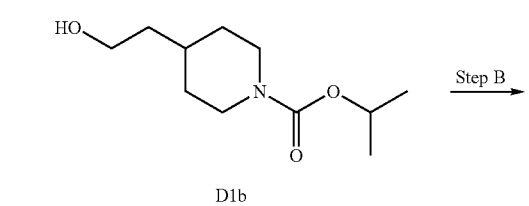

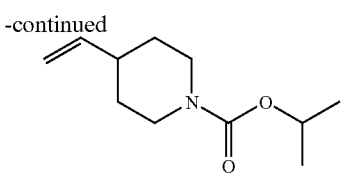

D1c

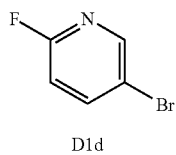

D1d

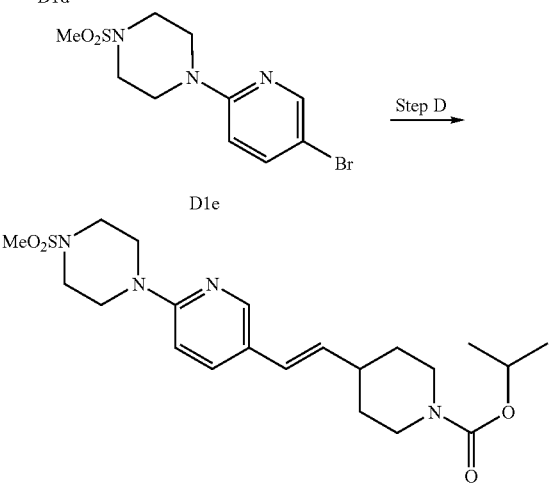

Example D1

Step A: A solution of D1a (10 g, 0.077 mol) in dichloromethane (100 mL) is treated with a solution of isopropyl chloroformate in toluene (93 mL of a 1M solution) dropwise. The reaction is then stirred at room temperature for 2.5 hours and quenched with saturated aqueous ammonium chloride solution. The phases are separated and the aqueous phase is extracted once more with dichloromethane and discarded. The combined organics are extracted once with 1M HCl, once with saturated aqueous sodiumhydrogencarbonate, dried over MgSO$_4$, filtered and evaporated to afford D1b; ESIMS m/z for (M+H)$^+$ C$_7$H$_{16}$NO calcd.: 130.1. found: 130.1.

Step B: A cold (ice/water bath) solution of D1b (9.9 g, 0.046 mol) and triethylamine (6.7 mL, 0.048 mol) in dichloromethane is treated with the dropwise addition of methanesulfonyl chloride (3.7 mL, 0.048 mol) and stirred for 2 hours. The mixture is treated with water and extracted with dichloromethane. The organics are pooled, dried over MgSO$_4$, filtered and concentrated. The crude material is diluted in acetone (10 mL) and added dropwise to a slurry of lithium bromide (12 g, 0.138 mol) in acetone (50 mL). The reaction is heated to 35° C. and maintained overnight. After cooling to room temperature, the reaction is concentrated, diluted with ethyl acetate and washed with water. The organic phase is collected, dried over MgSO$_4$, and concentrated. This residue is diluted in tetrahydrofuran (150 mL) and treated with the portionwise addition of potassium tert-butoxide (23.05 g, 0.2054 mol) every 30 min for 3 hours. Reaction is then heated to 40° C. and maintained overnight. Once the reaction had cooled to room temperature, saturated aqueous ammonium chloride is introduced and the reaction extracted with Et$_2$O. Organics are collected, dried over MgSO$_4$, concentrated, and purified via distillation (68°-70° C., 180 mTorr) to afford D1c. ESIMS m/z for (M+H)$^+$ C$_{11}$H$_{20}$NO$_2$ calcd.: 198.3 found: 198.1.

Step C: A solution of D1d (321 mg, 1.8 mmol) and methanesulfonylpiperazine (300 mg, 1.8 mmol) in N-methylpyrrolidinone (2 mL) is treated with K$_2$CO$_3$ (380 mg, 2.7 mmol) and heated to 160° C. for 5 minutes. The reaction is then partitioned between ethyl acetate and water and the organics are extracted with water again, dried over MgSO$_4$, filtered, evaporated and purified on silica gel using 0-100% ethyl acetate in hexane to afford D1e; ESIMS m/z for (M+H)$^+$ C$_{10}$H$_{15}$BrN$_3$O$_2$S calcd.: 320.0. found: 320.1.

Step D: A solution of D1e (50 mg, 0.18 mmol), D1c (44 mg, 0.22 mmol) Pd$_2$dba$_3$ (5 mg, 0.006 mmol) and tri-tert-butylphosphonium tetrafluoroborate (3.2 mg, 0.011 mmol) and dicyclohexylmethylamine (72 mg, 0.37 mmol) in dioxane (1 mL) is heated to 120° C. for 1 hour. The reaction is then partitioned between ethyl acetate and water and the organics are extracted with water once more, dried over MgSO$_4$, filtered, evaporated and purified on silica gel using a gradient of 0-100% ethyl acetate in hexane to afford D1; $^1$H NMR (CDCl$_3$, 400 MHz): δ 8.11 (d, J=2.3, 1H), 7.57 (dd, J=8.8, 2.4, 1H), 6.63 (d, J=8.8, 1H), 6.27 (d, J=15.9, 1H), 5.99 (dd, J=16.0, 6.9, 1H), 4.91 (m, 1H), 4.17 (m, 2H), 3.67 (m, 4H), 3.32 (m, 4H), 2.80 (m, 2H), 2.80 (s, 3H), 2.23 (m, 1H), 1.77 (m, 2H), 1.38 (m, 2H), 1.24, d, J=6.2, 6H); ESIMS m/z for (M+H)$^+$ C$_{21}$H$_{33}$N$_4$O$_4$S calcd.: 437.2. found: 437.2.

Example D2

Isopropyl 4-(2-(6-(4-(methylsulfonyl)piperazin-1-yl) pyridin-3-yl)ethyl)piperidine-1-carboxylate

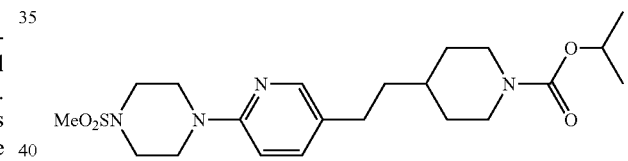

A solution of D2 (25 mg, 0.057 mmol) in methanol (2 mL) is treated with 10% Pd/C (5 mg) and hydrogenated for 1 hour. The atmosphere is exchanged back for nitrogen and the reaction is filtered though a plug of Celite® and the solvent is removed to afford D2; $^1$H NMR (CDCl$_3$, 400 MHz): δ 8.02 (d, J=2.2, 1H), 7.35 (dd, J=8.6, 2.4, 1H), 6.63 (d, J=8.6, 1H), 4.90 (m, 1H), 4.12 (m, 2H), 3.62 (m, 4H), 3.32 (m, 4H), 2.80 (s, 3H), 2.68 (m, 2H), 2.52 (m, 2H), 1.70 (m, 2H), 1.52 (m, 2H), 1.42 (m, 1H), 1.23 (d, J=6.2, 6H), 1.12 (m, 2H); ESIMS m/z for (M+H)$^+$ C$_{21}$H$_{35}$N$_4$O$_4$S calcd.: 439.2. found: 439.3.

Example D3

(E)-Isopropyl 4-(2-(2-(4-(methylsulfonyl)piperazin-1-yl)pyrimidin-5-yl)vinyl)piperidine-1-carboxylate

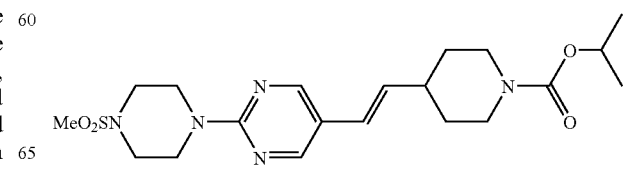

By following a similar procedure as the one used for preparing D1 from D1a except substituting 2-chloro-5-bromopyrimidine for D1d, D3 is prepared; $^1$H NMR (CDCl$_3$, 400 MHz): δ 8.38 (s, 2H), 6.18 (d, J=16.2 Hz, 1H), 6.05 (dd, J=16.1, 6.6 Hz, 1H), 4.92 (m, 1H), 4.18 (m, 2H), 3.98 (m, 4H), 3.30 (m, 4H), 2.80 (s, 3H), 2.80 (m, 2H), 2.29 (m, 1H), 1.76 (m, 2H), 1.38 (m, 2H), 1.24 (d, J=6.2 Hz, 6H); ESIMS m/z for (M+H)$^+$ C$_{20}$H$_{32}$N$_5$O$_4$S calcd.: 438.2. found: 438.3.

Example E1

5-Ethyl-2-(4-((6-(4-(methylsulfonyl)piperazin-1-yl)pyridin-3-yloxy)methyl)piperidin-1-yl)pyrimidine

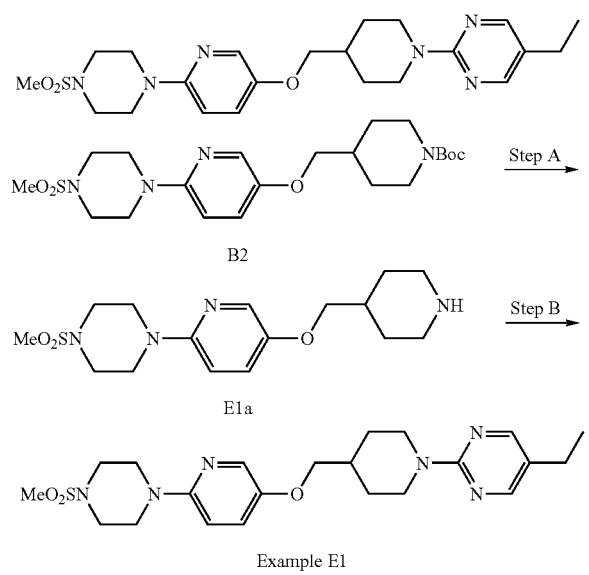

Step A: A sample of B2 (202 mg, 0.445 mmol) is treated with 4 M HCl in dioxane (3 mL) and aged for 1 hour. The solvent is then removed and the residue is partitioned between ethyl acetate and 1 M NaOH. The aqueous phase is isolated, extracted once more with ethyl acetate and discarded. The combined organics are dried over MgSO$_4$, filtered and evaporated to afford E1a; ESIMS m/z for (M+H)$^+$ C$_{16}$H$_{27}$N$_4$O$_3$S calcd.: 355.2. found: 355.2.

Step B: The resulting material is treated with 2-chloro-5-ethylpyrimidine (121 mg, 0.85 mmol), CuI (12 mg, 0.063 mmol), diisopropylethylamine (176 mg, 1.4 mmol) and N-methylpyrrolidinone (2 mL). The resulting solution is sealed in a reaction vial and heated to 160° C. for 10 minutes using a microwave reactor. The reaction is then diluted with ethyl acetate and extracted with water once, 1 M HCl once and saturated aqueous sodiumhydrogencarbonate once, dried over MgSO$_4$, filtered, evaporated and purified on silica gel using a linear gradient of 0-100% ethyl acetate in hexane followed by lyophilization from 1 M HCl to afford E1 as the HCl salt; $^1$H NMR (DMSO-d6, 400 MHz): δ 8.27 (s, 2H), 7.82 (d, J=2.9, 1H), 7.50 (m, 1H), 7.05 (m, 1H), 4.63 (m, 2H), 3.86 (d, J=6.4, 2H), 3.57 (m, 4H), 3.22 (m, 4H), 2.91 (s, 3H), 2.91 (m, 2H), 2.43 (dd, J=15.1, 7.6, 2H), 2.03 (s, 1H), 1.82 (m, 2H), 1.22 (m, 2H), 1.13 (dd, J=7.6, 7.6, 36H); ESIMS m/z for (M+H)$^+$ C$_{22}$H$_{33}$N$_6$O$_3$S calcd.: 461.2. found: 461.2.

Example E2

1-(Methylsulfonyl)-4-(5-((1-(5-(trifluoromethyl)pyridin-2-yl)piperidin-4-yl)methoxy)pyridin-2-yl)piperazine

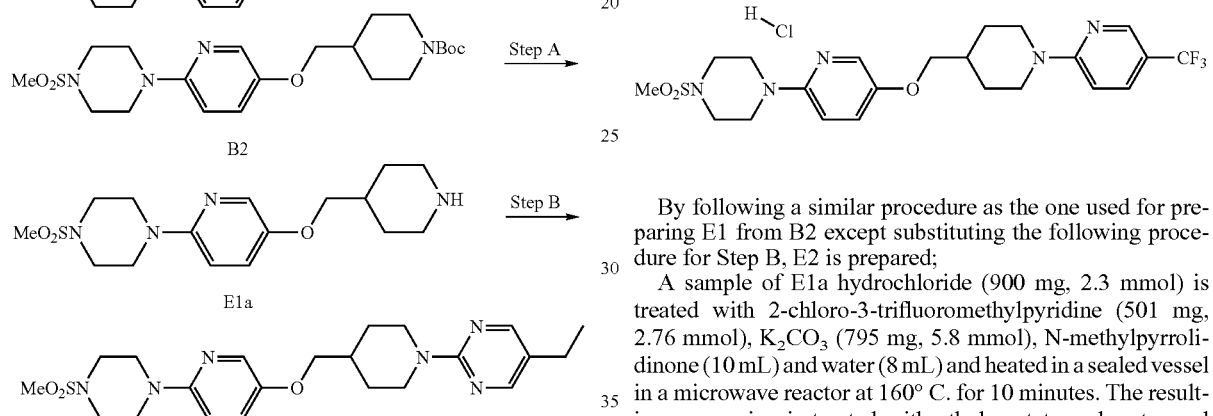

By following a similar procedure as the one used for preparing E1 from B2 except substituting the following procedure for Step B, E2 is prepared;

A sample of E1a hydrochloride (900 mg, 2.3 mmol) is treated with 2-chloro-3-trifluoromethylpyridine (501 mg, 2.76 mmol), K$_2$CO$_3$ (795 mg, 5.8 mmol), N-methylpyrrolidinone (10 mL) and water (8 mL) and heated in a sealed vessel in a microwave reactor at 160° C. for 10 minutes. The resulting suspension is treated with ethyl acetate and water and filtered. The resulting solid is washed with water and ethyl acetate, dissolved in 1 M HCl and lyophilized to afford E2; $^1$H NMR (CDCl$_3$, 400 MHz): δ8.22 (m, 1H), 8.10 (dd, J=9.8, 2.3, 1H), 7.86 (dd, J=9.9, 2.9, 1H), 7.60 (d, J=2.9, 1H), 7.53 (d, J=9.8, 1H), 7.42 (d, J=9.1, 1H), 4.30 (m, 2H), 3.94 (d, J=6.2, 1H), 3.71 (m, 4H), 3.37 (m, 4H), 2.86 (s, 3H), 2.28 (m, 1H), 2.06 (m, 2H), 1.57 (m, 2H); ESIMS m/z for (M+H)$^+$ C$_{22}$H$_{29}$F$_3$N$_5$O$_3$S calcd.: 500.2. found: 500.2.

Example E3

1-Methylcyclopropyl 4-((5-(4-(methylsulfonyl)piperazin-1-yl)pyrazin-2-yloxy)methyl)piperidine-1-carboxylate

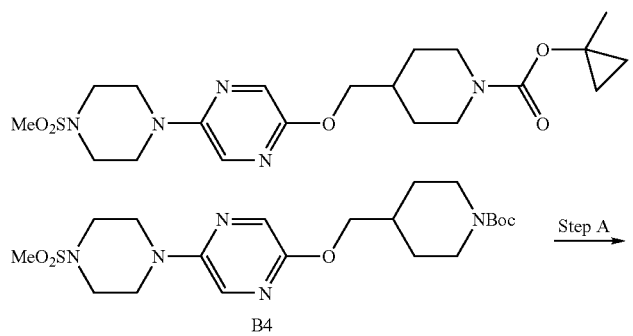

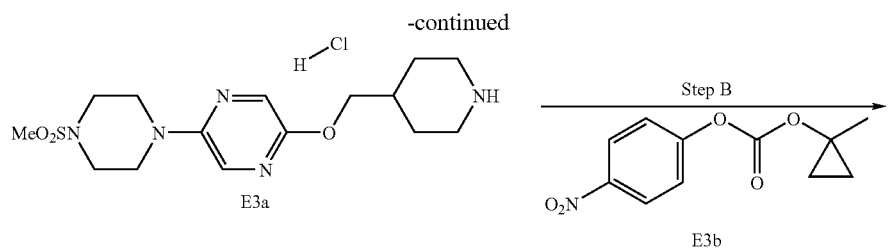

E3a

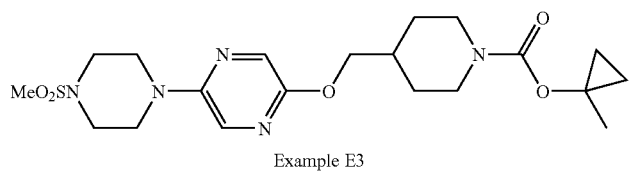

E3b

→ Step B

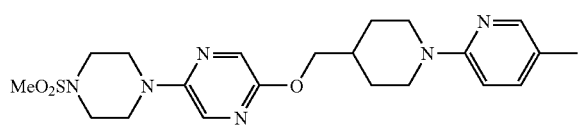

Example E3

Step A: A sample of B4 (745 mg, 0.16 mmol) is treated with 4 M HCl in dioxane and stirred for 3 hours. The solvent is decanted and the residue is lyophilized from water to afford E3a; ESIMS m/z for (M+H)+ $C_{15}H_{26}N_5O_3S$ calcd.: 356.2. found: 356.2.

Step B: A sample of E3a (181.8 mg, 0.46 mmol) is treated with N,N-dimethylformamide (1.5 mL), E3b (110 mg, 0.46 mmol) and diisopropylethylamine (242 μL, 1.4 mmol) and stirred overnight. The reaction is then partitioned between ethyl acetate and water and the organics are isolated, extracted with 1 M NaOH three times, dried over MgSO$_4$, filtered, evaporated and purified on silica gel using a linear gradient of 0-100% ethyl acetate in hexane to afford E3; $^1$H NMR (CDCl$_3$, 400 MHz): δ 7.87 (d, J=1.5, 1H), 7.62 (d, J=1.4, 1H), 4.18 (m, 2H), 4.08 (d, J=6.5, 2H), 3.52 (m, 4H), 3.36 (m, 4H), 2.82 (s, 3H), 2.72 (m, 2H), 1.93 (m, 1H), 1.80 (m, 2H), 1.56 (d, J=9.9, 3H), 1.23 (m, 2H), 0.87 (m, 2H), 0.62 (m, 2H); ESIMS m/z for (M+H)+ $C_{20}H_{32}N_5O_5S$ calcd.: 454.2. found: 454.2.

Example E4

5-Ethyl-2-(4-((5-(4-(methylsulfonyl)piperazin-1-yl)pyrazin-2-yloxy)methyl)piperidin-1-yl)pyrimidine

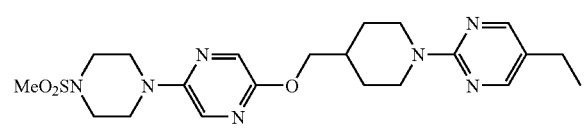

By following a similar procedure as the one used for preparing E1 from E1a except substituting E3a for E1a, E4 is prepared; $^1$H NMR (CDCl$_3$, 400 MHz): δ 8.17 (s, 2H), 7.88 (d, J=1.4, 1H), 7.63 (d, J=1.5, 1H), 4.76 (m, 2H), 4.11 (d, J=6.6, 2H), 3.52 (m, 4H), 3.37 (m, 4H), 2.90 (m, 2H), 2.82 (s, 3H), 2.45 (dd, J=15.2, 7.6, 2H), 2.08 (m, 2H), 1.90 (m, 2H), 1.33 (ddd, J=24.9, 12.4, 4.2, 2H), 1.18 (dd, J=7.6, 7.6, 3H); ESIMS m/z for (M+H)+ $C_{21}H_{32}N_7O_3S$ calcd.: 462.2. found: 462.3.

Example E5

2-((1-(5-Methylpyridin-2-yl)piperidin-4-yl)methoxy)-5-(4-(methylsulfonyl)piperazin-1-yl)pyrazine

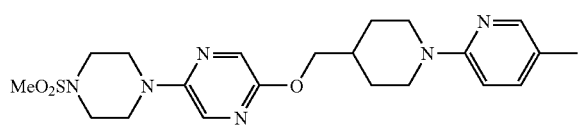

A mixture of E3a (103 mg, 0.26 mmol), 2-bromo-5-methylpyridine (45.3 mg, 0.26 mmol), Pd$_2$ dba$_3$ (4.8 mg, 0.005 mmol), xantphos (9.1 mg, 0.016 mmol), sodium tert-butoxide (78 mg, 0.815 mmol) and toluene (1.5 mL) is purged with nitrogen for 5 minutes and heated in an oil bath at 100° C. overnight. The reaction is cooled to room temperature and diluted with water and ethyl acetate. The organics are dried over MgSO$_4$, filtered, evaporated and purified by silica gel column chromatography using a linear gradient of 0-100% ethyl acetate in hexane to afford E5; $^1$H NMR (CDCl$_3$, 400 MHz): δ 8.01 (m, 1H), 7.88 (d, J=1.4, 1H), 7.30 (m, 1H), 6.62 (d, J=8.6, 1H), 4.27 (m, 2H), 4.11 (d, J=6.6, 1H), 3.53 (m, 4H), 3.37 (m, 4H), 2.82 (m, 2H), 2.82 (s, 3H), 2.19 (s, 3H), 2.02 (m, 1H), 1.91 (m, 2H), 1.42 (m, 2H); ESIMS m/z for (M+H)+ $C_{21}H_{31}N_6O_3S$ calcd.: 447.2. found: 447.3.

Example E6

1-Methylcyclopropyl 4-((5-(4-(methylsulfonyl)piperazin-1-yl)pyridin-2-yloxy)methyl)piperidine-1-carboxylate

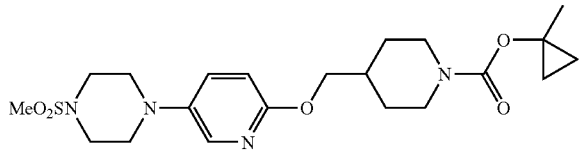

By following a similar procedure as the one used for preparing E3 from B4 except substituting tert-butyl 4-((5-(4-(methylsulfonyl)piperazin-1-yl)pyridin-2-yloxy)methyl)piperidine-1-carboxylate for B4, E6 is prepared; tert-Butyl 4-((5-(4-(methylsulfonyl)piperazin-1-yl)pyridin-2-yloxy)methyl)piperidine-1-carboxylate is prepared in an analogous fashion to B4 except using 2-fluoro-5-bromopyridine instead of A1d; $^1$H NMR (CDCl$_3$, 400 MHz): δ 7.78 (d, J=2.9, 1H), 7.28 (dd, J=8.9, 3.0, 1H), 6.68 (d, J=8.9, 1H), 4.18 (m, 2H), 4.08 (d, J=6.5, 2H), 3.38 (m, 4H), 3.14 (m, 4H), 2.83 (s, 3H), 2.73 (m, 2H), 1.93 (m, 1H), 1.79 (m, 2H), 1.54 (s, 3H), 1.23 (m, 2H), 0.86 (m, 2H), 0.61 (m, 2H); ESIMS m/z for (M+H)$^+$ C$_{21}$H$_{33}$N$_4$O$_5$S calcd: 453.2. found: 453.3.

Example E7

5-Ethyl-2-(4-((5-(4-(methylsulfonyl)piperazin-1-yl)pyridin-2-yloxy)methyl)piperidin-1-yl)pyrimidine

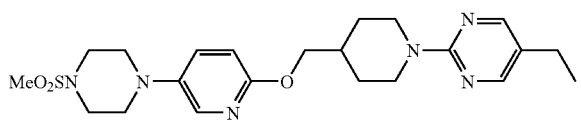

By following a similar procedure as the one used for preparing E1 from E1a except substituting tert-butyl 4-((5-(4-(methylsulfonyl)piperazin-1-yl)pyridin-2-yloxy)methyl)piperidine-1-carboxylate for E1a, E7 is prepared; tert-Butyl 4-((5-(4-(methylsulfonyl)piperazin-1-yl)pyridin-2-yloxy)methyl)piperidine-1-carboxylate is prepared in an analogous fashion to B4 except using 2-fluoro-5-bromopyridine instead of A1d; $^1$H NMR (CDCl$_3$, 400 MHz): δ 8.16 (s, 2H), 7.78 (d, J=2.9, 1H), 7.28 (dd, J=8.9, 3.0, 1H), 6.69 (d, J=9.0, 1H), 4.73 (m, 2H), 4.11 (d, J=6.6, 1H), 3.38 (m, 4H), 3.14 (m, 4H), 2.89 (m, 2H), 2.83 (s, 3H), 2.44 (dd, J=15.2, 7.6, 2H), 2.08 (m, 1H), 1.90 (m, 2H), 1.34 (ddd, J=24.8, 12.4, 4.1, 2H), 1.73 (dd, J=7.6, 7.6, 3H); ESIMS m/z for (M+H)$^+$ C$_{22}$H$_{33}$N$_6$O$_3$S calcd.: 461.2. found: 461.3.

Example E8

3-Isopropyl-5-(4-((5-(4-(methylsulfonyl)piperazin-1-yl)pyrazin-2-yloxy)methyl)piperidin-1-yl)-1,2,4-oxadiazole

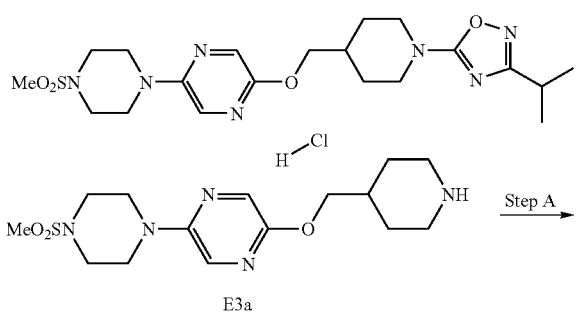

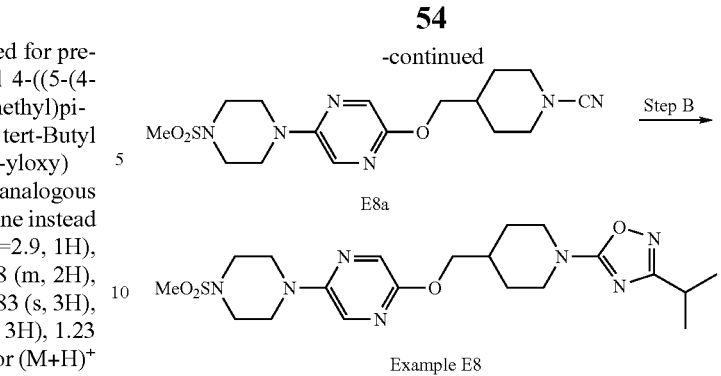

Step A: A cold (ice/water bath) solution of E3a (256 mg, 0.65 mmol) in dichloromethane (5 mL) is treated with a solution of K$_2$CO$_3$ (298 mg, 2.2 mmol) in water (5 mL). The vigorously stirred solution is treated with a solution of cyanogen bromide (76.1 mg, 0.72 mmol) in dichloromethane (2 mL) and the reaction is allowed to stir cold for 3 hours. The phases are then separated and the organic phase is dried over MgSO$_4$, filtered and evaporated to afford E8a which is used without further purification; ESIMS m/z for (M+H)$^+$ C$_{16}$H$_{25}$N$_6$O$_3$S calcd.: 381.2. found: 381.1.

Step B: A solution of E3a (215.5 mg, 0.57 mmol) in dioxane (2 mL) is treated with N'-hydroxyisobutyrimidamide (86.8 mg, 0.85 mmol) and ZnCl$_2$ (115.8 mgL, 0.85 mmol) and stirred at 100° C. overnight. The reaction is then partitioned between ethyl acetate and 1 M NaOH and the organics are isolated, dried over MgSO$_4$, filtered, evaporated and purified on silica gel using a linear gradient of 0-100% ethyl acetate in hexane to afford E8; $^1$H NMR (CDCl$_3$, 400 MHz): δ 7.88 (d, J=1.4, 1H), 7.62 (d, J=1.4, 1H), 4.19 (m, 2H), 4.11 (d, J=6.5, 2H), 3.53 (m, 4H), 3.37 (m, 4H), 3.08 (ddd, J=12.9, 12.9, 2.8, 2H), 2.87 (m, 1H), 2.82 (s, 3H), 2.03 (m, 1H), 1.91 (m, 2H), 1.43 (ddd, J=25.2, 12.5, 4.4, 2H), 1.28 (d, J=7.0, 3H); ESIMS m/z for (M+H)$^+$ C$_{20}$H$_{32}$N$_7$O$_4$S calcd.: 466.2. found: 466.3.

Example E9

3-Isopropyl-5-(4-((5-(4-(methylsulfonyl)piperazin-1-yl)pyridin-2-yloxy)methyl)piperidin-1-yl)-1,2,4-oxadiazole

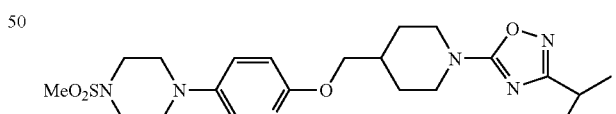

By following a similar procedure as the one used for preparing E8 from B4 except substituting tert-butyl 4-((5-(4-(methylsulfonyl)piperazin-1-yl)pyridin-2-yloxy)methyl)piperidine-1-carboxylate for B4, E9 is prepared; tert-Butyl 4-((5-(4-(methylsulfonyl)piperazin-1-yl)pyridin-2-yloxy)methyl)piperidine-1-carboxylate is prepared in an analogous fashion to B4 except using 2-fluoro-5-bromopyridine instead of A1d; $^1$H NMR (CDCl$_3$, 400 MHz): δ 7.78 (d, J=2.9, 1H), 7.29 (dd, J=8.9, 3.0, 1H), 6.69 (d, J=8.9, 1H), 4.17 (m, 2H), 4.13 (d, J=6.5, 1H), 3.40 (m, 4H), 3.17 (m, 4H), 3.08 (ddd, J=12.9, 12.9, 2.8, 2H), 2.88 (m, 1H), 2.84 (s, 3H), 2.03 (m, 1H), 1.91 (m, 2H), 1.34 (ddd, J=25.1, 12.5, 4.4, 2H), 1.28 (d, J=7.0, 3H); ESIMS m/z for (M+H)⁺ $C_{21}H_{33}N_6O_4S$ calcd.: 465.2. found: 465.3.

Example E10

1-Methylcyclopropyl 4-((6-(4-(methylsulfonyl)piperazin-1-yl)pyridin-3-yloxy)methyl)piperidine-1-carboxylate

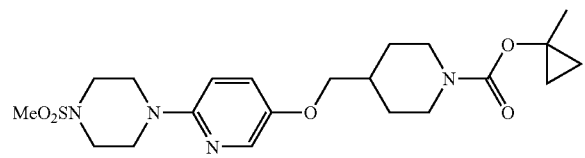

By following a similar procedure as the one used for preparing E3 from B4 except substituting B2 for B4, E10 is prepared; ¹H NMR (CDCl₃, 400 MHz): δ 7.90 (d, J=2.9, 1H), 7.14 (dd, J=9.1, 3.0, 1H), 6.65 (d, J=9.0, 1H), 4.12 (m, 2H), 3.77 (d, J=6.3, 1H), 3.54 (m, 4H), 3.33 (m, 4H), 2.80 (s, 3H), 2.73 (m, 2H), 1.92 (m, 1H), 1.89 (m, 2H), 1.54 (s, 3H), 1.23 (m, 2H), 0.86 (m, 2H), 0.62 (m, 2H); ESIMS m/z for (M+H)⁺ $C_{21}H_{33}N_4O_5S$ calcd.: 453.2. found: 453.2.

Example E11

5-Isopropyl-3-(4-((6-(4-(methylsulfonyl)piperazin-1-yl)pyridin-3-yloxy)methyl)piperidin-1-yl)-1,2,4-oxadiazole

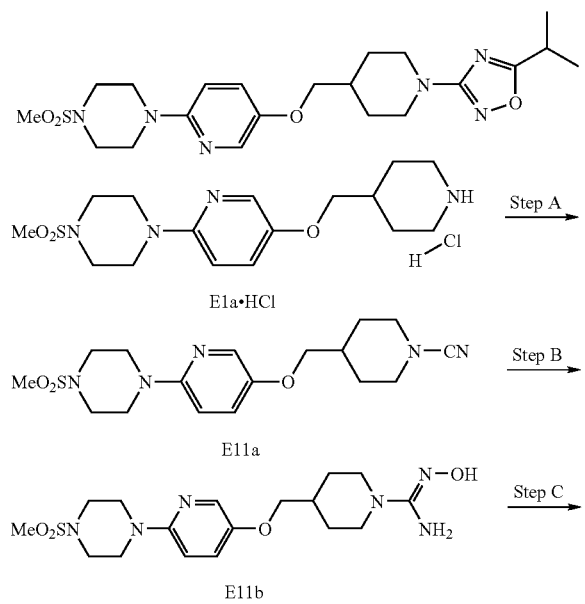

Example E11

Step A: A mixture of E1a.HCl (202.3 mg, 0.52 mmol) and K₂CO₃ (143 mg, 1.0 mmol) in water (3 mL) is cooled to ice/water bath temperature and treated dropwise with a solution of cyanogen bromide (60.3 mg, 0.57 mmol) in dichlormethane (3 mL) and stirred for 2 hours while cooled. The reaction is then diluted with dichloromethane, extracted with water, dried over MgSO₄, filtered and evaporated to afford E11a which is used without further purification; ESIMS m/z for (M+H)⁺ $C_{17}H_{26}N_5O_3S$ calcd.: 380.2. found: 380.2.

Step B: A solution of E11a (152.4 mg, 0.40 mmol) and hydroxylamine (492 μL of a 50% aqueous solution, 0.80 mmol) in ethanol (2 mL) is heated to 60° C. in a sealed vessel overnight. The reaction is cooled to room temperature and the resulting sample of E11b; ESIMS m/z for (M+H)⁺ $C_{17}H_{29}N_6O_4S$ calcd.: 413.2. found: 413.2.

Step C: A solution of E11b (134.2 mg, 0.32 mmol) and isobutyric anhydride (50 mg, 0.32 mmol) in dioxane is heated at 400 W in a microwave reactor for 10 minutes (~120° C.). The reaction is cooled to room temperature, evaporated and partitioned between ethyl acetate and saturated aqueous sodium hydrogencarbonate. The organics are isolated, dried over MgSO₄, filtered, evaporated and purified on silica gel using a linear gradient of 0-100% ethyl acetate in hexane and lyophilized from 1 M HCl to afford E11 as an HCl salt; ¹H NMR (CDCl₃, 400 MHz): δ 7.92 (d, J=3.0, 1H), 7.16 (dd, J=9.1, 3.0, 1H), 6.65 (d, J=9.1, 1H), 4.06 (m, 2H), 3.80 (d, J=6.4, 1H), 3.54 (m, 4H), 3.33 (m, 4H), 3.07 (m, 1H), 2.92 (ddd, J=12.7, 12.7, 2.7, 1H), 2.80 (s, 3H), 2.73 (m, 2H), 1.99 (m, 1H), 1.88 (m, 2H), 1.42 (m, 2H), 1.34 (d, J=7.0, 6H); ESIMS m/z for (M+H)⁺ $C_{21}H_{33}N_6O_4S$ calcd.: 465.2. found: 453.3.

Example E12

2-((1-(5-Fluoropyridin-2-yl)piperidin-4-yl)methoxy)-5-(4-(methylsulfonyl)piperazin-1-yl)pyrazine

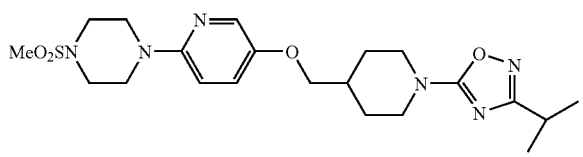

By following a similar procedure as the one used for preparing E5 from E3a except substituting 2-bromo-5-fluoropyridine for 2-bromo-5-methylpyridine and dicyclohexyl(2',6'-dimethoxybiphenyl-4-yl)phosphine for xantphos, E12 is prepared; ESIMS m/z for (M+H)⁺ $C_{20}H_{28}FN_6O_3S$ calcd: 451.2. found: 451.2.

Example F1

3-Isopropyl-5-(4-((6-(4-(methylsulfonyl)piperazin-1-yl)pyridin-3-yloxy)methyl)piperidin-1-yl)-1,2,4-oxadiazole

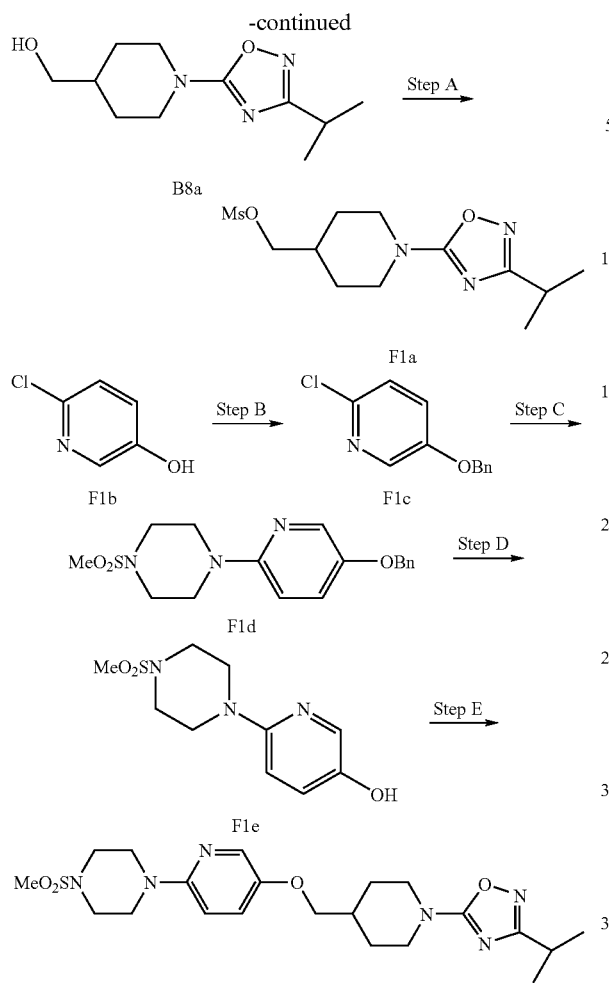

Example F1

Step A: By following a similar procedure as the one used for preparing B5c from B5b except substituting B8a for B5b, F1a is prepared; ESIMS m/z for $(M+H)^+$ $C_{12}H_{22}N_3O_4S$ calcd: 304.1. found: 304.1.

Step B: A solution of F1b (3.00 g, 23.0 mmol) and benzyl chloride (2.93 mL, 25.5 mmol) in acetonitrile (50 mL) is treated with $Cs_2CO_3$ (15.0 g, 46.0 mmol) and the reaction mixture is heated at 90° C. for 2 hours, cooled and filtered. The solvents are evaporated and the crude compound purified on silica gel using a linear gradient of 0-100% ethyl acetate in hexane to afford F1c; $^1$H-NMR (400 MHz, CDCl$_3$) δ 8.15 (dd, J=0.8, 2.8 Hz, 1H), 7.42 (m, 4H), 7.39 (m, 1H), 7.25 (m, 2H), 5.12 (s, 2H); ESIMS calcd. for $[M+H]^+$ $C_{12}H_{11}ClNO$: 220.1 found: 220.1.

Step C: F1c (2.67 g, 12.2 mmol), 1-methanesulfonyl piperazine (3 g, 18.3 mmol), $Pd(OAc)_2$ (548 mg, 2.4 mmol), ((2-dicyclohexyl)phosphino)biphenyl (1.7 g, 4.8 mmol), NaOtBu (3.5 g, 36.6 mmol) and toluene (20 mL) are charged to a sealed flask and degassed with bubbling Ar for 30 minutes. The mixture is heated at 120° C. for 18 h, then is hot filtered to remove particulates. The filter cake is washed with ethyl acetate (10 mL) and water (20 mL) and the filtrates are combined and extracted with ethyl acetate (20 mL). The organic layer is extracted with 1N HCl (3×20 mL) and discarded. The acidic layer is then basified with NaOH and extracted with ethyl acetate (3×20 mL). The remaining organic layers are combined, dried (MgSO$_4$), filtered and concentrated. The residue is recrystallized from ethyl acetate/Hexane to provide F1d; ESIMS calcd. for $[M+H]^+$ $C_{17}H_{22}N_3O_3S$: 348.1 found: 348.1.

Step D: A solution of F1d (1.3 g, 3.88 mmol) in EtOH is treated with Pd/C (0.2 g of 10%, wet). The reaction is stirred under H$_2$ (1 atmosphere) for 12 hours. The mixture is filtered and concentrated to provide F1e which is used without further purification: ESIMS calcd. for $[M+H]^+$ $C_{10}H_{16}N_3O_3S$: 258.1 found: 258.1.

Step E: A solution of F1e (97.7 mg, 0.38 mmol) and F1a (115.2 mg, 0.38 mmol) in N,N-dimethylformamide (1.5 mL) is treated with $Cs_2CO_3$ (185.6 mg, 0.57 mmol) and heated to 60° C. overnight. The reaction is cooled to room temperature, diluted with ethyl acetate, extracted with water, dried over MgSO$_4$, filtered, evaporated and purified by silica gel column chromatography using a linear gradient of 0 to 100% ethyl acetate in hexane and then lyophilized from HCl to afford F1 as an HCl salt; $^1$H NMR (CDCl$_3$, 400 MHz): δ 8.01 (m, 0.5H), 7.92 (d, J=2.8, 1H), 7.16 (dd, J=9.1, 3.1, 1H), 6.66 (d, J=9.1, 1H), 4.20 (m, 2H), 3.81 (d, J=6.3, 1H), 3.54 (m, 4H), 3.33 (m, 4H), 3.09 (m, 2H), 2.88 (m, 1H), 2.81 (s, 3H), 2.00 (m, 1H), 1.92 (m, 2H), 1.44 (m, 2H), 1.28 (d, J=7.0, 3H); ESIMS m/z for $(M+H)^+$ $C_{21}H_{33}N_6O_4S$ calcd.: 465.2. found: 465.3.

Example G1 tert-Butyl 4-((5-(4-(methylsulfonyl)-1,4-diazepan-1-yl)pyrazin-2-yloxy)methyl)piperidine-1-carboxylate

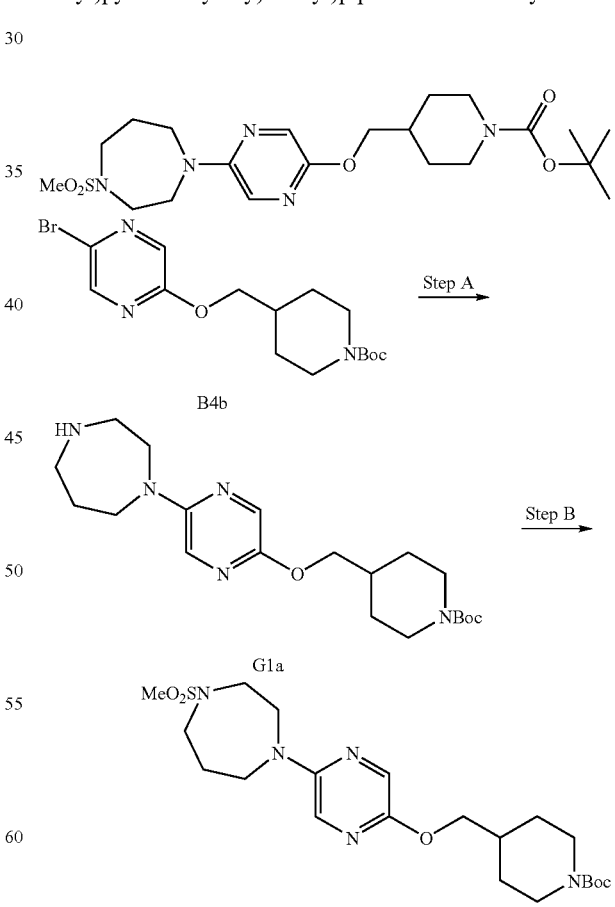

Example G1

Step A: A mixture of B4b (307.5 mg, 0.83 mmol), homopiperazine (248.2 mg, 2.5 mmol), xantphos (28.7 mg, 0.050 mmol), sodium tert-butoxide 119 mg, 1.2 mmol) and toluene (5 mL) is sparged with nitrogen for 5 minutes and treated with Pd₂dba₃ (15.1 mg, 0.017 mmol). The reaction is then sealed and dipped into a pre-heated oil bath at 100° C. The reaction is stirred at this temperature for 4 hours, cooled to room temperature, diluted with ethyl acetate and extracted with water twice. The organics are dried over MgSO₄, filtered, evaporated and purified on a silica gel column using 0-10% methanol in dichloromethane to afford G1a; ESIMS m/z for (M+H)⁺ $C_{21}H_{35}N_4O_3$ calcd.: 391.3. found: 391.3.

Step B: A solution of G1a (139 mg, 3.6 mmol) in dichloromethane (0.25 m L) is cooled to ice/water bath temperature and treated with triethylamine (37.4 mg, 0.37 mmol) followed by methanesulfonyl chloride (42.3 mg, 0.37 mmol) and stirred overnight. The reaction is then poured into water and extracted with dichloromethane twice. The combined organics are dried over MgSO₄, filtered, evaporated and purified on a silica gel column using 0-100% ethyl acetate in hexane to afford G1; ¹H NMR (CDCl₃, 400 MHz): δ 7.79 (d, J=2.9, 1H), 7.49 (d, J=1.5, 1H), 4.13 (m, 2H), 4.14 (d, J=6.5, 1H), 3.82 (m, 2H), 3.74 (dd, J=6.3, 6.3, 2H), 3.49 (m, 2H), 3.26 (m, 2H), 2.78 (s, 3H), 2.73 (m, 2H), 2.07 (m, 2H), 1.94 (m, 1H), 1.79 (m, 1H), 1.46 (s, 9H), 1.25 (m, 2H); ESIMS m/z for (M+H)⁺ $C_{21}H_{36}N_5O_5S$ calcd.: 470.2. found: 370.2 (M-Boc+H⁺).

Example G2 tert-Butyl 4-((5-(3-(methylsulfonyloxy) pyrrolidin-1-yl)pyrazin-2-yloxy)methyl)piperidine-1-carboxylate

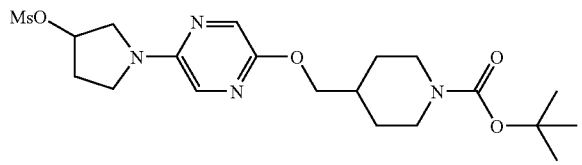

By following a similar procedure as the one used for preparing G1 from B4b except substituting pyrrolidin-3-ol for homopiperazine, G2 is prepared; ¹H NMR (CDCl₃, 400 MHz): δ 7.82 (d, J=1.5, 1H), 7.38 (d, J=1.5, 1H), 5.43 (m, 1H), 4.03 (m, 2H), 4.06 (d, J=6.6, 1H), 3.82 (m, 21H), 3.74 (dd, J=12.4, 4.4, 1H), 3.58 (m, 2H), 3.05 (s, 3H), 2.72 (m, 2H), 2.47 (m, 1H), 2.33 (m, 1H), 1.93 (m, 1H), 1.79 (m, 2H), 1.46 (s, 9H), 1.26 (m, 2H); ESIMS m/z for (M-Boc+H)⁺ $C_{15}H_{25}N_4O_4S$ calcd.: 357.2. found: 357.2.

Example G3

Tert-butyl 4-((5-(4-(methylsulfonyl)piperidin-1-yl) pyrazin-2-yloxy)methyl)piperidine-1-carboxylate

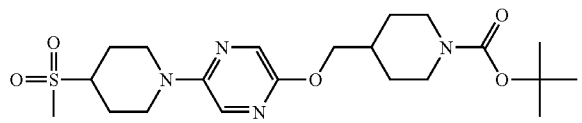

By following a similar procedure as the one used for preparing G1a from B4b except substituting 4-(methylsulfonyl) piperidine for homopiperazine, G3 is prepared; ESIMS m/z for (M-ᵗBu+H)⁺ $C_{16}H_{27}N_4O_3S$ calcd: 355.2. found: 355.2

Example G4

1-Methylcyclopropyl 4-((5-(4-(methylsulfonyl)piperidin-1-yl)pyrazin-2-yloxy)methyl)piperidine-1-carboxylate

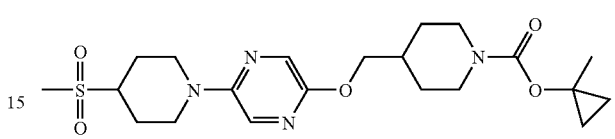

By following a similar procedure as the one used for preparing E3 from B4 except substituting G3 for B4, G4 is prepared; ESIMS m/z for (M+H)⁺ $C_{21}H_{34}N_4O_5S$ calcd: 454.2. found: 454.2.

Example H1 tert-Butyl 4-(2-(3-(4-(methylsulfonyl)piperazin-1-yl)-1,2,4-oxadiazol-5-yl)ethyl)piperidine-1-carboxylate

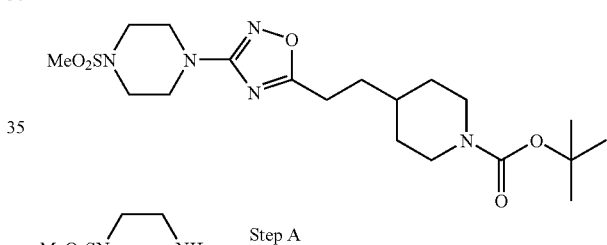

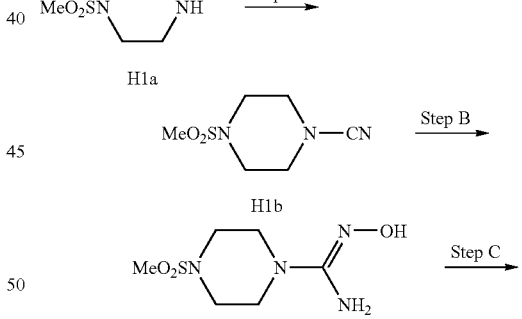

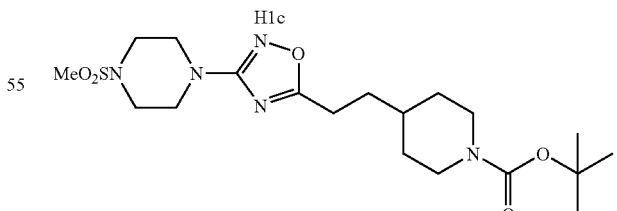

Example H1

Step A: To a stirred a solution of potassium carbonate (2.78 g, 20.0 mol) in water (20 mL) is added H1a (3.0 g, 18.3 mmol). The solution is cooled to 10° C., then a solution of cyanogen bromide (2.12 g, 20.0 mmol) in dichloromethane (20 mL) is added dropwise over 30 min. The reaction is warmed to room temperature and stirred for 2 hours, then extracted into dichloromethane. The organic layer is washed with 1N HCl (30 mL), dried over MgSO₄, filtered and concentrated. The product is used without further purification.

Step B: A solution of H1b (2.6 g, 13.7 mmol) and hydroxylamine (1 mL, 15.1 mmol) in EtOH (10 mL) is heated in a sealed vial at 90° C. for 12 hours. The mixture is concentrated in vacuo to provide H1c, which is used without further purification.

Step C: A solution of 1-Boc-piperidin-4-yl propionic acid acid (112 mg, 0.44 mmol) and N,N-carbonyl dimidazole (71 mg, 0.44 mmol) in N,N-dimethylformamide (0.5 mL) is stirred at room temperature for 30 min. H1c (107 mg, 0.48 mmol) is added, the tube is sealed and heated at 115° C. for 18 hours. The reaction mixture is cooled, extracted into ethyl acetate (10 mL), washed with water (2×10 mL), then brine (10 mL). The organic layer is dried over MgSO₄, filtered, concentrated, and purified by mass triggered reverse phase HPLC to provide H1; $^1$H NMR (CDCl₃, 400 MHz): δ 4.10 (br.s, 2H), 3.59 (m, 4H), 3.32 (m, 4H), 2.82 (s, 3H), 2.79 (t, J=8.0 Hz, 2H), 2.68 (m, 2H), 1.71 (m, 4H), 1.46 (s, 9H), 1.15 (m, 2H); ESIMS m/z for (M+H+Na)⁺ $C_{19}H_{33}N_5O_5SNa$ calcd.: 466.2. found: 466.2.

Example H2 tert-Butyl 4-(3-(3-(4-(methylsulfonyl)piperazin-1-yl)-1,2,4-oxadiazol-5-yl)propyl)piperidine-1-carboxylate

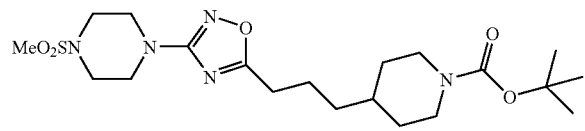

By following a similar procedure as the one used for preparing H1 from H1a except substituting 4-(1-Boc-piperidin-4-yl) butanoic acid for 1-Boc-piperidin-4-yl propionic acid acid, H2 is prepared; $^1$H NMR (CDCl₃, 400 MHz): δ 4.08 (d, J=13.2 Hz, 2H), 3.59 (m, 4H), 3.32 (m, 4H), 2.82 (s, 3H), 2.75 (t, J=7.6 Hz, 2H), 2.68 (dt, J=2.4, 13.2 Hz, 2H), 1.80 (m, 2H), 1.68 (s, 1H), 1.65 (s, 1H), 1.46 (s, 9H), 1.42 (m, 1H), 1.34 (s, 2H), 1.11 (m, 2H); ESIMS m/z for (M+H+Na)⁺ $C_{20}H_{35}N_5O_5SNa$ calcd.: 480.2. found: 480.3.

Example H3

5-(3-(1-(5-Ethylpyrimidin-2-yl)piperidin-4-yl)propyl)-3-(4-(methylsulfonyl)piperazin-1-yl)-1,2,4-oxadiazole

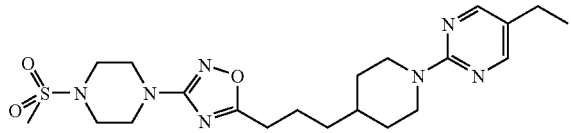

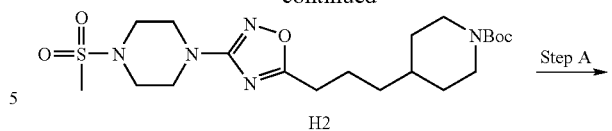

H2

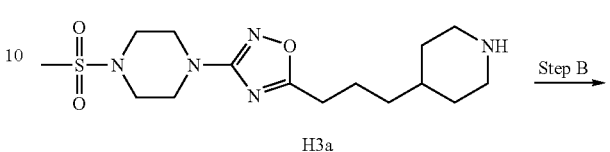

H3a

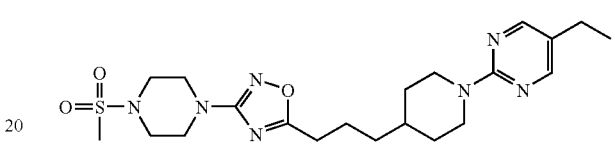

Example H3

Step A: A solution of H2 (261 mg, 0.57 mmol) in tetrahydrofuran (5 mL) is treated with HCl (5 mL of 4N in dioxane) and stirred at room temperature for 1 hour. The reaction is concentrated, dissolved in dichloromethane (5 mL) and concentrated in vacuo to remove traces of acid and provide H3a, which is used without further purification; ESIMS m/z for (M+H)⁺ $C_{15}H_{28}N_5O_3S$ calcd.: 358.2. found: 358.2.

Step B: H3a (53 mg, 0.15 mmol) and 2-chloro-5-ethylpyrimidine (22 μL, 0.18 mmol) are dissolved in 1,4-dioxane (1 mL). Cesium carbonate (120 mg, 0.37 mmol) is added and the tube is sealed and heated at 150° C. for 2 hours. The reaction mixture is cooled, filtered, and purified by mass triggered reverse phase HPLC to provide H3; $^1$H NMR (CDCl₃, 400 MHz): δ 8.27 (s, 2H), 4.70 (d, J=13.2 Hz, 2H), 3.60 (m, 4H), 3.33 (m, 4H), 2.93 (dt, J=2.0, 13.2 Hz, 2H), 2.83 (s, 3H), 2.77 (t, J=7.6 Hz, 2H), 2.51 (q, J=7.6 Hz, 2H), 1.84 (m, 4H), 1.58 (m, 1H), 1.37 (m, 3H), 1.22 (t, J=7.6 Hz, 3H; ESIMS m/z for (M+H)⁺ $C_{21}H_{34}N_7O_3S$ calcd.: 464.2. found: 464.2.

Example H4

Isopropyl 4-(3-(3-(4-(methylsulfonyl)piperazin-1-yl)-1,2,4-oxadiazol-5-yl)propyl)piperidine-1-carboxylate

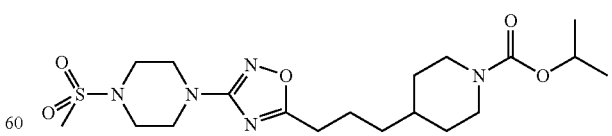

By following a similar procedure as the one used for preparing H1 from H1a except substituting H4b (see scheme below) for 1-Boc-piperidin-4-yl propionic acid acid, H4 is prepared; ESIMS m/z for (M+H)⁺ $C_{19}H_{34}N_5O_5S$ calcd.: 444.2. found: 480.3.

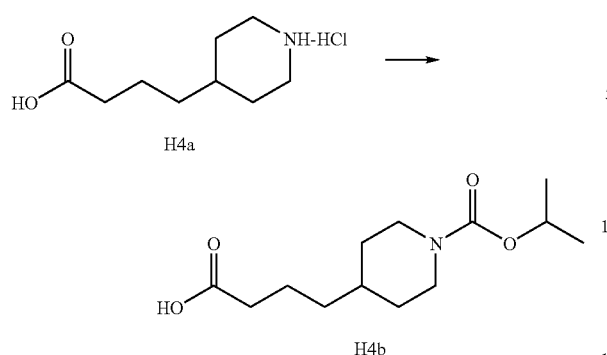

H4a

H4b

Commercially available H4a (20 g, 96 mmol) is suspended in dry dimethylacetamide (100 mL). Triethylamine (34 mL, 240 mmol) is added and the resulting mixture is cooled in an ice/water bath. A solution of isopropyl chloroformate in toluene (1.0M, 150 mL) is added dropwise, forming a white precipitate. The suspension is stirred at room temperature for 18 hours, then the white precipitate is filtered, washed with ethyl acetate, and discarded. The filtrate is concentrated in vacuo to yield H4b.

Example I1

3-Isopropyl-5-(4-(2-(5-(4-(methylsulfonyl)piperazin-1-yl)thiazol-2-yl)ethyl)piperidin-1-yl)-1,2,4-oxadiazole

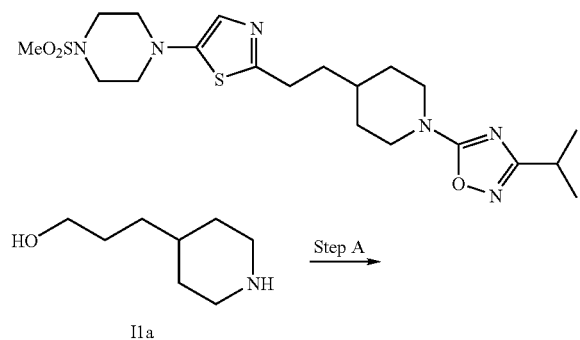

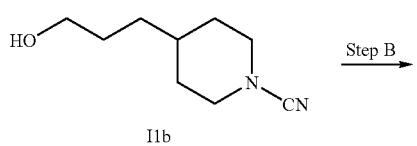

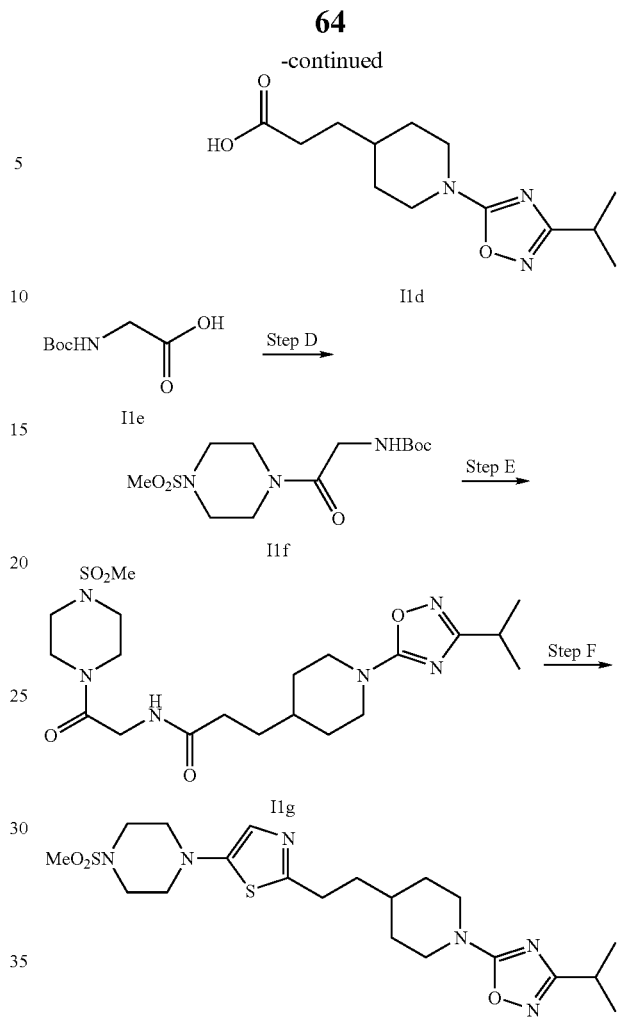

Example I1

Step A: To a stirred a suspension of sodiumhydrogencarbonate (2.80 g, 33.3 mmol) in water (1.5 mL) is added I1a hydrochloride salt (2.00 g, 11.1 mmol) and dichloromethane (2 mL). The mixture is cooled in ice/water bath and stirred. A solution of cyanogen bromide (1.42 g, 13.4 mmol) in dichloromethane (3 mL) is added over a period of 1 hour. The cold bath is removed and the reaction is stirred overnight. 0.33 g of $Na_2CO_3$ is added to ensure the reaction is basic. The reaction is diluted with dichloromethane (20 mL), dried with $MgSO_4$. The mixture is filtered, washed with dichloromethane, and evaporated to give I1b; ESIMS m/z for (M+H)$^+$ $C_9H_{17}N_2O$ calcd.: 169.1. found: 169.1.

Step B: A solution of I1b (1.87 g, 11.1 mmol) and N'-hydroxy isobutyrimidamide (1.70 g, 16.7 mmol) in ethyl acetate (40 mL) is treated with a solution of $ZnCl_2$ (16.7 mL, 1N in ether) dropwise. A white precipitate is formed. After stirring at room temperature for 15 minutes, the precipitate stuck on the flask and made stirring difficult. The solid is triturated with ether (40 mL) and stirred for 4 hours until a yellow suspension is obtained. The solid is collected by filtration, washed with ether (30 mL) and dried to give a yellow solid which is used without purification for the next step; ESIMS m/z for (M+H)$^+$ $C_{13}H_{27}N_4O_2$ calcd.: 271.2. found: 271.2. The intermediate material (422 mg) is treated with dioxane (10 mL) and 4M HCl in dioxane (0.5 mL) and heated to 100° C. for 1 hour. The reaction is then cooled to room temperature and the solvent is removed. The residue is diluted with ethyl acetate and extracted with 1 M HCl twice, dried over MgSO$_4$, filtered and evaporated to afford I1c; ESIMS m/z for (M+H)$^+$ C$_{13}$H$_{24}$N$_3$O$_2$ calcd.: 254.2. found: 254.2.

Step C: A solution of I1c (368 mg, 1.45 mmol) in acetonitrile (8 mL) is treated with NaH$_2$PO$_4$ (218 mg, 1.8 mmol), Na$_2$HPO$_4$ (258 mg, 1.8 mmol), TEMPO free radical (16 mg, 0.1 mmol), NaClO$_2$ (328 mg of an 80% pure sample, 2.91 mmol) and water (8 mL). After all the reagents went into solution, 10% bleach (22 µL, 0.03 mmol) is added and the reaction is stirred overnight. The acetonitrile is removed in vacuo and the resulting solution is extracted with ethyl acetate once and the organics are discarded. The aqueous phase is made acidic (pH<1) with concentrated HCl and extracted twice with ethyl acetate and discarded. The combined organics are dried over MgSO$_4$ and the solvent is removed to afford I1d; ESIMS m/z for (M+H)$^+$ C$_{13}$H$_{22}$N$_3$O$_3$ calcd.: 268.2. found: 268.1.

Step D. A solution of I1e (250 mg, 1.4 mol) and methanesulfonyl piperazine (258 mg, 1.6 mmol) in dichloromethane (4 mL) is treated with HOBt hydrate (328 mg, 2.1 mmol) followed by EDC (356 mg, 1.9 mmol). After stirring for 3 hours, the reaction is diluted with ethyl acetate and extracted with water, 1M HCl and 1 M NaOH, dried over MgSO$_4$, filtered and evaporated to afford I2f; ESIMS m/z for (M+H)$^+$ C$_{12}$H$_{24}$N$_3$O$_5$S calcd.: 322.1. found: 322.2.

Step E. A sample of I1f (388 mg, 1.2 mmol) is treated with 4 M HCl in dioxane (4 mL) and aged for 1 hour. The solvent is removed and the residue is treated with I1d (298 mg, 1.1 mmol), HATU (502 mg, 1.3 mmol) and N-methylpyrrolidinone (4 mL). The solution is then treated with triethylamine (0.39 mL, 2.8 mmol) and stirred for 2 hours. The reaction is then diluted with 1M NaOH and saturated with NaCl. The resulting solution is extracted 4 times with ethyl acetate and discarded. The combined organics are dried over MgSO$_4$, filtered, evaporated and further purified on a UV triggered HPLC to afford I1g; ESIMS m/z for (M+H)$^+$ C$_{20}$H$_{35}$N$_6$O$_5$S calcd.: 471.2. found: 471.1.

Step F. A suspension of I1g (354 mg, 0.75 mmol) and Lawesson's reagent (304 mg, 0.75 mmol) in m-xylene (3 mL) is dipped into an oil bath which is preheated to 140° C. and stirred for 5 minutes. The reaction is then cooled to room temperature and loaded onto silica gel and purified using a linear gradient of 0-100% ethyl acetate to afford F1; $^1$H NMR (CDCl$_3$, 400 MHz): δ 6.86 (s, 1H), 4.12, (2, 2H), 3.38 (m, 4H), 3.19 (m, 4H), 3.02 (m, 2H), 2.99 (m, 3H), 2.83 (s, 3H), 1.80 (m, 2H), 1.73 (dd, J=15.3, 7.1, 21H), 1.40 (m, 1H), 1.24 (m, 2H), 1.28 (d, J=7.0, 6H); ESIMS m/z for (M+H)$^+$ C$_{20}$H$_{33}$N$_6$O$_3$S$_2$ calcd.: 469.2. found: 469.1.

Example J1

Isopropyl 4-((4-(1-methanesulfonyl-1,2,3,6-tetrahydropyridin-4-yl)phenoxy)methyl)piperidine-1-carboxylate

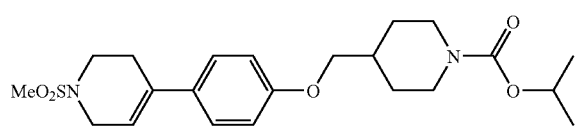

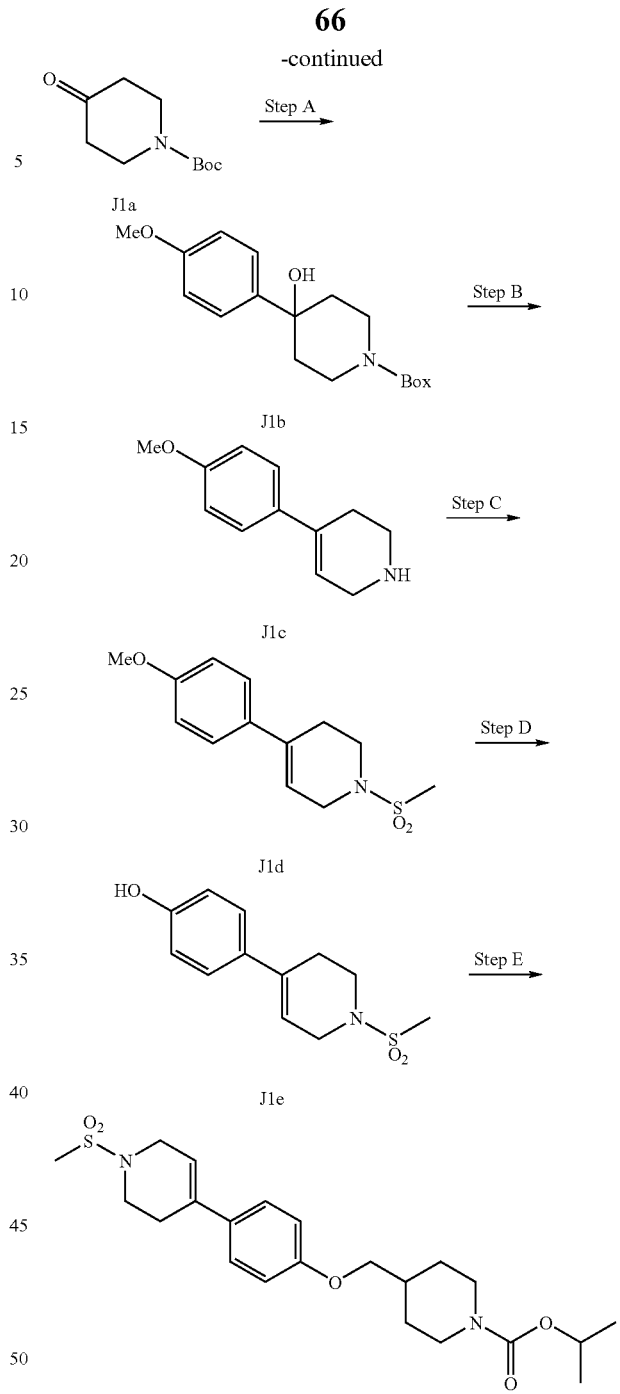

Example J1

Step A: 4-Bromoanisole (4.5 mL, 36.0 mmol) is dissolved in dry tetrahydrofuran (50 mL) and cooled to −78° C. under nitrogen. A solution of n-butyllithium (1.6 M in hexane (22.0 mL, 35.2 mmol) is slowly added with stirring. The mixture is stirred at −78° C. for 2 hours. A solution of J1a (7.28 g, 36.5 mmol) in dry tetrahydrofuran (80 mL) under nitrogen is cooled to −78° C. The suspension of organolithium prepared above is slowly cannulated with stirring into the solution of J1a, using a 20-mL tetrahydrofuran rinse. The resulting mixture is stirred at −78° C. for 30 minutes, then at 0° C. for 15 min. Addition of saturated ammonium chloride solution (60 mL) and extraction with ethyl acetate, washing with brine and concentration in vacuo yield an oil. The residue is purified using a linear gradient of 10-80% ethyl acetate in hexane to afford J1b; $^1$H NMR (CDCl$_3$, 400.13 MHz): δ 7.39 (d, J=8.9 Hz, 2H), 6.89 (d, J=8.9 Hz, 2H), 3.99 (br., 2H), 3.81 (s, 3H), 1.96 (br, 2H), 1.71 (m, 4H), 1.49 (s, 9H); no mass spectrum could be obtained.

Step B: To a solution of J1b (6.29 g, 20 mmol) in dichloromethane (120 mL) is added trifluoroacetic acid (20 mL), slowly, with stirring. The resulting solution is stirred at room temperature for 3 hours. Concentration, dilution with dichloromethane (50 mL), washing with saturated aqueous sodiumhydrogencarbonate solution, drying over MgSO$_4$ and concentration yields J1c; $^1$H NMR (CDCl$_3$, 400.13 MHz): δ 7.30 (d, J=8.8 Hz, 2H), 6.88 (d, J=8.8 Hz, 2H), 5.93 (m, 1H), 3.82 (s, 5H), 3.40 (t, J=6.0 Hz, 2H), 2.77 (m, 2H); ESIMS calcd. for C$_{12}$H$_{16}$NO (M+H$^+$) 190.1. found 190.0.

Step C: To a solution of J1c (3.41 g, 18 mmol) in dichloromethane (80 mL) is added triethylamine (4.5 mL, 32.0 mmol) in one portion. The resulting mixture is cooled in an ice/water bath and methanesulfonyl chloride (1.75 mL, 22.5 mmol) is added dropwise, with stirring, over 5 minutes. The resulting solution is stirred at room temperature for 30 min. The reaction mixture is added to water (40 mL) and extracted with dichloromethane (2×40 mL). The combined organic extracts are washed with saturated ammonium chloride aqueous solution, dried over MgSO$_4$, and concentrated to yield J1d; $^1$H NMR (CDCl$_3$, 400.13 MHz): δ 7.31 (d, J=8.8 Hz, 2H), 6.88 (d, J=8.8 Hz, 2H), 5.98 (m, 1H), 3.96 (q, J=3.2 Hz, 2H), 3.82 (s, 3H), 3.52 (t, J=5.7 Hz, 2H), 2.86 (s, 3H), 2.64 (m, 2H); ESIMS calcd. for C$_{13}$H$_{18}$NO$_3$S (M+H$^+$) 268.1. found 268.1.

Step D: A solution of J1d (3.71 g, 13.9 mmol) in dichloromethane (100 mL) is treated with boron tribromide (5.0 mL, 51.9 mmol) slowly and stirred at room temperature for 3 hours. The mixture is poured over crushed ice and, after the ice melts, it is extracted with dichloromethane. Washing with saturated aqueous sodiumhydrogencarbonate solution, water, and saturated ammonium chloride, drying over MgSO$_4$ and concentration yield J1e; $^1$H NMR (CDCl$_3$, 400.13 MHz): δ 7.27 (d, J=8.7 Hz, 2H), 6.81 (d, J=8.7 Hz, 2H), 5.97 (m, 1H), 4.85 (s, 1H), 3.95 (q, J=3.2 Hz, 2H), 3.52 (t, J=5.7 Hz, 2H), 2.86 (s, 3H), 2.63 (m, 2H); ESIMS calcd. for C$_{12}$H$_{16}$NO$_3$S (M+H$^+$) 254.1. found 254.1.

Step E: A solution of J1e (0.12 g, 0.47 mmol) in acetonitrile (3 mL) is treated with A1c (0.16 g, 0.57 mmol) followed by powdered cesium carbonate (0.20 g, 0.6 mmol) and stirred at 60° C. for 5 hours. Cooling, filtration and purification using mass-triggered reverse phase HPLC affords J1; $^1$H NMR (CDCl$_3$, 400.13 MHz): δ 7.30 (d, J=8.7 Hz, 2H), 6.86 (d, J=8.7 Hz, 2H), 5.97 (m, 1H), 4.92 (septet, J=6.2 Hz, 1H), 4.19 (br, 2H), 3.95 (dd, J=2.6, 5.9 Hz, 2H), 3.81 (d, J=6.3 Hz, 2H), 3.52 (t, J=5.8 Hz, 2H), 2.85 (s, 3H), 2.78 (m, 2H), 2.63 (m, 2H), 1.97 (m, 1H), 1.83 (dd, J=1.0, 13.4 Hz, 2H), 1.25 (m, 2H), 1.24 (d, J=6.2 Hz, 6H); ESIMS calcd. for C$_{22}$H$_{33}$N$_2$O$_5$S (M+H$^+$) 437.2. found 437.1.

By following a similar procedure as the one used for preparing J1 from HJ1a except substituting the appropriate methanesulfonate for intermediate A1c in Step E and/or 3-bromoanisole for 4-bromoanisole, the following examples are prepared;

| Example | Structure | Analytical data |
|---|---|---|
| J2 | 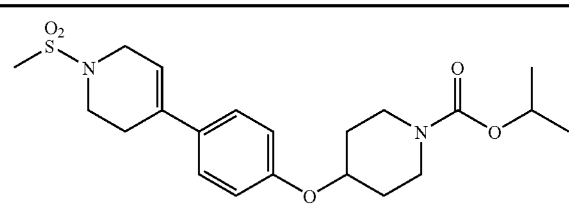 | ESIMS calcd. for C$_{21}$H$_{31}$N$_2$O$_5$S (M + H$^+$) 423.2, found 423.1. |
| J3 | 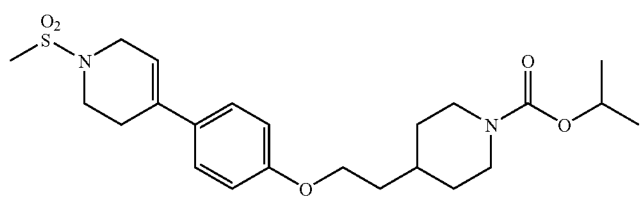 | $^1$H NMR (CDCl$_3$, 400.13 MHz): δ 7.30 (d, J = 8.7 Hz, 2H), 6.86 (d, J = 8.7 Hz, 2H), 5.97 (m, 1H), 4.92 (septet, J = 6.2 Hz, 1H), 4.12 (br, 2H), 4.02 (t, J = 5.8, 2H), 3.95 (dd, J = 2.6, 5.9 Hz, 2H), 3.52 (t, J = 5.8 Hz, 2H), 2.85 (s, 3H), 2.74 (m, 2H), 2.64 (m, 2H), 1.85 (m, 1H), 1.73 (dd, J = 1.0, 13.4 Hz, 2H), 1.24 (d, J = 6.2 Hz, 6H), 1.18 (m, 2H); ESIMS calcd. for C$_{23}$H$_{35}$N$_2$O$_5$S (M +H$^+$) 451.2, found 451.2. |
| J4 | 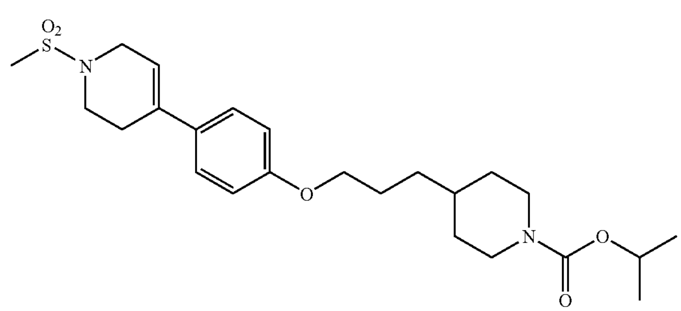 | $^1$H NMR (CDCl$_3$, 400.13 MHz): δ 7.29 (d, J = 8.7 Hz, 2H), 6.86 (d, J = 8.7 Hz, 2H), 5.97 (m, 1H), 4.91 (septet, J = 6.2 Hz, 1H), 4.13 (br, 2H), 3.52 (t, J = 5.8 Hz, 2H), 2.85 (s, 3H), 2.71 (m, 2H), 2.63 (m, 2H), 1.81 (m, 2H), 1.70 (m, 5H), 1.42 (m, 4H), 1.24 (d, J = 6.2 Hz, 6H), 1.12 (m, 2H); ESIMS calcd. for C$_{24}$H$_{37}$N$_2$O$_5$S (M + H$^+$) 465.2, found 465.1. |

| Example | Structure | Analytical data |
| --- | --- | --- |
| J5 | 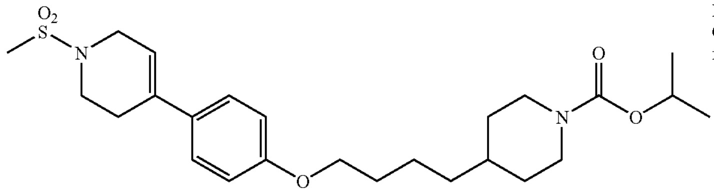 | ESIMS calcd. for $C_{25}H_{39}N_2O_5S$ (M + H$^+$) 479.3, found 479.1. |
| J6 | 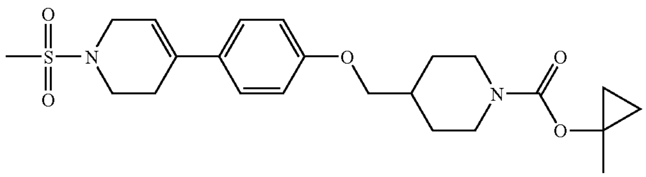 | $^1$H-NMR (400 MHz, DMSO-d6) δ 7.37 (m, 2H), 6.90 (m, 2H), 6.08 (m, 1H), 3.70-4.05 (m, 6H), 2.92 (s, 3H), 2.75 (m, 2H), 2.56 (m, 2H), 1.91 (m, 1H), 1.73 (m, 2H), 1.46 (s, 3H), 1.13 (m, 2H), 0.76 (m, 2H), 0.59 (m, 2H); ESIMS calcd. for $C_{23}H_{33}N_2O_5S$ (M + H$^+$) 449.2, found 448.8. |
| J7 | 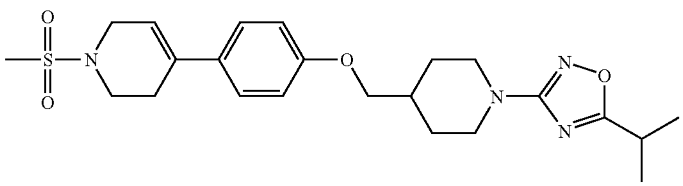 | $^1$H-NMR (400 MHz, DMSO-d6) δ 7.38 (m, 2H), 6.92 (m, 2H), 6.08 (m, 1H), 3.86 (m, 6H), 3.10 (h, 1H, J = 7.0 Hz), 2.92 (s, 3H), 2.91 (m, 2H), 2.56 (m, 2H), 1.97 (m, 1H), 1.82 (m, 2H), 1.30 (m, 2H), 1.26 (d, 6H, J = 7.0 Hz); ESIMS calcd. for $C_{23}H_{33}N_4O_4S$ (M + H$^+$) 461.2, found 460.8. |
| J8 | 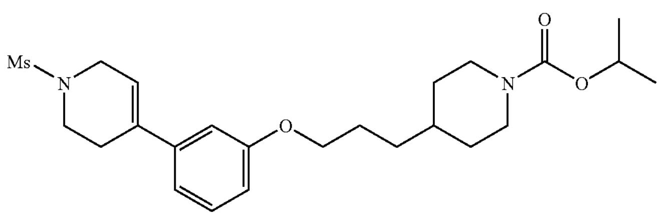 | $^1$H NMR (CDCl$_3$, 400.13 MHz): δ 7.25 (dd, J = 7.8, 8.2 Hz, 1H), 6.95 (dd, J = 2.2, 7.8 Hz, 1H), 6.89 (dd, J = 1.9, 2.2 Hz, 1H), 6.81 (dd, J = 1.9, 8.2 Hz, 1H), 6.07 (tt, J = 1.5, 3.5 Hz, 1H), 4.91 (septet, J = 6.2 Hz, 1H), 4.13 (br. s, 2H), 3.96 (m, 4H), 3.52 (t, J = 5.7 Hz, 2H), 2.86 (s, 3H), 2.73 (t, J = 12.4 Hz, 2H), 2.65 (m, 2H), 1.81 (m, 2H), 1.71 (d, J = 12.7 Hz, 2H), 1.46 (m, 1H), 1.41 (m, 2H), 1.24 (d, J = 6.3 Hz, 6H), 1.12 (ddd, J = 4.2, 12.7, 13.0 Hz, 2H); ESIMS calcd. for $C_{24}H_{37}N_2O_5S$ (M + H$^+$) 465.2, found 465.2. |
| J9 | 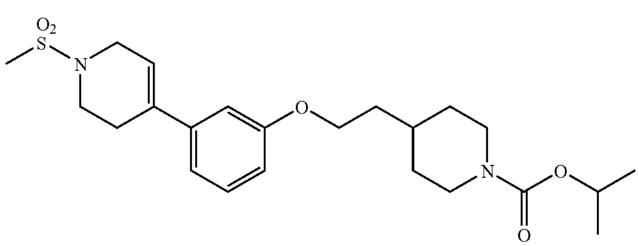 | $^1$H NMR (CDCl$_3$, 400.13 MHz): δ 7.26 (dd, J = 7.9, 8.1 Hz, 1H), 6.96 (d, J = 7.8 Hz, 1H), 6.89 (dd, J = 1.8, 2.2 Hz, 1H), 6.82 (dd, J = 2.0, 7.8 Hz, 1H), 6.07 (m, 1H), 4.91 (septet, J = 6.2 Hz, 1H), 4.13 (br, 2H), 4.02 (t, J = 5.8 Hz, 2H), 3.97 (dd, J = 2.7, 6.0 Hz, 2H), 3.52 (t, J = 5.7 Hz, 2H), 2.86 (s, 3H), 2.74 (t, J = 12.4 Hz, 2H), 2.66 (m, 2H), 1.80 (m, 2H), 1.74 (m, 3H), 1.24 (d, J = 6.2 Hz, 6H), 1.20 (m, 2H); ESIMS calcd. for $C_{23}H_{35}N_2O_5S$ (M + H$^+$) 451.2, found 451.2. |

Example J10

Isopropyl 4-((4-(1-methanesulfonylpiperidin-4-yl)phenoxy)methyl)piperidine-1-carboxylate

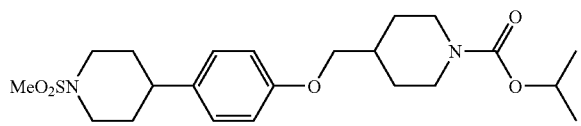

A solution of J1 (0.18 g, 0.4 mmol) in ethanol (10 mL) and ethyl acetate (2 mL) is treated with palladium(0) on charcoal (5%, 0.12 g). The mixture is stirred under 1 atm hydrogen for 18 hours. Filtration, concentration, and purification using mass-triggered reverse phase HPLC yields J9; $^1$H NMR (CD$_3$CN, 400.13 MHz): δ 7.19 (d, J=8.7 Hz, 2H), 6.88 (d, J=8.7 Hz, 2H), 4.95 (septet, J=6.2 Hz, 1H), 4.16 (br, 2H), 3.83 (d, J=6.4 Hz, 2H), 3.78 (m, 2H), 2.81 (s, 3H), 2.78 (m, 4H), 2.61 (tt, J=3.6, 12.1 Hz, 1H), 2.01 (m, 1H), 1.90 (m, 2H), 1.81 (m, 2H), 1.71 (m, 2H), 1.23 (d, J=6.2 Hz, 6H), 1.22 (m, 2H); ESIMS calcd. for C$_{22}$H$_{35}$N$_2$O$_5$S (M+H$^+$) 439.2. found 439.2.

By following a similar procedure as the one used for preparing J10 from J1 except substituting the olefin for intermediate J1 or by following a similar procedure as the one used for preparing J1 from J1a except substituting 4-(4-methoxyphenyl)piperidine or 4-(3-methoxyphenyl)piperidine for J1c, the following examples are prepared;

| Example | Structure | Analytical data |
|---|---|---|
| J11 | 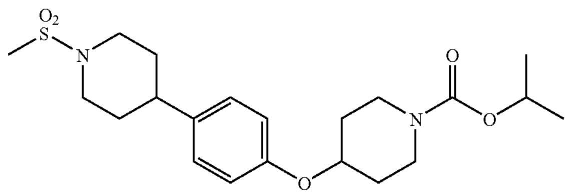 | ESIMS calcd. for C$_{21}$H$_{33}$N$_2$O$_5$S (M + H$^+$) 425.2, found 425.0. |
| J12 | 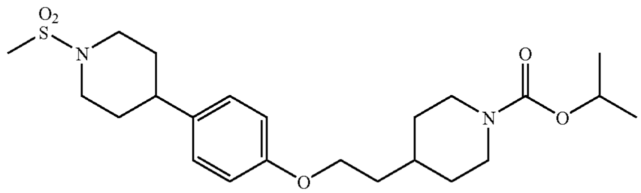 | ESIMS calcd. for C$_{23}$H$_{37}$N$_2$O$_5$S (M + H$^+$) 453.2, found 453.2. |
| J13 | 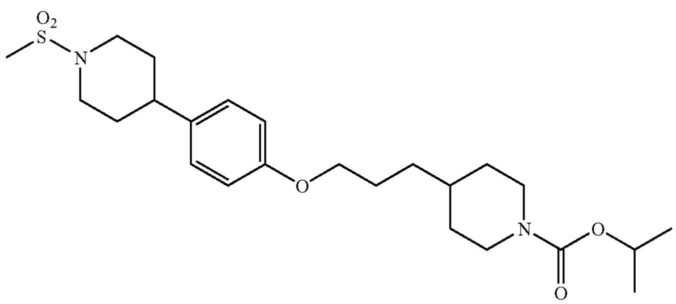 | ESIMS calcd. for C$_{24}$H$_{39}$N$_2$O$_5$S (M + H$^+$) 467.3, found 467.2. |
| J14 | 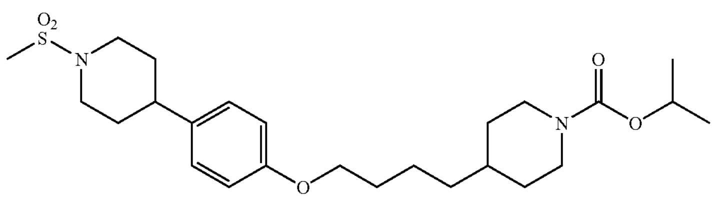 | ESIMS calcd. for C$_{25}$H$_{41}$N$_2$O$_5$S (M + H$^+$) 481.3, found 481.1. |
| J15 | 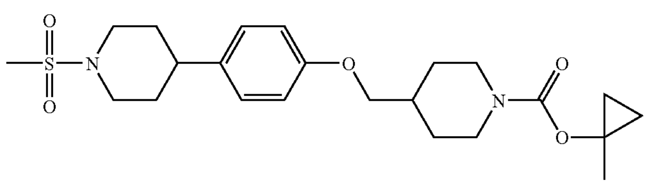 | $^1$H-NMR (400 MHz, CDCl$_3$) δ 7.11 (m, 2H), 6.83 (m, 2H), 4.12 (m, 2H), 3.93 (m, 2H), 3.77 (d, 2H, J = 6.3 Hz), 2.81 (s, 3H), 2.75 (m, 2H), 2.55 (tt, 1H, J = 3.5, 12.1 Hz), 1.93 (m, 2H), 1.81 (m, 4H), 1.55 (s, 3H), 1.26 (m, 2H), 0.86 (m, 2H), 0.62 (m, 2H). ESIMS calcd. for C$_{23}$H$_{35}$N$_2$O$_5$S (M + H$^+$) 451.2, found 451.2. |

-continued

| Example | Structure | Analytical data |
|---|---|---|
| J16 | 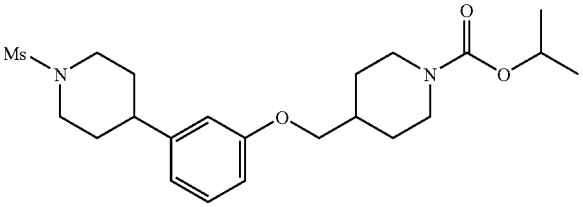 | ESIMS calcd. for $C_{22}H_{35}N_2O_5S$ (M + H$^+$) 439.2, found 439.1. |
| J17 | 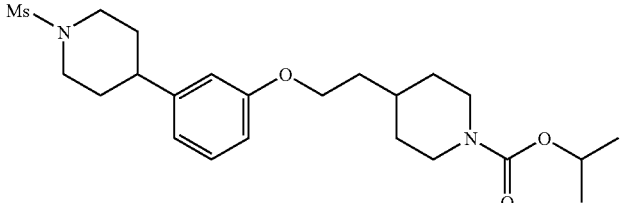 | ESIMS calcd. for $C_{23}H_{37}N_2O_5S$ (M + H$^+$) 453.2, found 453.1. |
| J18 | 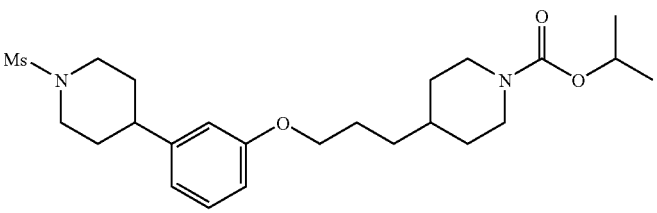 | ESIMS calcd. for $C_{24}H_{39}N_2O_5S$ (M + H$^+$) 467.3, found 467.1. |
| J19 | 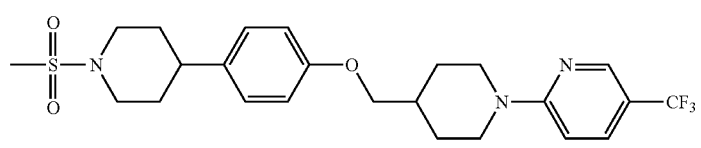 | $^1$H-NMR (400 MHz, DMSO-d6) δ 8.38 (m, 1H), 7.75 (dd, 1H, J = 2.5, 9.2 Hz), 7.16 (m, 2H), 6.96 (d, 1H, J = 9.2 Hz), 6.86 (m, 2H), 4.46 (m, 2H), 3.82 (d, 2H, J = 6.4 Hz), 3.65 (m, 2H), 2.95 (m, 2H), 2.88 (s, 3H), 2.78 (m, 2H), 2.56 (tt, 1H, J = 3.5, 12.3 Hz), 2.07 (m, 1H), 1.83 (m, 4H), 1.62 (m, 2H), 1.24 (m, 2H). ESIMS calcd. for $C_{24}H_{31}F_3N_3O_3S$ (M + H$^+$) 498.2, found 497.8 |
| J20 | 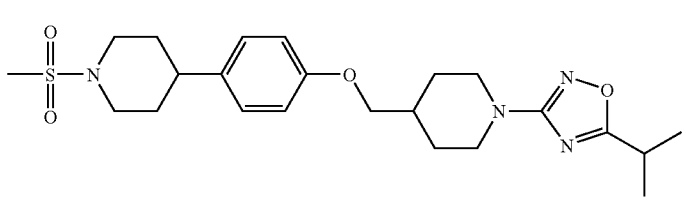 | $^1$H-NMR (400 MHz, DMSO-d6) δ 7.16 (m, 2H), 6.86 (m, 2H), 3.87 (m, 2H), 3.82 (d, 2H, J = 6.5 Hz), 3.65 (m, 2H), 3.10 (h, 1H, J = 7.0 Hz), 2.90 (m, 2H), 2.89 (s, 3H), 2.78 (m, 3H), 2.56 (tt, 1H, J = 3.4, 12.2 Hz), 1.95 (m, 1H), 1.82 (m, 4H), 1.62 (m, 2H), 1.29 (m, 2H), 1.26 (d, 6H, J = 7.0 Hz). ESIMS calcd. for $C_{23}H_{35}N_4O_4S$ (M + H$^+$) 463.2, found 463.2. |
| J21 | 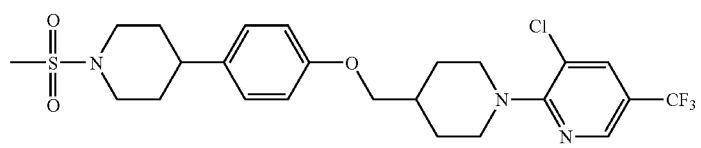 | $^1$H-NMR (400 MHz, DMSO-d6) δ 8.54 (m, 1H), 8.16 (d, 1H, J = 2.0 Hz), 7.17 (m, 2H), 6.88 (m, 2H), 4.04 (m, 2H), 3.86 (d, 2H, J = 6.4 Hz), 3.65 (m, 2H), 2.93 (m, 2H), 2.89 (s, 3H), 2.78 (m, 2H), 2.56 (tt, 1H, J = 3.5, 12.2 Hz), 2.01 (m, 1H), 1.86 (m, 4H), 1.62 (m, 2H), 1.43 (m, 2H). ESIMS calcd. for $C_{24}H_{30}ClF_3N_3O_3S$ (M + H$^+$) 532.2, found 531.9. |

-continued

| Example | Structure | Analytical data |
|---|---|---|
| J22 | 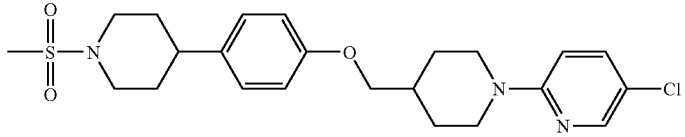 | $^1$H-NMR (400 MHz, DMSO-d6) δ 8.08 (d, 1H, J = 2.5 Hz), 7.56 (dd, 1H, J = 2.7, 9.1 Hz), 7.16 (m, 2H), 6.87 (m, 3H), 4.29 (m, 2H), 3.81 (d, 2H, J = 6.4 Hz), 3.65 (m, 2H), 2.88 (s, 3H), 2.81 (m, 4H), 2.56 (tt, 1H, J = 3.4, 11.9 Hz), 2.00 (m, 1H), 1.82 (m, 4H), 1.62 (m, 2H), 1.25 (m, 2H). ESIMS calcd. for $C_{23}H_{31}ClN_3O_3S$ (M + H$^+$) 464.2, found 464.2. |
| J23 | 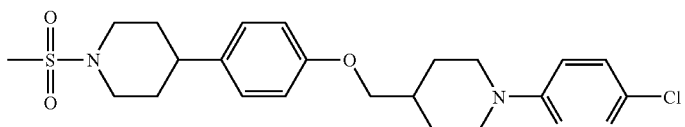 | $^1$H-NMR (400 MHz, DMSO-d6) δ 7.50 (d, 1H, J = 9.6 Hz), 7.41 (d, 1H, J = 9.7 Hz), 7.16 (m, 2H), 6.87 (m, 2H), 4.37 (m, 2H), 3.82 (d, 2H, J = 6.4 Hz), 3.64 (m, 2H), 2.96 (m, 2H), 2.88 (s, 3H), 2.78 (m, 2H), 2.56 (tt, 1H, J = 3.4, 11.9 Hz), 2.06 (m, 1H), 1.84 (m, 4H), 1.62 (m, 2H), 1.29 (m, 2H). ESIMS calcd. for $C_{22}H_{30}ClN_4O_3S$ (M + H$^+$) 465.2, found 465.2. |
| J24 | 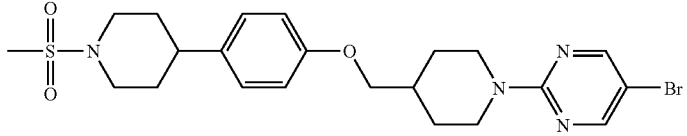 | $^1$H-NMR (400 MHz, DMSO-d6) δ 8.43 (s, 2H), 7.16 (m, 2H), 6.86 (m, 2H), 4.61 (m, 2H), 3.81 (d, 2H, J = 6.6 Hz), 3.65 (m, 2H), 2.93 (m, 2H), 2.88 (s, 3H), 2.78 (m, 2H), 2.55 (m, 1H), 2.05 (m, 1H), 1.82 (m, 4H), 1.62 (m, 2H), 1.22 (m, 2H). ESIMS calcd. for $C_{22}H_{30}BrN_4O_3S$ (M + H$^+$) 509.1, found 508.9. |
| J25 | 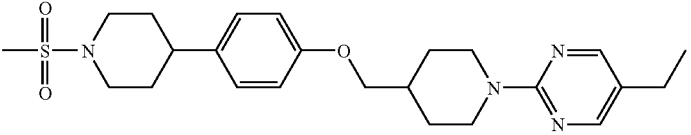 | $^1$H-NMR (400 MHz, DMSO-d6) δ 8.24 (s, 2H), 7.16 (m, 2H), 6.86 (m, 2H), 4.65 (m, 2H), 3.81 (d, 2H, J = 6.4 Hz), 3.65 (m, 2H), 2.87 (m, 2H), 2.89 (s, 3H), 2.78 (m, 2H), 2.56 (tt, 1H, J = 3.5, 11.9 Hz), 2.42 (q, 2H, J = 7.6 Hz), 2.03 (m, 1H), 1.82 (m, 4H), 1.62 (m, 2H), 1.20 (m, 2H), 1.12 (t, 3H, J = 7.6). ESIMS calcd. for $C_{24}H_{35}N_4O_3S$ (M + H$^+$) 459.2, found 459.2. |
| J26 | 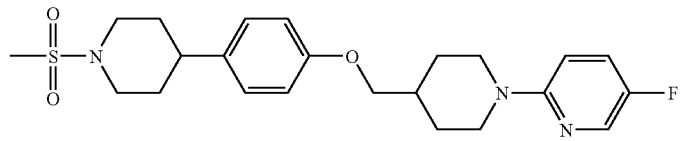 | $^1$H-NMR (400 MHz, DMSO-d6) δ 8.07 (d, 1H, J = 3.1 Hz), 7.49 (ddd, 1H, J = 3.1, 8.4, 9.2 Hz), 7.16 (m, 2H), 6.88 (m, 3H), 4.23 (m, 2H), 3.82 (d, 2H, J = 6.4 Hz), 3.65 (m, 2H), 2.89 (s, 3H), 2.79 (m, 4H), 2.57 (tt, 1H, J = 3.5, 12.0 Hz), 1.98 (m, 1H), 1.82 (m, 4H), 1.62 (m, 2H), 1.27 (m, 2H). ESIMS calcd. for $C_{23}H_{31}FN_3O_3S$ (M + H$^+$) 448.2, found 448.2. |

| Example | Structure | Analytical data |
|---|---|---|
| J27 | 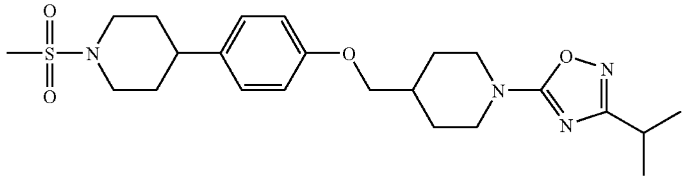 | ¹H-NMR (400 MHz, DMSO-d6) δ 7.16 (m, 2H), 6.87 (m, 2H), 3.99 (m, 2H), 3.83 (d, 2H, J = 6.4 Hz), 3.65 (m, 2H), 3.12 (m, 2H), 2.89 (s, 3H), 2.79 (m, 3H), 2.56 (tt, 1H, J = 3.5, 11.9 Hz), 1.99 (m, 1H), 1.84 (m, 4H), 1.62 (m, 2H), 1.31 (m, 2H), 1.18 (d, 6H, J = 6.9 Hz). ESIMS calcd. for $C_{23}H_{35}N_4O_4S$ (M + H⁺) 463.2, found 463.2. |
| J28 | 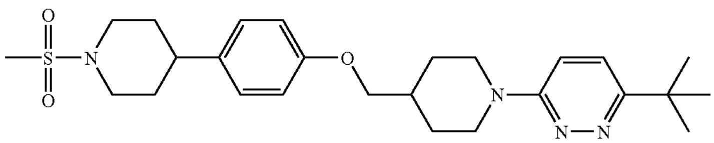 | ¹H-NMR (400 MHz, DMSO-d6) δ 8.10 (d, 1H, J = 10.0 Hz), 8.01 (d, 1H, J = 10.0 Hz), 7.17 (m, 2H), 6.87 (m, 2H), 4.31 (m, 2H), 3.84 (d, 2H, J = 6.4 Hz), 3.66 (m, 2H), 3.25 (m, 2H), 2.89 (s, 3H), 2.78 (m, 2H), 2.56 (tt, 1H, J = 3.4, 12.3 Hz), 2.16 (m, 1H), 1.92 (m, 2H), 1.82 (m, 2H), 1.62 (m, 2H), 1.41 (m, 2H), 1.32 (s, 9H). ESIMS calcd. for $C_{26}H_{39}N_4O_3S$ (M + H⁺) 486.3, found 486.3. |
| J29 | 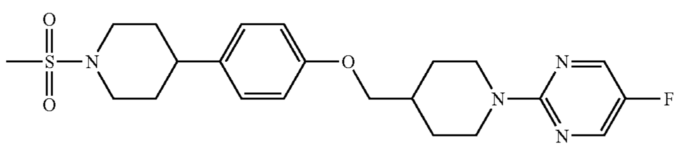 | ¹H-NMR (400 MHz, DMSO-d6) δ 8.42 (d, 2H, J = 0.8 Hz), 7.16 (m, 2H), 6.86 (m, 2H), 4.60 (m, 2H), 3.82 (d, 2H, J = 6.4 Hz), 3.65 (m, 2H), 2.91 (m, 2H), 2.88 (s, 3H), 2.78 (m, 2H), 2.56 (tt, 1H, J = 3.5, 11.9 Hz), 2.03 (m, 1H), 1.82 (m, 4H), 1.62 (m, 2H), 1.21 (m, 2H). ESIMS calcd. for $C_{22}H_{30}FN_4O_3S$ (M + H⁺) 449.2, found 448.8. |

Example J30

2-(4-((2-Bromo-4-(1-(methylsulfonyl)piperidin-4-yl)phenoxy)methyl)piperidin-1-yl)-5-fluoropyrimidine

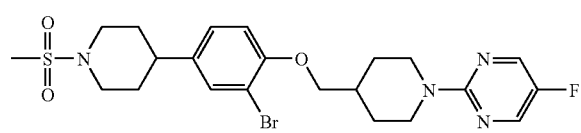

This material is prepared when a large scale preparation of J28 from 4-(4-methoxyphenyl)piperidine in place of J1c following the scheme outlined for J1 yielded a brominated byproduct in step D: ¹H-NMR (400 MHz, DMSO-d₆) δ 8.43 (d, 2H, J=0.8 Hz), 7.45 (d, 1H, J=2.1 Hz), 7.21 (dd, 1H, J=2.1, 8.6 Hz), 7.04 (d, 1H, J=8.6 Hz), 4.61 (m, 2H), 3.91 (d, 2H, J=6.3 Hz), 3.65 (m, 2H), 2.93 (m, 2H), 2.89 (s, 3H), 2.77 (m, 2H), 2.59 (tt, 1H, J=3.5, 12.0 Hz), 2.07 (m, 1H), 1.84 (m, 4H), 1.62 (m, 2H), 1.27 (m, 2H). ESIMS calcd. for $C_{22}H_{29}BrFN_4O_3S$ (M+H⁺) 527.1. found 527.1.

Example K1

1-Methylcyclopropyl 4-methoxy-4-((5-(4-(methylsulfonyl)piperazin-1-yl)pyrazin-2-yloxy)methyl)piperidine-1-carboxylate

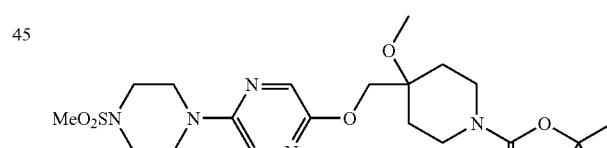

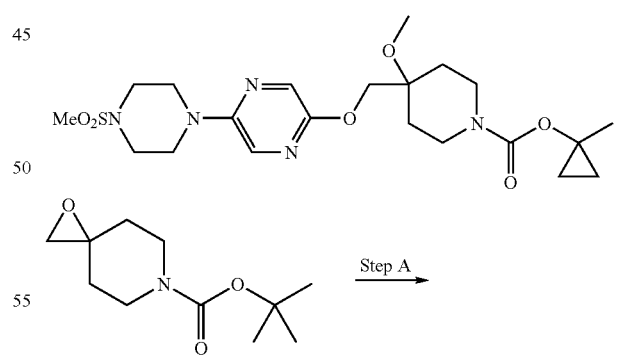

K1a

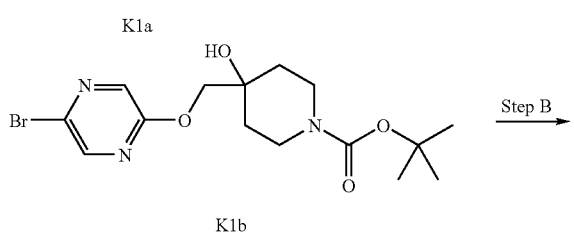

K1b

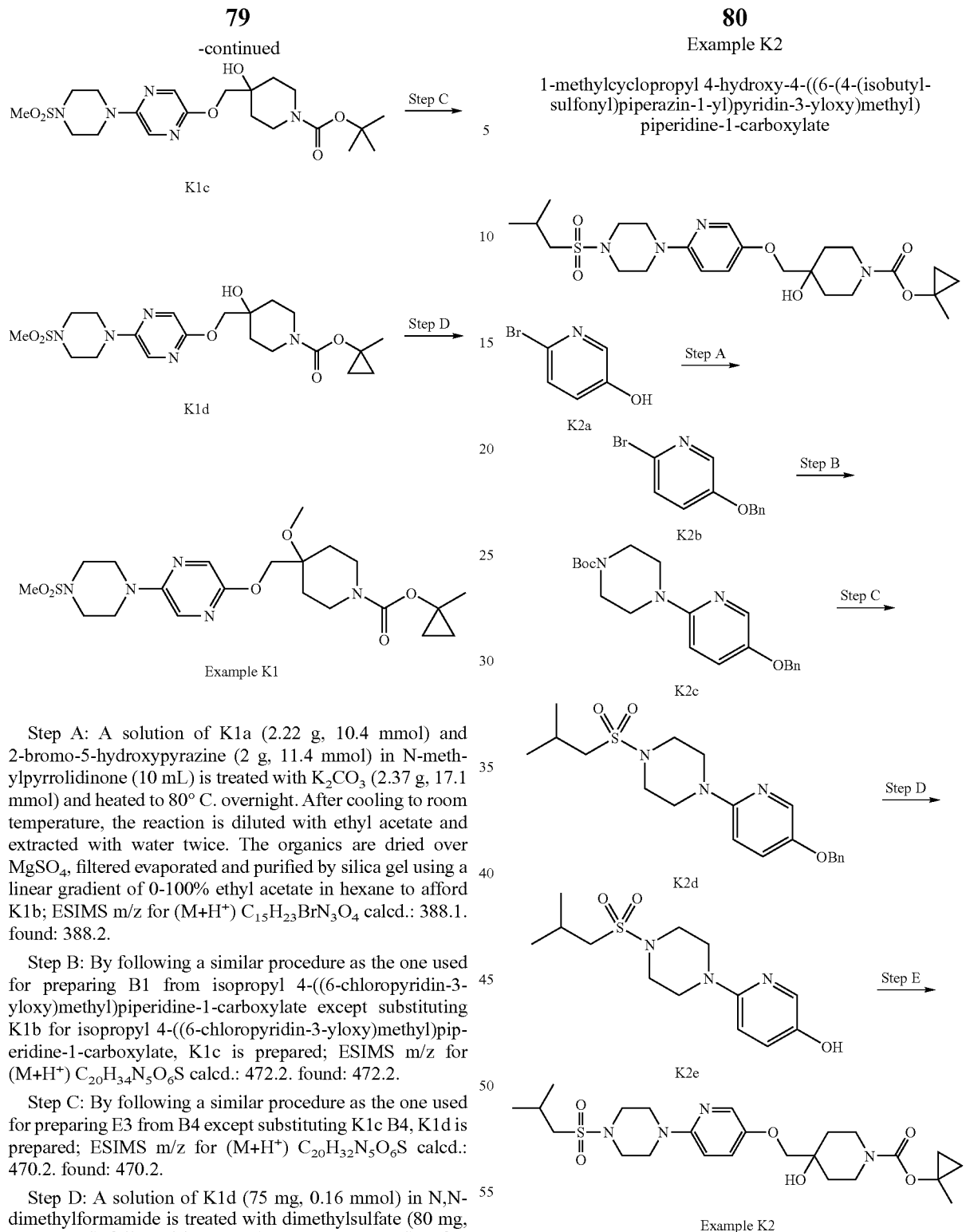

Example K2

1-methylcyclopropyl 4-hydroxy-4-((6-(4-(isobutyl-sulfonyl)piperazin-1-yl)pyridin-3-yloxy)methyl) piperidine-1-carboxylate Step A: A solution of K1a (2.22 g, 10.4 mmol) and 2-bromo-5-hydroxypyrazine (2 g, 11.4 mmol) in N-methylpyrrolidinone (10 mL) is treated with $K_2CO_3$ (2.37 g, 17.1 mmol) and heated to 80° C. overnight. After cooling to room temperature, the reaction is diluted with ethyl acetate and extracted with water twice. The organics are dried over $MgSO_4$, filtered evaporated and purified by silica gel using a linear gradient of 0-100% ethyl acetate in hexane to afford K1b; ESIMS m/z for (M+H$^+$) $C_{15}H_{23}BrN_3O_4$ calcd.: 388.1. found: 388.2.

Step B: By following a similar procedure as the one used for preparing B1 from isopropyl 4-((6-chloropyridin-3-yloxy)methyl)piperidine-1-carboxylate except substituting K1b for isopropyl 4-((6-chloropyridin-3-yloxy)methyl)piperidine-1-carboxylate, K1c is prepared; ESIMS m/z for (M+H$^+$) $C_{20}H_{34}N_5O_6S$ calcd.: 472.2. found: 472.2.

Step C: By following a similar procedure as the one used for preparing E3 from B4 except substituting K1c B4, K1d is prepared; ESIMS m/z for (M+H$^+$) $C_{20}H_{32}N_5O_6S$ calcd.: 470.2. found: 470.2.

Step D: A solution of K1d (75 mg, 0.16 mmol) in N,N-dimethylformamide is treated with dimethylsulfate (80 mg, 0.63 mmol) followed by NaH (30 mg, 1.25 mmol). After stirring at room temperature for 1 hour, the reaction is treated with water and ethyl acetate. The organics are isolated, washed with water, dried over $MgSO_4$, filtered evaporated and purified by silica gel using a linear gradient of 50-100% ethyl acetate in hexane to afford K1; $^1$H NMR (CDCl$_3$, 400.13 MHz): δ 7.94 (d, J=1.5 Hz, 1H), 7.61 (d, J=1.4 Hz, 1H), 4.20 (m, 2H), 3.91 (m, 2H), 3.54 (m, 4H), 3.37 (m, 4H), 3.29 (s, 3H), 3.13 (m, 2H), 2.82 (s, 3H), 1.89 (m, 2H), 1.55 (m, 2H), 1.55 s, 3H), 0.87 (m, 2H), 0.62 (m, 2H); ESIMS calcd. for $C_{21}H_{34}N_5O_6S$ (M+H$^+$) 484.2. found 484.1.

Step A: A solution of K2a (2.0 g, 11.5 mmol) and benzyl bromide (2.36 g, 13.8 mmol) in N-methylpyrrolidinone (15 mL) is treated with $K_2CO_3$ (2.38 g, 17.2 mmol) and stirred at 60° C. overnight. The reaction is cooled to room temperature, diluted with ethyl acetate and extracted with water twice. The organics are then dried over $MgSO_4$, filtered evaporated and purified on silica gel using a linear gradient of 0-100% ethyl acetate in hexane to afford K2b; $^1$H NMR (CDCl$_3$, 400.13 MHz): δ 8.13 (d, J=3.1 Hz, 1H), 7.38 (m, 6H), 7.15 (dd, J=3.2, 8.7 Hz, 1H), 5.09 (s, 2H); ESIMS m/z for (M+H)$^+$ C$_{12}$H$_{11}$BrNO calcd: 264.0. found: 264.0.

Step B: A roundbottom flask is charged with K2b (2.55 g, 9.65 mmol), Pd$_2$dba$_3$ (177 mg, 0.19 mmol), xantphos (335 mg, 0.58 mmol) and tert-butyl piperazine-1-carboxylate (2.16 g, 11.6 mmol) followed by dry toluene (30 mL). The flask is sparged with dry nitrogen, treated with NaOtBu (1.39 g, 14.5 mmol), sealed, dipped into a pre heated 100° C. oil bath and stirred for 2 hours. The reaction is then cooled to room temperature, diluted with ethyl acetate and extracted with water twice. The organics are then dried over MgSO$_4$, filtered evaporated and purified on silica gel using a linear gradient of 0-100% ethyl acetate in hexane to afford K2c; ESIMS m/z for (M+H)$^+$ C$_{21}$H$_{28}$N$_3$O$_3$ calcd: 370.2. found: 370.1.

Step C: A solution of K2c (970 mg, 2.2 mmol) in 1:1 TFA/dichloromethane (10 mL) is aged for 1 hour and the solvent is removed. The resulting residue is partitioned between ethyl acetate and 1 M HCl. The aqueous phase is collected and the organics are extracted once more with 1 M HCl and discarded. The combined aqueous extracts are made basic with solid Na$_2$CO$_3$ and extracted three times with dichloromethane. The combined organics are dried over MgSO$_4$, filtered, evaporated, dissolved in dichloromethane (10 mL) and treated with triethylamine (337 mg, 3.33 mmol) followed by isobutanesulfonyl chloride (452 mg, 2.89 mmol). After stirring for 30 minutes, the reaction is diluted with ethyl acetate, extracted with saturated aqueous sodiumhydrogencarbonate twice, dried over MgSO$_4$, filtered and evaporated to afford K2d; $^1$H NMR (CDCl$_3$, 400.13 MHz): δ 7.99 (d, J=2.8 Hz, 1H), 7.38 (m, 5H), 7.22 (dd, J=3.2, 9.1 Hz, 1H), 6.64 (d, J=9.0 Hz, 1H), 5.04 (s, 2H), 3.52 (m, 4H), 3.37 (m, 4H), 2.76 (d, J=6.6 Hz, 2H), 1.12 (d, J=6.7 Hz, 6H); ESIMS m/z for (M+H)$^+$ C$_{20}$H$_{28}$N$_3$O$_3$S calcd: 390.2. found: 390.2.

Step D: A solution of K2d (0.80 g, 2.0 mmol) in ethanol (10 mL) is treated with Pd(OH)$_2$ (50 mg) and hydrogenated overnight. The catalyst is removed by filtration through Celite® and resubjected to hydrogenation with 100 mg of 10% Pd/C overnight. The catalyst is removed by filtration through Celite® and the solvent is removed. The resulting material is slurried in hexane, collected and dried to afford K2e; ESIMS m/z for (M+H)$^+$ C$_{13}$H$_{22}$N$_3$O$_3$S calcd: 300.1. found: 300.1.

Step E: A solution of K2e (75 mg, 0.25 mmol) and K1a (64 mg, 0.30 mmol) in N-methylpyrrolidinone (2 mL) is treated with K$_2$CO$_3$ (52 mg, 0.38 mmol) and stirred at 80° C. overnight. The reaction is then cooled to room temperature, partitioned between ethyl acetate and water and extracted with water once more. The organics are dried over MgSO$_4$, filtered, evaporated, dissolved in dichloromethane (2 mL) and treated with TFA (2 mL). After stirring for 1 hour, the solvent is removed and the residue is dissolved in dichloromethane, treated with E3b (59 mg, 0.25 mmol) and excess triethylamine and stirred overnight. The reaction is then partitioned between ethyl acetate and water and extracted with water once more. The organics are dried over MgSO$_4$, filtered, evaporated and purified on silica gel using a linear gradient of 0-100% ethyl acetate in hexane to afford K2; $^1$H NMR (CDCl$_3$, 400.13 MHz): δ 7.93 (d, J=3.0 Hz, 1H), 7.18 (dd, J=3.1, 9.1 Hz, 1H), 6.65 (d, J=9.2 Hz, 1H), 3.99 (m, 2H), 3.77 (s, 2H), 3.52 (m, 4H), 3.37 (m, 4H), 3.20 (m, 2H), 2.77 (d, J=6.6 Hz, 2H), 2.32 (m, 1H), 2.12 (s, 1H), 1.72 (m, 2H), 1.55 (m, 3H), 1.12 (d, J=6.7 Hz, 6H), 0.87 (m, 2H), 0.63 (m, 2H); ESIMS m/z for (M+H)$^+$ C$_{24}$H$_{38}$N$_4$O$_6$S calcd: 510.3. found: 511.5.

Example K3

(+/−)-(cis)-1-methylcyclopropyl 3-hydroxy-4-((6-(4-(isobutylsulfonyl)piperazin-1-yl)pyridin-3-yloxy)methyl)piperidine-1-carboxylate

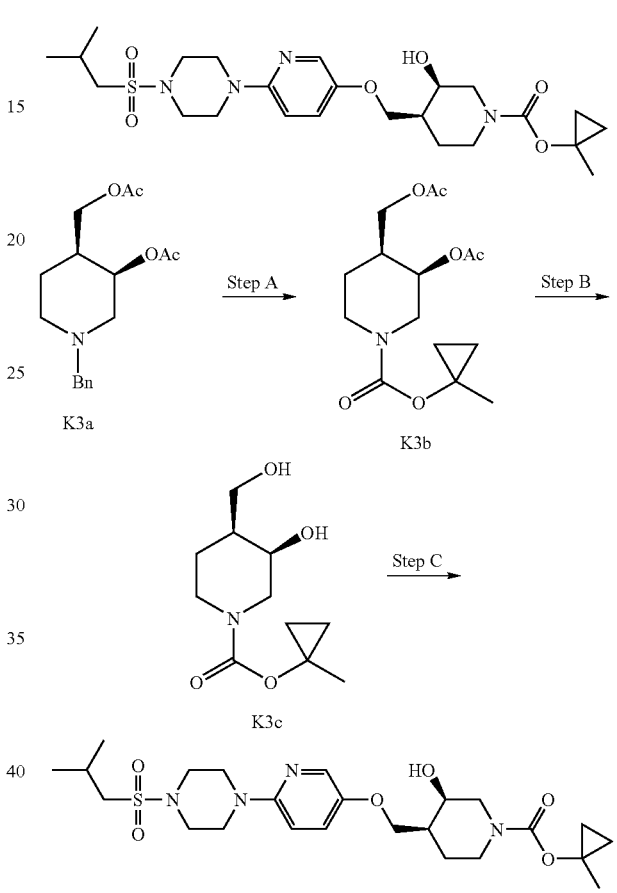

Example K3

Step A: A solution of K3a (420 mg, 1.4 mmol) (Helv. Chim. Acta 2004, 87, 2629) in EtOH containing 1% by volume TFA (150 mL) is hydrogenated in an H-Cube apparatus at 50 atmospheres of H$_2$ and 70° C. The solvent is then removed and the residue is co-evaporated twice with toluene, dissolved in dichloromethane (10 mL) and treated with E3b (342 mg, 1.4 mmol), excess triethylamine and a few crystals of DMAP. The reaction is stirred overnight, partitioned between ethyl acetate and saturated aqueous sodiumhydrogencarbonate and extracted with saturated aqueous sodium carbonate twice. The organics are then dried over MgSO$_4$, filtered evaporated and purified on silica gel using a linear gradient of 0-100% ethyl acetate in hexane to afford K3b; ESIMS m/z for (M+H)$^+$ C$_{15}$H$_{24}$NO$_6$ calcd: 314.2. found: 314.1.

Step B: A solution of K3b (333 mg, 1.1 mmol) in MeOH is treated with a solution of Mg(OMe)$_2$ (5.6 mL of a 0.57 M solution, 3.2 mmol) and stirred for 1 hour. The reaction is then quenched with excess prewashed Amberlite IR-120H$^+$ resin and filtered. The solvent is removed to afford K3c; ESIMS m/z for (M+H)$^+$ C$_{11}$H$_{20}$NO$_4$ calcd: 230.1. found: 230.1.

Step C: A solution of DIAD (88 mg, 0.22 mmol) in dichloromethane (0.5 mL) is cooled in an ice bath and treated with a solution of PPh₃ (114 mg, 0.44 mmol) in dichloromethane (1 mL). The solution is stirred for 15 minutes and treated with a solution of K3c (50 mg, 0.22 mmol) and K2d (65 mg, 0.22 mmol) in dichloromethane (1.5 mL). The reaction is sealed and heated to 50° C. overnight. The reaction is cooled to room temperature and loaded onto a silica gel column and purified using a linear gradient of 0-100% ethyl acetate in hexane. The product fractions are partitioned between ethyl acetate and 1 M HCl. The aqueous phase is collected and the organics are extracted once more with 1 M HCl and discarded. The combined aqueous extracts are made basic with solid Na$_2$CO$_3$ and extracted three times with ethyl acetate. The combined organics are dried over MgSO$_4$, filtered and evaporated to afford K3; $^1$H NMR (CDCl$_3$, 400.13 MHz): δ 7.93 (d, J=2.9 Hz, 1H), 7.17 (dd, J=3.1, 9.1 Hz, 1H), 6.64 (d, J=9.1 Hz, 1H), 4.19 (m, 2H), 4.09 (m, 1H), 4.03 (dd, J=7.6, 9.1 Hz, 1H), 3.84 (dd, J=6.0, 9.1 Hz, 1H), 3.51 (m, 4H), 3.37 (m, 4H), 2.91 (m, 1H), 2.78 (m, 1H), 2.76 (d, J=6.6 Hz, 2H), 2.32 (m, 1H), 2.00 (m, 1H), 1.86 (m, 1H), 1.68 (m, 1H), 1.55 (s, 3H), 1.12 (d, J=6.7 Hz, 6H), 0.88 (m, 2H), 0.62 (m, 2H); ESIMS m/z for (M+H)$^+$ C$_{24}$H$_{39}$N$_4$O$_6$S calcd: 511.3. found: 511.4.

Example K4

(+/−)-(cis)-1-Methylcyclopropyl 4-((6-(4-(isobutylsulfonyl)piperazin-1-yl)pyridin-3-yloxy)methyl)-3-methoxypiperidine-1-carboxylate

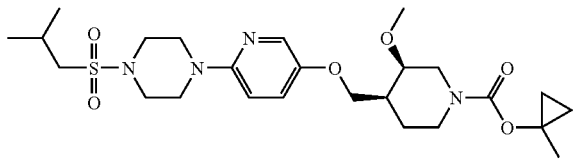

A solution of K3 (25 mg, 0.22 mmol) in N,N-dimethylformamide (2 mL) is treated with excess (~100 uL) dimethylsulfate and excess (~40 mg) of NaH. The reaction is stirred for 1 hour and then diluted with ethyl acetate and water. The organics are isolated and washed once more with water, dried over MgSO4, filtered, evaporated and purified on silica gel using a linear gradient of 0-100% ethyl acetate in hexane to afford K4; $^1$H NMR (CDCl$_3$, 400.13 MHz): δ 7.93 (d, J=2.9 Hz, 1H), 7.16 (dd, J=3.0, 9.1 Hz, 1H), 6.64 (d, J=9.1 Hz, 1H), 4.53 (m, 0.5H), 4.28 (m, 1H), 4.00 (m, 1.5H), 3.78 (m, 1H), 3.52 (m, 4H), 3.75 (m, 7H), 2.76 (d, J=6.6 Hz, 2H), 2.72 (m, 2H), 2.32 (m, 1H), 2.03 (m, 1H), 1.59 (m, 1H), 1.55 (s, 3H), 1.48 (m, 1H), 1.12 (d, J=6.7 Hz, 6H), 0.87 (m, 2H), 0.61 (m, 2H); ESIMS m/z for (M+H)$^+$ C$_{25}$H$_{41}$N$_4$O$_6$S calcd: 525.3. found: 525.2.

Example K5

(+/−)-(Trans)-1-methylcyclopropyl 3-hydroxy-4-((6-(4-(isobutylsulfonyl)piperazin-1-yl)pyridin-3-yloxy)methyl)piperidine-1-carboxylate

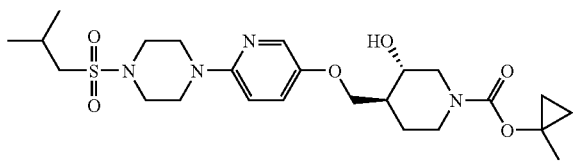

By following a similar procedure as the one used for preparing K3 from K3a except substituting the trans-isomer of K3a (Helv. Chim. Acta 2004, 87, 2629) for K3a, K5 is prepared; $^1$H NMR (CDCl$_3$, 400.13 MHz): δ 7.93 (d, J=3.0 Hz, 1H), 7.24 (dd, J=3.0, 9.1 Hz, 1H), 6.69 (d, J=9.2 Hz, 1H), 4.17 (m, 3H), 4.05 (m, 2H), 3.56 (m, 5H), 3.37 (m, 4H), 2.77 (d, J=6.6 Hz, 2H), 2.72 (m, 1H), 2.58 (m, 1H), 2.31 (m, 1H), 1.90 (m, 1H), 1.78 (m, 1H), 1.55 (s, 3H), 1.40 (m, 1H), 1.12 (d, J=6.7 Hz, 6H), 0.87 (m, 2H), 0.61 (m, 2H); ESIMS m/z for (M+H)$^+$ C$_{24}$H$_{39}$N$_4$O$_6$S calcd: 511.3. found: 511.4.

Example L1

1-methylcyclopropyl 4-((6-formyl-5-(4-(methylsulfonyl)piperazin-1-yl)pyrazin-2-yloxy)methyl)piperidine-1-carboxylate

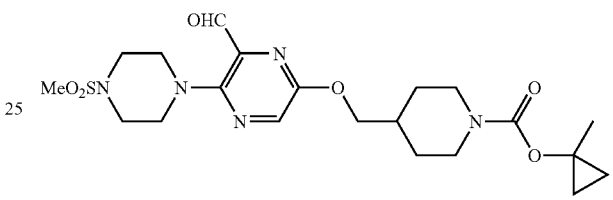

A solution of E3 (109 mg, 0.24 mmol) in N,N-dimethylformamide (2.2 mL) is treated with POCl$_3$ (165 mg, 1.1 mmol) and heated to 70° C. for 2 hours. The reaction is then cooled to room temperature, quenched with water and diluted with ethyl acetate. The organics are extracted with water twice more, dried over MgSO$_4$, filtered evaporated and purified by silica gel using a linear gradient of 50-100% ethyl acetate in hexane to afford L1; $^1$H NMR (CDCl$_3$, 400.13 MHz): δ 9.93 (s, 1H), 8.04 (s, 1H), 4.19 (d, J=6.4 Hz, 1H), 4.15 (m, 2H), 3.50 (m, 4H), 3.43 (m, 4H), 2.83 (s, 3H), 2.74 (m, 2H), 1.97 (m, 1H), 1.81 (m, 2H), 1.55 (s, 3H), 1.27 (m, 2H), 0.86 (m, 2H), 0.62 (m, 2H); ESIMS calcd. for C$_{21}$H$_{32}$N$_5$O$_6$S (M+H$^+$) 482.2. found 482.1.

Example L2

1-Methylcyclopropyl 4-((6-chloro-5-(4-(methylsulfonyl)piperazin-1-yl)pyrazin-2-yloxy)methyl)piperidine-1-carboxylate

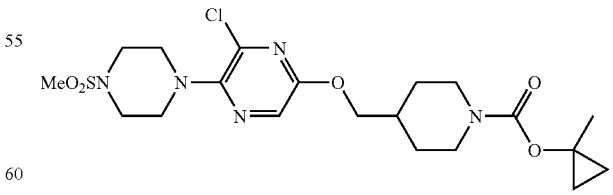

By following a similar procedure as the one used for preparing L1 from E3 except using NCS at 50° C. in dichloroethane overnight as the reaction conditions, K5 is prepared; ESIMS m/z for (M+H)$^+$ C$_{20}$H$_{31}$ClN$_5$O$_5$S calcd: 488.2. found: 487.7.

Example M1

1-Methylcyclopropyl 4-((5-(4-(3-methoxy-3-oxopropylsulfonyl)piperazin-1-yl)pyrazin-2-yloxy)methyl)piperidine-1-carboxylate

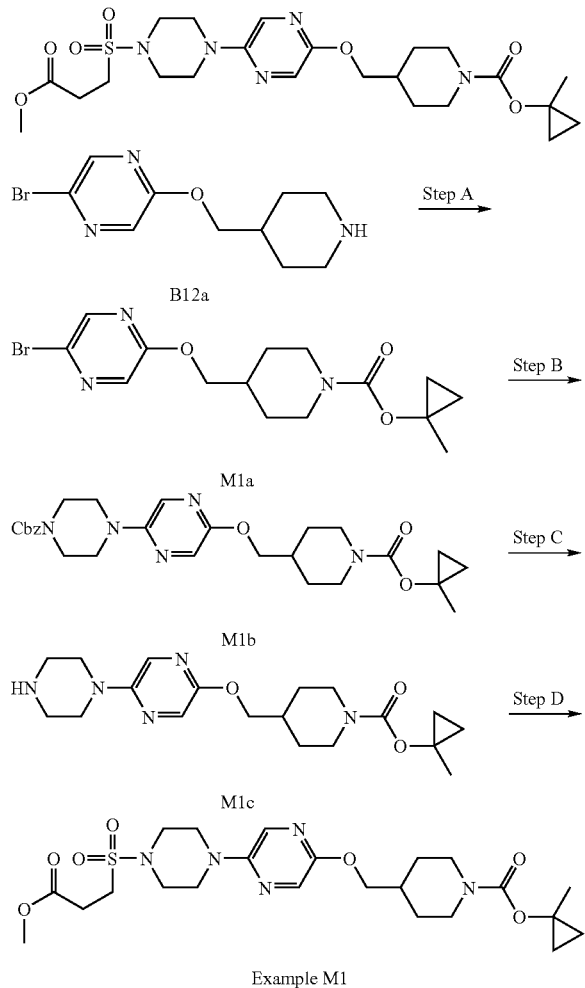

Step A: By following a similar procedure as the one used for preparing E3 from E3a except substituting B12a for E3a, M1a is prepared; ESIMS m/z for $(M+H)^+$ $C_{15}H_{22}BrN_3O_3$ calcd: 371.2. found: 371.1.

Step B: By following a similar procedure as the one used for preparing B1 from isopropyl 4-((6-chloropyridin-3-yloxy)methyl)piperidine-1-carboxylate except substituting M1a for isopropyl 4-((6-chloropyridin-3-yloxy)methyl)piperidine-1-carboxylate and benzyl piperazine-1-carboxylate for 1-(methylsulfonyl)piperazine, M1b is prepared; $^1$H NMR (400 MHz, CDCl$_3$) δ 7.85 (d, J=1.5 Hz, 1H), 7.59 (d, J=1.4 Hz, 1H), 7.35 (m, 5H), 5.16 (s, 2H), 4.18 (m, 2H), 4.06 (d, J=6.6 Hz, 2H), 3.65 (m, 4H), 3.38 (m, 4H), 2.74 (m, 2H), 1.94 (m, 1H), 1.79 (m, 2H), 1.54 (s, 3H), 1.24 (m, 2H), 0.86 (m, 2H), 0.62 (m, 2H); ESIMS m/z for $(M+H)^+$ $C_{27}H_{36}N_5O_5$ calcd: 510.3. found: 510.0.

Step C: A mixture of M1b (494 mg, 0.969 mmol) and 10% Pd/C (45 mg) in ethanol (5 mL) is purged with H$_2$ (g) for 30 minutes and then left to stir at room temperature under an atmosphere of H$_2$ overnight. The crude reaction is then filtered through a pad of Celite® and M1c is obtained with 95%+purity. ESIMS m/z for $(M+H)^+$ $C_{19}H_{30}N_5O_3$ calcd: 376.2. found: 376.0.

Step D: A solution of M1c (100 mg, 0.266 mmol) in dichloromethane (1 mL) is treated with triethylamine (74.2 mL, 0.533 mmol) followed by methyl 3-(chlorosulfonyl)propanoate (50 mg, 0.27 mmol) and stirred at room temperature for 4 hours. The crude reaction is then concentrated and purified directly via a mass-directed HPLC to afford M1; $^1$H NMR (400 MHz, CDCl$_3$) δ 7.86 (d, J=1.5 Hz, 1H), 7.61 (d, J=1.5 Hz, 1H), 4.18 (m, 2H), 4.07 (d, J=6.5 Hz, 2H), 3.73 (s, 3H), 3.49 (m, 4H), 3.42 (m, 4H), 3.28 (t, J=7.3H, 2H), 2.85 (t, J=7.7 Hz, 2H), 2.74 (m, 2H), 1.93 (m, 1H), 1.81 (m, 2H), 1.54 (s, 3H), 1.24 (m, 2H), 0.86 (m, 2H), 0.62 (m, 2H); ESIMS m/z for $(M+H)^+$ $C_{23}H_{36}N_5O_7S$ calcd: 526.2. found: 526.2.

By following a similar procedure as the one used for preparing M1 from E12a except substituting commercially available sulfonyl chlorides for methyl 3-(chlorosulfonyl)propanoate (in the case of M5, also substituting B4bB for M1a), the following examples are prepared;

| Example | Structure | Analytical data |
|---|---|---|
| M2 | 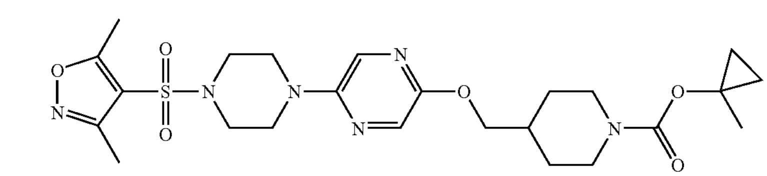 | ESIMS m/z for $(M + H)^+$ $C_{24}H_{35}N_6O_6S$ calcd: 535.2, found: 535.2. |
| M3 | 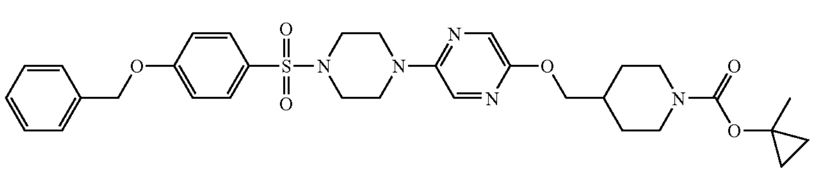 | ESIMS m/z for $(M)^+$ $C_{32}H_{39}N_5O_6S$ calcd: 621.3, found: 621.7. |

-continued

| Example | Structure | Analytical data |
|---|---|---|
| M4 | 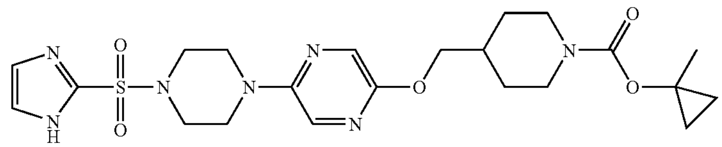 | ESIMS m/z for (M + H)+ C22H32N7O5S calcd: 506.2, found: 506.2. |
| M5 | 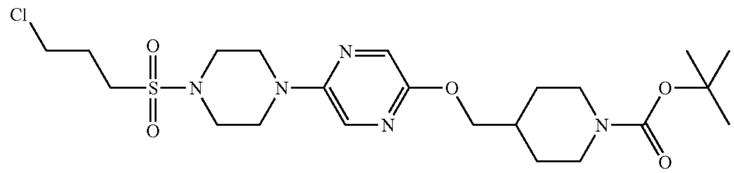 | 1H NMR (400 MHz, CD3CN) δ 7.87 (d, J = 1.4 hz, 1H), 7.62 (d, J − 1.5 Hz, 1H), 4.15 (m, 2H), 4.08 (d, J = 6.6 Hz, 2H), 3.70 (t, J = 6.1 Hz, 2H), 3.51 (m, 4H), 3.43 (m, 4H), 3.11 (t, J = 7.4 Hz, 2H), 2.73 (m, 2H), 2.32 (m, 2H), 1.94 (m, 1H), 1.79 (m, 2H), 1.46 (s, 9H), 1.26 (m, 2H); ESIMS m/z for (M − Boc + H)+ C17H29ClN5O3S calcd: 418.2, found: 418.2. |
| M6 | 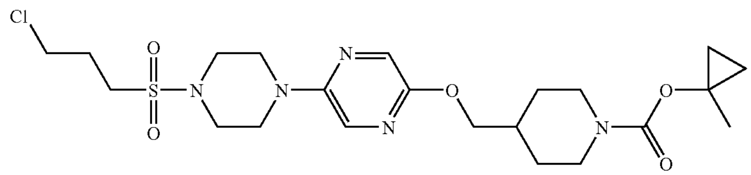 | 1H-NMR (400 MHz, CDCl3) δ 7.87 (d, I = 1.4 Hz, 1H), 7.63 (d, J = 1.4 Hz, 1H), 4.21 (m, 2H), 4.08 (d, J = 6.5 Hz, 2H), 3.70 (t, J = 6.1 Hz, 2H), 3.51 (m, 4H), 3.44 (m, 4H), 3.12 (m, 2H), 2.74 (dd, J = 12.3, 12.2 Hz, 2H), 2.32 (m, 2H), 1.95 (m, 1H), 1.79 (m, 2H), 1.55 (s, 3H), 1.25 (m, 2H), 0.86 (m, 2H), 0.62 (m, 2H); ESIMS calcd. for C22H35ClN5O5S [M]+ 516.2, found 516.0. |
| M7 | 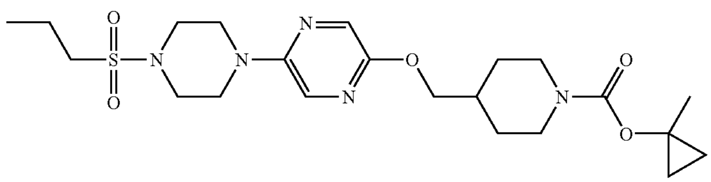 | 1H NMR (400 MHz, CD3CN) δ 7.89 (d, J = 1.4 Hz, 1H), 7.82 (d, J = 1.2 Hz, 1H), 4.19 (m, 2H), 4.10 (d, J = 6.5 Hz, 2H), 3.51 (m, 8H), 2.93 (m, 2H), 2.74 (dd, J = 12.7, 12.0 Hz, 1H), 1.91 (m, 3H), 1.79 (m, 2H), 1.55 (s, 3H), 1.25 (m, 2H), 1.07 (t, J = 7.4 Hz, 3H), 0.86 (m, 2H), 0.62 (m, 2H); ESIMS m/z for (M + H)+ C22H36N5O5S calcd: 482.3, found: 482.2. |
| M8 | 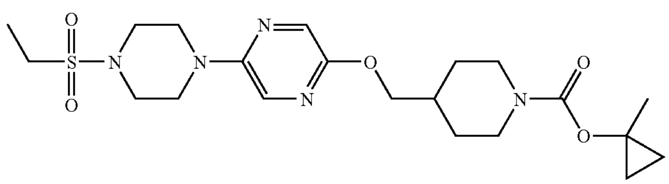 | 1H NMR (400 MHz, CD3CN) δ 7.96 (s, 1H), 7.91 (d, J = 1.4 Hz, 1H), 4.17 (m, 2H), 4.11 (d, J = 6.5 Hz, 2H), 3.58 (m, 4H), 3.54 (m, 4H), 3.01 (m, 2H), 2.74 (dd, J = 12.2, 11.9 Hz, 2H), 1.95 (m, 1H), 1.79 (m, 2H), 1.55 (s, 3H), 1.40 (t, J = 7.4 Hz, 3H), 1.25 (m, 2H), 0.86 (m, 2H), 0.62 (m, 2H); ESIMS m/z for (M + H)+ C21H34N5O5S calcd: 468.2, found: 468.2. |
| M9 | 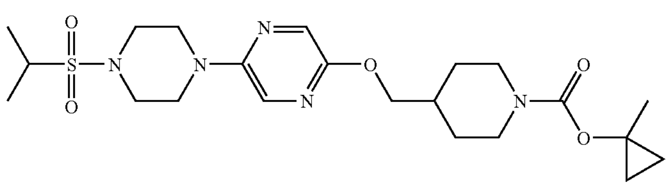 | 1H NMR (400 MHz, CD3CN) δ 7.91 (m, 2H), 4.18 (m, 2H), 4.11 (d, J = 6.5 Hz, 2H), 3.63 (m, 4H), 3.50 (m, 4H), 3.25 (sept., J = 6.8 Hz, 1H), 2.74 (dd, J = 12.2, 12.1 Hz, 2H), 1.94 (m, 1H), 1.78 (m, 2H), 1.55 (s, 3H), 1.37 (d, J = 6.9 Jz, 6H), 1.25 (m, 2H), 0.86 (m, 2H), 0.62 (m, 2H); ESIMS m/z for (M + H)+ C22H36N5O5S calcd: 482.2, found: 482.2. |

-continued

| Example | Structure | Analytical data |
|---|---|---|
| M10 | 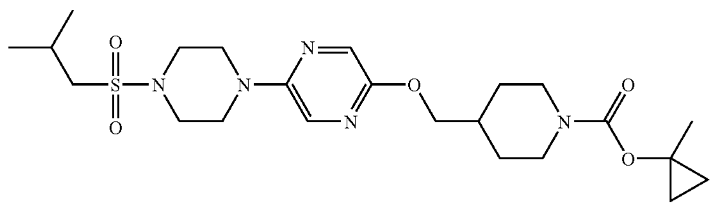 | ¹H NMR (400 MHz, CD₃CN) δ 7.89 (d, J = 1.4 Hz, 1H), 7.81 (d, J = 1.1 Hz, 1H), 4.18 (m, 2H), 4.10 (d, J = 6.5 Hz, 2H), 3.53 (m, 4H), 3.47 (m, 4H), 2.79 (d, J = 6.6 Hz, 2H), 2.74 (m, 2H), 2.32 (m, 1H), 1.95 (m, 1H), 1.78 (m, 2H), 1.55 (s, 3H), 1.24 (m, 2H), 1.12 (d, J = 6.7 Hz, 6H), 0.86 (m, 2H), 0.62 (m, 2H); ESIMS m/z for (M + H)⁺ C₂₃H₃₈N₅O₅S calcd: 496.3, found: 496.3. |
| M11 | 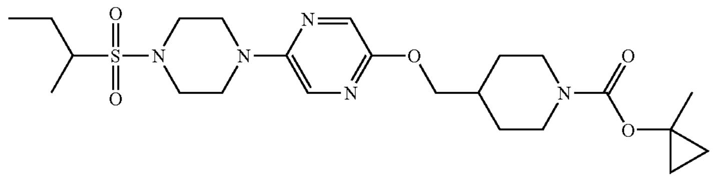 | ¹H NMR (400 MHz, CD₃CN) δ 7.87 (d, J = 1.5 Hz, 1H), 7.62 (d, J = 1.5 Hz, 1H), 4.19 (m, 2H), 4.07 (d, J = 6.5 Hz, 2H), 3.50 (m, 4H), 3.46 (m, 4H), 2.98 (m, 1H), 2.75 (dd, J = 12.2, 12.1 Hz, 2H), 2.03 (m, 1H), 1.80 (m, 1H), 1.79 (m, 2H), 1.56 (m, 1H), 1.55 (s, 3H), 1.35 (d, J = 6.9 Hz, 3H), 1.26 (m, 2H), 1.03 (t, J = 7.5 hz, 3H), 0.87 (m, 2H), 0.62 (m, 2H); ESIMS m/z for (M + H)⁺ C₂₃H₃₈N₅O₅S calcd: 496.3, found: 496.2. |
| M12 | 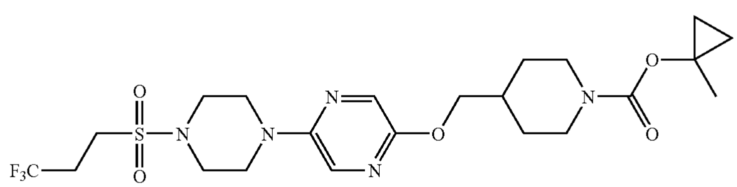 | ¹H-NMR (400 MHz, CDCl₃) δ 7.87 (d, J = 1.4 Hz, 1H), 7.62 (d, 1 = 1.4 Hz, 1H), 4.20 (m, 2H), 4.08 (d, J = 6.5 Hz, 2H), 3.52 (m, 4H), 3.45 (m, 2H), 3.13 (m, 2H), 2.74 (dd, J = 12.2, 12.2 Hz, 2H), 2.66 (m, 2H), 1.94 (m, 1H), 1.79 (m, 2H), 1.56 (s, 3H), 1.25 (m, 2H), 0.86 (m, 2H), 0.62 (m, 2H); ESIMS calcd. C₂₂H₃₃F₃N₅O₅S [M + H]⁺ 536.2, found 536.3. |

Example M13

3-(4-(5-((1-((1-Methylcyclopropoxy)carbonyl)piperidin-4-yl)methoxy)pyrazin-2-yl)piperazin-1-ylsulfonyl)propanoic acid

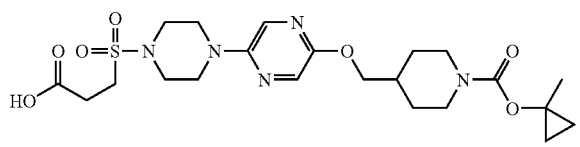

Example M14

1-Methylcyclopropyl 4-((5-(4-(3-hydroxypropylsulfonyl)piperazin-1-yl)pyrazin-2-yloxy)methyl)piperidine-1-carboxylate

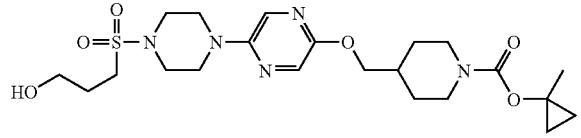

A solution of M1 (18.8 mg, 0.035 mmol) in TETRAHYDROFURAN (1 mL) and water (0.25 mL) is treated with LiOH (3 mg) and stirred overnight. The crude reaction is then concentrated and purified directly via a mass-directed HPLC to afford M13. ESIMS m/z for (M+H)⁺ C₂₂H₃₄N₅O₇S calcd: 512.2. found: 512.3.

A solution of M1 (18.8 mg, 0.035 mmol) in 2 M LiBH₄ in tetrahydrofuran (1 mL) is heated to 50° C. and stirred overnight. The crude reaction is then concentrated and purified directly via a mass-directed HPLC to afford M14. ESIMS m/z for (M+H)⁺ C₂₂H₃₆N₅O₆S calcd: 498.2. found: 498.3.

Example M15

1-Methylcyclopropyl 4-((5-(4-(4-hydroxyphenylsulfonyl)piperazin-1-yl)pyrazin-2-yloxy)methyl)piperidine-1-carboxylate

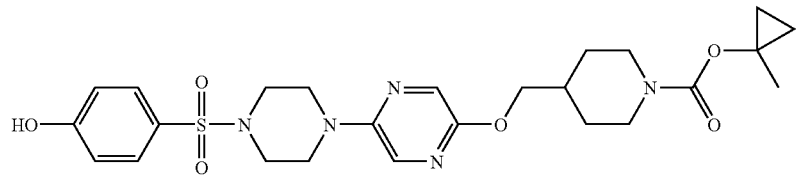

A solution of M3 (44.5 mg, 0.071 mmol) in ethanol (2 mL) is treated with 5% Pd/C (10 mg) and hydrogenated under atmospheric pressure overnight. The catalyst is removed by filtration through Celite® and the reaction is concentrated and purified directly via a mass-directed HPLC to afford M15. ESIMS m/z for $(M+H)^+$ $C_{25}H_{33}N_5O_6S$ calcd: 531.2. found: 531.7.

Example M16

1-Methylcyclopropyl 4-((5-(4-(3-cyanopropylsulfonyl)piperazin-1-yl)pyrazin-2-yloxy)methyl)piperidine-1-carboxylate

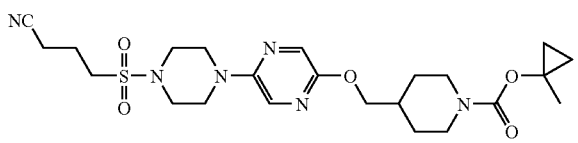

A solution of M6 (19 mg, 0.037 mmol) in N,N-dimethylformamide (0.5 mL) is treated with KCN (3.6 mg, 0.055 mmol) and cesium carbonate (24 mg, 0.077 mmol) and heated to 80° C. for 1.5 hours. The reaction is then diluted with water and extracted with ethyl acetate three times and diethyl ether twice. The combined organics are dried over MgSO$_4$, filtered evaporated and purified by silica gel using a linear gradient of 50-100% ethyl acetate in hexane to afford M16. $^1$H NMR (400 MHz, CDCl$_3$) δ 7.87 (d, J=1.6 Hz, 1H), 7.62 (d, J=1.6 Hz, 1H), 4.28-3.95 (m, 2H), 4.08 (d, J=6.4 Hz, 2H), 3.53-3.50 (m, 4H), 3.44-3.42 (m, 4H), 3.07 (t, J=6.8 Hz, 2H), 2.74 (br t, J=12.0 Hz, 2H), 2.64 (t, J=7.2 Hz, 2H), 2.24 (quintet, J=7.2 Hz, 2H), 2.01-1.89 (m, 1H), 1.81-1.77 (m, 2H), 1.54 (s, 3H), 1.30-1.17 (m, 2H), 0.88-0.84 (m, 2H), 0.64-0.60 (m, 2H); ESIMS m/z for $(M+H)^+$ $C_{23}H_{35}N_6O_5S$ calcd: 507.2. found: 507.2.

Example M17

1-Methylcyclopropyl 4-((5-(4-(3-(1H-tetrazol-5-yl)propylsulfonyl)piperazin-1-yl)pyrazin-2-yloxy)methyl)piperidine-1-carboxylate

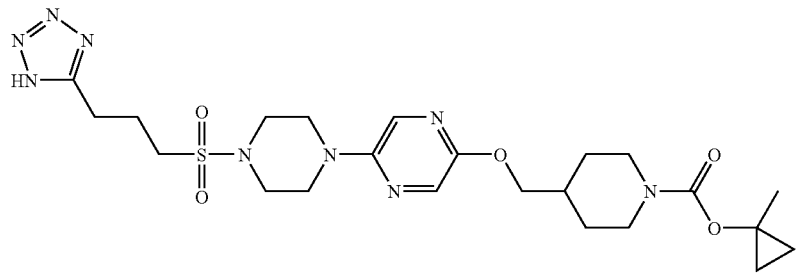

A solution of M16 (12 mg, 0.024 mmol) in isopropanol (0.1 mL) and water (0.3 mL) is treated with ZnBr$_2$ (27 mg, 0.12 mmol) and NaN$_3$ (7.7 mg, 0.12 mmol) and heated to 150° C. overnight. The reaction is filtered through a syringe filter and purified directly via a mass-directed HPLC to afford M17; $^1$H NMR (400 MHz, CD$_3$CN) δ 7.83 (d, J=1.6 Hz, 1H), 7.71 (d, J=1.6 Hz, 1H), 4.16-3.89 (m, 2H), 4.06 (d, J=6.4 Hz, 2H), 3.49-3.46 (m, 4H), 3.35-3.32 (m, 4H), 3.12-3.04 (m, 4H), 2.81-2.70 (m, 2H), 2.28-2.20 (m, 2H), 1.78-1.71 (m, 3H), 1.48 (s, 3H), 1.22-1.12 (m, 2H), 0.81-0.78 (m, 2H), 0.60-0.57 (m, 2H); ESIMS m/z for $(M+H)^+$ $C_{23}H_{36}N_9O_5S$ calcd: 550.3. found: 550.3.

Example M18

1-Methylcyclopropyl 4-((5-(4-(3-aminopropylsulfonyl)piperazin-1-yl)pyrazin-2-yloxy)methyl)piperidine-1-carboxylate

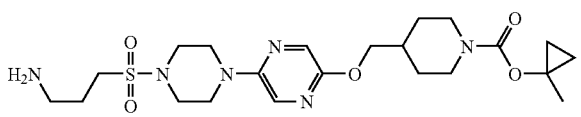

A solution of M6 (113 mg, 0.22 mmol) in N,N-dimethylformamide (1 mL) is treated with NaN$_3$ (42.7 mg, 0.67 mmol) and heated to 90° C. overnight. The reaction is cooled to room temperature, partitioned between water and ethyl acetate. The organics are extracted with water twice more, dried over MgSO$_4$, filtered evaporated and purified by silica gel using a linear gradient of 0-100% ethyl acetate in hexane to afford the intermediate azide which is dissolved in ethanol (1 mL) and treated with 10% Pd/C (20 mg) and hydrogenated at room temperature overnight. The catalyst is removed by filtration through Celite® and the reaction is concentrated and purified directly via a mass-directed HPLC to afford M18. $^1$H NMR (400 MHz, CD$_3$CN) δ 7.86 (d, J=1.4 Hz, 1H), 7.61 (d, J=1.5 Hz, 1H), 4.19 (m, 2H), 4.07 (d, J=6.5 Hz, 2H), 3.50 (m, 4H), 3.42 (m, 4H), 3.05 (m, 2H), 2.88 (t, J=6.7 Hz, 2H), 2.74 (dd, J=13.0, 12.0 Hz, 2H), 1.98 (m, 3H), 1.79 (m, 2H), 1.54 (s, 3H), 1.24 (m, 2H), 0.86 (m, 2H), 0.62 (m, 2H); ESIMS m/z for (M+H)$^+$ C$_{22}$H$_{37}$N$_6$O$_5$S calcd: 497.3. found: 497.6.

Example M19

Tert-butyl 4-((5-(4-(3-acetoxypropylsulfonyl)piperazin-1-yl)pyrazin-2-yloxy)methyl)piperidine-1-carboxylate

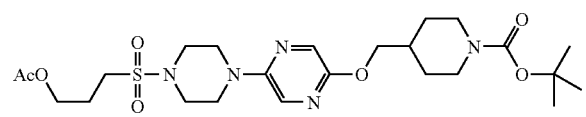

A solution of M5 (154 mg, 0.30 mmol) in N,N-dimethylformamide (2 mL) is treated with sodium acetate (73 mg, 0.89 mmol) and sodium iodide (45 mg, 0.30 mmol) and heated to 120° C. overnight. The reaction is cooled to room temperature, partitioned between water and ethyl acetate. The organics are extracted with water twice more, dried over MgSO$_4$, filtered evaporated and purified by silica gel using a linear gradient of 0-100% ethyl acetate in dichloromethane to afford M19; $^1$H NMR (400 MHz, CD$_3$CN) δ 7.87 (d, J=1.4 Hz, 1H), 7.83 (d, J=1.5 Hz, 1H), 4.20 (t, J=6.1 Hz, 2H), 1.14 (m, 2H), 4.08 (d, J=6.6 Hz, 1H), 3.51 (m, 4H), 3.44 (m, 4H), 3.02 (m, 2H), 2.74 (m, 2H), 2.19 (m, 2H), 2.07 (s, 3H), 1.95 (m, 1H), 1.80 (m, 2H), 1.46 (s, 9H), 1.26 (m, 2H); ESIMS m/z for (M-Boc+H)$^+$ C$_{19}$H$_{32}$N$_5$O$_5$S calcd: 442.2. found: 442.3.

Example M20

1-Methylcyclopropyl 4-((5-(4-(3-methoxypropylsulfonyl)piperazin-1-yl)pyrazin-2-yloxy)methyl)piperidine-1-carboxylate

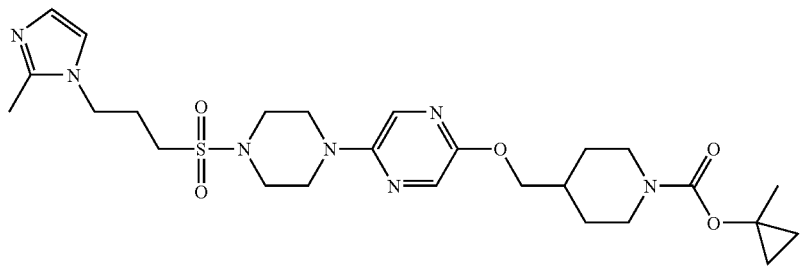

A solution of M6 (26 mg, 0.049 mmol) in methanol (1 mL) is treated with a 0.5 M solution of sodium methoxide in methanol (0.2 mL, 0.1 mmol) and heated to 65° C. overnight and at 95° C. for 10 hours. The reaction is cooled to room temperature, the solvent is removed in vacuo and the crude residue is purified by silica gel using a linear gradient of 0-80% ethyl acetate in hexane to afford M20. $^1$H NMR (400 MHz, CDCl$_3$) δ 7.86 (d, J=1.2 Hz, 1H), 7.61 (d, J=1.6 Hz, 1H), 4.15 (m, 2H), 4.07 (d, J=6.4 Hz, 2H), 3.49 (m, 6H), 3.42 (m, 4H), 3.33 (s, 3H), 3.04 (m, 2H), 2.74 (t, J=12.4 Hz, 2H), 2.09 (m, 2H), 1.94 (m, 1H), 1.79 (d, J=12.4 Hz, 2H), 1.54 (s, 3H), 1.24 (m, 2H), 0.86 (m, 2H), 0.62 (m, 2H); ESIMS m/z for (M+H)$^+$ C$_{23}$H$_{37}$N$_5$O$_6$S calcd: 511.3. found: 512.2.

Example M21

1-Methylcyclopropyl 4-((5-(4-(3-(2-methyl-1H-imidazol-1-yl)propylsulfonyl)piperazin-1-yl)pyrazin-2-yloxy)methyl)piperidine-1-carboxylate A solution of M6 (53 mg, 0.10 mmol) in tetrahydrorfuran (1 mL) is treated with 2-methylimidazole (8.5 mg, 0.10 mmol) and heated to 65° C. overnight. The reaction is cooled to room temperature, the solvent is removed in vacuo and the crude residue is purified directly via a mass-directed HPLC to afford M21. $^1$H NMR (400 MHz, CD$_3$CN) δ7.86 (d, J=1.4 Hz, 1H), 7.62 (d, J=1.4 Hz, 1H), 7.29 (d, J=2.0 Hz, 1H), 7.18 (d, J=1.8 Hz, 1H), 4.34 (t, J=7.0 Hz, 2H), 4.18 (m, 2H), 4.07 (d, J=6.5 Hz, 2H), 3.51 (m, 4H), 3.41 (m, 4H), 2.93 (m, 2H), 2.83 (s, 3H), 2.74 (m, 2H), 2.42 (m, 2H), 1.94 (m, 1H), 1.79 (m, 2H), 1.54 (s, 3H), 1.25 (m, 2H), 0.86 (m, 2H), 0.62 (m, 2H); ESIMS m/z for (M+H)$^+$ C$_{26}$H$_{40}$N$_7$O$_5$S calcd: 562.3. found: 562.5.

By following the procedure for M21 using the appropriate amine nucleophiles, the following examples are obtained:

| Example | Structure | Analytical data |
|---|---|---|
| M22 | 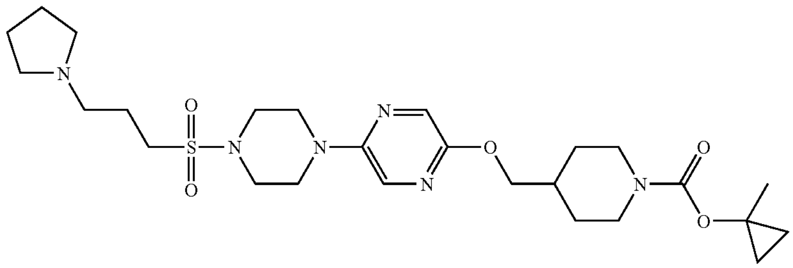 | $^1$H NMR (400 MHz, CD$_3$CN) δ 7.85 (d, J = 1.4 Hz, 1 H), 7.61 (d, J = 1.5 Hz, 1 H), 4.18 (m, 2 H), 4.07 (d, J = 6.5 Hz, 2 H), 3.51 (m, 4 H), 3.43 (m, 4 H), 3.19 (m, 6 H), 2.74 (dd, J = 12.4, 12.3 Hz, 2 H), 2.36 (m, 2 H), 2.08 (m, 5 H), 1.94 (m, 2 H), 1.79 (m, 2 H), 1.54 (s, 3 H), 1.25 (m, 2 H), 0.86 (m, 2 H), 0.62 (m, 2 H); ESIMS m/z for (M + H)$^+$ C$_{26}$H$_{43}$N$_6$O$_5$S calcd: 551.3, found: 551.5. |
| M23 | 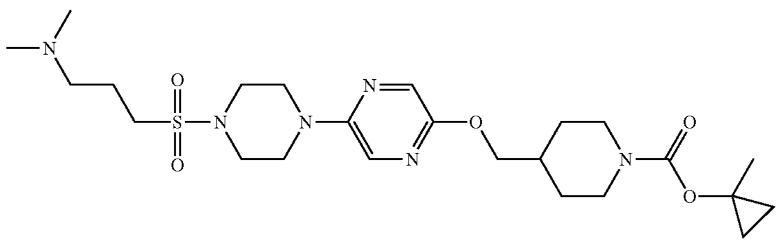 | $^1$H NMR (400 MHz, CD$_3$CN) δ 7.85 (d, J = 1.5 Hz, 1 H), 7.61 (d, J = 1.5 Hz, 1 H), 4.18 (m, 2 H), 4.07 (d, J = 6.6 Hz, 2 H), 3.51 (m, 4 H), 3.44 (m, 4 H), 3.18 (m, 2 H), 2.98 (m, 2 H), 2.74 (dd, J = 12.4, 12.3, Hz, 2 H), 2.63 (s, 6 H), 2.30 (m, 2 H), 1.94 (m, 1 H), 1.79 (m, 2 H), 1.54 (s, 3 H), 1.25 (m, 2 H), 0.86 (m, 2 H), 0.62 (m, 2 H); ESIMS m/z for (M + H)$^+$ C$_{24}$H$_{41}$N$_6$O$_5$S calcd: 525.3, found: 525.3. |
| M-24 | 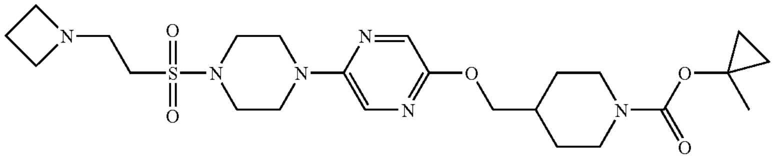 | $^1$H NMR (400 MHz, CD$_3$CN) δ 7.86 (d, J = 1.2 Hz, 1 H), 7.82 (d, J = 1.6 Hz, 1 H), 4.10 (d, J = 6.4 Hz, 2 H), 4.07 (m, 2 H), 3.55 (m, 2 H), 3.41 (m, 2 H), 3.15 (t, J = 7.2 Hz, 4 H), 3.01 (m, 2 H), 2.83 (m, 2 H), 2.74 (m, 2 H), 1.95 (m, 3 H), 1.78 (m, 2 H), 1.50 (s, 3 H), 1.22 (m, 2 H), 0.79 (m, 2 H), 0.58 (m, 2 H); ESIMS m/z for (M + H)$^+$ C$_{24}$H$_{38}$N$_6$O$_5$S calcd: 522.3, found: 523.2. |
| M-25 | 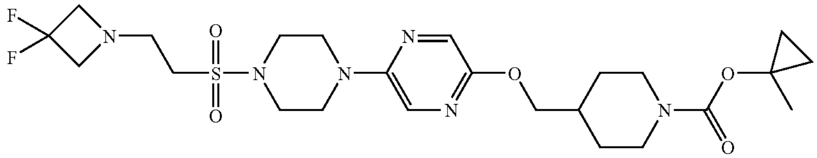 | $^1$H NMR (400 MHz, CD$_3$CN) δ 7.83 (d, J = 1.2 Hz, 1 H), 7.71 (d, J = 1.6 Hz, 1 H), 4.06 (d, J = 6.8 Hz, 2 H), 4.00 (m, 2 H), 3.59 (t, J = 12.4 Hz, 4 H), 3.48 (m, 4 H), 3.32 (m, 4 H), 3.06 (m, 2 H), 2.95 (m, 2 H), 2.74 (m, 2 H), 2.10 (m, 1 H), 1.76 (m, 2 H), 1.49 (s, 3 H), 1.17 (m, 2 H), 0.79 (m, 2 H), 0.59 (m, 2 H); ESIMS m/z for (M + H)$^+$ C$_{24}$H$_{36}$F$_2$N$_6$O$_5$S calcd: 558.2, found: 559.2. |

Example M26

1-Methylcyclopropyl 4-((5-(4-(vinylsulfonyl)piperazin-1-yl)pyrazin-2-yloxy)methyl)piperidine-1-carboxylate

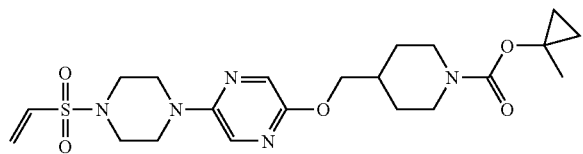

A solution of M1c (308 mg, 0.82 mmol) in tetrahydrorfuran (4 mL) is cooled in an ice/water bath and treated with triethylamine (299 mg, 3.0 mmol) followed by 2-chloroethanesulfonyl chloride (401 mg, 2.5 mmol) added over 10 minutes. The reaction is stirred for an hour and then evaporated and partitioned between water and ethyl acetate. The organics are extracted with water twice more, dried over $MgSO_4$, filtered evaporated and purified by silica gel using a linear gradient of 0-100% ethyl acetate in hexane to afford M26; $^1H$ NMR (400 MHz, $CD_3CN$) δ 7.91 (d, J=2.9 Hz, 1H), 7.15 (dd, J=9.1, 3.1 Hz, 1H), 6.65 (d, J=9.1 Hz, 1H), 4.19 (m, 2H), 3.81 (d, J=6.3 Hz, 2H), 3.54 (m, 4H), 3.34 (m, 4H), 3.08 (ddd, J=13.1, 2.8, 2.8 Hz, 2H), 2.80 (s, 3H), 2.04 (m, 1H), 1.92 (m, 2H), 1.44 (m, 2H), 1.28 (m, 6H); ESIMS m/z for $(M+H)^+$ $C_{21}H_{32}N_5O_5S$ calcd: 466.2. found: 466.2.

Example M27

1-Methylcyclopropyl 4-((5-(4-(2-ethoxyethylsulfonyl)piperazin-1-yl)pyrazin-2-yloxy)methyl)piperidine-1-carboxylate

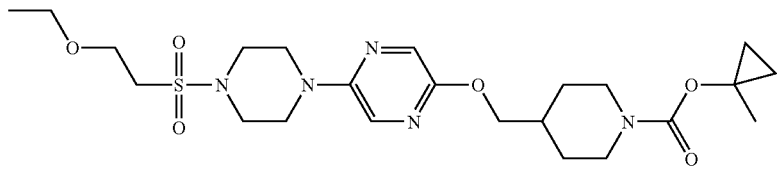

By following a similar procedure as the one used for preparing M20 from M6 except substituting M26 for M6, M27 is prepared; $^1H$ NMR (400 MHz, $CD_3CN$) δ 7.86 (d, J=1.5 Hz, 1H), 7.61 (d, J=1.5 Hz, 1H), 4.18 (m, 2H), 4.07 (d, J=6.6 Hz, 2H), 3.80 (t, J=6.0 Hz, 2H), 3.51 (m, 6H), 3.43 (m, 4H), 3.24 (t, J=5.9 Hz, 2H), 2.74 (dd, J=12.3, 12.0 Hz, 2H), 1.94 (m, 1H), 1.79 (m, 2H), 1.54 (s, 3H), 1.23 (m, 2H), 1.17 (t, J=7.0 Hz, 3H), 0.86 (m, 2H), 0.62 (m, 2H); ESIMS m/z for $(M+H)^+$ $C_{23}H_{38}N_5O_6S$ calcd: 512.3. found: 512.6.

Example M28

1-Methylcyclopropyl 4-((5-(4-(2-(piperidin-1-yl)ethylsulfonyl)piperazin-1-yl)pyrazin-2-yloxy)methyl)piperidine-1-carboxylate

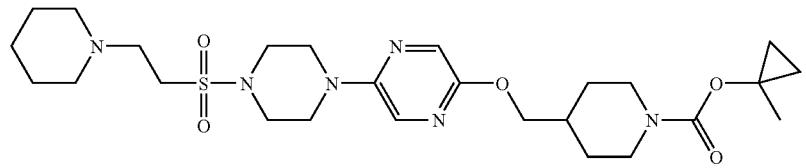

A solution of M26 (27 mg, 0.058 mmol) in ethanol (0.5 mL) is treated with piperidine (13.3 mg, 0.12 mmol) and stirred at room temperature overnight. The reaction is diluted with N,N-dimethylformamide and purified directly via a mass-directed HPLC to afford M27; $^1H$ NMR (400 MHz, $CD_3CN$) δ 7.87 (d, J=1.4 Hz, 1H), 7.64 (d, J=1.4 Hz, 1H), 4.19 (m, 2H), 4.07 (d, J=6.5 Hz, 2H), 3.70 (m, 2H), 3.49 (m, 8H), 3.42 (m, 4H), 2.75 (m, 4H), 1.93 (m, 6H), 1.80 (m, 2H), 1.54 (s, 3H), 1.45 (m, 1H), 1.24 (m, 2H), 0.86 (m, 2H), 0.62 (m, 2H); ESIMS m/z for $(M+H)^+$ $C_{26}H_{43}N_6O_5S$ calcd: 551.3. found: 551.3.

By following a similar procedure as the one used for preparing M28 from M26 except substituting a commercially available amine for piperidine, the following examples are prepared;

| Example | Structure | Analytical data |
|---|---|---|
| M29 | 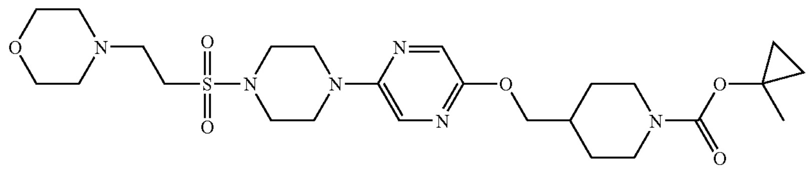 | $^1$H NMR (400 MHz, CD$_3$CN) δ 7.86 (s, 1 H), 7.62 (s, 1 H), 4.19 (m, 2 H), 4.07 (d, J = 6.5 Hz, 2 H), 3.97 (m, 5 H), 3.49 (m, 5 H), 3.42 (m, 5 H), 2.74 (m, 2 H), 1.94 (m, 1 H), 1.79 (m, 2 H), 1.54 (s, 3 H), 1.24 (m, 2 H), 0.86 (m, 2 H), 0.61 (m, 2); ESIMS m/z for (M + H)$^+$ C$_{25}$H$_{41}$N$_6$O$_6$S calcd: 553.3, found: 553.2. |
| M30 | 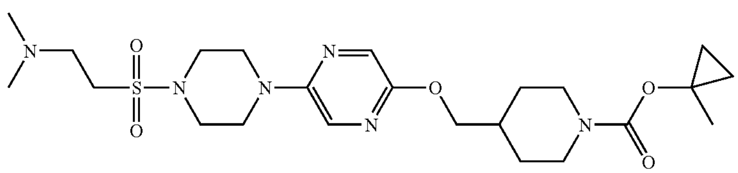 | $^1$H NMR (400 MHz, CD$_3$CN) δ 7.88 (s, 1 H), 7.64 (s, 1 H), 4.18 (m, 2 H), 4.07 (d, J = 6.5 Hz, 2 H), 3.51 (m, 8 H), 3.44 (m, 4 H), 2.94 (s, 6 H), 2.76 (m, 2 H), 1.96 (m, 1 H), 1.80 (m, 2 H), 1.54 (s, 3 H), 1.24 (m, 2 H), 0.87 (m, 2 H), 0.62 (m, 2 H); ESIMS m/z for (M + H)$^+$ C$_{23}$H$_{39}$N$_6$O$_5$S calcd: 511.3, found: 511.2. |
| M31 | 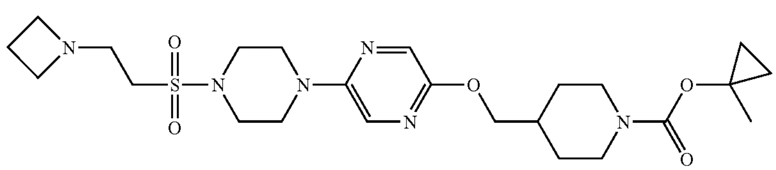 | $^1$H NMR (400 MHz, CD$_3$CN) δ 7.86 (d, J = 1.2 Hz, 1 H), 7.82 (d, J = 1.6 Hz, 1 H), 4.10 (d, J = 6.4 Hz, 2 H), 4.07 (m, 2 H), 3.55 (m, 2 H), 3.41 (m, 2 H), 3.15 (t, J = 7.2 Hz, 4 H), 3.01 (m, 2 H), 2.83 (m, 2 H), 2.74 (m, 2 H), 1.95 (m, 3 H), 1.78 (m, 2 H), 1.50 (s, 3 H), 1.22 (m, 2 H), 0.79 (m, 2 H), 0.58 (m, 2 H); ESIMS m/z for (M + H)$^+$ C$_{24}$H$_{38}$N$_6$O$_5$S calcd: 522.3, found: 523.2. |
| M32 | 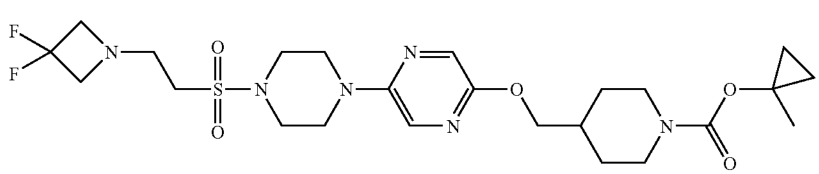 | $^1$H NMR (400 MHz, CD$_3$CN) δ 7.83 (d, J = 1.2 Hz, 1 H), 7.71 (d, J = 1.6 Hz, 1 H), 4.06 (d, J = 6.8 Hz, 2 H), 4.00 (m, 2 H), 3.59 (t, J = 12.4 Hz, 4 H), 3.48 (m, 4 H), 3.32 (m, 4 H), 3.06 (m, 2 H), 2.95 (m, 2 H), 2.74 (m, 2 H), 2.10 (m, 1 H), 1.76 (m, 2 H), 1.49 (s, 3 H), 1.17 (m, 2 H), 0.79 (m, 2 H), 0.59 (m, 2 H); ESIMS m/z for (M + H)$^+$ C$_{24}$H$_{36}$F$_2$N$_6$O$_5$S calcd: 558.2, found: 559.2. |

Example M33

1-Methylcyclopropyl 4-((5-(4-((1-(dimethylamino)cyclopropyl)methylsulfonyl)piperazin-1-yl)pyrazin-2-yloxy)methyl)piperidine-1-carboxylate

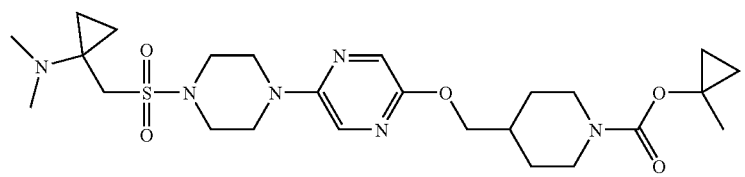

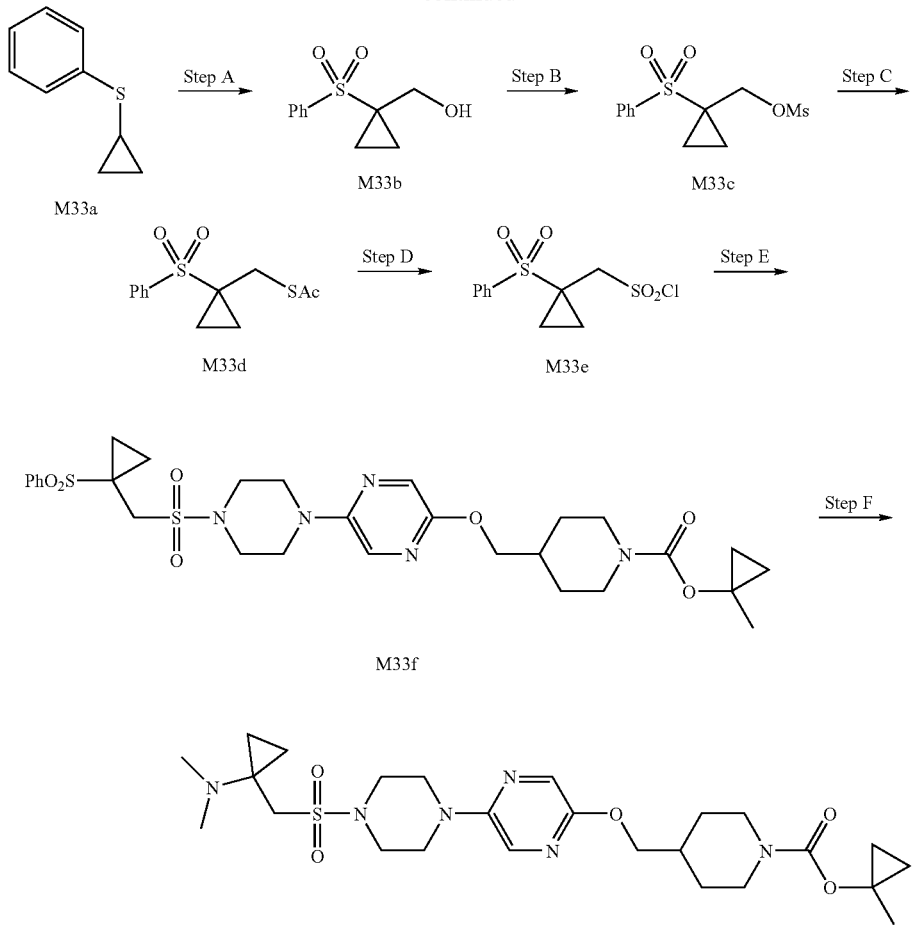

Example 33

Step A: A solution of M33a (5.0 g, 33 mmol) in acetic acid (50 mL) is treated with 30% aqueous hydrogen peroxide (7.92 g of solution, 70 mmol) and stirred at 100° C. for 1 hour. The solvent was then removed and the reaction was coevaporated with toluene 3 times.

A sample of M33a (4 g, 22 mmol) in tetrahydrofuran (40 mL) is cooled in an ice/water bath and treated with BuLi in hexane (13.2 mL of a 2 M solution, 26 mmol) and stirred for 20 minutes. The resulting yellow solution is treated with paraformaldehyde (1.65 g, 55 mmol) and allowed to stir for 1 hour. The reaction is then quenched with saturated aqueous ammonium chloride and filtered through a pad of Celite® using ethyl acetate. The organics are isolated, dried over $MgSO_4$, filtered, evaporated and purified on silica gel using a linear gradient of 0-100% ethyl acetate in hexane to afford M33b; $^1$H NMR (400 MHz, $CDCl_3$) δ 7.91 (m, 2H), 7.68 (m, 1H), 7.59 (m, 2H), 3.64 (d, J=6.4 Hz, 2H), 2.72 (dd, J=6.4, 6.4 Hz, 1H), 1.64 (m, 2H), 1.07 (m, 2H); ESIMS m/z for $(M+H)^+$ $C_{10}H_{13}O_3S$ calcd: 213.1. found: 213.0.

Step B: A solution of M33b (4.2 g, 20 mmol) in dichloromethane (40 mL) is treated with triethylamine (3.0 g of solution, 30 mmol), cooled in an ice/water bath and treated methanesulfonyl chloride (2.95 g, 26 mmol). The solution is stirred overnight an allowed to come to room temperature. The reaction is then quenched with aqueous 1 M HCl and extracted with dichloromethane twice. The organics are dried over $MgSO_4$, filtered, evaporated and triturated with diethyl ether to afford M33c; $^1$H NMR (400 MHz, $CDCl_3$) δ 7.92 (m, 2H), 7.68 (m, 1H), 7.59 (m, 2H), 4.41 (s, 2H), 2.82 (s, 3H), 1.80 (m, 2H), 1.21 (m, 2H); ESIMS m/z for $(M+H)^+$ $C_{11}H_{15}O_5S_2$ calcd: 291.0. found: 291.0.

Step C: A solution of M33c (3 g, 10 mmol) in N,N-dimethylformide (30 mL) is treated with potassium thioacetate (1.3 g, 11 mmol) and water (20 mL) and stirred at 60° C. overnight. The reaction is diluted with ethyl acetate and extracted with water twice. The organics are isolated, dried over $MgSO_4$, filtered, evaporated and purified on silica gel using a linear gradient of 0-100% ethyl acetate in hexane to afford M33d; $^1$H NMR (400 MHz, $CDCl_3$) δ 7.88 (m, 2H), 7.69 (m, 1H), 7.59 (m, 2H), 3.26 (s, 2H), 2.26 (m, 3H), 1.68 (m, 2H), 1.02 (m, 2H); ESIMS m/z for $(M+H)^+$ $C_{12}H_{15}O_3S_2$ calcd: 271.1. found: 271.0.

Step D: A cold (ice/water bath) solution of acetonitrile (2.1 mL) and 2 M HCl (419 µL, 0.84 mmol) is treated with NCS (838 mg, 6.27 mmol), allowed to stir for 5 minutes and treated dropwise with a solution of M33d (358 mg, 1.6 mmol) in acetonitrile (419 µL). After 30 minutes of stirring, the reaction is diluted with diethyl ether and extracted with brine, water and saturated sodium thiosulfate. The organics are isolated, dried over $MgSO_4$, filtered and to afford M33e; ESIMS m/z for $(M+H)^+$ $C_{10}H_{12}ClO_4S_2$ calcd: 295.0. found: 294.9.

Step E: A cold (ice/water bath) solution of M1c (524 mg, 1.4 mmol) and triethylamine (282 mg, 2.8 mmol) in dichloromethane (5 mL) is treated with a solution of M33e (solution of the crude from the last step) in dichlormethane (3 mL). After 2 hours of stirring, the reaction is evaporated and purified silica gel using a linear gradient of 0-100% ethyl acetate in hexane to afford M33f; ESIMS m/z for (M+H)+ $C_{29}H_{40}N_5O_7S_2$ calcd: 634.2. found: 634.2.

Step F: A solution of M33f (157 mg, 0.25 mmol) in 2 M dimethylamine in tetrahydrofuran (2 mL, 4 mmol) is treated with potassium tert-butoxide (28 mg, 0.25 mmol) and stirred for 1 hour. The reaction is evaporated, diluted with methanol and purified directly via a mass-directed HPLC to afford M33; $^1$H-NMR (400 MHz, CDCl$_3$) δ 7.86 (d, J=1.4 Hz, 1H), 7.61 (d, J=1.4 Hz, 1H), 4.20 (m, 2H), 4.07 (d, J=6.5 Hz, 2H), 3.50 (m, 4H), 3.39 (m, 4H), 3.07 (s, 2H), 2.74 (dd, J=12.4, 12.3 Hz, 2H), 2.37 (s, 6H), 1.94 (m, 1H), 1.79 (m, 2H), 1.55 (s, 3H), 1.25 (m, 2H), 0.93 (m, 2H), 0.86 (m, 4H); ESIMS calcd. for $C_{25}H_{41}N_6O_5S$ [M+H]+ 537.3. found 537.4.

By following the procedure for M33 using the appropriate amine nucleophiles in step F, the following examples are obtained:

7.86 (d, J=1.4 Hz, 1H), 7.61 (d, J=1.4 Hz, 1H), 4.20 (m, 2H), 4.07 (d, J=6.5 Hz, 2H), 3.50 (m, 4H), 3.39 (m, 4H), 3.07 (s, 2H), 2.74 (dd, J=12.4, 12.3 Hz, 2H), 2.37 (s, 6H), 1.94 (m, 1H), 1.79 (m, 2H), 1.55 (s, 3H), 1.25 (m, 2H), 0.93 (m, 2H), 0.86 (m, 4H); ESIMS calcd. for $C_{23}H_{37}N_6O_5S$ [M+H]+ 509.3. found 509.5.

Example M37

1-methylcyclopropyl 4-((5-(4-((1-(benzyloxy)cyclopropyl)methylsulfonyl)piperazin-1-yl)pyrazin-2-yloxy)methyl)piperidine-1-carboxylate

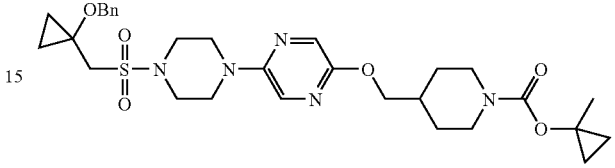

| Example | Structure | Analytical data |
|---|---|---|
| M34 | 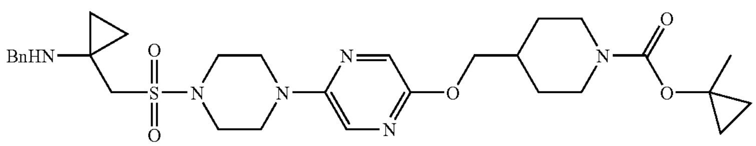 | $^1$H-NMR (400 MHz, CDCl$_3$) δ 7.86 (d, J = 1.5 Hz, 1 H), 7.61 (d, J = 1.5 Hz, 1 H), 7.31 (m, 5 H), 4.14 (m, 2 H), 4.09 (d, J = 6.5 Hz, 2 H), 3.83 (s, 2 H), 3.49 (m, 4 H), 3.38 (m, 4 H), 3.06 (s, 2 H), 2.75 (m, 2 H), 1.94 (m, 1 H), 1.79 (m, 2 H), 1.55 (s, 3 H), 1.26 (m, 2 H), 0.92 (m, 2 H), 0.87 (m, 2 H), 0.71 (m, 2 H), 0.62 (m, 2 H); ESIMS calcd. for $C_{30}H_{43}N_6O_5S$ [M + H]+ 599.3, found 599.5. |
| M35 | 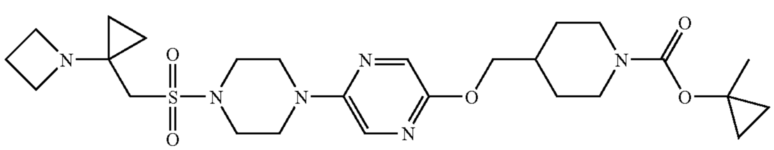 | $^1$H-NMR (400 MHz, CDCl$_3$) δ 7.86 (d, J = 1.4 Hz, 1 H), 7.61 (d, J = 1.4 Hz, 1 H), 3.82-4.21 (m, 6 H), 4.07 (d, J = 6.5 Hz, 2 H), 3.49 (m, 7 H), 3.41 (m, 5 H), 2.74 (dd, J = 12.5, 12.3 Hz, 2 H), 1.94 (m, 1 H), 1.79 (m, 2 H), 1.55 (s, 3 H), 1.24 (m, 6 H), 0.86 (m, 2 H), 0.62 (m, 2 H); ESIMS calcd. for $C_{26}H_{41}N_6O_5S$ [M + H]+ 549.3, found 549.4. |

Example M36

1-Methylcyclopropyl 4-((5-(4-((1-aminocyclopropyl)methylsulfonyl)piperazin-1-yl)pyrazin-2-yloxy)methyl)piperidine-1-carboxylate

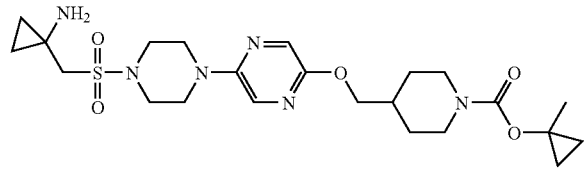

A solution of M34 (29 mg, 0.048 mmol) in ethanol (1 mL) and acetic acid (0.1 mL) is treated with 10% Pd/C (Degussa type) and hydrogenated at room pressure for 2 hours. The atmosphere is exchanged for nitrogen and the catalyst is removed by filtration through Celite®. The crude material is diluted with methanol and purified directly via a mass-directed HPLC to afford M36; $^1$H-NMR (400 MHz, CDCl$_3$) δ

A solution of M33f (147 mg, 0.23 mmol) in benzyl alcohol (1 mL) is treated with sodium hydride (12 mg, 0.5 mmol) and stirred for 24 hours. The reaction is purified directly via a mass-directed HPLC to afford M37; $^1$H-NMR (400 MHz, CDCl$_3$) δ 7.84 (d, J=1.4 Hz, 1H), 7.56 (d, J=1.4 Hz, 1H), 7.25 (m, 5H), 4.55 (s, 2H), 4.20 (m, 2H), 4.07 (d, J=6.5 Hz, 2H), 3.46 (m, 8H), 3.31 (s, 2H), 2.75 (dd, J=12.3, 12.3 Hz, 2H), 1.94 (m, 1H), 1.80 (m, 2H), 1.54 (s, 3H), 1.25 (m, 2H), 1.08 (m, 2H), 0.87 (m, 4H), 0.62 (m, 2H); ESIMS calcd. for $C_{30}H_{42}N_5O_6S$ [M+H]+ 600.3. found 600.5.

Example M38

1-Methylcyclopropyl 4-((5-(4-((1-hydroxycyclopropyl)methylsulfonyl)piperazin-1-yl)pyrazin-2-yloxy)methyl)piperidine-1-carboxylate

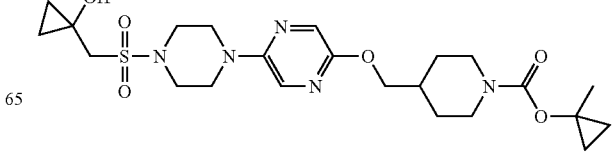

A solution of M33f (11.6 mg, 0.018 mmol) in tetrahydrofuran (0.5 mL) is treated with potassium tert-butoxide (2 mg, 0.02 mmol) and stirred for 5 minutes. The reaction is then treated with water (50 μL) and trimethylphosphine (9 μL of a 1 M solution in tetrahydrofuran, 0.009 mmol) and stirred at 45° C. overnight. The reaction is diluted with ethyl acetate and washed with water. The organics are dried over MgSO$_4$, filtered evaporated and purified via a mass-directed HPLC to afford M38; $^1$H-NMR (400 MHz, CDCl$_3$) δ 7.87 (s, 1H), 7.62 (s, 1H), 4.18 (m, 2H), 4.07 (d, J=6.5 Hz, 2H), 3.51 (m, 8H), 3.21 (s, 2H), 2.75 (dd, J=12.4, 12.4 Hz, 2H), 2.34 (bs, 1H), 1.94 (m, 1H), 1.79 (m, 2H), 1.54 (s, 3H), 1.28 (m, 2H), 1.10 (m, 2H), 0.86 (m, 4H), 0.62 (m, 2H); ESIMS calcd. for C$_{23}$H$_{36}$N$_5$O$_6$S [M+H]$^+$ 510.2. found 510.4.

Example M39

1-Methylcyclopropyl 4-((5-(4-(2-hydroxyethylsulfonyl)piperazin-1-yl)pyrazin-2-yloxy)methyl)piperidine-1-carboxylate

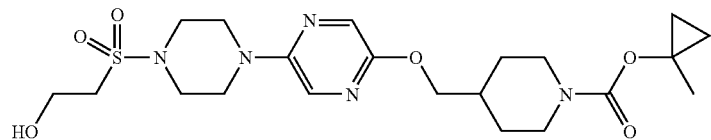

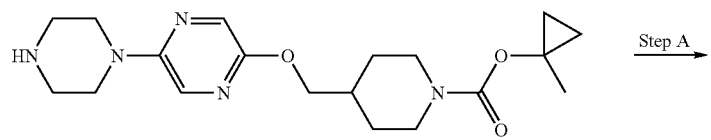

M1c

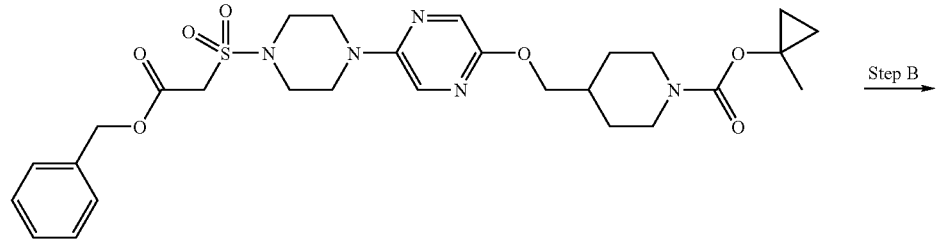

M39a

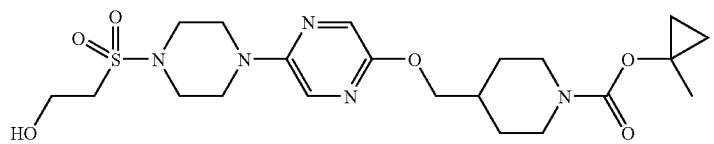

Example M39

Step A: By following a similar procedure as the one used for preparing M1 from M1c except substituting benzyl 2-(chlorosulfonyl)acetate for methyl 3-(chlorosulfonyl)propanoate, M39a is prepared; ESIMS m/z for (M+H)$^+$ C$_{28}$H$_{38}$N$_5$O$_7$S calcd: 588.3. found: 588.2.

Step B: A solution of M39a (20 mg, 0.034 mmol) in methanol (3 mL) is treated with sodium borohydride (13 mg, 0.34 mmol) and heated at 80° C. for 2 hours. The mixture is cooled, diluted with water and extracted with ethyl acetate. The organic layer is washed with brine, dried (MgSO$_4$), filtered, concentrated and purified using mass-triggered reverse phase HPLC to afford M39; $^1$H NMR (400 MHz, CDCl$_3$) δ 7.89 (d, J=1.6 Hz, 1H), 7.64 (d, J=1.6 Hz, 1H), 4.11 (s, 4H), 3.54 (m, 4H), 3.47 (m, 4H), 3.21 (m, 2H), 2.77 (m, 2H), 1.96 (m, 1H), 1.82 (m, 2H), 1.57 (s, 3H), 1.28 (m, 2H), 0.89 (m, 2H), 0.65 (m, 2H); ESIMS m/z for (M+H)$^+$ C$_{21}$H$_{34}$N$_5$O$_6$S calcd: 484.2. found: 484.2.

Example M40

1-Methylcyclopropyl 4-((5-(4-(1-hydroxy-2-methyl-propan-2-ylsulfonyl)piperazin-1-yl)pyrazin-2-yloxy)methyl)piperidine-1-carboxylate

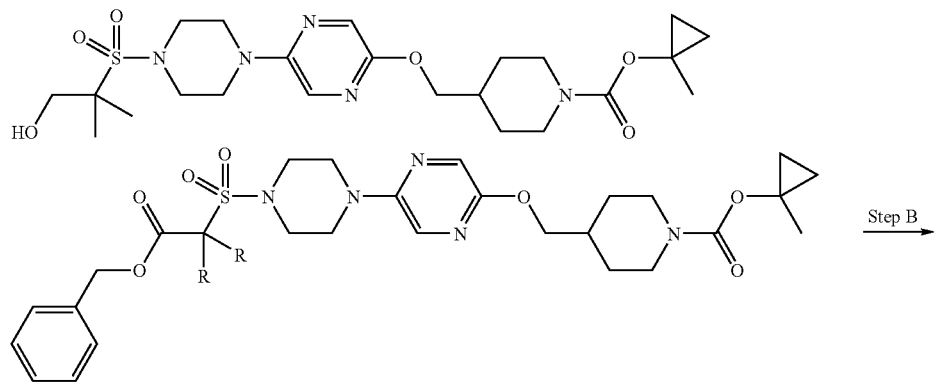

Example M40

Step A: A solution of M39a (40 mg, 0.068 mmol) in dimethylformamide (2 mL) is treated with potassium carbonate (50 mg, 0.36 mmol) and methyl iodide (46 mg, 0.32 mmol) and heated to 60° C. for 2 hours. The reaction is then partitioned between ethyl acetate and water. The organics are washed with water and brine, dried over MgSO$_4$, filtered evaporated and used crude for the next step; ESIMS m/z for (M+H)$^+$ C$_{30}$H$_{42}$N$_5$O$_7$S calcd: 616.3. found: 616.3.

By following a similar procedure as the one used for preparing M39 from M39a except substituting M40a for M39a, M40 is prepared; $^1$H NMR (400 MHz, CDCl$_3$) δ7.89 (d, J=1.6 Hz, 1H), 7.62 (d, J=1.6 Hz, 1H), 4.10 (d, J=6.4 Hz, 2H), 3.75 (s, 2H), 3.59 (m, 4H), 3.48 (m, 4H), 2.76 (m, 2H), 1.97 (m, 1H), 1.81 (m, 2H), 1.57 (s, 3H), 1.40 (m, 6H), 1.27 (m, 2H), 0.89 (m, 2H), 0.64 (m, 2H); ESIMS m/z for (M+H)$^+$ C$_{23}$H$_{38}$N$_5$O$_6$S calcd: 512.3. found: 512.2.

Example M41

1-Methylcyclopropyl 4-((5-(4-((3-methyloxetan-3-yl)methylsulfonyl)piperazin-1-yl)pyrazin-2-yloxy)methyl)piperidine-1-carboxylate

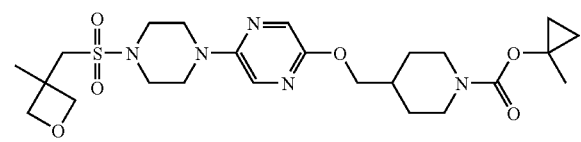

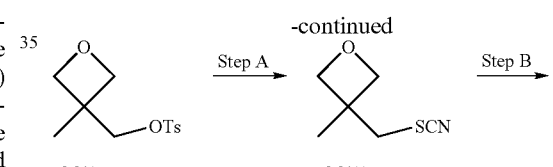

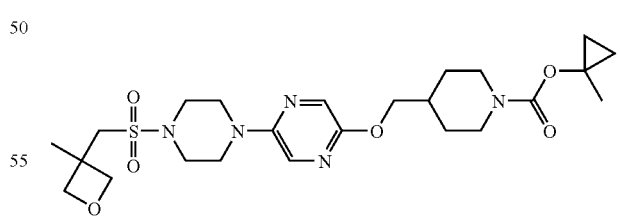

Example M41

Step A: A solution of M41a (1.01 g, 3.9 mmol) in ethanol (25 mL) is treated with potassium thiocyanate (767 mg, 7.9 mmol) and stirred at reflux overnight. The solvent is then removed to afford M41b which is used crude. ESIMS m/z for (M+H)$^+$ C$_6$H$_{10}$NOS calcd: 144.1. found: 144.0.

Step B: A suspension of M41b (crude from step A) in water (5 mL) is cooled in an ice/water bath and treated with a slow stream of chlorine gas for 30 minutes. The reaction is then extracted with diethyl ether and the organics are washed with saturated aqueous sodium bisulfate solution followed by saturated aqueous sodiumhydrogencarbonate solution. The organics are then dried over $Na_2SO_4$, filtered and evaporated to afford M41b which was used crude in the next reaction; ESIMS m/z for $(M+H)^+$ $C_5H_{10}ClO_3S$ calcd: 185.0. found: 185.0.

Step C: By following a similar procedure as the one used for preparing M1 from M1c except substituting M41c for methyl 3-(chlorosulfonyl)propanoate, M41 is prepared; $^1$H-NMR (400 MHz, $CDCl_3$) δ 7.87 (d, J=1.4 Hz, 1H), 7.62 (d, J=1.5 Hz, 1H), 4.64 (d, J=6.3 Hz, 2H), 4.46 (d, J=6.4 Hz, 2H), 4.22 (m, 2H), 4.08 (d, J=6.6 Hz, 2H), 3.53 (m, 4H), 3.40 (m, 4H), 3.25 (s, 2H), 2.74 (dd, J=12.4, 12.4 Hz, 2H), 1.94 (m, 1H), 1.79 (m, 2H), 1.65 (s, 3H), 1.55 (s, 3H), 1.25 (m, 2H), 0.86 (m, 2H), 0.62 (m, 2H); ESIMS calcd. for $C_{24}H_{38}N_5O_6S$ $[M+H]^+$ 524.3. found 524.2.

sodiumhydrogencarbonate solution. The organics are then dried over $MgSO_4$, filtered and evaporated to afford M42c which was used crude in the next reaction; ESIMS m/z for $(M+H)^+$ $C_8H_{14}NO_2S$ calcd: 188.1. found: 188.1.

Step C: By following a similar procedure as the one used for preparing M41 from M41b except substituting M42c for M41b, M42 is obtained; $^1$H NMR (400 MHz, $CD_3CN$) δ 7.86 (d, J=1.4 Hz, 1H), 7.61 (d, J=1.4 Hz, 1H), 4.19 (m, 2H), 4.07 (d, J=6.5 Hz, 2H), 4.00 (s, 2H), 3.50 (m, 5H), 3.37 (m, 4H), 2.86 (s, 2H), 2.73 (dd, J=12.4, 12.3 Hz, 2H), 2.08 (s, 3H), 1.94 (m, 1H), 1.79 (m, 2H), 1.54 (s, 3H), 1.27 (m, 2H), 1.22 (s, 6H), 0.86 (m, 2H), 0.62 (m, 2H); ESIMS m/z for $(M+H)^+$ $C_{26}H_{42}N_5O_7S$ calcd: 568.3. found: 568.4.

Example M43

1-Methylcyclopropyl 4-((5-(4-(3-hydroxy-2,2-dimethylpropylsulfonyl)piperazin-1-yl)pyrazin-2-yloxy)methyl)piperidine-1-carboxylate

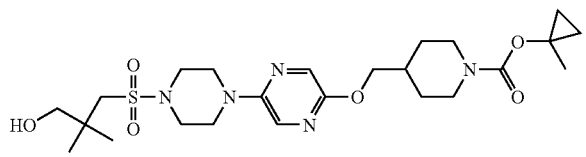

Example M42

1-Methylcyclopropyl 4-((5-(4-(3-acetoxy-2,2-dimethylpropylsulfonyl)piperazin-1-yl)pyrazin-2-yloxy)methyl)piperidine-1-carboxylate

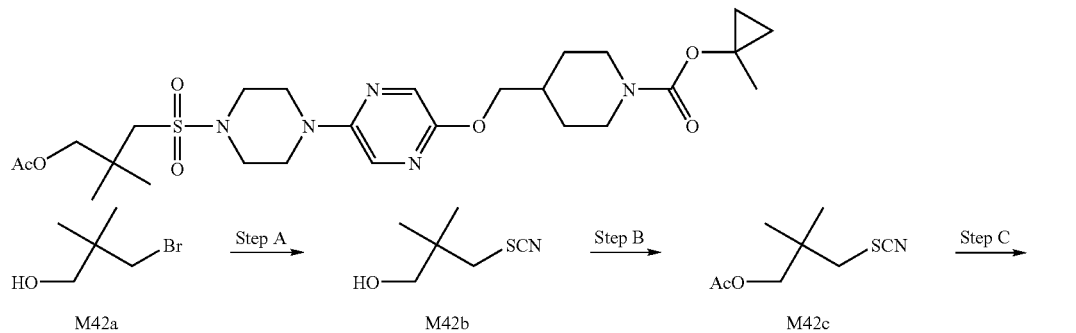

Example M42

Step A: A solution of M42a (2 g, 12 mmol) in N,N-dimethylformamide (7.2 mL) is treated with potassium thiocyanate (1.75 g, 18 mmol) and stirred at 140° C. for 4 hours. The reaction is cooled to room temperature and partitioned between diethyl ether and water. The aqueous phase is extracted with diethyl ether once more and discarded. The combined organics are dried over $MgSO_4$, filtered, evaporated and distilled on a Kugelrohr apparatus to afford M42b; ESIMS m/z for $(M+H)^+$ $C_6H_{12}NOS$ calcd: 146.1. found: 146.1.

Step B: A solution of M42b (1.54 g, 10.6 mmol) in pyridine (10 mL) is cooled in an ice/water bath and treated with acetic anhydride (10 mL). The reaction is allowed to stir overnight as the ice bath melts. The solvent is removed and the residue is partitioned between ethyl acetate and water. The organics are washed with 1 M HCl twice and then saturated aqueous Step A: A solution of M42 (48 mg, 0.085 mmol) in tetrahydrofuran (1.5 mL) is treated with lithium hydroxide (7 mg, 0.17 mmol) and stirred for 1 day. The solvent is removed and the residue is purified on silica gel using a linear gradient of 0-100% ethyl acetate in hexane to afford M43; $^1$H NMR (400 MHz, $CD_3CN$) δ 7.89 (d, J=1.4 Hz, 1H), 7.67 (s, 1H), 4.36 (s, 2H), 4.17 (m, 2H), 4.07 (d, J=6.5 Hz, 2H), 3.51 (m, 4H), 3.37 (m, 4H), 2.87 (s, 2H), 2.76 (dd, J=12.2, 11.6 Hz, 2H), 1.94 (m, 2H), 1.80 (m, 2H), 1.53 (s, 3H), 1.26 (m, 2H), 1.24 (s, 6H), 1.14 (s, 1H), 0.87 (m, 2H), 0.62 (m, 2H); ESIMS m/z for $(M+H)^+$ $C_{24}H_{40}N_5O_6S$ calcd: 526.3. found: 526.2.

Example M44

1-Methylcyclopropyl 4-((5-(4-(3-acetoxy-3-methyl-butylsulfonyl)piperazin-1-yl)pyrazin-2-yloxy)methyl)piperidine-1-carboxylate

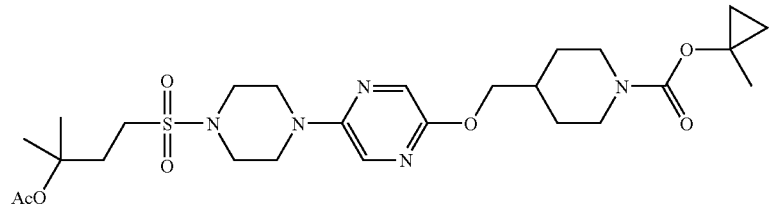

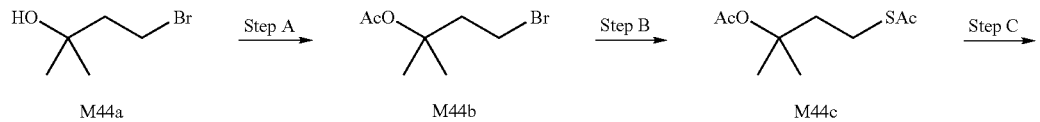

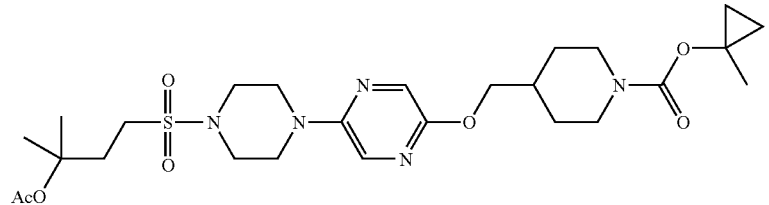

Example M44

Step A: A solution of M44a (1.48 g, 8.9 mmol) in dichloromethane (49 mL) is cooled in an ice/water bath and treated with pyridine (913 mg, 12 mmol) and acetyl chloride (868 mg, 11 mmol) and the reaction is allowed to stir overnight as the ice bath melts. The reaction is then quenched with water. The organic phase is isolated, dried over $MgSO_4$, filtered, evaporated and the residue is purified on silica gel using a linear gradient of 0-100% ethyl acetate in hexane to afford M44b; A satisfactory ESIMS could not be obtained.

Step B: A solution of M44b (750 mg, 3.6 mmol) in N,N-dimethylfromamide (10 mL) is cooled in an ice/water bath and treated with potassium thioacetate (410 mg, 3.6 mmol). The reaction is stirred overnight and partitioned between ethyl acetate and water. The organics are extracted with water once more, dried over $MgSO_4$, filtered and evaporated to afford M44c which is used in the next step crude; ESIMS m/z for $(M+Na)^+$ $C_9H_{16}NaO_3S$ calcd: 227.1. found: 227.0.

Step C: By following a similar procedure as the one used for preparing M32 from M32d except substituting M44c for M32d, M44 is prepared; $^1$H-NMR (400 MHz, $CDCl_3$) δ 7.86 (d, J=1.4 Hz, 1H), 7.61 (d, J=1.5 Hz, 1H), 4.20 (m, 2H), 4.07 (d, J=6.5 Hz, 2H), 3.50 (m, 4H), 3.44 (m, 4H), 3.02 (m, 2H), 2.74 (dd, J=13.2, 12.6 Hz, 2H), 2.22 (m, 2H), 1.98 (s, 3H), 1.96 (m, 1H), 1.80 (m, 2H), 1.55 (s, 3H), 1.48 (s, 6H), 1.25 (m, 2H), 0.86 (m, 2H), 0.62 (m, 2H); ESIMS calcd. for $C_{24}H_{38}N_5O_5S$ $[M-OAc]^+$ 508.3. found 508.4.

Example M45

1-Methylcyclopropyl 4-((5-(4-(3-hydroxy-3-methyl-butylsulfonyl)piperazin-1-yl)pyrazin-2-yloxy)methyl)piperidine-1-carboxylate

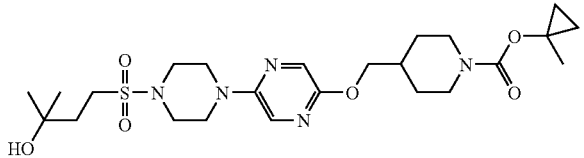

A solution of M44 (199 mg, 0.35 mmol) in methanol (3.9 mL) is treated with NaOMe (1.1 mL of a 6.4M solution, 7 mmol) and stirred for 2.5 hours. The reaction is quenched with saturated aqueous ammonium chloride and the solvent is removed. The residue is dissolved in dichloromethane and washed with water, dried over $MgSO_4$, filtered, evaporated and the residue is purified on silica gel using a linear gradient of 0-100% ethyl acetate in hexane to afford M45; $^1$H-NMR (400 MHz, $CDCl_3$) δ 7.86 (d, J=1.5 Hz, 1H), 7.62 (d, J=1.5 Hz, 1H), 4.20 (m, 2H), 4.07 (d, J=6.5 Hz, 2H), 3.50 (m, 4H), 3.44 (m, 4H), 3.09 (m, 2H), 2.74 (dd, J=12.9, 12.7 Hz, 2H), 1.92-2.01 (m, 3H), 1.79 (m, 2H), 1.55 (s, 3H), 1.27 (m, 8H), 0.86 (m, 2H), 0.62 (m, 2H); ESIMS calcd. for $C_{24}H_{40}N_5O_6S$ $[M+H]^+$ 526.3. found 526.2.

Example M46

1-Methylcyclopropyl 4-((5-(4-(2-(1-acetoxycyclo-propyl)ethylsulfonyl)piperazin-1-yl)pyrazin-2-yloxy)methyl)piperidine-1-carboxylate

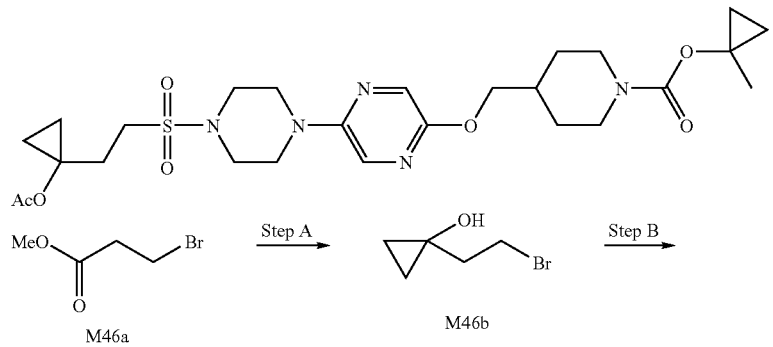

Example M46

Step A: A solution of M46a (1.99 g, 12 mmol) in diethyl ether (40 mL) is treated with titanium(IV) isopropoxide (369 mg, 1.2 mmol) followed by dropwise addition of ethylmagnesium bromide (8.8 mL of a 3 M solution in diethyl ether, 26 mmol). The reaction is quenched into ice cold 10% sulfuric acid and the aqueous phase is extracted with ether once more. The combined organics are dried over MgSO$_4$, filtered, evaporated and the residue is purified on silica gel using a linear gradient of 0-100% ethyl acetate in hexane to afford M46b; $^1$H-NMR (400 MHz, CDCl$_3$) δ 3.60 (dd, J=7.3, 7.3 Hz, 2H), 2.41 (s, 1H), 2.10 (dd, J=7.3, 7.3 Hz, 2H), 0.78 (m, 2H), 0.52 (m, 2H); A satisfactory ESIMS spectrum could not be obtained.

Step B: By following a similar procedure as the one used for preparing M33 from M33c except substituting M46b for M33c, M46 is prepared; $^1$H-NMR (400 MHz, CDCl$_3$) δ 7.86 (d, J=1.4 Hz, 1H), 7.61 (d, J=1.4 Hz, 1H), 4.20 (m, 2H), 4.07 (d, J=6.5 Hz, 2H), 3.49 (m, 4H), 3.41 (m, 4H), 3.11 (ddd, J=8.2, 5.2, 5.2 Hz, 2H), 2.74 (dd, J=12.2, 12.0 Hz, 2H), 2.25 (ddd, J=8.2, 4.7, 4.7 Hz, 2H), 2.00 (s, 3H), 1.94 (m, 1H), 1.79 (m, 2H), 1.54 (s, 3H), 1.25 (m, 2H), 0.93 (m, 2H), 0.86 (m, 2H), 0.76 (m, 2H), 0.62 (m, 2H); ESIMS calcd. for C$_{26}$H$_{40}$N$_5$O$_7$S [M+H]$^+$ 566.3. found 566.4.

Example M47

1-Methylcyclopropyl 4-((5-(4-(2-(1-hydroxycyclo-propyl)ethylsulfonyl)piperazin-1-yl)pyrazin-2-yloxy)methyl)piperidine-1-carboxylate

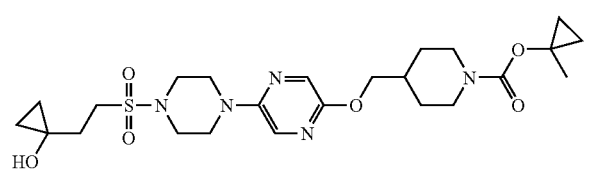

By following a similar procedure as the one used for preparing M43 from M42 except substituting M46 for M42, M47 is prepared; $^1$H-NMR (400 MHz, CDCl$_3$) δ 7.87 (d, J=1.5 Hz, 1H), 7.62 (d, J=1.4 Hz, 1H), 4.19 (m, 2H), 4.08 (d, J=6.5 Hz, 2H), 3.51 (m, 4H), 3.43 (m, 4H), 3.21 (m, 2H), 2.74 (dd, J=12.3, 12.3 Hz, 2H), 2.27 (bs, 1H), 2.08 (m, 2H), 1.94 (m, 1H), 1.79 (m, 2H), 1.55 (s, 3H), 1.25 (m, 2H), 0.86 (m, 4H), 0.62 (m, 2H), 0.56 (m, 2H); ESIMS calcd. for C$_{24}$H$_{38}$N$_5$O$_6$S [M+H]$^+$ 524.3. found 524.5.

Example M48

(R)-1-methylcyclopropyl 4-((5-(4-(pyrrolidin-3-yl-sulfonyl)piperazin-1-yl)pyrazin-2-yloxy)methyl)piperidine-1-carboxylate

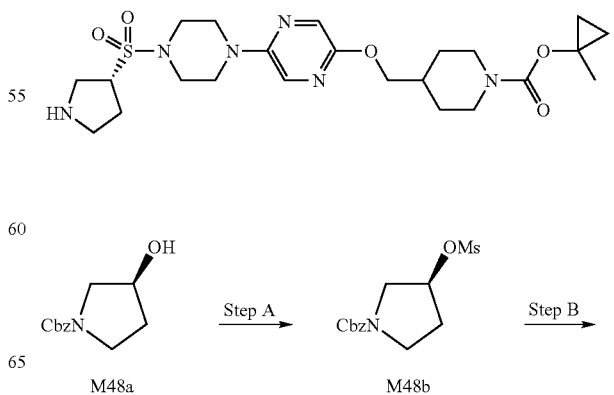

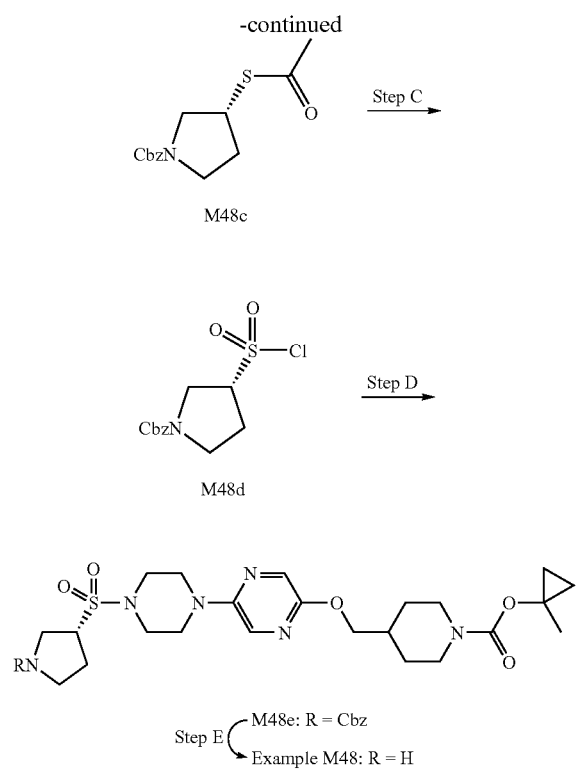

Step A: A solution of M48a (10 g, 45.2 mmol) in dichloromethane (200 mL) is cooled in an ice/water bath and treated with diisopropylethylamine (9.4 mL, 54.3 mmol) followed by dropwise addition of methanesulfonyl chloride (3.8 mL, 50 mmol). The resulting solution is stirred at 0° C. for 1 hour, concentrated and purified on silica gel using a linear gradient of 0-100% ethyl acetate in hexane to afford M48b; ESIMS m/z for (M+H)$^+$ C$_{13}$H$_{18}$NO$_5$S calcd: 300.1. found: 300.0.

Step B: A solution of M48b (14.1 g, 45 mmol) and thiolacetic acid (6.4 mL, 90 mmol) in dimethylformamide (200 mL) is treated with Cs$_2$CO$_3$ (30 g, 90 mmol) and heated at 60° C. for 14 hours. The mixture is diluted with water and extracted with ethyl acetate (3×). The organic layers are combined, washed with water (2×) and brine, dried over MgSO$_4$, filtered, concentrated, and purified on silica gel using a linear gradient of 0-100% ethyl acetate in hexane to afford M48c; ESIMS m/z for (M+H)$^+$ C$_{14}$H$_{18}$NO$_3$S calcd: 280.1. found: 280.0.

Step C: A solution of N-chlorosuccinimide (16.7 g, 125 mmol) in 2N HCl (24 mL) and acetonitrile (120 mL) is cooled in an ice/water bath and treated dropwise with a solution of M48c (9.2 g, 31 mmol) in acetonitrile (20 mL) over 1 hour. The solution is concentrated and partitioned between ethyl acetate and a saturated aqueous sodiumhydrogencarbonate solution. The organic layer is washed with aqueous sodium thiosulfate and brine, dried (MgSO$_4$), filtered and concentrated to provide M48d as a golden oil; ESIMS m/z for (M+H)$^+$ C$_{12}$H$_{15}$ClNO$_4$S calcd: 304.0. found: 304.0.

Step D: A solution of M1c (74 mg, 0.2 mmol) and M48d (67 mg, 0.22 mmol) in dichloromethane (5 mL) is treated with diisopropylethylamine (69 µL, 0.4 mmol) and stirred at room temperature for 3 hours. The mixture is concentrated and purified on silica gel using 0-100% ethyl acetate in hexane to afford M48e; ESIMS m/z for (M+H)$^+$ C$_{31}$H$_{43}$N$_6$O$_7$S calcd: 643.3. found: 643.2.

Step E: A solution of M48e (104 mg, 0.16 mmol) in methanol (10 mL) is treated with Pd/C (10%, wet) and stirred under 1 atm H$_2$ for 14 hours. The mixture is filtered through Celite®, concentrated, and purified on silica gel using 0-10% MeOH in dichloromethane to afford M48: $^1$H NMR (400 MHz, CDCl$_3$) δ 7.79 (d, J=1.2 Hz, 1H), 7.54 (d, J=1.2 Hz, 1H), 4.01 (d, J=4.8 Hz, 2H), 3.52 (m, 1H), 3.40 (m, 9H), 3.14 (m, 1H), 3.07 (dd, J=5.2, 8.4 Hz, 1H), 2.80 (m, 1H), 2.67 (m, 2H), 2.08 (m, 2H), 1.98 (s, 2H), 1.87 (m, 1H), 1.72 (m, 2H), 1.48 (s, 3H), 1.18 (m, 2H), 0.79 (m, 2H), 0.55 (m, 2H); ESIMS m/z for (M+H)$^+$ C$_{23}$H$_{37}$N$_6$O$_5$S calcd: 509.3. found: 509.2.

By following the procedure for making M48 from M48a using the appropriate commercially available starting alcohols in place of M48a and in some cases performing reductive methylations, the following examples are prepared;

| Example | Structure | Analytical data |
|---|---|---|
| M49 | 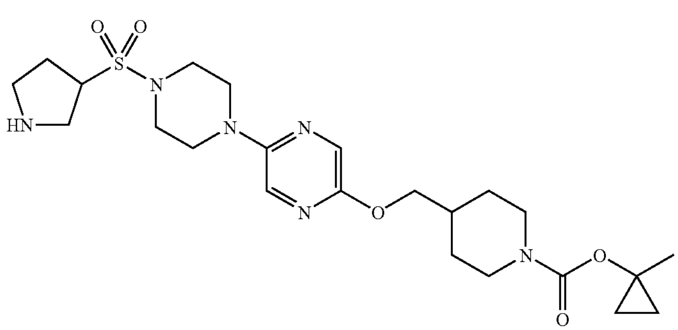 | $^1$H NMR (400 MHz, CD$_3$CN) δ 7.82 (d, J = 1.6 Hz, 1 H), 7.70 (d, J = 1.6 Hz, 1 H), 4.06 (d, J = 6.8 Hz, 2 H), 4.00 (m, 2 H), 3.63 (m, 1 H), 3.46 (m, 4 H), 3.36 (m, 4 H), 3.12 (m, 2 H), 2.95 (m, 1 H), 2.77 (m, 3 H), 2.10 (m, 5 H), 1.76 (m, 2 H), 1.73 (s, 3 H), 1.18 (m, 2 H), 0.79 (m, 2 H), 0.59 (m, 2 H); ESIMS m/z for (M + H)$^+$ C$_{23}$H$_{32}$N$_6$O$_5$S calcd: 509.3, found: 509.2. |

| Example | Structure | Analytical data |
|---|---|---|
| M50 | 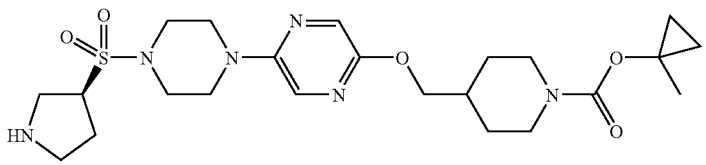 | $^1$H NMR (400 MHz, CDCl$_3$) δ 7.79 (d, J = 0.8 Hz, 1 H), 7.54 (d, J = 0.8 Hz, 1 H), 4.01 (d, J = 4.8 Hz, 2 H), 3.53 (m, 1 H), 3.40 (m, 9 H), 3.14 (m, 1 H), 3.08 (dd, J = 5.2, 8.4 Hz, 1 H), 2.81 (m, 1 H), 2.68 (m, 2 H), 2.08 (m, 2 H), 2.00 (s, 2 H), 1.87 (m, 1 H), 1.72 (m, 2 H), 1.48 (s, 3 H), 1.18 (m, 2 H), 0.79 (m, 2 H), 0.55 (m, 2 H); ESIMS m/z for (M + H)$^+$ C$_{23}$H$_{32}$N$_6$O$_5$S calcd: 509.3, found: 509.2. |
| M51 | 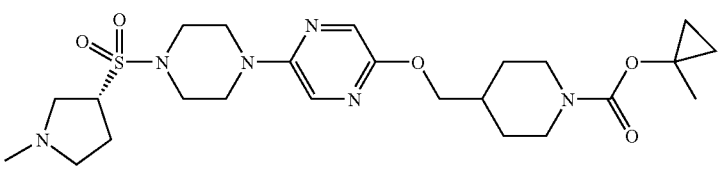 | $^1$H NMR (400 MHz, CDCl$_3$) δ 7.79 (d, J = 1.2 Hz, 1 H), 7.54 (d, J = 1.2 Hz, 1 H), 4.01 (d, J = 4.8 Hz, 2 H), 3.64 (m, 1 H), 3.40 (m, 8 H), 2.87 (m, 1 H), 2.73 (m, 1 H), 2.67 (m, 2 H), 2.61 (m, 1 H), 2.31 (s, 3 H), 2.00 (m, 2 H), 1.98 (s, 2 H), 1.72 (m, 2 H), 1.48 (s, 3 H), 1.18 (m, 2 H), 0.79 (m, 2 H), 0.55 (m, 2 H); ESIMS m/z for (M + H)$^+$ C$_{24}$H$_{39}$N$_6$O$_5$S calcd: 523.3, found: 523.2. |
| M52 | 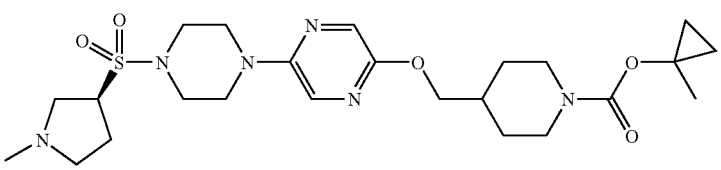 | $^1$H NMR (400 MHz, CDCl$_3$) δ 7.79 (d, J = 1.2 Hz, 1 H), 7.54 (d, J = 1.2 Hz, 1 H), 4.01 (d, J = 4.8 Hz, 2 H), 3.64 (m, 1 H), 3.40 (m, 8 H), 2.87 (m, 1 H), 2.73 (m, 1 H), 2.67 (m, 2 H), 2.61 (m, 1 H), 2.31 (s, 3 H), 2.00 (m, 2 H), 1.98 (s, 2 H), 1.72 (m, 2 H), 1.48 (s, 3 H), 1.18 (m, 2 H), 0.79 (m, 2 H), 0.55 (m, 2 H); ESIMS m/z for (M + H)$^+$ C$_{24}$H$_{39}$N$_6$O$_5$S calcd: 523.3, found: 523.2. |
| M53 | 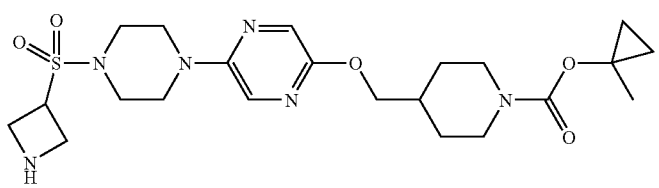 | $^1$H NMR (400 MHz, CDCl$_3$) δ 7.78 (d, J = 1.0 Hz, 1 H), 7.53 (d, J = 1.0 Hz, 1 H), 4.09 (m, 1 H), 4.05 (m, 2 H), 4.01 (d, J = 4.4 Hz, 2 H), 3.40 (m, 4 H), 3.38 (m, 4 H), 2.67 (m, 2 H), 1.94 (br s, 1 H), 1.87 (m, 1 H), 1.71 (m, 2 H), 1.48 (s, 3 H), 1.18 (m, 2 H), 0.79 (m, 2 H), 0.55 (m, 2 H); ESIMS m/z for (M + H)$^+$ C$_{22}$H$_{35}$N$_6$O$_5$S calcd: 495.2, found: 495.2. |
| M54 | 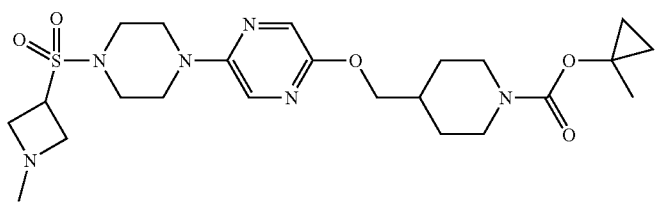 | $^1$H NMR (400 MHz, CDCl$_3$) δ 7.79 (d, J = 0.8 Hz, 1 H), 7.53 (d, J = 0.8 Hz, 1 H), 4.00 (d, J = 4.4 Hz, 2 H), 3.85 (m, 1 H), 3.57 (m, 2 H), 3.41 (m, 4 H), 3.34 (m, 4 H), 2.67 (m, 2 H), 2.29 (s, 3 H), 1.87 (m, 1 H), 1.72 (m, 2 H), 1.48 (s, 3 H), 1.18 (m, 2 H), 0.79 (m, 2 H), 0.55 (m, 2 H); ESIMS m/z for (M + H)$^+$ C$_{23}$H$_{37}$N$_6$O$_5$S calcd: 509.3, found: 509.2. |

| Example | Structure | Analytical data |
|---|---|---|
| M55 | 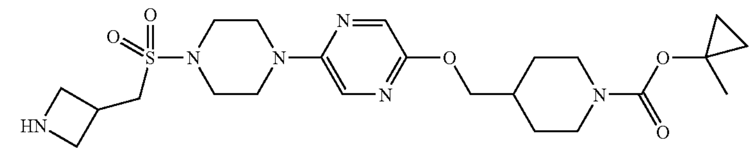 | $^1$H NMR (400 MHz, CDCl$_3$) δ 7.79 (d, J = 1.4 Hz, 1 H), 7.53 (d, J = 1.4 Hz, 1 H), 4.01 (d, J = 6.8 Hz, 2 H), 3.75 (m, 2 H), 3.43 (m, 6 H), 3.33 (m, 4 H), 3.16 (m, 2 H), 2.67 (m, 2 H), 1.87 (m, 1 H), 1.72 (m, 2 H), 1.48 (s, 3 H), 1.18 (m, 3 H), 0.79 (m, 2 H), 0.54 (m, 2 H); ESIMS m/z for (M + H)$^+$ C$_{23}$H$_{37}$N$_6$O$_5$S calcd: 509.3, found: 509.2 |
| M56 | 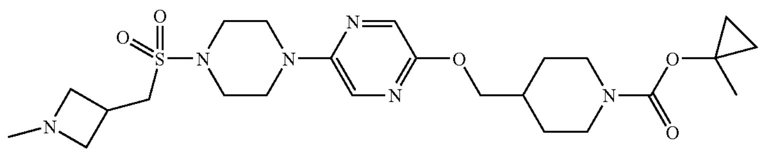 | $^1$H NMR (400 MHz, CDCl$_3$) δ 7.79 (d, J = 1.6 Hz, 1 H), 7.53 (d, J = 1.6 Hz, 1 H), 4.01 (d, J = 6.8 Hz, 2 H), 3.42 (m, 6 H), 3.33 (m, 4 H), 3.14 (d, J = 7.2 Hz, 2 H), 2.98 (m, 2 H), 2.69 (m, 2 H), 2.25 (s, 3 H), 1.87 (m, 1 H), 1.72 (m, 2 H), 1.48 (s, 3 H), 1.18 (m, 3 H), 0.80 (m, 2 H), 0.54 (m, 2 H); ESIMS m/z for (M + H)$^+$ C$_{24}$H$_{39}$N$_6$O$_5$S calcd: 523.3, found: 523.2 |

Example M57

1-Methylcyclopropyl 4-((5-(4-(2-(pyridin-3-yl)ethyl-sulfonyl)piperazin-1-yl)pyrazin-2-yloxy)methyl)piperidine-1-carboxylate

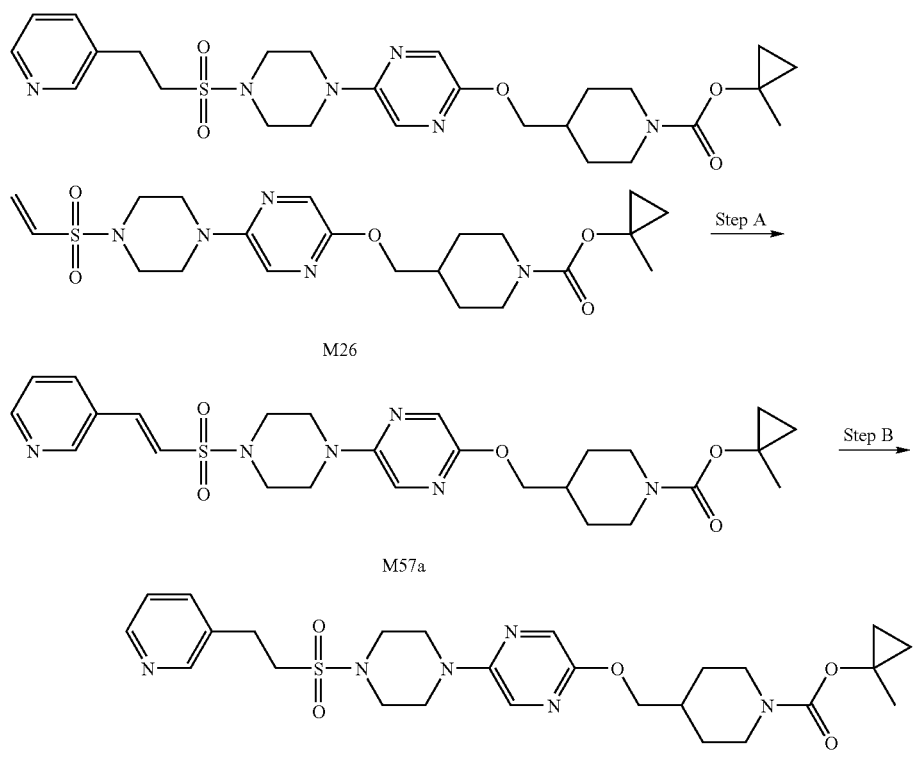

Step A: A sealed vessel containing M26 (50 mg, 0.11 mmol), 3-bromopyridine (10 μL, 0.11 mmol), Pd$_2$dba$_3$ (3.0 mg, 0.0032 mmol), tri-t-butylphosphonium tetrafluoroborate (2.0 mg, 0.0064 mmol), dicyclohexylmethylamine (45 mL, 0.21 mmol), and dioxane (1 mL) is heated at 120° C. overnight. The reaction is cooled to room temperature and is diluted with water and extracted with ethyl acetate. The organic phase is dried over MgSO$_4$, filtered, evaporated, and purified on silica gel using a linear gradient of 0 to 100% ethyl acetate in dichloromethane to afford M57a; ESIMS m/z for (M+H)$^+$ C$_{26}$H$_{34}$N$_6$O$_5$S calcd: 543.2. found: 543.2.

Step B: A solution of M57a from the previous step in ethanol (1 mL) is sparged with H$_2$ (g) for 30 minutes and then left under an atmosphere of H$_2$ (g) overnight. The reaction is filtered over Celite®, concentrated, and purified by mass directed HPLC using a linear gradient of 10 to 90% acetonitrile in water to afford M57; $^1$H NMR (CDCl$_3$, 400 MHz): δ 8.79 (s, 1H), 8.65 (m, 1H), 8.09 (m, 1H), 7.86 (d, J=1.4 Hz, 1H), 7.68 (m, 1H), 7.61 (d, J=1.4 Hz, 1H), 4.20 (m, 2H), 4.08 (d, J=6.5 Hz, 2H), 3.50 (m, 4H), 3.42 (m, 2H), 3.33 (m, 2H), 3.24 (m, 2H), 2.74 (m, 2H), 1.79 (m, 2H), 1.55 (s, 3H), 1.25 (m, 3H), 0.86 (m, 2H), 0.62 (m, 2H); ESIMS m/z for (M+H)$^+$ C$_{26}$H$_{37}$N$_6$O$_5$S calcd.: 545.3. found: 545.3.

Example M58

1-Methylcyclopropyl 4-((5-(4-(2-(pyridin-4-yl)ethylsulfonyl)piperazin-1-yl)pyrazin-2-yloxy)methyl)piperidine-1-carboxylate

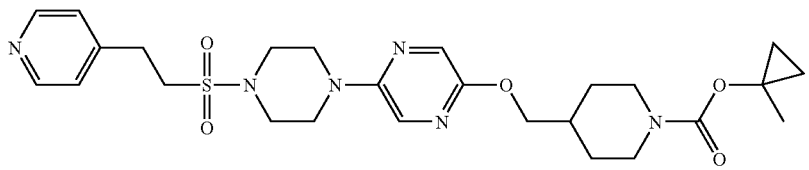

By following a similar procedure as for the preparation of M57 from M26 except substituting 4-bromopyridine for 3-bromopyridine, M58 is prepared; $^1$H NMR (CDCl$_3$, 400 MHz): δ 8.80 (s, 2H), 7.87 (s, 1H), 7.74 (s, 2H), 7.63 (s, 1H), 4.20 (m, 2H), 4.07 (d, J=6.5 Hz, 2H), 3.50 (m, 4H), 3.43 (m, 4H), 3.40 (m, 2H), 3.26 (m, 2H), 2.74 (m, 2H), 1.94 (m, 1H), 1.78 (m, 2H), 1.54 (s, 3H), 1.24 (m, 2H), 0.86 (m, 2H), 0.62 (m, 2H); ESIMS m/z for (M+H)$^+$ C$_{26}$H$_{37}$N$_6$O$_5$S calcd.: 545.3. found: 545.4.

Example M59

1-Methylcyclopropyl 4-((5-(4-sulfamoylpiperazin-1-yl)pyrazin-2-yloxy)methyl)piperidine-1-carboxylate

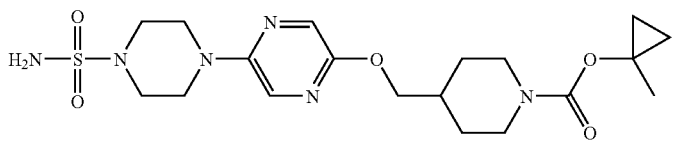

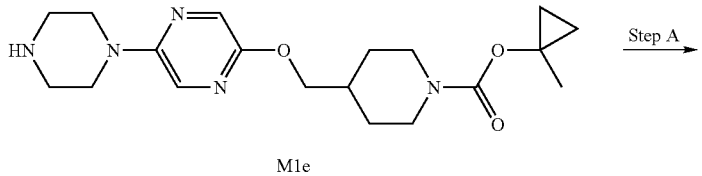

M1e

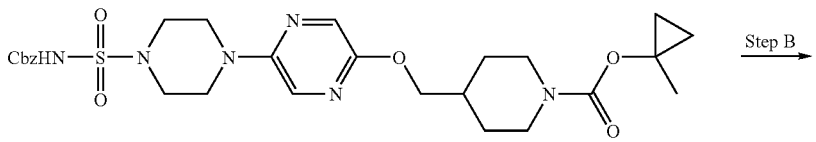

M59a

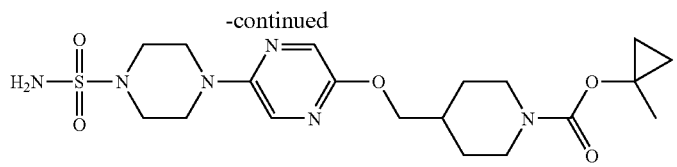

Example M59

Step A: A solution of chlorosulfonyl isocyanate (230 μL, 2.65 mmol) in n-hexanes (2.4 mL) is added dropwise to a solution M1c (1.0 g, 2.7 mmol) in n-hexanes (5 mL) and stirred at room temperature for 45 minutes. A solution of benzyl alcohol (274 μL, 2.65 mmol) and triethylamine (554 μL, 3.97 mmol) in tetrahydrofuran (10 mL) is then introduced dropwise. After 2 hr., the reaction is treated with water and extracted with dichloromethane. The organic phase is dried (MgSO$_4$), filtered, evaporated and chromatographed on silica gel using a linear gradient of 0 to 100% ethyl acetate in dichloromethane to afford M59a. ESIMS m/z for (M+H)$^+$ $C_{27}H_{37}N_6O_7S$ calcd.: 589.2. found: 589.3.

Step B: A solution of M59a (300 mg, 0.509 mmol) in ethanol (5 mL) is treated with 5% Pd/C (30 mg) and subjected to a H$_2$ (g) flush for 30 minutes. The reaction is left under an atmosphere of H$_2$ (g) overnight and is then filtered over Celite® and concentrated to afford M59; ESIMS m/z for (M+H)$^+$ $C_{19}H_{31}N_6O_5S$ calcd.: 455.2. found: 455.3.

Example M60 tert-Butyl 4-((5-(4-(morpholinosulfonyl)piperazin-1-yl)pyrazin-2-yloxy)methyl)piperidine-1-carboxylate

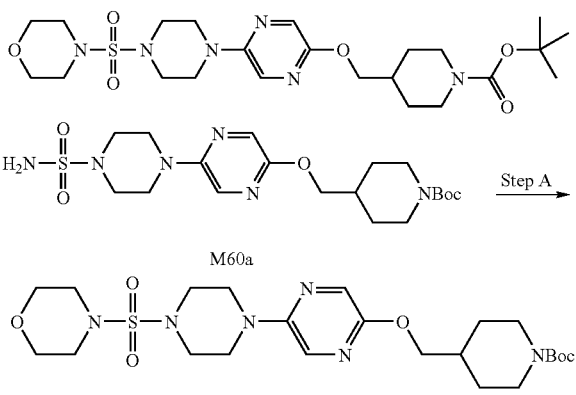

Example 60

A sample of M60a is prepared in an analogous manner to M30. A microwave reaction vial is charged M60a (64 mg, 0.14 mmol), 2-bromoethyl ether (18 μL, 0.14 mmol), potassium carbonate (40 mg, 0.28 mmol) and N,N-dimethylformamide (2 mL), sealed and heated to 150° C. for 5 minutes via microwave. The reaction is cooled to room temperature and poured over water and extracted with ethyl acetate. The organic phase is dried (MgSO$_4$), filtered, evaporated, and purified on silica gel using a linear gradient of 0 to 100% ethyl acetate in hexane to afford M60; $^1$H NMR (CDCl$_3$, 400 MHz): δ 7.95 (s, 1H), 7.91 (s, 1H), 4.16 (m, 2H), 4.11 (d, J=6.5 Hz, 2H), 3.74 (m, 4H), 3.53 (m, 6H), 3.44 (m, 1H), 3.27 (m, 5H), 2.73 (m, 2H), 1.96 (m, 1H), 1.78 (m, 2H), 1.46 (s, 9H), 1.26 (m, 2H). ESIMS m/z for (M+H—CO$_2$$^t$Bu)$^+$ $C_{18}H_{31}N_6O_4S$ calcd.: 427.2. found: 427.2.

Example M61

1-Methylcyclopropyl 4-((6-(4-(ethylsulfonyl)piperazin-1-yl)pyridin-3-yloxy)methyl)piperidine-1-carboxylate

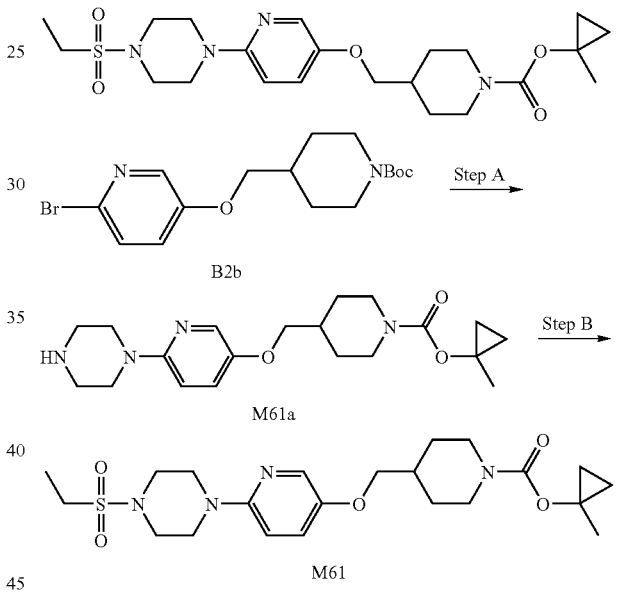

Step A: By following a similar procedure as for the one used for the preparation of M1c from B12a except substituting B2b for B12a, M61a is prepared; ESIMS m/z for (M+H)$^+$ $C_{20}H_{31}N_4O_3$ calcd.: 375.2. found: 375.2.

Step A: By following a similar procedure as the one used for preparing M1 from M1c except substituting M61a for M1c and ethanesulfonyl chloride for methyl 3-(chlorosulfonyl)propanoate, M61 is prepared; $^1$H NMR (400 MHz, CD$_3$CN) δ 7.80 (m, 1H), 7.26 (m, 1H), 6.65 (m, 1H), 4.05 (m, 2H), 3.70 (d, J=6.3 Hz, 2H), 3.52 (m, 3H), 3.37 (m, 4H), 3.21 (m, 1H), 2.92 (m, 2H), 2.67 (dd, J=12.4, 12.4 Hz, 2H), 1.86 (m, 1H), 1.72 (m, 2H), 1.47 (s, 3H), 1.31 (t, J=7.3 Hz, 3H), 1.17 (m, 2H), 0.79 (m, 2H), 0.55 (m, 2H); ESIMS m/z for (M+H)$^+$ $C_{22}H_{35}N_4O_5S$ calcd: 467.2. found: 467.2.

By following a similar procedure as for the one used for the preparation of M61 from M61a except substituting commercially available sulfonyl chlorides for M61a, the following examples are obtained:

| Example | Structure | Analytical data |
|---|---|---|
| M62 | 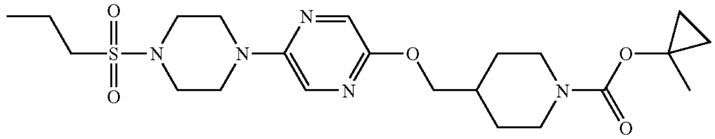 | $^1$H NMR (400 MHz, CD$_3$CN) δ 7.88 (m, 1 H), 7.24 (m, 1 H), 6.71 (m, 1 H), 4.13 (m, 2 H), 3.78 (d, J = 6.3 Hz, 2 H), 3.59 (m, 3 H), 3.43 (m, 4 H), 3.28 (m, 1 H), 2.91 (m, 2 H), 2.74 (dd, J = 12.2, 12.1 Hz, 2 H), 1.89 (m, 3 H), 1.80 (m, 2 H), 1.55 (s, 3 H), 1.24 (m, 2 H), 1.07 (t, J = 7.4 Hz, 3 H), 0.86 (m, 2 H), 0.62 (m, 2 H); ESIMS m/z for (M + H)$^+$ C$_{23}$H$_{32}$N$_4$O$_5$S calcd: 481.2, found: 481.2. |
| M63 | 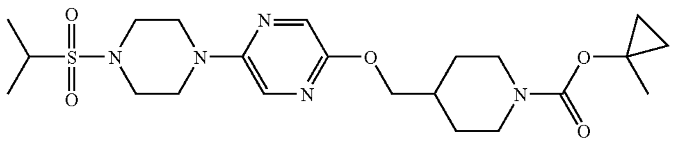 | $^1$H NMR (400 MHz, CD$_3$CN) δ 7.89 (d, J = 2.8 Hz, 1 H), 7.24 (m, 1 H), 6.67 (d, J = 8.9 Hz, 1 H), 4.12 (m, 2 H), 3.77 (d, J = 6.3 Hz, 2 H), 3.50 (m, 8 H), 3.22 (sept., J = 6.8 Hz, 1 H), 2.74 (dd, J = 12.4, 12.3 Hz, 2 H), 1.93 (m, 1 H), 1.80 (m, 2 H), 1.55 (s, 3 H), 1.36 (d, J = 6.9 Hz, 6 H), 1.23 (m, 2 H), 0.86 (m, 2 H), 0.62 (m, 2 H); ESIMS m/z for (M + H)$^+$ C$_{23}$H$_{32}$N$_4$O$_5$S calcd: 481.2, found: 481.2. |
| M64 | 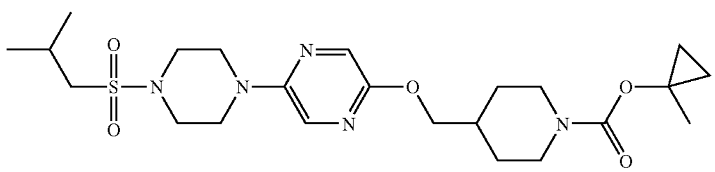 | $^1$H NMR (400 MHz, CD$_3$CN) δ 7.88 (m, 1 H), 7.24 (m, 1 H), 6.71 (m, 1 H), 4.13 (m, 2 H), 3.78 (d, J = 6.3 Hz, 2 H), 3.59 (m, 3 H), 3.40 (m, 4 H), 3.29 (m, 1 H), 2.77 (d, J = 6.6 Hz, 2 H), 2.74 (dd, J = 12.6, 12.6 Hz, 2 H), 2.31 (m, 1 H), 1.94 (m, 1 H), 1.80 (m, 2 H), 1.55 (s, 3 H), 1.24 (m, 2 H), 1.12 (d, J = 6.7 Hz, 6 H), 0.86 (m, 2 H), 0.62 (m, 2 H); ESIMS m/z for (M + H)$^+$ C$_{24}$H$_{39}$N$_4$O$_5$S calcd: 495.3, found: 495.3. |

Example M65

1-Methylcyclopropyl 4-((6-(4-(3-hydroxypropylsulfonyl)piperazin-1-yl)pyridin-3-yloxy)methyl)piperidine-1-carboxylate

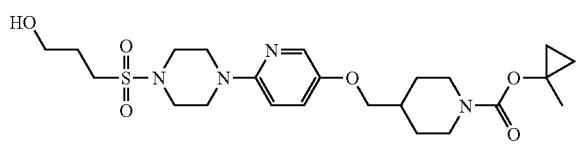

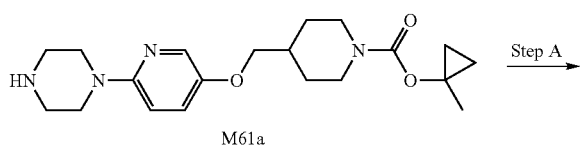

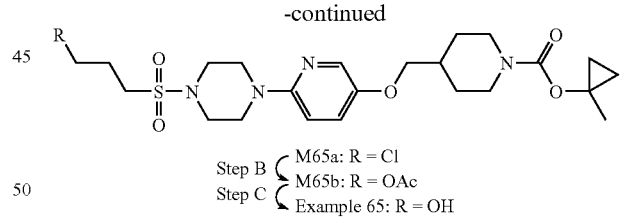

Step B ⎰ M65a: R = Cl
Step C ⎱ M65b: R = OAc
         Example 65: R = OH

Step A: By following a similar procedure as for the one used for the preparation of M6 from M1c except substituting M61a for M1c, M65a is prepared; ESIMS m/z for (M+H)$^+$ C$_{23}$H$_{36}$ClN$_4$O$_5$S calcd.: 515.2. found: 515.2.

Step B: By following a similar procedure as the one used for preparing M19 from M5 except substituting M65a for M5, M65b is prepared; ESIMS m/z for (M+H)$^+$ C$_{25}$H$_{39}$N$_4$O$_7$S calcd: 539.3. found: 539.2.

Step C: By following a similar procedure as the one used for preparing M43 from M42 except substituting M65b for M42, Example 65 is prepared; $^1$H NMR (400 MHz, CD$_3$CN) δ 7.88 (d, J=3.0 Hz, 1H), 7.19 (dd, J=9.2, 2.8 Hz, 1H), 6.68 (d, J=9.1 Hz, 1H), 4.11 (m, 2H), 3.77 (m, 4H), 3.55 (m, 4H), 3.41 (m, 4H), 3.08 (m, 2H), 2.74 (dd, J=12.3, 12.3 Hz, 2H), 2.08 (m, 2H), 1.92 (m, 2H), 1.80 (m, 2H), 1.54 (s, 3H), 1.24 (m, 2H), 0.85 (m, 2H), 0.62 (m, 2H); ESIMS m/z for (M+H)+ $C_{23}H_{37}N_4O_6S$ calcd: 497.2. found: 497.3.

Example M66

1-Methylcyclopropyl 4-((6-(4-(3-aminopropylsulfonyl)piperazin-1-yl)pyridin-3-yloxy)methyl)piperidine-1-carboxylate

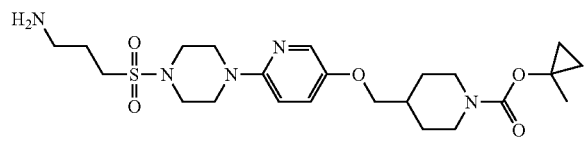

By following a similar procedure as for the one used for the preparation of M18 from M16 except substituting M65a for M16, M66 is prepared; ESIMS m/z for (M+H)+ $C_{23}H_{38}N_5O_5S$ calcd: 496.3. found: 496.3.

Example M67

1-Methylcyclopropyl 4-((6-(4-(3-(azetidin-1-yl)propylsulfonyl)piperazin-1-yl)pyridin-3-yloxy)methyl)piperidine-1-carboxylate

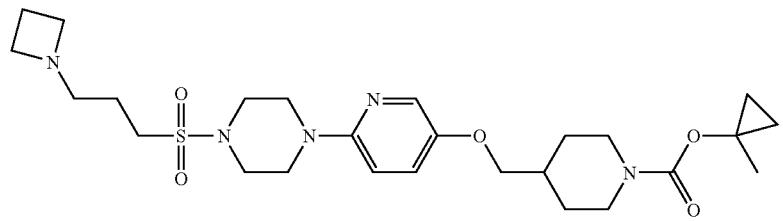

By following a similar procedure as for the one used for the preparation of M21 from M6 except substituting M65a for M21 and azetidine for 2-methylimidazole, M67 is prepared; $^1$H NMR (400 MHz, Acetone-$d_6$) δ 7.91 (d, J=3.2 Hz, 1H), 7.27 (dd, J=3.2, 9.2 Hz, 1H), 6.84 (d, J=8.8 Hz, 1H), 4.06 (m, 2H), 3.85 (d, J=6.4 Hz, 2H), 3.52 (m, 4H), 3.34 (m, 4H), 3.09 (t, J=6.8 Hz, 4H), 3.05 (m, 2H), 2.80 (m, 2H), 2.44 (d, J=6.8 Hz, 2H), 1.96 (m, 3H), 1.78 (m, 4H), 1.50 (s, 3H), 1.23 (m, 2H), 0.79 (m, 2H), 0.58 (m, 2H); ESIMS m/z for (M+H)+ $C_{26}H_{41}N_5O_5S$ calcd: 535.3. found: 536.3

Example M68

1-Methylcyclopropyl 4-((6-(4-((1-(azetidin-1-yl)cyclopropyl)methylsulfonyl)piperazin-1-yl)pyridin-3-yloxy)methyl)piperidine-1-carboxylate

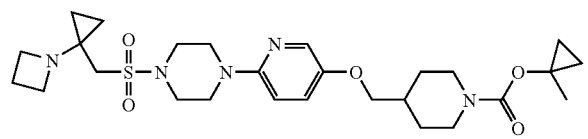

By following a similar procedure as for the one used for the preparation of M35 from M1c except substituting M61a for M1c, M68 is prepared; $^1$H-NMR (400 MHz, CDCl$_3$) δ 7.92 (d, J=2.9 Hz, 1H), 7.14 (dd, J=9.1, 3.0 Hz, 1H), 6.64 (d, J=9.1 Hz, 1H), 4.13 (m, 2H), 3.77 (d, J=6.3 Hz, 2H), 3.54 (m, 4H), 3.49 (m, 4H), 3.06 (m, 4H), 3.01 (s, 2H), 2.74 (m, 2H), 1.91 (m, 2H), 1.85 (m, 2H), 1.80 (m, 2H), 1.55 (s, 3H), 1.25 (m, 2H), 0.86 (m, 4H), 0.70 (m, 2H), 0.62 (m, 2H); ESIMS calcd. for $C_{27}H_{42}N_5O_5S$ [M+H]+ 548.3. found 548.4.

Example M69

1-Methylcyclopropyl 4-((6-(4-(2-hydroxy-2-methylpropylsulfonyl)piperazin-1-yl)pyridin-3-yloxy)methyl)piperidine-1-carboxylate

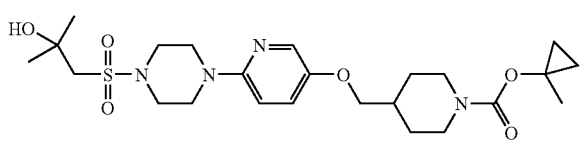

A solution of E10 (50 mg, 0.11 mmol) in tetrahydrofuran (3 mL) is cooled to −78° C. and treated excess butyllithium in hexane (2M, 250 μL). After stirring for 15 minutes, excess dry acetone is added and the reaction is stirred for an additional 30 minutes. The reaction is quenched with saturated aqueous ammonium chloride solution, warmed to room temperature and partitioned between ethyl acetate and water. The organics are isolated, dried over MgSO$_4$, filtered, evaporated and purified on silica gel using a linear gradient of 0-100% ethyl acetate in hexane to afford M69; $^1$H NMR (400 MHz, CDCl$_3$) δ 7.90 (d, J=2.8 Hz, 1H), 7.15 (dd, J=3.0, 9.1 Hz, 1H), 6.64 (d, J=9.1 Hz, 1H), 4.13 (m, 2H), 3.77 (d, J=6.3 Hz, 2H), 3.52 (m, 5H), 3.36 (m, 4H), 3.04 (s, 2H), 2.73 (m, 2H), 1.93 (m, 1H), 1.80 (m, 2H), 1.54 (s, 3H), 1.44 (s, 6H), 1.25 (m, 2H), 0.87 (m, 2H), 0.61 (m, 2H); ESIMS m/z for (M+H)+ $C_{24}H_{39}N_4O_6S$ calcd: 511.3. found: 511.5.

Example N1

1-Methylcyclopropyl 4-((5-fluoro-6-(4-(methylsulfonyl)piperazin-1-yl)pyridin-3-yloxy)methyl)piperidine-1-carboxylate

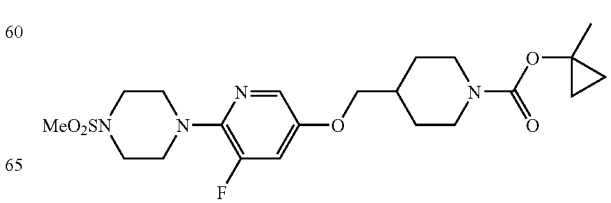

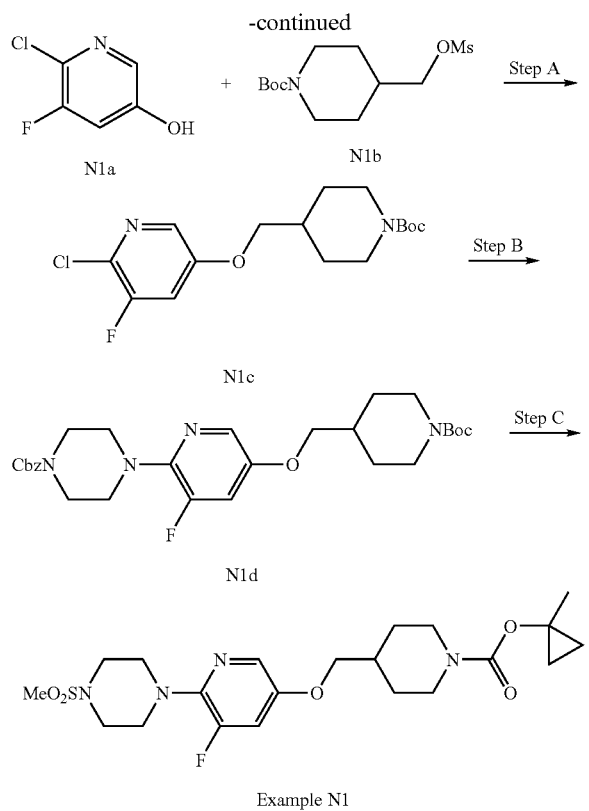

Example N1

Step A: A solution of N1a (100 mg, 0.678 mmol) and N1b (219 mg, 0.746 mmol) in N-methylpyrrolidinone (2 mL) is treated with Cs$_2$CO$_3$ (331 mg, 1.01 mmol) and heated to 80° C. for 2 hours. The reaction is cooled to room temperature, diluted with ethyl acetate and extracted with water twice. The organics are dried over MgSO$_4$, filtered, evaporated and purified on silica using a linear gradient of 0 to 50% ethyl acetate in hexanes to afford N1c. ESIMS m/z for (M+H)$^+$ C$_{16}$H$_{23}$ClFN$_2$O$_3$ calcd: 345.1. found: 289.0 (M-tBu+H$^+$).

Step B: By following a similar procedure as the one used for preparing B1 from isopropyl 4-((6-chloropyridin-3-yloxy)methyl)piperidine-1-carboxylate except substituting N1c for isopropyl 4-((6-chloropyridin-3-yloxy)methyl)piperidine-1-carboxylate and benzyl piperazine-1-carboxylate for 1-(methylsulfonyl)piperazine, N1d is prepared; ESIMS m/z for (M+H)$^+$ C$_{28}$H$_{38}$FN$_4$O$_5$ calcd: 529.3. found: 529.2.

Step C: A solution of N1d (132 mg, 0.25 mmol) in a mixture of methanol and dioxane (2 mL, 1:1) is treated with 10 mg of 5% Pd/C and hydrogenated overnight at balloon pressure. The atmosphere in the reaction is then exchanged back to N$_2$ and the reaction is filtered through Celite® and the solvent is removed. The resulting oil is coevaporated with toluene twice, dissolved in dichloromethane (2 mL) containing triethylamine (51 mg, 0.50 mmol) and treated with methanesulfonyl chloride (43 mg, 0.38 mmol) as a solution in dichloromethane (1 mL) and stirred for 1 hour. The solvent is removed and the reaction is treated with neat trifluoroacetic acid (3 mL). After 20 minutes of stirring, the solvent is removed and the reaction is coevaporated with toluene twice and treated with dichlormethane (2 mL), E3b (71 mg, 0.30 mmol) and excess triethylamine. After 2 h of stirring, the reaction is diluted with ethyl acetate, extracted with 1 M NaOH twice, saturated sodiumhydrogencarbonate once, dried over MgSO$_4$, filtered, evaporated and purified on silica gel using a linear gradient of 0 to 100% ethyl acetate in hexane; $^1$H NMR (400 MHz, CDCl$_3$) δ 7.73 (d, J=2.5 Hz, 1H), 7.07 (dd, J=2.5, 13.0 Hz, 1H), 4.14 (m, 2H), 3.80 (d, J=6.3 Hz, 2H), 3.53 (m, 4H), 3.40 (m, 4H), 2.82 (s, 3H), 2.74 (m, 2H), 1.95 (m, 1H), 1.80 (m, 2H), 1.55 (s, 3H), 1.26 (m, 2H), 0.86 (m, 2H), 0.62 (m, 2H); ESIMS m/z for (M+H)$^+$ C$_{21}$H$_{32}$FN$_4$O$_5$S calcd: 471.2. found: 471.2.

Example O1 tert-Butyl 4-((5-(4-(methylsulfonyl)-2-oxopiperazin-1-yl)pyrazin-2-yloxy)methyl)piperidine-1-carboxylate

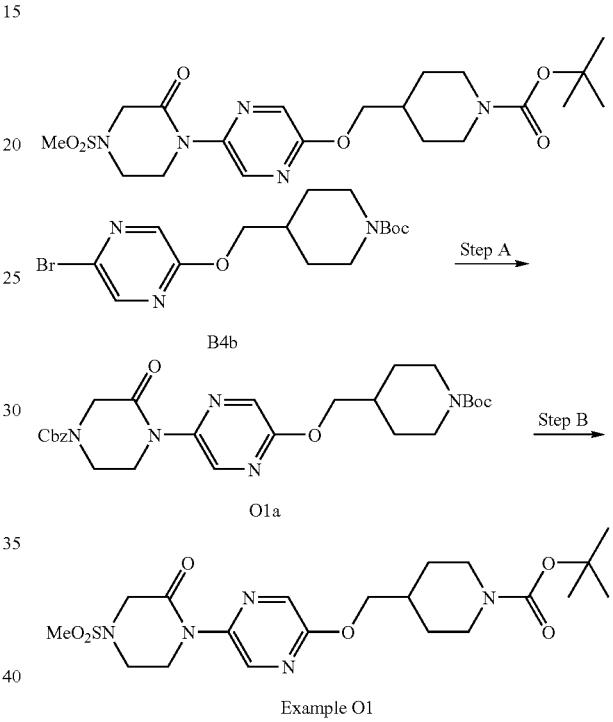

Example O1

Step A: A sealable flask is charged with B4b (4.00 g, 11 mmol) and benzyl 3-oxopiperazine-1-carboxylate (3.02 g, 13 mmol), Pd$_2$dba$_3$ (295 mg, 0.32 mmol), Xantphos (560 mg, 0.97 mmol) and Cs$_2$CO$_3$ (10.5 g, 32 mmol). The flask is evacuated and back filled with nitrogen, sealed, treated with dioxane (60 mL) and dipped into a pre-heated 120° C. bathours. After 2 hours, the reaction is cooled to room temperature, diluted with ethyl acetate and extracted with water twice. The organics are dried over MgSO$_4$, filtered, evaporated and purified on silica using a step gradient of 25, 50 and 75% ethyl acetate in hexanes to afford O1a; ESIMS m/z for (M-Boc+H)$^+$ C$_{22}$H$_{28}$N$_5$O$_4$ calcd: 426.2. found: 426.1.

Step B: A solution of O1a (80 mg, 0.15 mmol) in MeOH (2 mL) is treated with 10 mg of 5% Pd/C and hydrogenated at balloon pressure overnight. The catalyst is removed by filtration through Celite® and the solvent is removed. The residue is coevaporated with toluene twice, dissolved in dichloromethane (2 mL) and treated with excess triethylamine followed by methanesulfonyl chloride (21 mg, 0.18 mmol) dissolved in dichloromethane (1 mL). After 1 hour of stirring, the reaction is diluted with ethyl acetate and extracted with water twice. The organics are dried over MgSO$_4$, filtered, evaporated and purified on silica using a linear gradient of 30 to 100% ethyl acetate in hexanes to afford O1; $^1$H NMR (400

MHz, CDCl$_3$) δ 8.66 (d, J=1.4 Hz, 1H), 8.02 (d, J=1.4 Hz, 1H), 4.19 (d, J=6.5 Hz, 2H), 4.15 (m, 2H), 4.13 (s, 2H), 4.08 (m, 2H), 3.68 (m, 2H), 2.92 (s, 3H), 2.74 (m, 2H), 1.98 (m, 1H), 1.79 (m, 2H), 1.46 (s, 9H), 1.27 (m, 2H); ESIMS m/z for (M+Na)$^+$ C$_{20}$H$_{31}$N$_5$NaO$_6$S calcd: 492.2. found: 492.2.

Example O2

1-Methylcyclopropyl 4-((5-(4-(methylsulfonyl)-2-oxopiperazin-1-yl)pyrazin-2-yloxy)methyl)piperidine-1-carboxylate

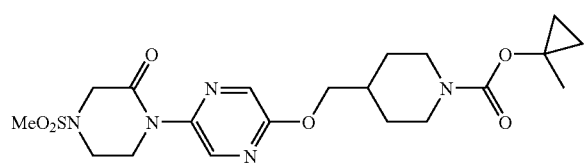

A sample of O1 (50 mg, 0.11 mmol) is treated with trifluoroacetic acid (1 mL) and aged for 20 minutes. The solvent is removed and the residue is treated with dichloromethane (2 mL), excess triethylamine and E3b (30.3 mg, 0.13 mmol). After stirring for 3 hours, the reaction is diluted with ethyl acetate, extracted with 1 M NaOH twice, saturated sodium-hydrogencarbonate once, dried over MgSO$_4$, filtered, evaporated and purified on silica gel using a linear gradient of 0 to 100% ethyl acetate in hexane; $^1$H NMR (400 MHz, CDCl$_3$) δ 8.65 (d, J=1.4 Hz, 1H), 8.02 (d, J=1.4 Hz, 1H), 4.18 (d, J=6.5 Hz, 2H), 4.12 (s, 2H), 4.12 (m, 2H), 4.07 (m, 2H), 3.67 (m, 2H), 2.93 (s, 3H), 2.72 (m, 2H), 1.98 (m, 1H), 1.79 (m, 2H), 1.54 (s, 3H), 1.25 (m, 2H), 0.87 (m, 2H), 0.62 (m, 2H); ESIMS m/z for (M+H)$^+$ C$_{20}$H$_{30}$N$_5$O$_6$S calcd: 468.2. found: 468.1.

Example O3

1-Methylcyclopropyl 4-((5-(2-oxo-4-(propylsulfonyl)piperazin-1-yl)pyrazin-2-yloxy)methyl)piperidine-1-carboxylate

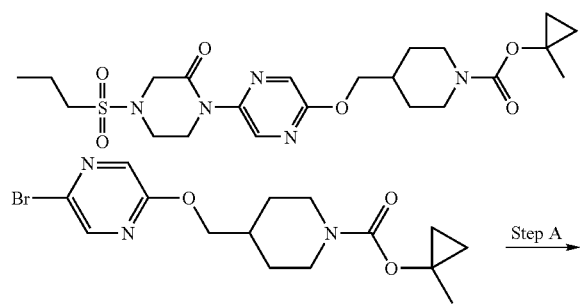

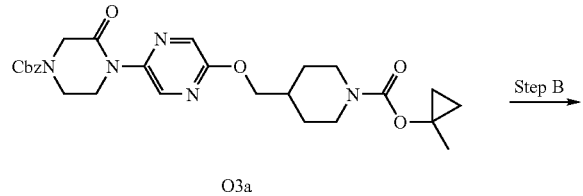

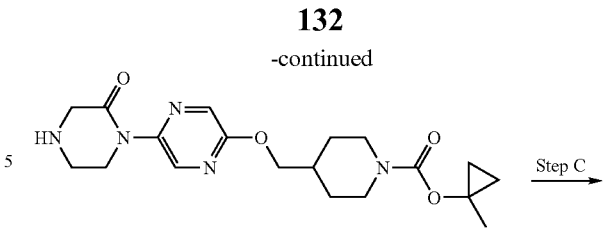

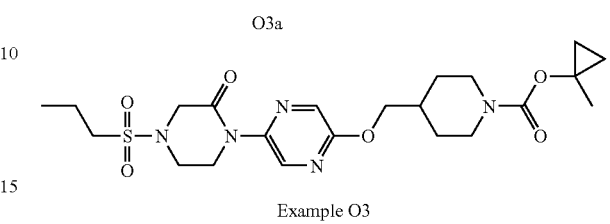

Step A: By following a similar procedure as the one used for preparing O1a from B4b except substituting M1a for B4b, O3a is prepared; ESIMS m/z for (M+H)$^+$ C$_{27}$H$_{34}$N$_5$O$_6$ calcd: 524.2. found: 524.2.

Step B: A solution of O3a (3.01 g, 0.15 mmol) in MeOH (30 mL) is treated with 101 mg of 20% Pd(OH)$_2$/C and hydrogenated at balloon pressure for 5 hours. The catalyst is removed by filtration through Celite® and the solvent is removed to afford O3b; ESIMS m/z for (M+H)$^+$ C$_{19}$H$_{28}$N$_5$O$_4$ calcd: 390.2. found: 390.1.

Step C: A solution of O3b (203 mg, 0.52 mmol) in dichloromethane (1.5 mL) is treated with triethylamine (55 mg, 0.54 mmol) and n-propanesulfonyl chloride (77 mg, 0.54 mmol) and stirred for 4 hours. Then, another identical portion of triethylamine and n-propylsulfonyl chloride is added and the reaction is stirred overnight. The reaction mixture is then loaded directly onto a silica gel column and eluted with a linear gradient of 0 to 100% ethyl acetate in hexane to afford O3; $^1$H NMR (400 MHz, CDCl$_3$) δ 8.65 (d, J=1.4 Hz, 1H), 8.02 (d, J=1.4 Hz, 1H), 4.18 (d, J=6.5 Hz, 1H), 4.17 (m, 2H), 4.15 (s, 2H), 4.05 (m, 2H), 3.70 (m, 2H), 3.01 (m, 2H), 2.75 (dd, J=12.3, 12.2 Hz, 2H), 1.98 (m, 1H), 1.89 (m, 2H), 1.79 (m, 2H), 1.55 (s, 3H), 1.26 (m, 2H), 1.09 (t, J=7.4 Hz, 3H), 0.86 (m, 2H), 0.62 (m, 2H); ESIMS m/z for (M+H)$^+$ C$_{22}$H$_{34}$N$_5$O$_6$S calcd: 496.2. found: 496.2.

Example O4

1-Methylcyclopropyl 4-((5-(4-(isopropylsulfonyl)-2-oxopiperazin-1-yl)pyrazin-2-yloxy)methyl)piperidine-1-carboxylate

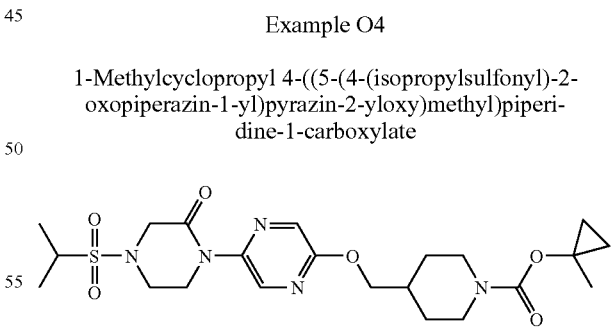

By following a similar procedure as the one used for preparing O3 from O3b except substituting 3-chloropropanesulfonyl chloride for n-propanesulfonyl chloride, O4 is prepared; $^1$H NMR (400 MHz, CDCl$_3$) δ 8.65 (d, J=1.4 Hz, 1H), 8.02 (d, J=1.4 Hz, 1H), 4.21 (s, 2H), 4.19 (m, 2H), 4.19 (d, J=6.5 Hz, 2H), 4.04 (m, 2H), 3.75 (m, 2H), 3.28 (sept., J=6.8 Hz, 1H), 2.75 (dd, J=12.3, 12.3 Hz, 2H), 1.98 (m, 1H), 1.78 (m, 2H), 1.55 (s, 3H), 1.40 (d, J=6.8 Hz, 6H), 1.26 (m, 2H), 0.87 (m, 2H), 0.62 (m, 2H); ESIMS m/z for (M+H)$^+$ C$_{22}$H$_{34}$N$_5$O$_6$S calcd: 496.2. found: 496.2.

Example O5

1-Methylcyclopropyl 4-((5-(4-(3-chloropropylsulfonyl)-2-oxopiperazin-1-yl)pyrazin-2-yloxy)methyl)piperidine-1-carboxylate

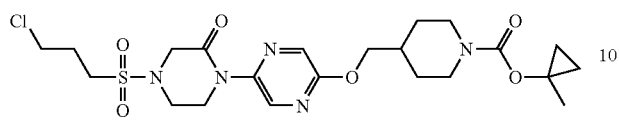

By following a similar procedure as the one used for preparing O3 from O3b except substituting iso-propylsulfonyl chloride for n-propylsulfonyl chloride, O5 is prepared; $^1$H-NMR (400 MHz, CDCl$_3$) δ 8.65 (d, J=1.4 Hz, 1H), 8.02 (d, J=1.4 Hz, 1H), 4.21 (m, 2H), 4.18 (d, J=6.6 Hz, 2H), 4.17 (s, 2H), 4.07 (m, 2H), 3.71 (m, 4H), 3.21 (m, 2H), 2.75 (dd, J=12.4, 12.3 Hz, 2H), 2.33 (m, 2H), 1.97 (m, 1H), 1.79 (m, 2H), 1.55 (s, 3H), 1.26 (m, 2H), 0.86 (m, 2H), 0.62 (m, 2H); ESIMS calcd. for C$_{22}$H$_{33}$ClN$_5$O$_6$S [M+H]$^+$ 530.2. found 530.3.

Example O6

1-Methylcyclopropyl 4-((5-(2-oxo-4-(3-(pyrrolidin-1-yl)propylsulfonyl)piperazin-1-yl)pyrazin-2-yloxy)methyl)piperidine-1-carboxylate

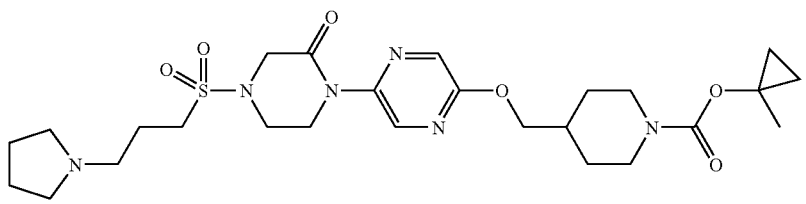

A solution of O5 (15 mg, 0.03 mmol) in N,N-dimethylformamide (700 μL) is treated with pyrrolidine (23 μL, 0.28 mmol) and subjected to microwave irradiation (200° C., 5 min). The solution is purified using mass directed reverse phase HPLC to afford O6; $^1$H NMR (400 MHz, CDCl$_3$) δ 8.67 (d, J=1.2 Hz, 1H), 8.04 (d, J=1.2 Hz, 1H), 4.20 (d, J=6.8 Hz, 2H), 4.18 (s, 2H), 4.07 (m, 2H), 3.72 (m, 2H), 3.18 (m, 2H), 2.77 (m, 2H), 2.66 (m, 2H), 2.59 (br s, 3H), 2.07 (m, 3H), 1.83 (m, 5H), 1.57 (s, 3H), 1.28 (m, 2H), 0.89 (m, 2H), 0.65 (m, 2H); ESIMS m/z for (M+H)$^+$ C$_{26}$H$_{41}$N$_6$O$_6$S calcd: 565.3. found: 565.2.

By following a similar procedure as for the one used for the preparation of O6 from O5 except substituting the appropriate amines for pyrrolidine, the following examples are obtained:

| | | |
|---|---|---|
| O7 | 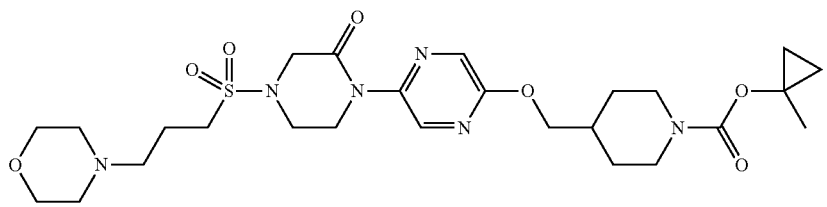 | $^1$H NMR (400 MHz, CDCl$_3$) δ 8.64 d, J = 1.6 Hz, 1H), 8.04 (d, J = 1.6 Hz, 1H), 4.20 (d, J = 6.4 Hz, 2H), 4.18 (s, 2H), 4.07(m, 2H), 3.72 (m, 4H), 3.32 (m, 8H), 3.15 (m, 2H), 2.77 (m, 2H), 2.46 (m, 4H), 2.02 (m, 4H), 1.80 (m, 2H), 1.56 (s, 3H), 1.29 (m, 2H), 0.87 (m, 2H), 0.64 (m, 2H); ESIMS m/z for (M + H)$^+$ C$_{26}$H$_{41}$N$_6$O$_7$S calcd: 581.3, found: 581.2. |
| O8 | 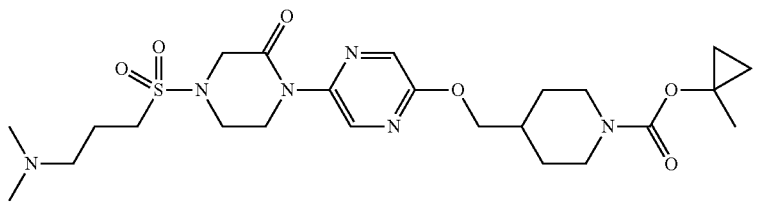 | $^1$H NMR (400 MHz, CDCl$_3$) δ 8.49 d, J = 1.4 Hz, 1H), 7.86 (d, J = 1.4 Hz, 1H), 4.03 d, J = 6.4 Hz, 2H), 4.00 (s, 2H), 3.89 (m, 2H), 3.54 (m, 2H), 2.97 (m, 2H), 2.59 (m, 2H), 2.33 (m, 2H), 2.12 (s, 6H), 1.87 (m, 4H), 1.64 (m, 2H), 1.39 (s, 3H), 1.10 (m, 2H), 0.71 (m, 2H), 0.46 (m, 2H); ESIMS m/z for (M + H)$^+$ C$_{24}$H$_{39}$N$_6$O$_6$S calcd: 539.3, found: 539.2. |

-continued

| | | |
|---|---|---|
| O9 | 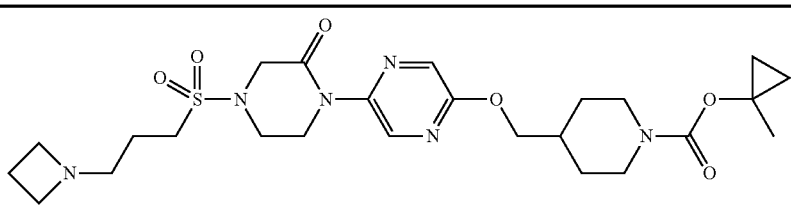 | $^1$H NMR (400 MHz, CDCl$_3$) δ 8.44 (d, J = 1.6 Hz, 1H), 7.81 (d, J = 1.6 Hz, 1H), 3.98 (d, J = 6.8 Hz, 2H), 3.94 (s, 2H), 3.84 (m, 2H), 3.48 (m, 2H), 2.98 (m, 3H), 2.89 (m, 2H), 2.54 (m, 2H), 2.31 (m, 2H), 1.86 (m, 2H), 1.78 (m, 1H), 1.65 (m, 4H), 1.34 (s, 3H), 1.05 (m, 2H), 0.66 (m, 2H), 0.41 (m, 2H); ESIMS m/z for (M + H)$^+$ C$_{25}$H$_{37}$F$_2$N$_6$O$_6$S calcd: 551.3, found: 551.3. |
| O10 | 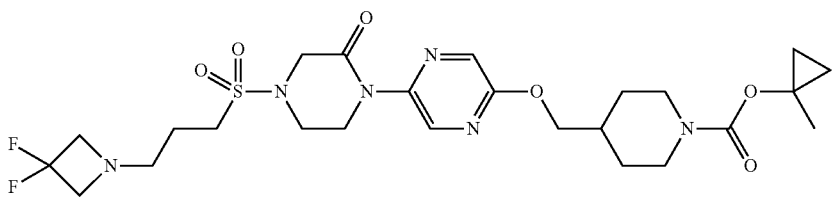 | $^1$H NMR (400 MHz, CDCl$_3$) δ 8.51 (d, J = 1.2 Hz, 1H), 7.88 (d, J = 1.2 Hz, 1H), 4.04 (d, J = 6.4 Hz, 2H), 4.01 (s, 2H), 3.91 (m, 3H), 3.56 (m, 2H), 3.43 (t, J = 12.0 Hz, 4H), 2.97 (m, 2H), 2.56 (m, 4H), 1.84 (m, 1H), 1.78 (m, 2H), 1.66 (m, 2H), 1.41 (s, 3H), 1.13 (m, 2H), 0.73 (m, 2H), 0.48 (m, 2H); ESIMS m/z for (M + H)$^+$ C$_{25}$H$_{37}$F$_2$N$_6$O$_6$S calcd: 587.3, found: 587.2. |
| O11 | 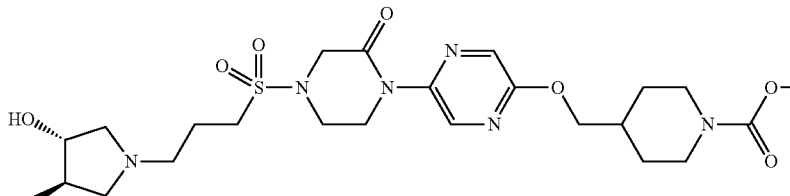 | $^1$H NMR (400 MHz, CDCl$_3$) δ 8.57 (d, J = 1.4 Hz, 1H), 7.95 (d, J = 1.4 Hz, 1H), 4.12 (d, J = 6.4 Hz, 2H), 4.10 (s, 2H), 4.06 (m, 2H), 3.98 (m, 3H), 3.64 (m, 2H), 3.07 (m, 2H), 2.94 (m, 2H), 2.68 (m, 2H), 2.58 (m, 2H), 2.43 (dd, J = 3.6, 10.4 Hz, 2H), 1.95 (m, 4H), 1.72 (m, 2H), 1.48 (s, 3H), 1.18 (m, 2H), 0.80 (m, 2H), 0.56 (m, 2H); ESIMS m/z for (M + H)$^+$ C$_{26}$H$_{41}$N$_6$O$_8$S calcd: 597.3, found: 597.3. |
| O12 | 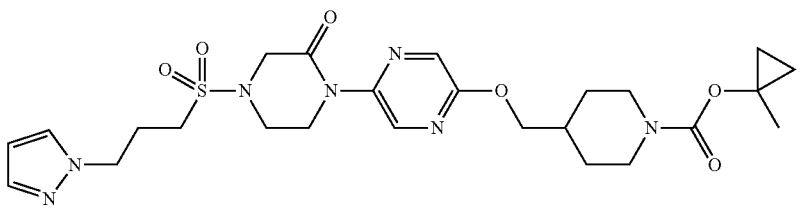 | $^1$H NMR (400 MHz, CDCl$_3$) δ 8.67 (d, J = 1.2 Hz, 1H), 8.04 (d, J = 1.2 Hz, 1H), 7.54 (d, J = 1.6 Hz, 1H), 7.46 (d, J = 1.6 Hz, 1H), 6.29 (m, 1H), 4.35 (m, 2H), 4.20 (d, J = 6.4 Hz, 2H), 4.12 (s, 2H), 4.05 (m, 3H), 3.68 (m, 2H), 2.99 (m, 2H), 2.77(m, 2H), 2.45 (m, 2H), 2.00 (m, 1H), 1.82 (m, 2H), 1.57 (s, 3H), 1.28 (m, 2H), 0.89 (m, 2H), 0.64 (m, 2H); ESIMS m/z for (M + H)$^+$ C$_{25}$H$_{36}$N$_7$O$_6$S calcd: 562.2, found: 562.3. |

Example O13

1-Methylcyclopropyl 4-((5-(2-oxo-4-(2-(pyrrolidin-1-yl)ethylsulfonyl)piperazin-1-yl)pyrazin-2-yloxy)methyl)piperidine-1-carboxylate

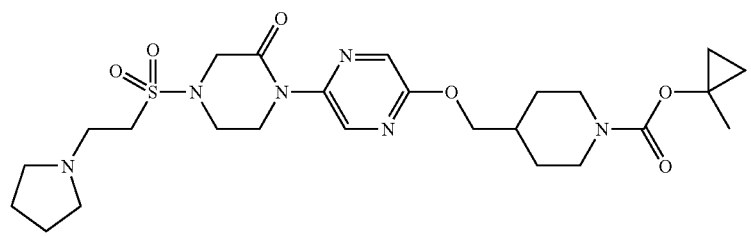

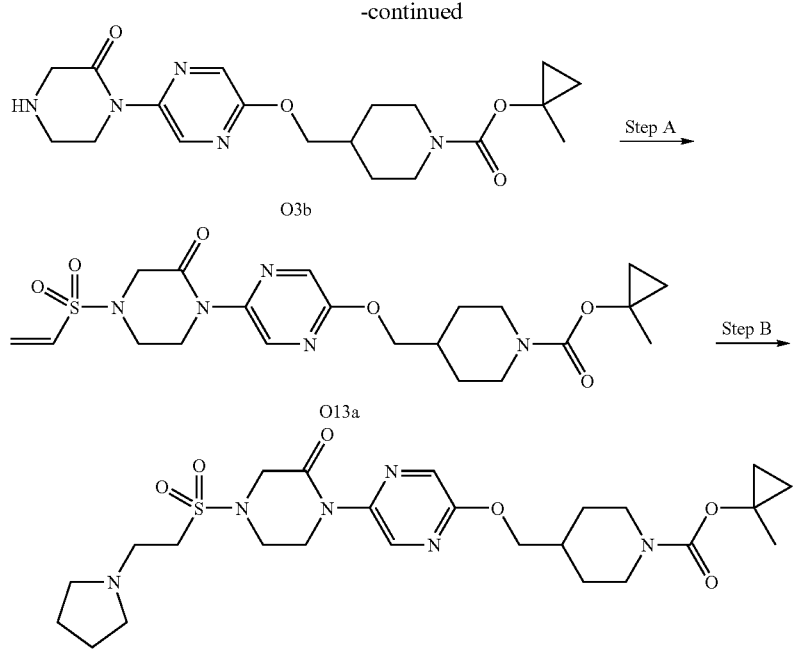

Example O13

Step A: A solution of O3b (600 mg, 1.51 mmol) in dichloromethane (10 mL) is treated with N,N-diisopropylethylamine (521 μL, 3.02 mmol) and 2-chloroethanesulfonyl chloride (173 μL, 1.66 mmol) and stirred for 2 hours. The reaction mixture is then loaded directly onto a silica gel column and eluted with a linear gradient of 0 to 100% ethyl acetate in hexane to afford O13a. ESIMS m/z for (M+H)+ $C_{21}H_{30}N_5O_6S$ calcd: 480.2. found: 480.2.

Step B: A solution of O13a (15 mg, 0.03 mmol) in N,N-dimethylformamide (1 mL) is treated with pyrrolidine (26 μL, 0.31 mmol) and stirred for 16 hours at room temperature. The solution is purified using mass-triggered reverse phase HPLC to afford O13. $^1$H NMR (400 MHz, CDCl$_3$) δ 8.68 (d, J=1.4 Hz, 1H), 8.04 (d, J=1.4 Hz, 1H), 4.20 (m, 4H), 4.06 (m, 3H), 3.72 (m, 2H), 3.34 (m, 2H), 3.04 (m, 2H), 2.75 (m, 6H), 2.00 (m, 1H), 1.83 (m, 6H), 1.57 (s, 3H), 1.28 (m, 2H), 0.89 (m, 2H), 0.64 (m, 2H); ESIMS m/z for (M+H)+ $C_{25}H_{39}N_6O_6S$ calcd: 551.3. found: 551.2.

By following a similar procedure as for the one used for the preparation of O13 from O13a except substituting the appropriate amines for pyrrolidine, the following examples are obtained:

| Ex. | Structure | Analytical data |
|---|---|---|
| O14 | 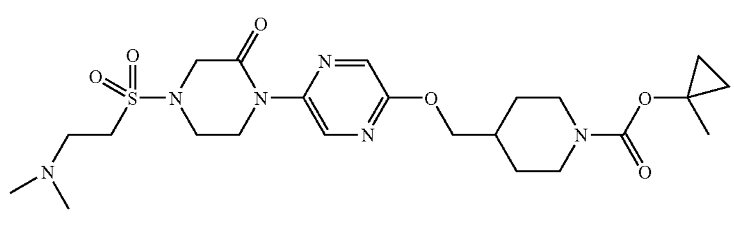 | $^1$H NMR (400 MHz, CDCl$_3$) δ 8.67 (d, J = 1.4 Hz, 1 H), 8.04 (d, J = 1.4 Hz, 1 H), 4.20 (m, 4 H), 4.06 (m, 3 H), 3.73 (m, 2 H), 3.26 (m, 2 H), 2.84 (m, 2 H), 2.77 (m, 2 H), 2.33 (s, 6 H), 2.00 (m, 1 H), 1.82 (m, 2 H), 1.57 (s, 3 H), 1.28 (m, 2 H), 0.89 (m, 2 H), 0.64 (m, 2 H); ESIMS m/z for (M + H)+ $C_{23}H_{37}N_6O_6S$ calcd: 525.3, found: 525.2. |
| O15 | 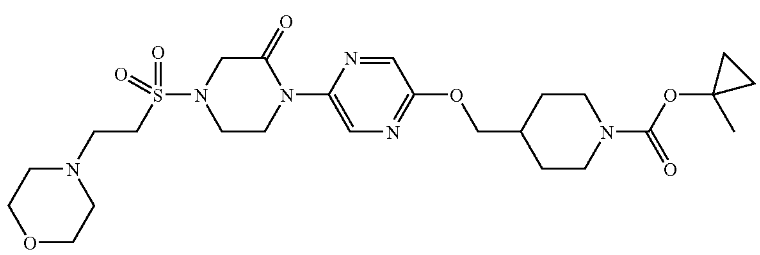 | $^1$H NMR (400 MHz, CDCl$_3$) δ 8.68 (d, J = 1.2 Hz, 1 H), 8.04 (d, J = 1.2 Hz, 1 H), 4.21 (m, 4 H), 4.08 (m, 2 H), 3.72 (m, 6 H), 3.25 (m, 2 H), 2.88 (m, 2 H), 2.77 (m, 2 H), 2.53 (m, 4 H), 2.00 (m, 1 H), 1.81 (m, 2 H), 1.57 (s, 3 H), 1.28 (m, 2 H), 0.89 (m, 2 H), 0.64 (m, 2 H); ESIMS m/z for (M + H)+ $C_{25}H_{39}N_6O_7S$ calcd: 567.3, found: 567.2. |

| Ex. | Structure | Analytical data |
|---|---|---|
| O16 | 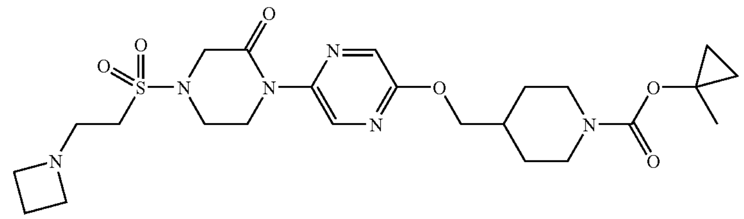 | $^1$H NMR (400 MHz, CDCl$_3$) δ 8.60 (d, J = 1.2 Hz, 1 H), 7.95 (d, J = 1.2 Hz, 1 H), 4.15 (s, 2 H), 4.12 (d, J = 6.4 Hz, 2 H), 3.97 (m, 2 H), 3.65 (m, 3 H), 3.15 (m, 3 H), 2.98 (m, 2 H), 2.77 (m, 2 H), 2.68 (m, 2 H), 1.98 (m, 2 H), 1.94 (m, 1 H), 1.73 (m, 2 H), 1.48 (s, 3 H), 1.19 (m, 2 H), 0.80 (m, 2 H), 0.55 (m, 2 H); ESIMS m/z for (M + H)$^+$ C$_{24}$H$_{37}$N$_6$O$_6$S calcd: 537.3, found: 567.3. |
| O17 | 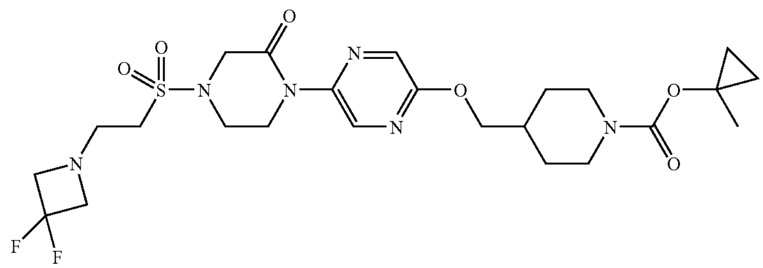 | $^1$H NMR (400 MHz, CDCl$_3$) δ 8.68 (d, J = 1.6 Hz, 1 H), 8.04 (d, J = 1.6 Hz, 1 H), 4.20 (m, 5 H), 4.07 (m, 3 H), 3.74 (m, 2 H), 3.66 (t, J = 11.6 Hz, 4 H), 3.09 (m, 4 H), 2.77 (m, 2 H), 2.00 (m, 1 H), 1.81 (m, 2 H), 1.57 (s, 3 H), 1.29 (m, 2 H), 0.89 (m, 2 H), 0.64 (m, 2 H); ESIMS m/z for (M + H)$^+$ C$_{24}$H$_{35}$F$_2$N$_6$O$_6$S calcd: 573.2, found: 573.2. |
| O18 | 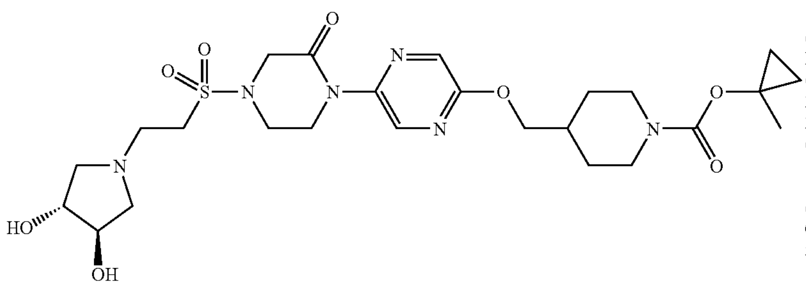 | $^1$H NMR (400 MHz, CDCl$_3$) δ 8.56 (d, J = 1.4 Hz, 1 H), 7.95 (d, J = 1.4 Hz, 1 H), 4.15 (s, 2 H), 4.12 (d, J = 6.4 Hz, 2 H), 4.03 (m, 2 H), 3.98 (m, 2 H), 3.66 (m, 2 H), 3.26 (m, 2 H), 2.95 (m, 4 H), 2.68 (m, 2 H), 2.48 (dd, J = 3.2, 10 Hz, 2 H), 1.91 (m, 1 H), 1.72 (m, 2 H), 1.48 (s, 3 H), 1.20 (m, 2 H), 0.80 (m, 2 H), 0.56 (m, 2 H); ESIMS m/z for (M + H)$^+$ C$_{25}$H$_{39}$N$_6$O$_8$S calcd: 583.3, found: 583.3. |
| O19 | 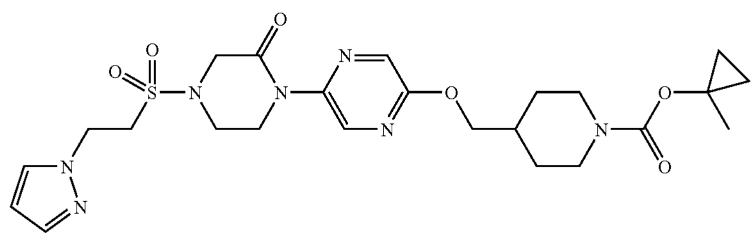 | $^1$H NMR (400 MHz, CDCl$_3$) δ 8.55 (d, J = 1.2 Hz, 1 H), 7.94 (d, J = 1.2 Hz, 1 H), 7.48 (d, J = 2.0 Hz, 1 H), 7.41 (d, J = 2.0 Hz, 1 H), 6.19 (m, 1 H), 4.52 (m, 2 H), 4.11 (d, J = 6.4 Hz, 2 H), 3.87 (s, 2 H), 3.85 (m, 2 H), 3.6 (m, 2 H), 3.40 (m, 2 H) 2.68 (m, 2 H), 1.91 (m, 1 H), 1.72 (m, 2 H), 1.48 (s, 3 H), 1.18 (m, 2 H), 0.80 (m, 2 H), 0.56 (m, 2 H); ESIMS m/z for (M + H)$^+$ C$_{24}$H$_{34}$N$_7$O$_6$S calcd: 548.2, found: 548.2. |

Example O20

1-methylcyclopropyl 4-((5-(4-((1-(dimethylamino)cyclopropyl)methylsulfonyl)-2-oxopiperazin-1-yl)pyrazin-2-yloxy)methyl)piperidine-1-carboxylate

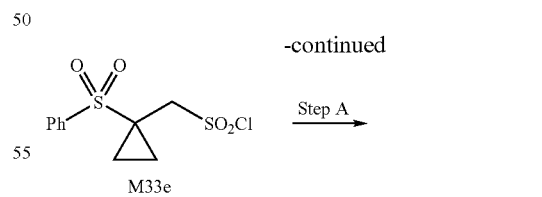

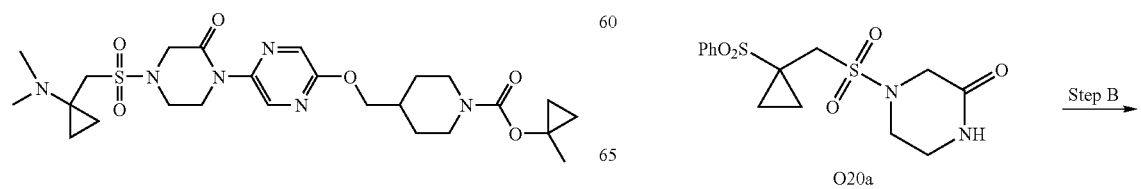

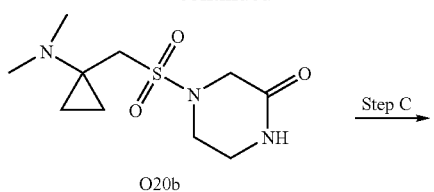

O20b

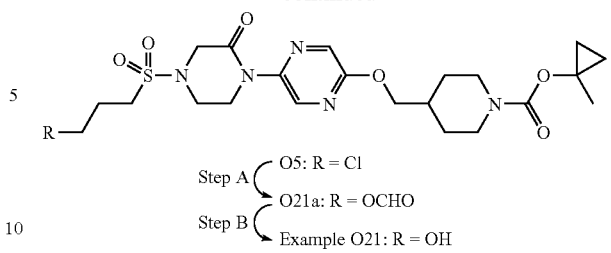

Step A ( O5: R = Cl
         O21a: R = OCHO
Step B ( Example O21: R = OH

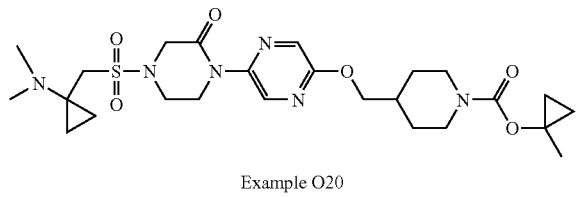

Example O20

Step A: A solution of piperazin-2-one (36.5 mg, 3.7 mmol) in dichloromethane (10 mL) is treated with triethylamine (74 mg, 0.73 mmol) followed by M33e (108 mg, 3.7 mmol) and stirred overnight. The solvent is removed and the residue is dissolved in dimethylformamide, filtered and purified by mass triggered reverse phase HPLC to afford O20a; ESIMS m/z for (M+H)$^+$ C$_{14}$H$_{19}$N$_2$O$_5$S$_2$ calcd: 359.1. found: 359.0.

Step B: A solution of O20a (71.7 mg, 0.20 mmol) in 2 M dimethylamine in tetrahydrofuran solution (6 mL, 12 mmol) is treated with potassium tert-butoxide (34 mg, 0.30 mmol) and stirred for 1 hour at room temperature The solvent is removed and the residue is dissolved in dimethylformamide, filtered and purified by mass triggered reverse phase HPLC to afford O20a; ESIMS m/z for (M+H)$^+$ C$_{10}$H$_{20}$N$_3$O$_3$S calcd: 262.1. found: 262.1.

Step C: By following a similar procedure as the one used for preparing O3a from M1a except substituting O20b for benzyl 3-oxopiperazine-1-carboxylate, O20 is prepared; $^1$H-NMR (400 MHz, CDCl$_3$) δ 8.65 (d, J=1.4 Hz, 1H), 8.02 (d, J=1.4 Hz, 1H), 4.25 (m, 2H), 4.19 (d, J=6.5 Hz, 2H), 4.17 (s, 2H), 4.04 (m, 2H), 3.70 (m, 2H), 3.16 (s, 2H), 2.75 (dd, J=15.2, 13.8 Hz, 2H), 2.29 (s, 6H), 1.98 (m, 1H), 1.80 (m, 2H), 1.55 (s, 3H), 1.27 (m, 2H), 0.88 (m, 6H), 0.62 (m, 2H); ESIMS calcd. for C$_{25}$H$_{39}$N$_6$O$_6$S [M+H]$^+$ 551.3. found 551.4.

Example O21

1-Methylcyclopropyl 4-((5-(4-(3-hydroxypropylsulfonyl)-2-oxopiperazin-1-yl)pyrazin-2-yloxy)methyl)piperidine-1-carboxylate

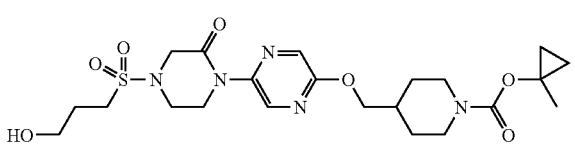

Step A: A solution of O5 (2.76 g, 5.2 mmol), NaI (790 mg, 5.3 mmol) and sodium formate (1.06 g, 15.6 mmol) in dimethylformamide (30 mL) is heated at 120° C. for 2 hours. The mixture is diluted with water, extracted with ethyl acetate (2×) and the organics are washed with water & brine, dried (MgSO$_4$), filtered and concentrated to provide crude O21a, which is used in the next step without further purification; ESIMS m/z for (M+H)$^+$ C$_{23}$H$_{34}$N$_5$O$_8$S calcd: 540.2. found: 540.2.

Step B: A solution of O21a (crude from the last step) in a 1:1 mixture of methanol and water (40 mL) is treated with sodiumhydrogencarbonate (2.2 g, 26.0 mmol) and stirred at room temperature for 1 hour. The mixture is extracted with ethyl acetate and the organics are washed with brine, dried (MgSO$_4$), filtered and concentrated. The residue is purified on silica gel using 0-10% methanol in dichloromethane to afford O21; $^1$H NMR (400 MHz, CDCl$_3$) □ 8.66 (d, J=1.4 Hz, 1H), 8.04 (d, J=1.4 Hz, 1H), 4.20 (m, 4H), 4.08 (m, 2H), 3.82 (m, 2H), 3.74 (m, 2H), 3.22 (m, 2H), 2.77 (m, 2H), 2.12 (m, 2H), 2.00 (m, 1H), 1.83 (m, 2H), 1.74 (t, J=4.8 Hz, 1H), 1.60 (s, 2H), 1.57 (s, 3H), 1.28 (m, 2H), 0.89 (m, 2H), 0.65 (m, 2H); ESIMS m/z for (M+H)$^+$ C$_{22}$H$_{34}$N$_5$O$_7$S calcd: 512.2. found: 512.2.

Example O22

1-Methylcyclopropyl 4-((5-(4-(3-acetoxypropylsulfonyl)-2-oxopiperazin-1-yl)pyrazin-2-yloxy)methyl)piperidine-1-carboxylate

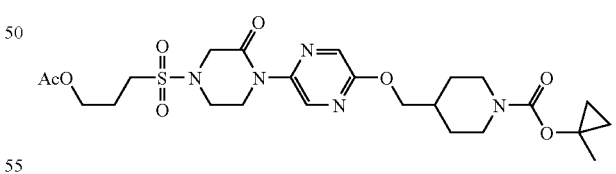

By following a similar procedure as the one used for preparing M19 from M5 except substituting O5 for M5, O22 is prepared; $^1$H-NMR (400 MHz, CDCl$_3$) δ 8.65 (d, J=1.4 Hz, 1H), 8.02 (d, J=1.4 Hz, 1H), 4.19 (m, 8H), 4.06 (m, 2H), 3.72 (m, 2H), 3.12 (m, 2H), 2.75 (dd, J=12.4, 12.4 Hz, 2H), 2.15-2.22 (m, 2H), 2.08 (s, 3H), 1.98 (m, 1H), 1.79 (m, 2H), 1.55 (s, 3H), 1.27 (m, 2H), 0.86 (m, 2H), 0.62 (m, 2H); ESIMS calcd. for C$_{24}$H$_{36}$N$_5$O$_8$S [M+H]$^+$ 554.2. found 554.2.

Example O23
1-Methylcyclopropyl 4-((5-(4-(2-(1-hydroxycyclopropyl)ethylsulfonyl)-2-oxopiperazin-1-yl)pyrazin-2-yloxy)methyl)piperidine-1-carboxylate
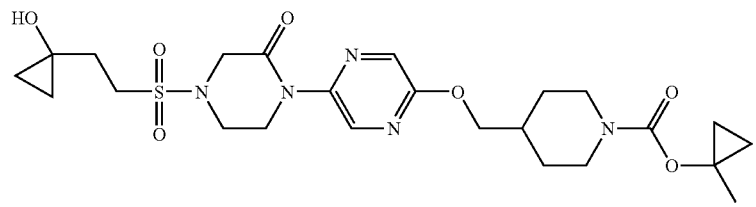
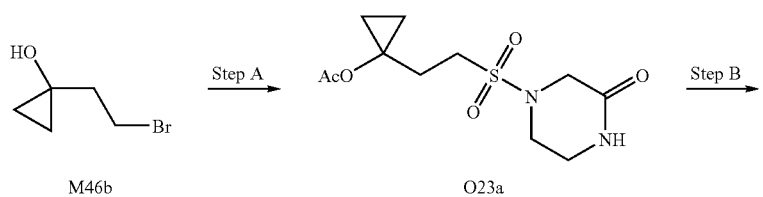
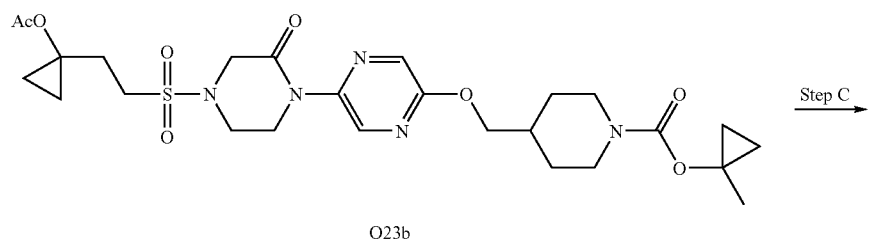
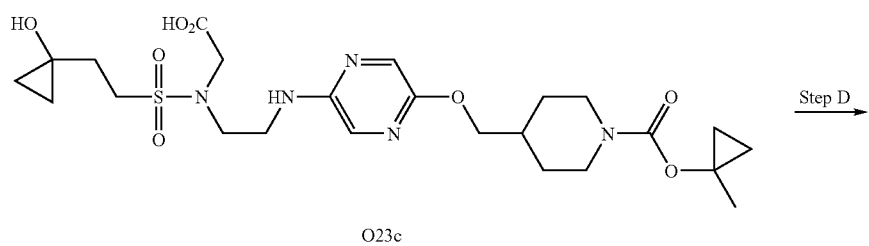
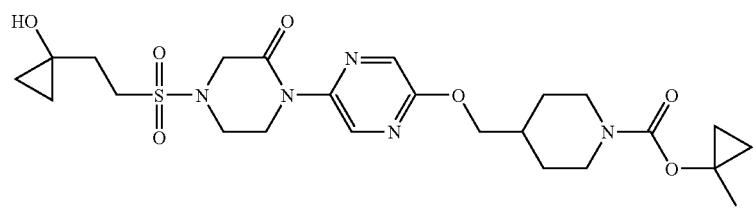
Example 23

Step A: By following a similar procedure as the one used for preparing M46 from M46b except substituting piperazin-2-one for M1c and purifying by HPLC, O23a is prepared; ESIMS calcd. for $C_{11}H_{19}N_2O_5S$ [M+H]$^+$ 291.1. found 291.1.

Step B: By following a similar procedure as the one used for preparing O3a from M1a except substituting O23b for benzyl 3-oxopiperazine-1-carboxylate, O23b is prepared; ESIMS calcd. for $C_{26}H_{38}N_5O_8S$ [M+H]$^+$ 580.2. found 580.3.

3H), 1.18 (br s, 2H), 1.06 (m, 2H), 0.67 (m, 2H), 0.42 (m, 2H); ESIMS m/z for (M+H)$^+$ $C_{22}H_{35}N_6O_6S$ calcd: 511.2. found: 511.2.

Example O25

1-Methylcyclopropyl 4-((5-(4-(2-(1,3-dioxoisoindo-lin-2-yl)ethylsulfonyl)-2-oxopiperazin-1-yl)pyrazin-2-yloxy)methyl)piperidine-1-carboxylate

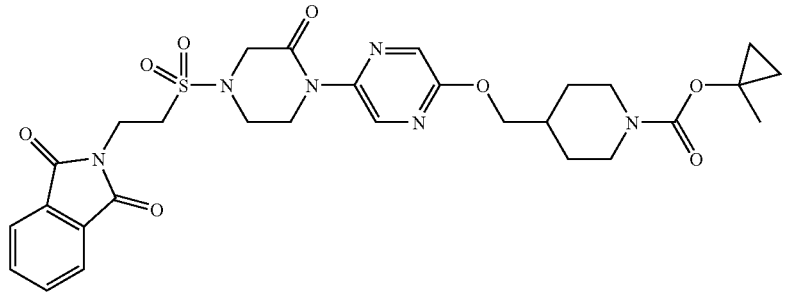

Step C: A solution of O23b (37.4 mg, 0.65 mmol) in methanol (1 mL) and water (0.1 mL) is treated with LiOH (5.7 mg, 0.1 mmol) and stirred overnight. The reaction is then purified directly by mass triggered reverse phase HPLC to afford O23c. ESIMS calcd. for $C_{24}H_{38}N_5O_8S$ [M+H]$^+$ 556.2. found 556.2.

Step D: A solution of O23c (20 mg, 0.036 mmol) in dichloromethane (1 mL) is treated with HATU (13.7 mg, 0.036 mmol) and N,N-diisopropylethylamine (4.6 mg, 0.036 mmol) and stirred overnight. The solvent is removed and the residue is dissolved in methanol and purified directly by mass triggered reverse phase HPLC. $^1$H-NMR (400 MHz, CDCl$_3$) δ 8.64 (d, J=1.4 Hz, 1H), 8.02 (d, J=1.4 Hz, 1H), 4.25 (m, 2H), 4.20 (s, 2H), 4.18 (s, 2H), 4.06 (m, 2H), 3.73 (m, 2H), 3.33 (ddd, J=7.7, 5.3, 5.3 Hz, 2H), 2.74 (dd, J=12.3, 12.1 Hz, 2H), 2.27 (s, 1H), 2.07 (ddd, J=7.7, 5.2, 5.2 Hz, 2H), 1.98 (m, 1H), 1.80 (m, 2H), 1.55 (s, 3H), 1.26 (m, 2H), 0.86 (m, 4H), 0.62 (m, 2H), 0.57 (m, 2H); ESIMS calcd. for $C_{24}H_{36}N_5O_7S$ [M+H]$^+$ 538.2. found 538.8.

Example O24

1-Methylcyclopropyl 4-((5-(4-(3-aminopropylsulfonyl)-2-oxopiperazin-1-yl)pyrazin-2-yloxy)methyl)piperidine-1-carboxylate

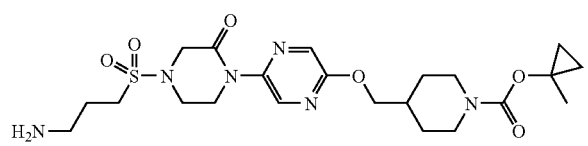

By following a similar procedure as the one used for preparing M18 from M6 except substituting O5 for M6, O23b is prepared; $^1$H NMR (400 MHz, CDCl$_3$) δ 8.45 (d, J=1.4 Hz, 1H), 7.82 (d, J=1.4 Hz, 1H), 3.99 (d, J=6.8 Hz, 2H), 3.97 (s, 2H), 3.86 (m, 2H), 3.51 (m, 2H), 2.96 (m, 2H), 2.68 (t, J=6.8 Hz, 2H), 2.55 (m, 2H), 1.78 (m, 3H), 1.60 (m, 2H), 1.35 (s, 3H), 1.18 (br s, 2H), 1.06 (m, 2H), 0.67 (m, 2H), 0.42 (m, 2H);

By following a similar procedure as the one used for preparing O3 from O3b except substituting 2-(1,3-dioxoisoindolin-2-yl)ethanesulfonyl chloride for n-propanesulfonyl chloride, O25 is prepared; $^1$H NMR (400 MHz, CDCl$_3$) δ 8.58 (d, J=1.4 Hz, 1H), 7.94 (d, J=1.4 Hz, 1H), 7.80 (m, 2H), 7.67 (m, 2H), 4.10 (s, 7H), 3.99 (m, 2H), 3.67 (m, 2H), 3.40 (t, J=6.8 Hz, 2H), 2.68 (m, 2H), 1.94 (m, 1H), 1.73 (m, 2H), 1.50 (s, 3H), 1.20 (m, 2H), 0.80 (m, 2H), 0.55 (m, 2H); ESIMS m/z for (M+H)$^+$ $C_{29}H_{35}N_6O_8S$ calcd: 627.2. found: 627.2.

Example O26

1-Methylcyclopropyl 4-((5-(4-(2-aminoethylsulfonyl)-2-oxopiperazin-1-yl)pyrazin-2-yloxy)methyl)piperidine-1-carboxylate

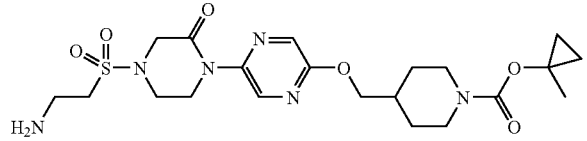

A solution of O25 (15 mg, 0.02 mmol) in ethanol (2 mL) is treated with hydrazine (8 μL, 0.24 mmol) and stirred for 1 hour. The solution is concentrated and purified using mass-triggered reverse phase HPLC to afford O26; $^1$H NMR (400 MHz, CDCl$_3$) δ 8.51 (d, J=1.4 Hz, 1H), 7.88 (d, J=1.4 Hz, 1H), 4.05 (m, 4H), 3.92 (m, 2H), 3.58 (m, 2H), 3.10 (m, 2H), 3.03 (m, 2H), 2.61 (m, 2H), 1.85 (m, 1H), 1.66 (m, 2H), 1.41 (s, 3H), 1.13 (m, 2H), 0.73 (m, 2H), 0.49 (m, 2H); ESIMS m/z for (M+H)$^+$ $C_{21}H_{33}N_6O_6S$ calcd: 497.2. found: 497.2.

Example O27

1-Methylcyclopropyl 4-((5-(4-(2-amino-2-oxoethylsulfonyl)-2-oxopiperazin-1-yl)pyrazin-2-yloxy)methyl)piperidine-1-carboxylate

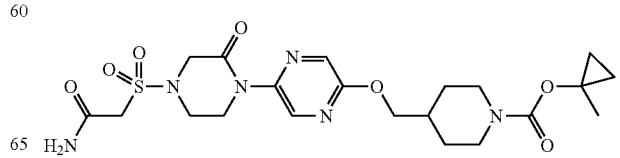

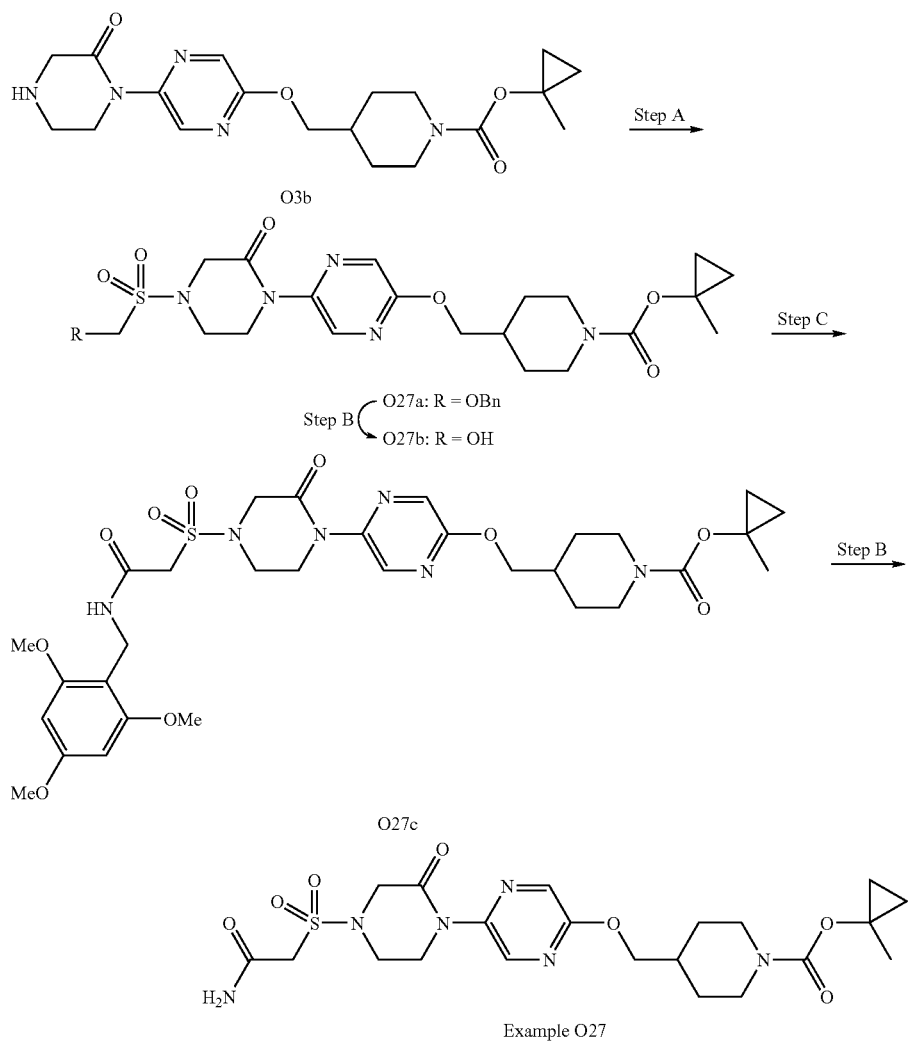

Step A: By following a similar procedure as the one used for preparing O3 from O3b except substituting benzyl 2-(chlorosulfonyl)acetate for n-propanesulfonyl chloride, O27a is prepared; ESIMS m/z for (M+H)$^+$ $C_{28}H_{36}N_5O_8S$ calcd: 602.2. found: 602.1.

Step B: By following a similar procedure as the one used for preparing M48 from M48e, O27b is prepared; $^1$H NMR (400 MHz, CDCl$_3$) δ 8.37 (d, J=1.2 Hz, 1H), 7.80 (d, J=1.2 Hz, 1H), 4.11 (s, 2H), 3.96 (m, 3H), 3.84 (m, 5H), 3.59 (m, 2H), 2.53 (m, 2H), 1.76 (m, 1H), 1.57 (m, 2H), 1.32 (s, 3H), 1.05 (m, 2H), 0.64 (m, 2H), 0.40 (m, 2H); ESIMS m/z for (M+H)$^+$ $C_{21}H_{30}N_5O_8S$ calcd: 512.2. found: 512.1.

Step C: A solution of O27b (60 mg, 0.12 mmol), HATU (89 mg, 0.23 mmol) and 2,4,6-trimethoxybenzylamine-HCl (33 mg, 0.14 mmol) in dichloromethane (10 mL) is treated with diisopropylethylamine (61 μL, 0.35 mmol) and the mixture is stirred at room temperature for 14 hours. The mixture is diluted with water and extracted with dichloromethane. The organics are dried, filtered, and concentrated to provide O27c, which was used without further purification. ESIMS m/z for (M+H)$^+$ $C_{31}H_{43}N_6O_{10}S$ calcd: 691.3. found: 691.2.

Step B: A solution of O27c (0.12 mmol) in dichloromethane (2 mL) is treated with TFA (1 mL) and aged for 1 hour at room temperature. The residue is concentrated and purified using mass-triggered reverse phase HPLC to afford O27; $^1$H NMR (400 MHz, CDCl$_3$) δ 8.59 (d, J=1.6 Hz, 1H), 7.95 (d, J=1.6 Hz, 1H), 4.19 (s, 2H), 4.12 (d, J=6.4 Hz, 2H), 3.99 (m, 2H), 3.90 (s, 2H), 3.72 (m, 2H), 2.68 (m, 3H), 1.89 (m, 1H), 1.72 (m, 2H), 1.48 (s, 3H), 1.13 (m, 2H), 0.80 (m, 2H), 0.55 (m, 2H); ESIMS m/z for (M+H)$^+$ $C_{21}H_{31}N_6O_7S$ calcd: 511.2. found: 511.2.

Example O28

1-Methylcyclopropyl 4-((5-(4-(2-(dimethylamino)-2-oxoethylsulfonyl)-2-oxopiperazin-1-yl)pyrazin-2-yloxy)methyl)piperidine-1-carboxylate

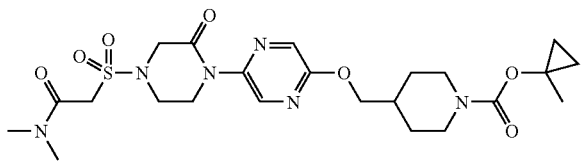

By following a similar procedure as the one used for preparing O27c from O27b except substituting dimethylamine-HCl for 2,4,6-trimethoxybenzylamine-HCl, O28 is prepared; $^1$H NMR (400 MHz, CDCl$_3$) δ 8.67 (d, J=1.6 Hz, 1H), 8.03 (d, J=1.6 Hz, 1H), 4.28 (s, 2H), 4.19 (m, 4H), 4.06 (m, 2H), 3.82 (s, 2H), 3.23 (s, 3H), 3.04 (s, 3H), 2.77 (m, 2H), 2.00 (m, 1H), 1.81 (m, 2H), 1.57 (s, 3H), 1.28 (m, 2H), 0.88 (m, 2H), 0.64 (m, 2H); ESIMS m/z for (M+H)$^+$ $C_{23}H_{35}N_6O_7S$ calcd: 539.2. found: 539.2.

Example O29

1-Methylcyclopropyl 4-((5-(4-(1-(dimethylamino)-2-methyl-1-oxopropan-2-ylsulfonyl)-2-oxopiperazin-1-yl)pyrazin-2-yloxy)methyl)piperidine-1-carboxylate

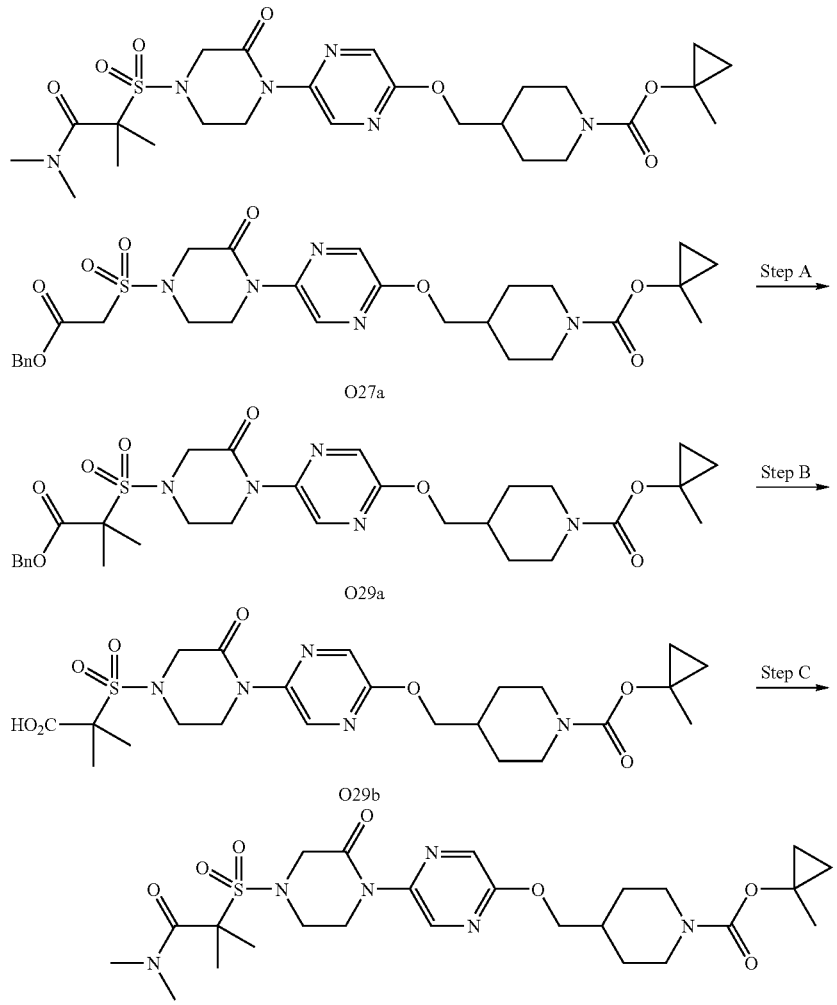

Example O29

Step A: A solution of O27a (200 mg, 0.33 mmol) in dimethylformamide (5 mL) is treated with potassium carbonate (138 mg, 1.0 mmol) and iodomethane (63 µL, 1.0 mmol) and heated at 70° C. for 1 hour. The mixture is diluted with water and extracted with ethyl acetate. The organic layer is washed with water and brine, dried (MgSO$_4$), filtered and concentrated to provide O29a; ESIMS m/z for (M+H)$^+$ C$_{30}$H$_{40}$N$_5$O$_8$S calcd: 630.3. found: 630.3.

Step B: A solution of O29a (crude from Step A) and ammonium formate (~1 mmol) in methanol (5 mL) is treated with Pd/C (wet, 10%) and heated at 80° C. for 1 hour. The mixture is cooled, filtered, and the filtrate is washed with water and ethyl acetate. The layers are separated and the organic layer is washed with 1N HCl and brine, then dried over MgSO$_4$, filtered and concentrated. The residue is purified using mass-triggered reverse phase HPLC to afford O29b; $^1$H NMR (400 MHz, CDCl$_3$) δ 8.61 (d, J=1.6 Hz, 1H), 8.05 (d, J=1.6 Hz, 1H), 4.43 (s, 2H), 4.21 (d, J=6.4 Hz, 2H), 4.05 (m, 2H), 3.87 (br s, 2H), 2.78 (m, 2H), 2.03 (m, 1H), 1.82 (s, 6H), 1.57 (s, 3H), 1.28 (m, 2H), 0.89 (m, 2H), 0.65 (m, 2H); ESIMS m/z for (M+H)$^+$ C$_{23}$H$_{34}$N$_5$O$_8$S calcd: 540.2. found: 540.1.

Step C: By following a similar procedure as the one used for preparing O27c from O27b except substituting dimethylamine-HCl for 2,4,6-trimethoxybenzylamine-HCl and O29b for O27c, O29 is prepared; $^1$H NMR (400 MHz, CDCl$_3$) δ 8.51 (d, J=1.4 Hz, 1H), 7.87 (d, J=1.4 Hz, 1H), 4.14 (s, 2H), 4.04 (d, J=6.4 Hz, 2H), 3.88 (m, 2H), 3.66 (s, 2H), 2.60 (m, 2H), 1.84 (m, 1H), 1.65 (m, 2H), 1.54 (s, 6H), 1.41 (s, 6H), 1.11 (m, 2H), 0.73 (m, 2H), 0.48 (m, 2H); ESIMS m/z for (M+H)$^+$ C$_{25}$H$_{39}$N$_6$O$_7$S calcd: 567.3. found: 567.2.

Example O30

1-Methylcyclopropyl 4-((5-(4-(1-amino-2-methyl-1-oxopropan-2-ylsulfonyl)-2-oxopiperazin-1-yl)pyrazin-2-yloxy)methyl)piperidine-1-carboxylate

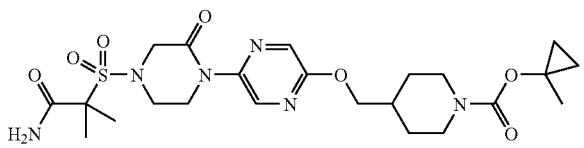

By following a similar procedure as the one used for preparing O27 from O27b except substituting O29b for O27b, O30 is prepared; $^1$H NMR (400 MHz, CDCl$_3$) δ 8.66 (d, J=1.4 Hz, 1H), 8.03 (d, J=1.4 Hz, 1H), 4.23 (s, 2H), 4.20 (d, J=6.4 Hz, 2H), 4.02 (m, 2H), 3.78 (s, 2H), 2.77 (m, 2H), 2.00 (m, 1H), 1.81 (s, 6H), 1.57 (s, 3H), 1.27 (m, 2H), 0.89 (m, 2H), 0.64 (m, 2H); ESIMS m/z for (M+H)$^+$ C$_{23}$H$_{35}$N$_6$O$_7$S calcd: 539.2. found: 539.2.

Example O31

1-Methylcyclopropyl 4-((5-(4-(2-(2-tert-butoxy-2-oxoethylamino)ethylsulfonyl)-2-oxopiperazin-1-yl)pyrazin-2-yloxy)methyl)piperidine-1-carboxylate

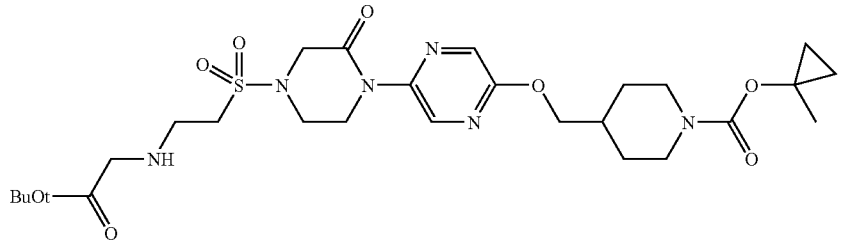

A solution of O13a (50 mg, 0.10 mmol), t-butylglycine-HCl (105 mg, 0.62 mmol) and diisopropylethylamine (108 μL, 0.62 mmol) in methanol (2 mL) and dimethylformamide (2 mL) and stirred at room temperature for 14 hours. The mixture is diluted with water and extracted with ethyl acetate. The organics are washed with water then brine, dried over MgSO$_4$, and filtered. The residue is concentrated and purified using mass-triggered reverse phase HPLC to afford O31; $^1$H NMR (400 MHz, CDCl$_3$) δ 8.66 (d, J=1.2 Hz, 1H), 8.04 (d, J=1.2 Hz, 1H), 4.20 (s, 4H), 4.07 (m, 2H), 3.76 (m, 2H), 3.48 (s, 2H), 3.40 (m, 2H), 3.28 (m, 2H), 2.77 (m, 2H), 2.00 (m, 1H), 1.82 (m, 2H), 1.57 (s, 3H), 1.49 (s, 9H), 1.28 (m, 2H), 0.89 (m, 2H), 0.64 (m, 2H); ESIMS m/z for (M+H)$^+$ C$_{27}$H$_{43}$N$_6$O$_8$S calcd: 611.3. found: 611.2.

Example O32

2-(2-(4-(5-((1-((1-Methylcyclopropoxy)carbonyl)piperidin-4-yl)methoxy)pyrazin-2-yl)-3-oxopiperazin-1-ylsulfonyl)ethylamino)acetic acid

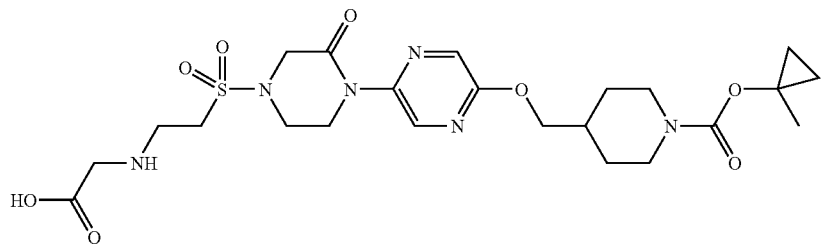

A solution of O31 (31 mg, 0.05 mmol) in dichloromethane (1 mL) is treated with HCl (1 mL of 4N in dioxane) and aged for 2 hours at room temperature. The mixture is concentrated and purified using mass-triggered reverse phase HPLC to afford the O32; $^1$H NMR (400 MHz, CDCl$_3$) δ 8.51 (d, J=1.4 Hz, 1H), 7.90 (d, J=1.4 Hz, 1H), 4.01 (m, 4H), 3.88 (m, 2H), 3.46 (m, 8H), 2.69 (m, 2H), 1.88 (m, 1H), 1.69 (m, 2H), 1.47 (s, 3H), 1.18 (m, 2H), 0.80 (m, 2H), 0.55 (m, 2H); ESIMS m/z for (M+H)$^+$ C$_{23}$H$_{35}$N$_6$O$_8$S calcd: 555.2. found: 555.1.

Example O33

1-Methylcyclopropyl 4-((5-(4-(2-guanidinoethylsulfonyl)-2-oxopiperazin-1-yl)pyrazin-2-yloxy)methyl)piperidine-1-carboxylate

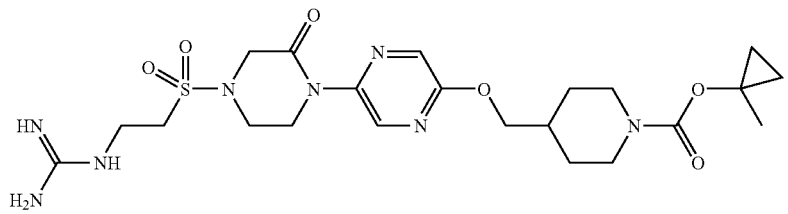

A solution of O26 (22 mg, 0.044 mmol) and 3,5-dimethoxypyrazole-1-carboxamidine nitrate (13 mg, 0.066 mmol) in dimethylformamide (3 mL) is treated with diisopropylethylamine (23 µL, 0.13 mmol) and stirred at room temperature for 14 hours. The mixture is diluted with aqueous sodiumhydrogencarbonate and extracted with ethyl acetate. The organic layer is washed with brine, dried over $MgSO_4$, filtered, concentrated and purified using mass-triggered reverse phase HPLC to afford O33; $^1$H NMR (400 MHz, $CDCl_3$) δ 8.48 (d, J=1.4 Hz, 1H), 7.93 (d, J=1.4 Hz, 1H), 4.11 (m, 4H), 4.06 (m, 2H), 3.92 (m, 2H), 3.62 (m, 3H), 2.68 (m, 2H), 1.80 (m, 1H), 1.72 (m, 2H), 1.18 (m, 3H), 0.80 (m, 2H), 0.56 (m, 2H); ESIMS m/z for (M+H)$^+$ $C_{22}H_{35}N_8O_6S$ calcd: 539.2. found: 539.2.

Example O34

1-Methylcyclopropyl 4-((5-(4-(3-methyl-3-nitrobutylsulfonyl)-2-oxopiperazin-1-yl)pyrazin-2-yloxy)methyl)piperidine-1-carboxylate

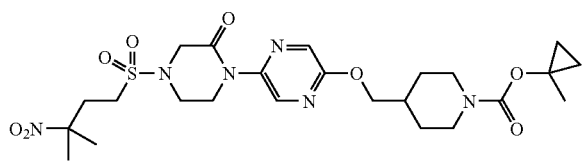

A solution of O13a (62 mg, 0.13 mmol) and 2-nitropropane (116 µL, 1.29 mmol) in methanol (0.5 mL) and tetrahydrofuran (1 mL) is treated with 1,8-diazabicyclo[5.4.0]undec-7-ene (154 µL, 1.03 mmol) and stirred at room temperature for 14 hours. The mixture is diluted with water, extracted with ethyl acetate, and washed with brine. The organic layer is dried ($MgSO_4$), filtered, concentrated and purified on silica gel using 0-100% ethyl acetate in dichloromethane to afford O34; $^1$H NMR (400 MHz, $CDCl_3$) δ 8.59 (d, J=1.4 Hz, 1H), 7.95 (d, J=1.4 Hz, 1H), 4.11 (m, 4H), 4.00 (m, 2H), 3.65 (m, 2H), 2.99 (m, 2H), 2.68 (m, 2H), 2.35 (m, 2H), 1.92 (m, 1H), 1.72 (m, 2H), 1.59 (s, 6H), 1.48 (s, 3H), 1.18 (m, 2H), 0.80 (m, 2H), 0.56 (m, 2H); ESIMS m/z for (M+H)$^+$ $C_{24}H_{37}N_6O_8S$ calcd: 569.2. found: 569.2.

Example O35

1-Methylcyclopropyl 4-((5-(4-(3-amino-3-methylbutylsulfonyl)-2-oxopiperazin-1-yl)pyrazin-2-yloxy)methyl)piperidine-1-carboxylate

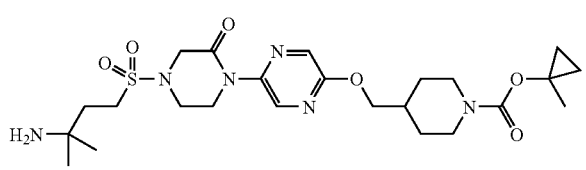

A solution of O34 (105 mg, 0.18 mmol) in a mixture of methanol (5 mL) and tetrahydrofuran (4 mL) is treated with $NiCl_2$ (72 mg, 0.55 mmol) followed by sodium borohydride (21 mg, 0.55 mmol) and the resulting mixture is stirred at room temperature for 3 hours. The mixture is diluted with ethyl acetate and filtered, then washed with saturated aqueous sodium hydrogencarbonate and brine. The organic layer is dried ($MgSO_4$), filtered, concentrated and purified using mass-triggered reverse phase HPLC to afford O35; $^1$H NMR (400 MHz, $CDCl_3$) δ 8.63 (d, J=1.2 Hz, 1H), 8.04 (d, J=1.2 Hz, 1H), 4.20 (d, J=6.4 Hz, 2H), 4.18 (s, 2H), 4.05 (m, 2H), 3.74 (m, 2H), 3.27 (m, 2H), 2.75 (m, 2H), 2.00 (m, 3H), 1.80 (m, 2H), 1.56 (s, 3H), 1.35 (m, 2H), 1.29 (s, 6H), 0.88 (m, 2H), 0.64 (m, 2H); ESIMS m/z for (M+H)$^+$ $C_{24}H_{39}N_6O_6S$ calcd: 539.3. found: 539.2.

Example O36

1-Methylcyclopropyl 4-((5-(4-(3-(dimethylamino)-3-methylbutylsulfonyl)-2-oxopiperazin-1-yl)pyrazin-2-yloxy)methyl)piperidine-1-carboxylate

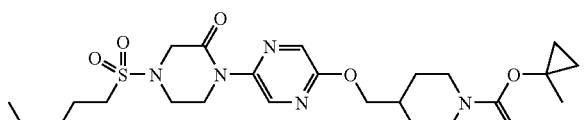

A solution of O35 (56 mg, 0.10 mmol) in dimethylformamide (2 mL) is treated with $K_2CO_3$ (43 mg, 0.31 mmol) and iodomethane (13 µL, 0.21 mmol) and stirred at room temperature for 3 hours. The mixture is diluted with water, extracted with ethyl acetate, and washed with water and brine. The organic extracts are dried ($MgSO_4$), filtered, concentrated and purified using mass-triggered reverse phase HPLC to afford O36; $^1$H NMR (400 MHz, $CDCl_3$) δ 8.66 (d, J=1.2 Hz, 1H), 8.04 (d, J=1.2 Hz, 1H), 4.20 (d, J=6.4 Hz, 2H), 4.18 (s, 2H), 4.07 (m, 2H), 3.72 (m, 2H), 3.21 (m, 2H), 2.77 (m, 2H), 2.35 (br s, 4H), 2.02 (m, 3H), 1.82 (m, 2H), 1.57 (s, 3H), 1.29 (m, 2H), 1.15 (br s, 6H), 0.88 (m, 2H), 0.64 (m, 2H); ESIMS m/z for (M+H)$^+$ $C_{26}H_{43}N_6O_6S$ calcd: 567.3. found: 567.2.

Example O37

1-Methylcyclopropyl 4-((5-(4-(1-benzylpyrrolidin-3-ylsulfonyl)-2-oxopiperazin-1-yl)pyrazin-2-yloxy)methyl)piperidine-1-carboxylate

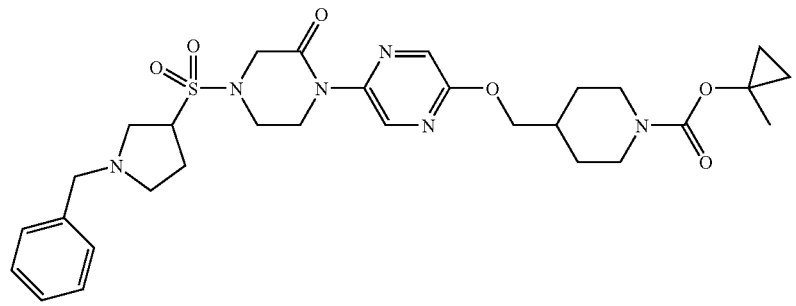

A solution of O13a (96 mg, 0.20 mmol) and N-trimethylsilyl-N-cyanomethylbenzylamine (104 μL, 0.42 mmol) in acetonitrile (5 mL) is treated with AgF (54 mg, 0.42 mmol) and heated at 75° C. for 4 hours. The mixture is filtered, washed with ethyl acetate, concentrated and purified on silica gel using 0-100% ethyl acetate in hexane to afford O37; ESIMS m/z for $(M+H)^+$ $C_{30}H_{41}N_6O_6S$ calcd: 613.3. found: 613.2.

Example O38

1-Methylcyclopropyl 4-((5-(2-oxo-4-(pyrrolidin-3-ylsulfonyl)piperazin-1-yl)pyrazin-2-yloxy)methyl)piperidine-1-carboxylate

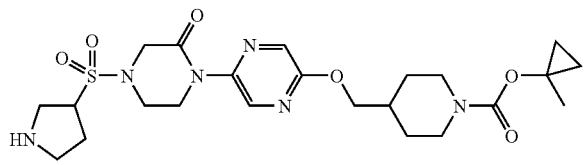

A solution of O37 (45 mg) in EtOH (5 mL) is hydrogenated in an H-cube® (Pd/C, 50 bar $H_2$, 70° C., 1 mL/min) device. The residue is concentrated to provide O38 $^1$H NMR (400 MHz, CDCl$_3$) δ 8.58 (d, J=1.4 Hz, 1H), 7.95 (d, J=1.4 Hz, 1H), 4.11 (m, 4H), 3.98 (m, 2H), 3.68 (m, 2H), 3.50 (m, 1H), 3.40 (dd, J=4.0, 13.2 Hz, 1H), 3.13 (m, 2H), 2.83 (m, 1H), 2.68 (m, 2H), 2.10 (m, 2H), 1.89 (m, 1H), 1.73 (m, 5H), 1.48 (s, 3H), 1.18 (m, 2H), 0.80 (m, 2H), 0.56 (m, 2H); ESIMS m/z for $(M+H)^+$ $C_{23}H_{35}N_6O_6S$ calcd: 523.2. found: 523.2.

Example O39

1-Methylcyclopropyl 4-((5-(4-(1-methylpyrrolidin-3-ylsulfonyl)-2-oxopiperazin-1-yl)pyrazin-2-yloxy)methyl)piperidine-1-carboxylate

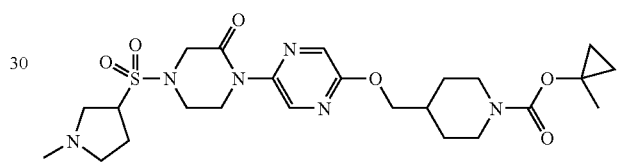

A solution of O38 (24 mg, 0.05 mmol) and paraformaldehyde (~0.25 mmol) in 1,2-dichloroethane (5 mL) was treated with acetic acid (50 μL) and heated at 80° C. for 1 hour. NaBH(OAc)$_3$ (20 mg, 0.09 mmol) is added and the mixture is stirred at 80° C. for an additional 2 hours. The mixture is cooled, diluted with saturated aqueous sodiumhydrogencarbonate, and extracted with dichloromethane (2×). The organic layers are dried over MgSO$_4$, filtered, concentrated, and purified using mass-triggered reverse phase HPLC to afford O39; $^1$H NMR (400 MHz, CDCl$_3$) δ 8.57 (d, J=1.4 Hz, 1H), 7.95 (d, J=1.4 Hz, 1H), 4.17 (d, J=7.2 Hz, 2H), 4.12 (d, J=6.4 Hz, 2H), 3.71 (m, 3H), 2.86 (m, 1H), 2.66 (m, 3H), 2.33 (s, 3H), 2.18 (m, 2H), 1.91 (m, 1H), 1.73 (m, 2H), 1.48 (s, 3H), 1.20 (m, 2H), 0.80 (m, 2H), 0.55 (m, 2H); ESIMS m/z for $(M+H)^+$ $C_{24}H_{37}N_6O_6S$ calcd: 537.3. found: 537.2.

Example O40

1-Methylcyclopropyl 4-((5-(4-(1-isobutylpyrrolidin-3-ylsulfonyl)-2-oxopiperazin-1-yl)pyrazin-2-yloxy)methyl)piperidine-1-carboxylate

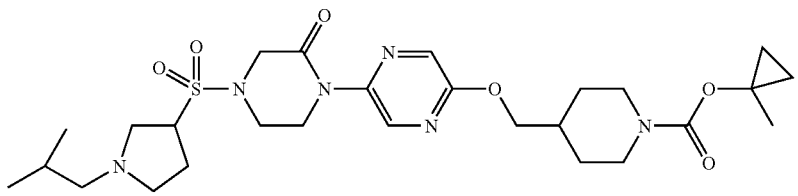

By following a similar procedure as the one used for preparing O39 from O38 except substituting isobutyraldehyde for paraformaldehyde, O40 is prepared; $^1$H NMR (400 MHz, CDCl$_3$) δ 8.58 (d, J=1.2 Hz, 1H), 7.94 (d, J=1.2 Hz, 1H), 4.18 (d, J=6.0 Hz, 2H), 4.12 (d, J=4.4 Hz, 2H), 3.96 (m, 2H), 3.69 (m, 2H), 2.80 (m, 2H), 2.68 (m, 2H), 2.58 (m, 2H), 2.17 (m, 3H), 1.91 (m, 1H), 1.73 (m, 2H), 1.65 (m, 1H), 1.48 (s, 3H), 1.20 (m, 2H), 0.84 (m, 6H), 0.79 (m, 2H), 0.55 (m, 2H); ESIMS m/z for (M+H)$^+$ C$_{27}$H$_{43}$N$_6$O$_6$S calcd: 579.3. found: 579.2

By following a similar procedure as the one used for preparing M48 from M48a except substituting the appropriate alcohol for M48a and O3b for M1c, followed in some cases by reductive aminations as in the preparation of O39 and O40, the following compounds are prepared;

| Ex. | Structure | Analytical data |
| --- | --- | --- |
| O41 | 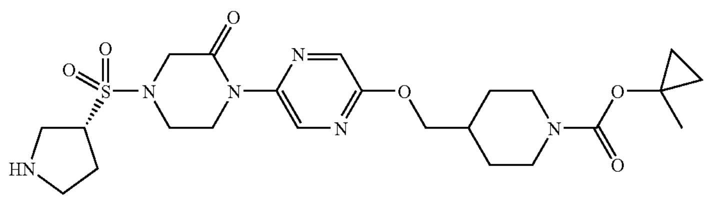 | $^1$H NMR (400 MHz, CDCl$_3$) δ 8.58 (d, J = 1.4 Hz, 1 H), 7.95 (d, J = 1.4 Hz, 1 H), 4.11 (m, 4 H), 3.97 (m, 2 H), 3.68 (m, 2 H), 3.60 (m, 1 H), 3.39 (dd, J = 4.0, 12.8 Hz, 1 H), 3.10 (m, 2 H), 2.82 (m, 1 H), 2.68 (m, 2 H), 2.08 (m, 2 H), 1.91 (s, 1 H), 1.72 (m, 2 H), 1.48 (s, 3 H), 1.20 (m, 2 H), 0.80 (m, 2 H), 0.55 (m, 2 H); ESIMS m/z for (M + H)$^+$ C$_{23}$H$_{35}$N$_6$O$_6$S calcd: 523.2, found: 523.2. |
| O42 | 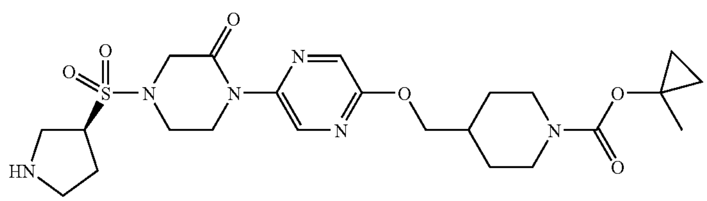 | $^1$H NMR (400 MHz, CDCl$_3$) δ 8.58 (d, J = 1.4 Hz, 1 H), 7.95 (d, J = 1.4 Hz, 1 H), 4.11 (m, 4 H), 3.97 (m, 2 H), 3.68 (m, 2 H), 3.60 (m, 1 H), 3.39 (dd, J = 4.0, 12.8 Hz, 1 H), 3.10 (m, 2 H), 2.82 (m, 1 H), 2.68 (m, 2 H), 2.08 (m, 2 H), 1.91 (s, 1 H), 1.72 (m, 2 H), 1.48 (s, 3 H), 1.20 (m, 2 H), 0.80 (m, 2 H), 0.55 (m, 2 H); ESIMS m/z for (M + H)$^+$ C$_{23}$H$_{35}$N$_6$O$_6$S calcd: 523.2, found: 523.2. |
| O43 | 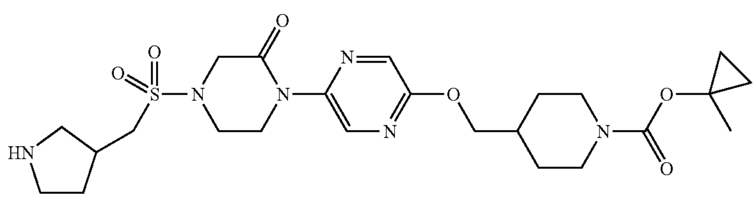 | $^1$H NMR (400 MHz, CDCl$_3$) δ 8.45 (d, J = 1.4 Hz, 1 H), 7.82 (d, J = 1.4 Hz, 1 H), 3.98 (d, J = 6.4 Hz, 2 H), 3.95 (s, 2 H), 3.85 (m, 2 H), 3.50 (m, 2 H), 3.13 (m, 2 H), 2.89 (m, 4 H), 2.61 (m, 5 H), 1.97 (m, 5 H), 1.78 (m, 2 H), 1.59 (m, 2 H), 1.44 (m, 2 H), 1.35 (s, 3 H), 1.05 (m, 2 H), 0.67 (m, 2 H), 0.43 (m, 2 H); ESIMS m/z for (M + H)$^+$ C$_{24}$H$_{37}$N$_6$O$_6$S calcd: 537.3, found: 537.3. |
| O44 | 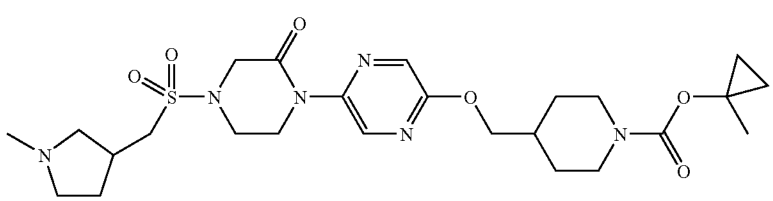 | $^1$H NMR (400 MHz, CDCl$_3$) δ 8.85 (d, J = 1.2 Hz, 1 H), 7.95 (d, J = 1.2 Hz, 1 H), 4.11 (d, J = 6.4 Hz, 2 H), 4.08 (s, 2 H), 3.98 (m, 2 H), 3.62 (m, 2 H), 3.04 (m, 2 H), 2.68 (m, 6 H), 2.50 (m, 2 H), 2.33 (s, 3 H), 2.17 (m, 1 H), 1.91 (m, 2 H), 1.72 (m, 5 H), 1.62 (m, 2 H), 1.48 (s, 3 H), 1.18 (m, 2 H), 0.79 (m, 2 H), 0.55 (m, 2 H); ESIMS m/z for (M + H)$^+$ C$_{25}$H$_{39}$N$_6$O$_6$S calcd: 551.3, found: 551.2. |
| O45 | 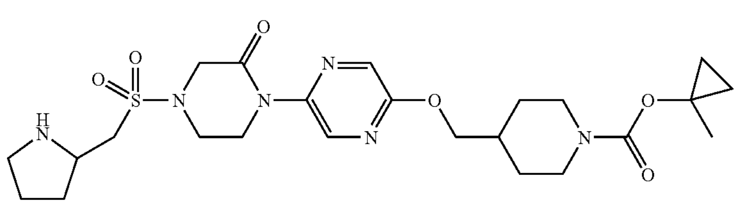 | $^1$H NMR (400 MHz, CDCl$_3$) δ 8.57 (d, J = 1.2 Hz, 1 H), 7.94 (d, J = 1.2 Hz, 1 H), 4.15 (m, 5 H), 3.99 (m, 2 H), 3.65 (m, 3 H), 3.24 (m, 1 H), 3.12 (dd, J = 4.0, 14.0 Hz, 1 H), 2.99 (m, 2 H), 2.68 (m, 2 H), 2.04 (m, 2 H), 1.85 (m, 9 H), 1.48 (s, 3 H), 1.20 (m, 2 H), 0.80 (m, 2 H), 0.56 (m, 2 H); ESIMS m/z for (M + H)$^+$ C$_{24}$H$_{37}$N$_6$O$_6$S calcd: 537.3, found: 537.3. |

| Ex. | Structure | Analytical data |
|---|---|---|
| O46 | 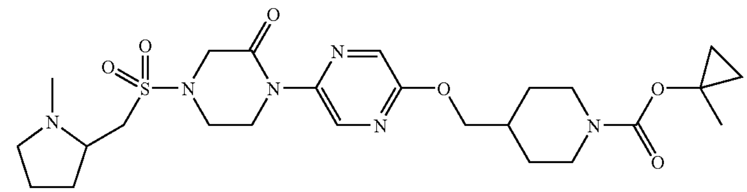 | ¹H NMR (400 MHz, CDCl₃) δ 8.58 (d, J = 1.2 Hz, 1 H), 7.95 (d, J = 1.2 Hz, 1 H), 4.11 (d, J = 6.4 Hz, 2 H), 4.10 (s, 2 H), 3.99 (m, 2 H), 3.64 (m, 2 H), 2.68 (m, 2 H), 2.37 (s, 2 H), 2.20 (s, 2 H), 1.90 (m, 1 H), 1.74 (m, 4 H), 1.48 (s, 3 H), 1.20 (m, 2 H), 0.79 (m, 2 H), 0.55 (m, 2 H); ESIMS m/z for (M + H)⁺ C₂₅H₃₉N₆O₆S calcd: 551.3, found: 551.2. |
| O47 | 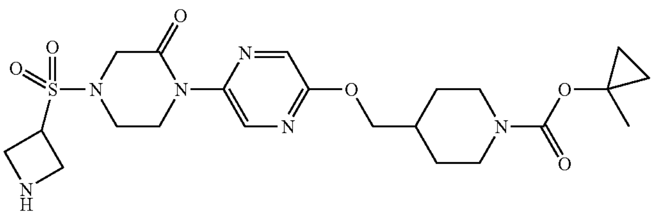 | ¹H NMR (400 MHz, CDCl₃) δ 8.57 (s, 1 H), 7.95 (s, 1 H), 4.16 (m, 2 H), 4.12 (m, 4 H), 4.02 (m, 2 H), 3.97 (m, 2 H), 3.82 (m, 2 H), 3.66 (m, 3 H), 2.68 (m, 2 H), 2.04 (m, 2 H), 1.91 (m, 1 H), 1.72 (m, 2 H), 1.48 (s, 3 H), 1.18 (m, 2 H), 0.80 (m, 2 H), 0.55 (m, 2 H); ESIMS m/z for (M + H)⁺ C₂₂H₃₃N₆O₆S calcd: 509.2, found: 509.2. |
| O48 | 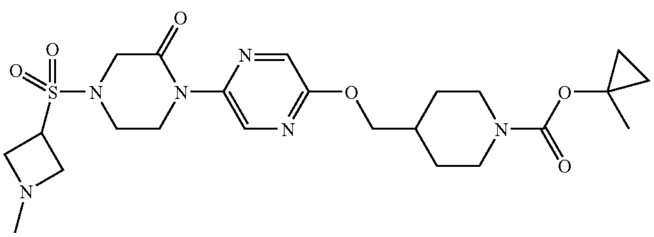 | ¹H NMR (400 MHz, CDCl₃) δ 8.57 (d, J = 1.0 Hz, 1 H), 7.95 (d, J = 1.0 Hz, 1 H), 4.14 (s, 2 H), 4.12 (d, J = 4.4 Hz, 2 H), 3.96 (m, 2 H), 3.90 (m, 1 H), 3.67 (m, 2 H), 3.54 (m, 2 H), 3.44 (m, 2 H), 2.68 (m, 2 H), 2.30 (s, 3 H), 1.91 (m, 1 H), 1.72 (m, 2 H), 1.48 (s, 3 H), 1.18 (m, 2 H), 0.80 (m, 2 H), 0.55 (m, 2 H); ESIMS m/z for (M + H)⁺ C₂₃H₃₅N₆O₆S calcd: 523.2, found: 523.2. |
| O49 | 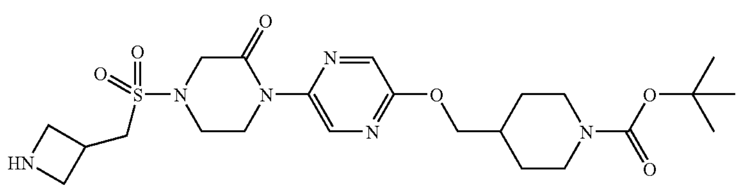 | ¹H NMR (400 MHz, CDCl₃) δ 8.59 (d, J = 1.2 Hz, 1 H), 7.94 (d, J = 1.4 Hz, 1 H), 4.12 (d, J = 6.8 Hz, 2 H), 4.06 (s, 2 H), 3.98 (m, 2 H), 3.77 (m, 2 H), 3.72 (m, 1 H), 3.62 (m, 2 H), 3.44 (m, 2 H), 3.26 (m, 2 H), 3.18 (m, 1 H), 2.68 (m, 2 H), 1.90 (m, 1 H), 1.73 (m, 2 H), 1.48 (s, 3 H), 1.20 (m, 3 H), 0.80 (m, 2 H), 0.55 (m, 2 H); ESIMS m/z for (M + H)⁺ C₂₃H₃₅N₆O₆S calcd: 523.2, found: 523.2. |
| O50 | 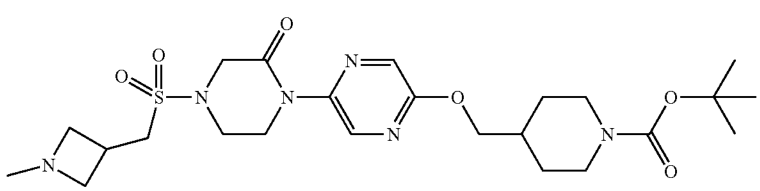 | ¹H NMR (400 MHz, CDCl₃) δ 8.59 (d, J = 1.6 Hz, 1 H), 7.94 (d, J = 1.6 Hz, 1 H), 4.12 (d, J = 6.8 Hz, 2 H), 3.98 (m, 3 H), 3.72 (m, 1 H), 3.62 (m, 2 H), 3.43 (m, 2 H), 3.23 (d, J = 7.2 Hz, 2 H), 2.95 (m, 2 H), 2.84 (m, 1 H), 2.68 (m, 2 H), 2.23 (s, 3 H), 1.91 (m, 1 H), 1.72 (m, 2 H), 1.48 (s, 3 H), 1.20 (m, 3 H), 0.80 (m, 2 H), 0.55 (m, 2 H); ESIMS m/z for (M + H)⁺ C₂₄H₃₇N₆O₆S calcd: 537.3, found: 537.2. |
| O51 | 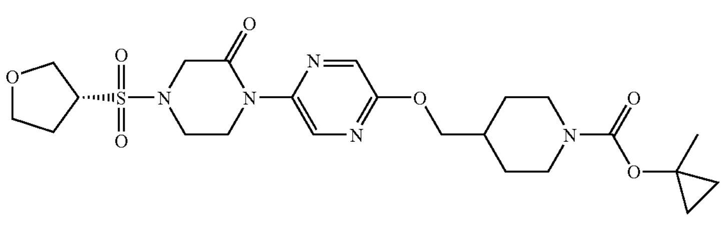 | ¹H-NMR (400 MHz, CDCl₃) δ 8.64 (d, J = 1.4 Hz, 1 H), 8.02 (d, J = 1.4 Hz, 1 H), 4.23 (m, 2 H), 4.19 (m, 2 H), 4.06-4.06 (m, 5 H), 3.84 (m, 2 H), 3.76 (m, 2 H), 2.74 (m, 2 H), 2.33 (m, 2 H), 1.98 (m, 1 H), 1.80 (m, 2 H), 1.55 (s, 3 H), 1.26 (m, 2 H), 0.86 (m, 2 H), 0.62 (m, 2 H); ESIMS calcd. for C₂₃H₃₄N₅O₇S [M + H]⁺ 524.2, found 524.3. |

| Ex. | Structure | Analytical data |
|---|---|---|
| O52 | 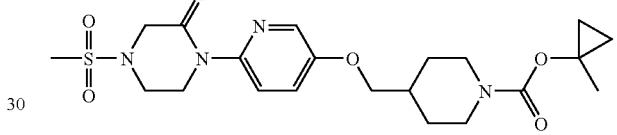 | $^1$H-NMR (400 MHz, CDCl$_3$) δ 8.65 (d, J = 1.4 Hz, 1 H), 8.02 (d, J = 1.4 Hz, 1 H), 4.21 (m, 2 H), 4.18 (d, J = 6.5 Hz, 2 H), 4.11-4.16 (m, 2 H), 3.98-4.06 (m, 5 H), 3.84 (m, 2 H), 3.76 (m, 2 H), 2.75 (dd, J = 12.3, 12.3 Hz, 2 H), 2.33 (m, 2 H), 1.97 (m, 1 H), 1.79 (m, 2 H), 1.55 (s, 3 H), 1.26 (m, 2 H), 0.86 (m, 2 H), 0.62 (m, 2 H); ESIMS calcd. for C$_{23}$H$_{34}$N$_5$O$_7$S [M + H]$^+$524.2, found 524.4. |
| O53 | 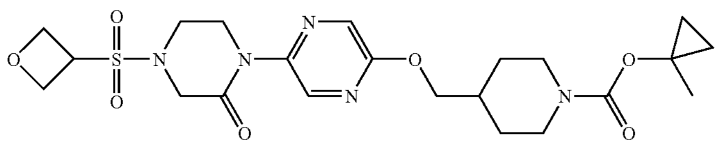 | $^1$H-NMR (400 MHZ, CDCl$_3$) δ 8.65 (d, J = 1.4 Hz, 1 H), 8.02 (d, J = 1.4 Hz, 1 H), 4.93 (m, 4 H), 4.51 (tt, J = 8.0, 6.4 Hz, 1 H), 3.95-4.30 (m, 8 H), 3.75 (m, 2 H), 2.75 (m, 2 H), 1.98 (m, 1 H), 1.79 (m, 2 H), 1.55 (s, 3 H), 1.26 (m, 2 H), 0.87 (m, 2 H), 0.63 (m, 2 H); ESIMS calcd. for C$_{22}$H$_{32}$N$_5$O$_7$S [M + H]$^+$ 510.2, found 510.2. |

Example O54

1-Methylcyclopropyl 4-((5-(4-(isopropylsulfonyl)-2-oxopiperazin-1-yl)pyrazin-2-yloxy)methyl)piperidine-1-carboxylate

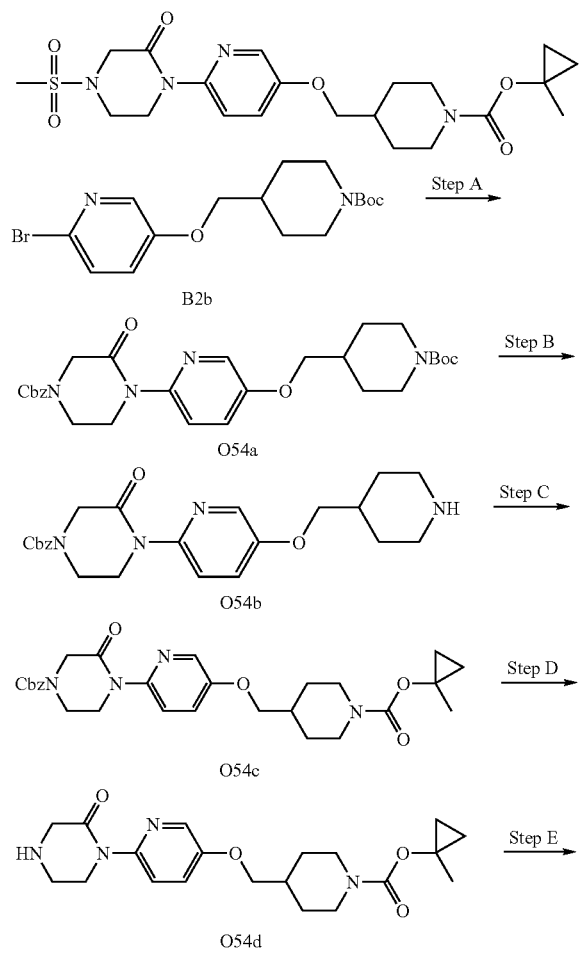

Example O54

Step A: By following a similar procedure as the one used for preparing O1a from B4b except substituting B2b for B4b, O54a is prepared; ESIMS m/z for (M+H)$^+$ C$_{28}$H$_{37}$N$_4$O$_6$ calcd: 525.3. found: 525.2.

Step B: A sample of O54a (200 mg, 0.38 mmol) is treated with trifluoroacetic acid (3 mL) and aged for 30 minutes. The solvent is removed and the reaction is treated with ethyl acetate and extracted with 1 M HCl three times. The organics are discarded and the aqueous layer is made basic with solid Na$_2$CO$_3$ and extracted with ethyl acetate three times. The combined organics are dried over MgSO$_4$, filtered and evaporated to afford O54b; ESIMS m/z for (M+H)$^+$ C$_{23}$H$_{29}$N$_4$O$_4$ calcd: 425.2. found: 425.2.

Step C: By following a similar procedure as the one used for preparing O2 from O1 except substituting O54b for O1, O54c is prepared; ESIMS m/z for (M+H)$^+$ C$_{28}$H$_{35}$N$_4$O$_6$ calcd: 523.3. found: 523.2.

Step D: By following a similar procedure as the one used for preparing O3b from O3a except substituting O54c for O3a, O54d is prepared; ESIMS m/z for (M+H)$^+$ C$_{20}$H$_{29}$N$_4$O$_4$ calcd: 389.2. found: 389.2.

Step E: By following a similar procedure as the one used for preparing O3 from O3b except substituting O54d for O3b and methanesulfonyl chloride for n-propanesulfonyl chloride, O54 is prepared; $^1$H NMR (400 MHz, CDCl$_3$) δ 8.00 (d, J=2.9 Hz, 1H), 7.66 (d, J=9.0 Hz, 1H), 7.17 (dd, J=2.9, 9.0, 1H), 4.10 (m, 2H), 4.05 (m, 2H), 4.03 (s, 2H), 3.77 (d, J=6.3 Hz, 2H), 3.58 (m, 2H), 2.48 (s, 3H), 2.69 (m, 2H), 1.90 (m, 1H), 1.74 (m, 2H), 1.48 (s, 3H), 1.20 (m, 2H)), 0.79 (m, 2H), 0.57 (m, 2H); ESIMS m/z for (M+H)$^+$ C$_{21}$H$_{31}$N$_4$O$_6$S calcd: 467.2. found: 467.2.

By following a similar procedure as the one used for preparing O54 from O54d except substituting the appropriate sulfonyl chloride for methanesulfonyl chloride, the following compounds are made;

| Ex. | Structure | Analytical data |
|---|---|---|
| O55 | 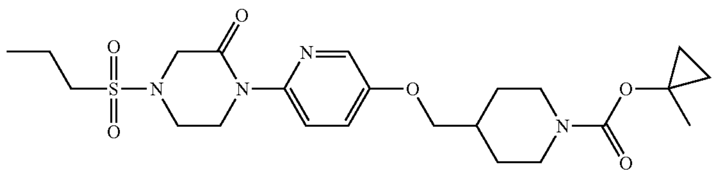 | $^1$H NMR (400 MHz, CDCl$_3$) δ 8.07 (d, J = 2.9 Hz, 1 H), 7.73 (d, J = 9.0 hz, 1 H), 7.24 (dd, J = 9.0, 3.0 Hz, 1 H), 4.20 (m, 2 H), 4.13 (s, 2 H), 4.09 (m, 2 H), 3.84 (d, J = 6.3 Hz, 2 H), 3.68 (m, 2 H), 3.00 (m, 2 H), 2.76 (dd, J = 12.4, 12.4 Hz, 2 H), 1.98 (m, 1 H), 1.89 (m, 2 H), 1.82 (m, 2 H), 1.55 (s, 3 H), 1.27 (m, 2 H), 1.08 (t, J = 7.5 Hz, 3 H), 0.87 (m, 2 H), 0.63 (m, 2 H); ESIMS m/z for (M + H)$^+$ C$_{23}$H$_{35}$N$_4$O$_6$S calcd.: 495.2, found: 495.6. |
| O56 | 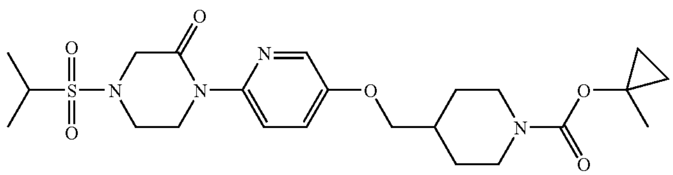 | $^1$H NMR (400 MHz, CDCl$_3$) δ 8.07 (d, J = 2.7 Hz, 1 H), 7.73 (d, J = 9.0 Hz, 1 H), 7.24 (dd, J = 9.0, 3.0 Hz, 1 H), 4.18 (s, 2 H), 4.16 (m, 2 H), 4.08 (m, 2 H), 3.84 (d, J = 6.3 Hz, 2 H), 3.73 (m, 2 H), 3.27 (sept., J = 6.8 Hz, 1 H), 2.76 (dd, J = 12.3, 12.3 Hz, 2 H), 1.97 (m, 1 H), 1.82 (m, 2 H), 1.55 (s, 3 H), 1.40 (d, J = 6.8 Hz, 6 H), 1.27 (m, 2 H), 0.87 (m, 2 H), 0.63 (m, 2 H); ESIMS m/z for (M + H)$^+$ C$_{23}$H$_{35}$N$_4$O$_6$S calcd.: 495.2, found: 495.6. |
| O57 | 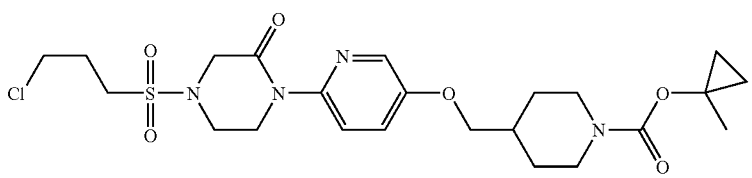 | $^1$H NMR (400 MHz, CDCl$_3$) δ 8.00 (d, J = 2.8 Hz, 1 H), 7.67 (d, J = 9.2 Hz, 1 H), 7.17 (dd, J = 9.2, 3.2 Hz, 1 H), 4.15 (m, 2 H), 4.08 (m, 2 H), 4.04 (m, 2 H), 3.78 (d, J = 6.4 Hz, 2 H), 3.63 (m, 2 H), 3.15 (m, 2 H), 2.69 (t, J = 12.4 Hz, 2 H), 2.26 (m, 2 H), 1.91 (m, 1 H), 1.75 (d, J = 12.4 Hz, 2 H), 1.49 (s, 3 H), 1.20 (m, 2 H), 0.80 (m, 2 H), 0.56 (m, 2 H); ESIMS m/z for (M + H)$^+$ C$_{23}$H$_{34}$ClN$_4$O$_6$S calcd.: 529.2, found: 529.1. |

Example O58

1-Methylcyclopropyl 4-((6-(4-(3-hydroxypropylsulfonyl)-2-oxopiperazin-1-yl)pyridin-3-yloxy)methyl)piperidine-1-carboxylate

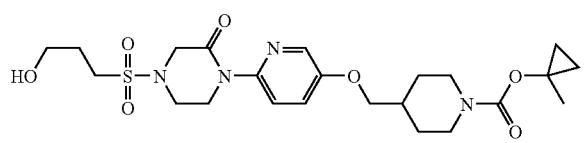

By following a similar procedure as the one used for preparing O21 from O5 except substituting O57 for O5, O58 is prepared; $^1$H NMR (400 MHz, CD$_3$CN) δ 8.09 (d, J=2.1 Hz, 1H), 7.65 (d, J=6.9 Hz, 1H), 7.34 (dd, J=3.0, 6.6 Hz, 1H), 4.02 (s, 2H), 4.01 (m, 2H), 3.96 (m, 2H), 3.90 (d, J=4.8 Hz, 2H), 3.63 (m, 2H), 3.59 (dd, J=4.5, 9.0 Hz, 2H), 3.16 (m, 2H), 2.79 (m, 3H), 1.92 (m, 1H), 1.77 (m, 2H), 1.49 (s, 3H), 1.19 (m, 2H), 0.80 (m, 2H), 0.59 (m, 2H); ESIMS m/z for (M+H)$^+$ C$_{23}$H$_{54}$N$_4$O$_7$S calcd.: 511.2. found: 511.1.

Example O59

1-Methylcyclopropyl 4-((6-(4-(3-(azetidin-1-yl)propylsulfonyl)-2-oxopiperazin-1-yl)pyridin-3-yloxy)methyl)piperidine-1-carboxylate

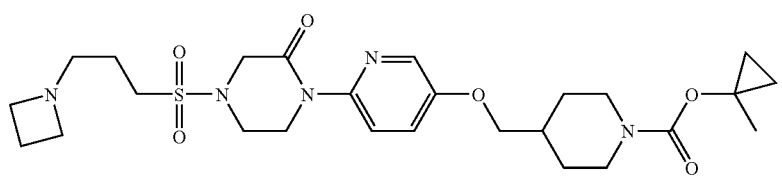

By following a similar procedure as the one used for preparing O16 from O5 except substituting O57 for O5, O59 is prepared; $^1$H NMR (400 MHz, CD$_3$CN) δ 8.09 (d, J=3.2 Hz, 1H), 7.66 (d, J=9.2 Hz, 1H), 7.33 (dd, J=9.2, 3.2 Hz, 1H), 4.02 (m, 2H), 4.01 (m, 2H), 3.97 (m, 2H), 3.90 (d, J=6.4 Hz, 2H), 3.63 (m, 2H), 3.41 (m, 2H), 3.19 (m, 2H), 2.70 (m, 4H), 2.10 (m, 4H), 1.80 (m, 4H), 1.49 (s, 3H), 1.20 (m, 2H), 0.80 (m, 2H), 0.59 (m, 2H); ESIMS m/z for (M+H)$^+$ C$_{26}$H$_{40}$N$_5$O$_6$S calcd.: 550.3. found: 550.1.

Example O60

1-(5-((1-(5-Ethylpyrimidin-2-yl)piperidin-4-yl)methoxy)pyrazin-2-yl)-4-(methylsulfonyl)piperazin-2-one

Example O61

1-(5-((1-(5-Ethylpyrimidin-2-yl)piperidin-4-yl)methoxy)pyridin-2-yl)-4-(methylsulfonyl)piperazin-2-one

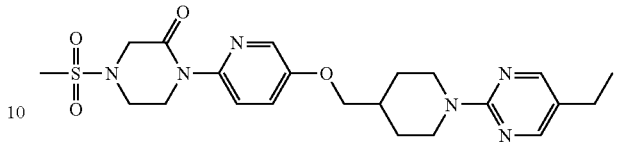

By following a procedure similar to the one used for preparing O60 from B4b, except substituting B2b for B4b, O61b is prepared; $^1$H NMR (400 MHz, CDCl$_3$) δ 8.18 (s, 2H), 8.09

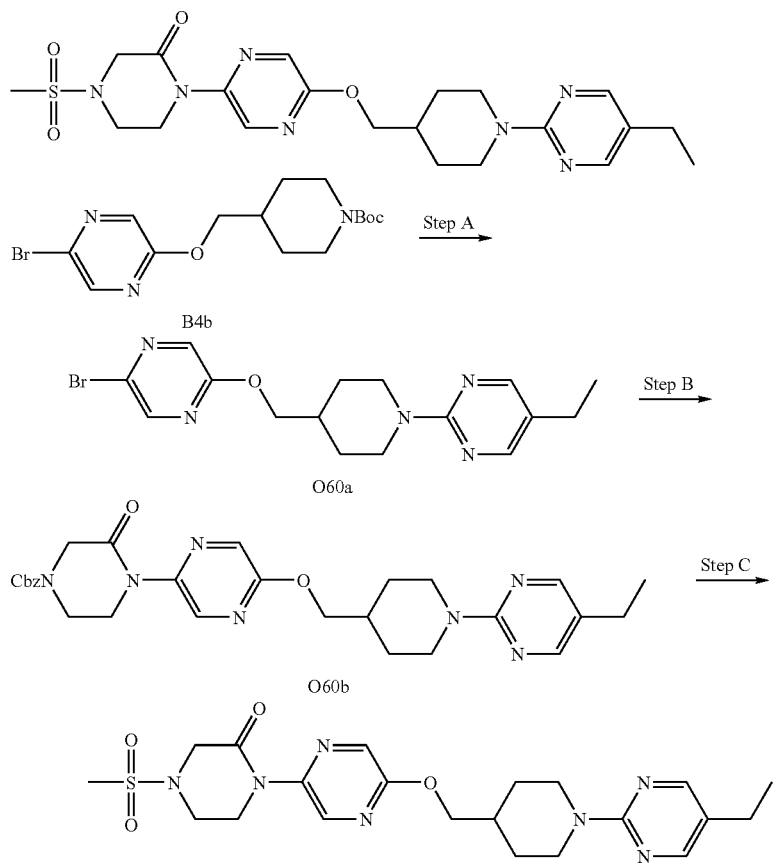

Step A: By following a procedure similar to the one used for preparing E1 from E1a, except substituting B4b for E1a, O60a is prepared; ESIMS m/z for (M+H)$^+$ C$_{16}$H$_{21}$BrN$_5$O calcd: 378.1. found: 378.1.

Step B: By following a procedure similar to the one used for preparing O1a from B4b, except substituting O60a for B4b, O60b is prepared; ESIMS m/z for (M+H)$^+$ C$_{28}$H$_{34}$N$_7$O$_4$ calcd: 532.3. found: 532.2.

Step C: By following a procedure similar to the one used for preparing O3 from O3b, except substituting O60b for O3b, and methanesulfonyl chloride for n-propanesulfonyl chloride, O60 is prepared; $^1$H NMR (400 MHz, CDCl$_3$) δ 8.65 (d, J=1.4 Hz, 1H), 8.41 (s, 2H), 8.04 (d, J=1.4 Hz, 1H), 4.72 (m, 2H), 4.25 (d, J=6.4, 2H), 4.14 (s, 2H), 4.09 (m, 2H), 3.68 (m, 2H), 3.21 (m, 2H), 2.94 (s, 3H), 2.60 (dd, J=15.2, 7.6, 2H), 2.22 (m, 1H), 2.05 (m, 2H), 1.48 (m, 2H), 1.26 (dd, J=7.6, 7.6, 3H); ESIMS m/z for (M+H)$^+$ C$_{21}$H$_{29}$N$_7$O$_4$S calcd: 476.2. found: 476.3.

(d, J=2.9 Hz, 1H), 7.73 (d, J=9.0 Hz, 1H), 7.25 (dd, J=9.0, 2.9), 4.79 (m, 2H), 4.12 (m, 2H), 4.10 (s, 2H), 3.87 (d, J=6.4, 2H), 3.64 (m, 2H), 2.92 (s, 3H), 2.91 (m, 2H), 2.46 (dd, J=15.2, 7.6, 2H), 2.11 (m, 1H), 1.93 (m, 2H), 1.37 (m, 2H), 1.19 (dd, J=7.6, 7.6, 3H); ESIMS m/z for (M+H)$^+$ C$_{22}$H$_{31}$N$_6$O$_4$S calcd: 475.2. found: 475.2.

Example O62

1-Methylcyclopropyl 4-((5-(4-(methylsulfonyl)-2-thioxopiperazin-1-yl)pyrazin-2-yloxy)methyl)piperidine-1-carboxylate

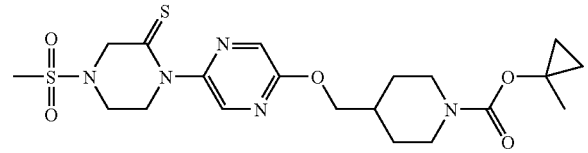

A solution of O2 (121 mg, 0.26 mmol) in tetrahydrofuran (3 mL) is treated with Lawesson's reagent (115 mg, 0.29 mmol), sealed in a reaction vessel and stirred at 90° C. overnight. The reaction is cooled to room temperature, evaporated to dryness and purified on silica gel using a linear gradient of 0-100% ethyl acetate in hexane to afford O62; $^1$H NMR (400 MHz, CDCl$_3$) δ 8.39 (d, J=1.3 Hz, 1H), 8.12 (d, J=1.4 Hz, 1H), 4.58 (s, 2H), 4.21 (m, 2H), 4.21 (d, J=6.5 Hz, 2H), 4.03 (m, 2H), 3.78 (m, 2H), 2.98 (s, 3H), 2.77 (m, 2H), 1.99 (m, 1H), 1.81 (m, 2H), 1.55 (s, 3H), 1.29 (m, 2H), 0.87 (m, 2H), 0.62 (m, 2H); ESIMS m/z for (M+Na)+C$_{20}$H$_{29}$N$_5$O$_5$S$_2$Na calcd: 506.2. found: 506.1 (M+Na$^+$).

Example O63

1-Methylcyclopropyl 4-((5-(2-(hydroxyimino)-4-(methylsulfonyl)piperazin-1-yl)pyrazin-2-yloxy)methyl)piperidine-1-carboxylate

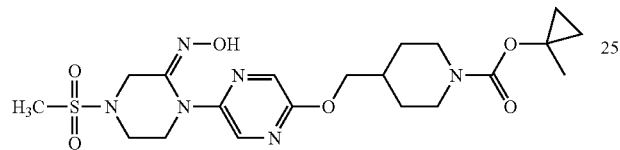

A solution of O62 (30 mg, 0.062 mmol) in ethanol (1 mL) is treated with hydroxylamine (7 μL of a 50% solution, 0.12 mmol) sealed in a reaction vessel and stirred at 80° C. overnight. The reaction is cooled to room temperature and evaporated to dryness to afford 63; $^1$H-NMR (400 MHz, CDCl$_3$) δ 8.46 (d, J=1.4 Hz, 1H), 7.96 (d, J=1.4 Hz, 1H), 4.47 (s, 2H), 4.21 (m, 2H), 4.14 (d, J=6.5 Hz, 2H), 3.87 (m, 2H), 3.62 (m, 2H), 3.52 (m, 1H), 2.92 (s, 3H), 2.74 (m, 2H), 1.95 (m, 1H), 1.79 (m, 2H), 1.55 (s, 3H), 1.26 (m, 2H), 0.86 (m, 2H), 0.62 (m, 2H); ESIMS calcd. for C$_{20}$H$_{31}$N$_6$O$_6$S [M+H]$^+$ 483.2. found 483.4.

Example P1 tert-Butyl 4-((2,6-difluoro-4-(1-(methylsulfonyl)piperidin-4-yl)phenoxy)methyl)piperidine-1-carboxylate

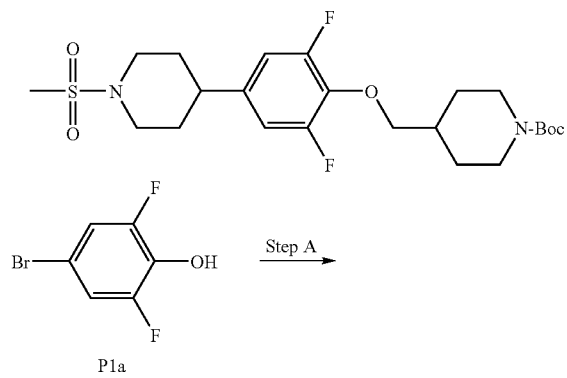

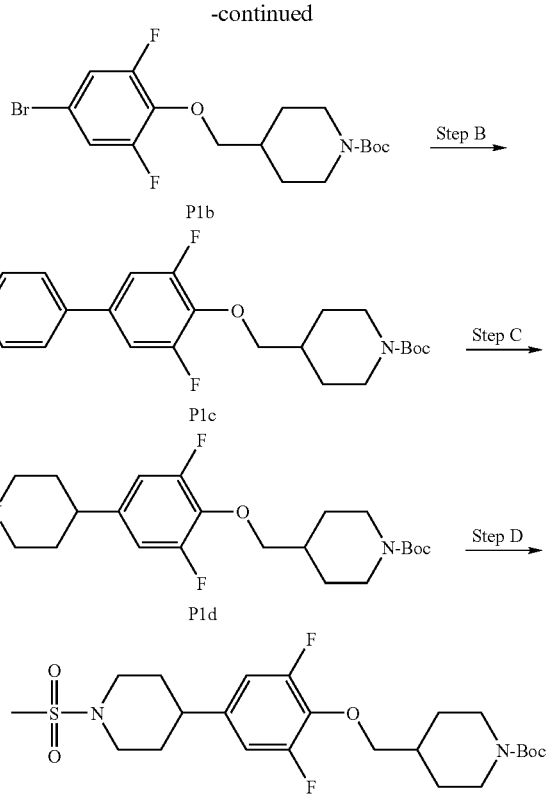

Step A: A mixture of P1a (1.67 g, 8 mmol), tert-butyl 4-((methylsulfonyloxy)methyl)piperidine-1-carboxylate (2.35 g, 8 mmol), and Cs$_2$CO$_3$ (3.91 g, 12 mmol) in N,N-dimethylformamide (30 mL) is heated at 90° C. overnight. The reaction mixture is poured into water (200 mL), extracted with ethyl acetate (3×50 mL), washed with water (2×30 mL), dried (Na$_2$SO$_4$) and concentrated to give P1b; ESIMS calcd. for C$_{17}$H$_{22}$BrF$_2$NNaO$_3$ (M+Na)$^+$ 428.1. found 428.2. The product is used without purification.

Step B: A mixture P1b (2.03 g, 5 mmol), pyridin-4-ylboronic acid (0.80 g, 6.5 mmol), Na$_2$CO$_3$ (2.65, 25 mmol), and Pd(PPh$_3$)$_4$ (289 mg, 0.25 mmol) in water (13 mL) and DME (52 mL)) is heated at 80° C. overnight under a nitrogen atmosphere. The reaction mixture is concentrated, water (200 mL) added, extracted with ethyl acetate (3×100 mL), washed with water (2×30 mL), dried (Na$_2$SO$_4$) and concentrated. Silica gel chromatography (0% to 5% gradient of MeOH in dichloromethane) gave P1c; ESIMS calcd. for C$_{22}$H$_{27}$F$_2$N$_2$O$_3$ (M+H)$^+$ 405.2. found 405.2.

Step C: A solution P1c (654 mg, 1.59 mmol) and TFA (118 μL, 1.59 mmol) in EtOH (100 ml) is hydrogenated using a 10% Pd/C cartridge on H-Cube (flow 1 mL/min) at 70 atm and 90° C. To the resulting solution is added a saturated solution of sodiumhydrogencarbonate (1 mL) and the EtOH is evaporated. To the residue is added water (50 mL) and dichloromethane (30 mL). The aqueous phase is further extracted with dichloromethane (2×30 mL) and discarded. The combined organics are dried over Na$_2$SO$_4$ and concentrated to yield P1d; ESIMS calcd. for C$_{22}$H$_{33}$F$_2$N$_2$O$_3$ (M+H)$^+$ 411.2. found 411.2.

Step D: Methanesulfonyl chloride (117 μL, 1.5 mmol) is added dropwise to a cold (ice/water bath) solution P1d (411 mg, 1 mmol) and Et$_3$N (418 μL, 3 mmol) in dry dichloromethane (6 mL). The resulting solution is stirred at room temperature for 2 hours. The reaction mixture is added to water (40 mL) and extracted with dichloromethane (3×40 mL). The combined organic layers are dried (Na$_2$SO$_4$) and concentrated to yield P1; $^1$H-NMR (600 MHz, CDCl$_3$) δ6.74 (m, 2H), 4.14 (m, 2H), 3.94 (m, 4H), 2.82 (s, 3H), 2.75 (td, J=12.1, 2.5 Hz, 4H), 2.53 (tt, J=12.1, 3.6 Hz, 1H), 1.93 (m, 3H), 1.84 (m, 2H), 1.74 (m, 2H), 1.46 (s, 9H), 1.25 (qd, J=12.4, 4.2 Hz, 2H). ESIMS calcd. for C$_{18}$H$_{27}$F$_2$N$_2$O$_3$S (M-Boc+H)$^+$ 389.2. found 389.2.

By following a procedure similar to the one used for preparing P1 from P1a, except substituting the appropriate commercially available halophenol for P1a, the following examples are prepared;

| | | |
|---|---|---|
| P2 | [structure] | $^1$H-NMR (600 MHz, CDCl$_3$) δ 6.97 (m, 2H), 6.73 (d, J = 8.2 Hz, 1H), 4.15 (m, 2H), 3.92 (dt, J = 11.7, 2.1 Hz, 2H), 3.79 (d, J = 6.2 Hz, 2H), 2.81 (s, 3H), 2.75 (m, 4H), 2.52 (tt, J = 12.1, 3.6 Hz, 1H), 2.21 (s, 3H), 1.98 (m, 1H), 1.92 (m, 2H), 1.80 (m, 4H), 1.47 (s, 9H), 1.30 (qd, J = 12.4, 4.2 Hz, 2H). ESIMS calcd. for C$_{19}$H$_{31}$N$_2$O$_3$S (M-Boc + H)$^+$ 367.2, found 367.2. |
| P3 | [structure] | $^1$H-NMR (600 MHz, CDCl$_3$) δ 7.02 (d, J = 8.1 Hz, 1H), 6.43 (m, 2H), 4.15 (m, 2H), 3.91 (m, 2H), 3.79 (m, 5H), 2.94 (tt, J = 12.2, 3.4 Hz, 1H), 2.91 (s, 3H), 2.77 (m, 4H), 1.95 (m, 1H), 1.89 (m, 2H), 1.83 (m, 2H), 1.77 (m, 2H), 1.47 (s, 9H), 1.28 (qd, J = 12.4, 4.2 Hz, 2H). ESIMS calcd. for C$_{19}$H$_{31}$N$_2$O$_4$S (M-Boc + H)$^+$ 383.2, found 383.2. |
| P4 | [structure] | $^1$H-NMR (600 MHz, CDCl$_3$) δ 7.26 (s, 2H), 4.17 (m, 2H), 3.92 (m, 2H), 3.58 (d, J = 6.3 Hz, 2H), 2.81 (s, 3H), 2.75 (m, 4H), 2.48 (tt, J = 12.2, 3.6 Hz, 1H), 2.24 (s, 6H), 1.98 (m, 1H), 1.90 (m, 4H), 1.79 (m, 2H), 1.47 (s, 9H), 1.33 (qd, J = 12.4, 4.1 Hz, 2H). ESIMS calcd. for C$_{20}$H$_{33}$N$_2$O$_3$S (M-Boc + H)$^+$ 381.2, found 381.2. |
| P5 | [structure] | $^1$H-NMR (600 MHz, CDCl$_3$) δ 6.94 (s, 1H), 6.58 (s, 1H), 4.15 (m, 2H), 3.94 (m, 2H), 3.77 (d, J = 6.2 Hz, 2H), 2.82 (s, 3H), 2.75 (m, 5H), 2.29 (s, 3H), 2.17 (s, 3H), 1.97 (m, 1H), 1.81 (m, 6H), 1.47 (s, 9H), 1.29 (m, 2H). ESIMS calcd. for C$_{20}$H$_{33}$N$_2$O$_3$S (M-Boc + H)$^+$ 381.2, found 381.2. |
| P6 | [structure] | $^1$H-NMR (400 MHz, CDCl$_3$) δ 7.63 (d, J = 2.4 Hz, 1H), 7.28 (dd, J = 8.7, 2.5 Hz, 1H), 6.89 (d, J = 8.6 Hz, 1H), 4.16 (m, 2H), 3.93 (m, 2H), 3.88 (s, 3H), 3.85 (d, J = 6.2 Hz, 2H), 2.82 (s, 3H), 2.75 (m, 4H), 2.58 (tt, J = 12.1, 3.6 Hz, 1H), 1.74-2.07 (m, 7H), 1.46 (s, 9H), 1.29 (m, 2H). ESIMS calcd. for C$_{20}$H$_{31}$N$_2$O$_5$S (M-Boc + H)$^+$ 411.2, found 410.8. |
| P7 | [structure] | $^1$H-NMR (400 MHz, CDCl$_3$) δ 7.20 (d, J = 2.2 Hz, 1H), 7.03 (dd, J = 8.4, 2.2 Hz, 1H), 6.85 (d, J = 8.5 Hz, 1H), 4.16 (m, 2H), 3.93 (m, 2H), 3.84 (d, J = 6.4 Hz, 2H), 2.82 (s, 3H), 2.75 (m, 4H), 2.53 (tt, J = 12.1, 3.6 Hz, 1H), 2.02 (m, 1H), 1.92 (m, 2H), 1.71 (m, 4H), 1.46 (s, 9H), 1.29 (m, 2H). ESIMS calcd. for C$_{18}$H$_{28}$ClN$_2$O$_3$S (M-Boc + H)$^+$ 387.2, found 386.8. |
| P8 | [structure] | $^1$H-NMR (400 MHz, CDCl$_3$) δ 7.08 (d, J = 8.2 Hz, 1H), 6.71 (m, 2H), 4.14 (m, 2H), 3.94 (m, 2H), 3.77 (d, J = 6.4 Hz, 2H), 2.82 (s, 3H), 2.76 (m, 5H), 2.31 (s, 3H), 1.93 (m, 1H), 1.81 (m, 6H), 1.46 (s, 9H), 1.25 (m, 2H). ESIMS calcd. for C$_{19}$H$_{31}$N$_2$O$_3$S (M-Boc + H)$^+$ 367.2, found 367.2. |
| P9 | [structure] | $^1$H-NMR (400 MHz, CDCl$_3$) δ 6.99 (d, J = 8.8 Hz, 1H), 6.69 (d, J = 8.7 Hz, 1H), 4.16 (m, 2H), 3.95 (m, 2H), 3.78 (d, J = 6.2 Hz, 2H), 2.72-2.84 (m, 8H), 2.24 (s, 3H), 2.18 (s, 3H), 1.83 (m, 7H), 1.47 (s, 9H), 1.30 (m, 2H). ESIMS calcd. for C$_{20}$H$_{33}$N$_2$O$_3$S (M-Boc + H)$^+$ 381.2, found 381.2. |

-continued

| | | |
|---|---|---|
| P10 | 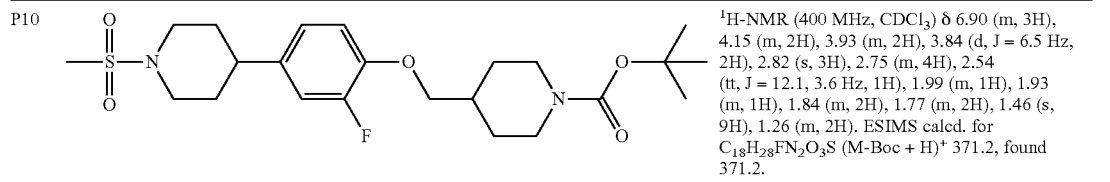 | ¹H-NMR (400 MHz, CDCl₃) δ 6.90 (m, 3H), 4.15 (m, 2H), 3.93 (m, 2H), 3.84 (d, J = 6.5 Hz, 2H), 2.82 (s, 3H), 2.75 (m, 4H), 2.54 (tt, J = 12.1, 3.6 Hz, 1H), 1.99 (m, 1H), 1.93 (m, 1H), 1.84 (m, 2H), 1.77 (m, 2H), 1.46 (s, 9H), 1.26 (m, 2H). ESIMS calcd. for $C_{18}H_{28}FN_2O_3S$ (M-Boc + H)⁺ 371.2, found 371.2. |
| P11 | 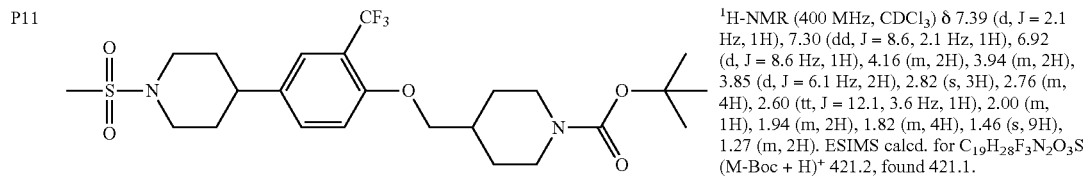 | ¹H-NMR (400 MHz, CDCl₃) δ 7.39 (d, J = 2.1 Hz, 1H), 7.30 (dd, J = 8.6, 2.1 Hz, 1H), 6.92 (d, J = 8.6 Hz, 1H), 4.16 (m, 2H), 3.94 (m, 2H), 3.85 (d, J = 6.1 Hz, 2H), 2.82 (s, 3H), 2.76 (m, 4H), 2.60 (tt, J = 12.1, 3.6 Hz, 1H), 2.00 (m, 1H), 1.94 (m, 2H), 1.82 (m, 4H), 1.46 (s, 9H), 1.27 (m, 2H). ESIMS calcd. for $C_{19}H_{28}F_3N_2O_3S$ (M-Boc + H)⁺ 421.2, found 421.1. |

Example P12

2-(4-((2,6-Difluoro-4-(1-(methylsulfonyl)piperidin-4-yl)phenoxy)methyl)piperidin-1-yl)-5-ethylpyrimidine Example P13

1-Methylcyclopropyl 4-((2,6-difluoro-4-(1-(methylsulfonyl)piperidin-4-yl)phenoxy)methyl)piperidine-1-carboxylate

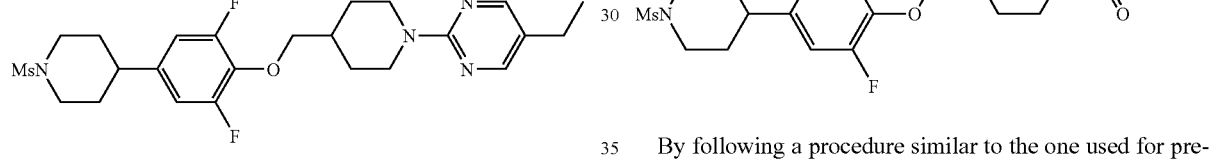

By following a procedure similar to the one used for preparing E1 from B2, except substituting P1 for B2, P12 is prepared; ¹H-NMR (400 MHz, CDCl₃) δ 8.18 (s, 2H), 6.67 (d, J=9.2 Hz, 2H), 4.70 (m, 2H), 2.91 (dt, J=2.0, 12.4 Hz, 2H), 2.75 (s, 3H), 2.68 (dt, J=2.4, 12.4 Hz, 2H), 2.43 (m, 3H), 2.01 (m, 3H), 1.70 (m, 2H), 1.31 (m, 2H), 1.13 (t, J=7.6 Hz, 3H); ESIMS calcd. for $C_{24}H_{33}F_2N_4O_3S$ [M+H]⁺ 495.2. found 495.2.

By following a procedure similar to the one used for preparing E3 from B4, except substituting P1 for B4, P12 is prepared; ¹H-NMR (400 MHz, CDCl₃) δ 6.74 (d, J=8.8 Hz, 2H), 4.22 (m, 2H), 3.95 (m, 4H), 2.83 (s, 3H), 2.76 (dt, J=2.4, 12.0 Hz, 4H), 2.55 (tt, J=3.6, 12.4 Hz, 1H), 1.94 (m, 3H), 1.85 (m, 2H), 1.78 (m, 2H), 1.56 (s, 3H), 1.26 (m, 2H), 0.87 (m, 2H), 0.63 (m, 2H); ESIMS calcd. for $C_{23}H_{33}F_2N_2O_5S$ [M+H]⁺ 487.2. found 487.2.

Example P14

3-(4-(4-((1-(5-Ethylpyrimidin-2-yl)piperidin-4-yl)methoxy)-3,5-difluorophenyl)piperidin-1-ylsulfonyl)propyl acetate

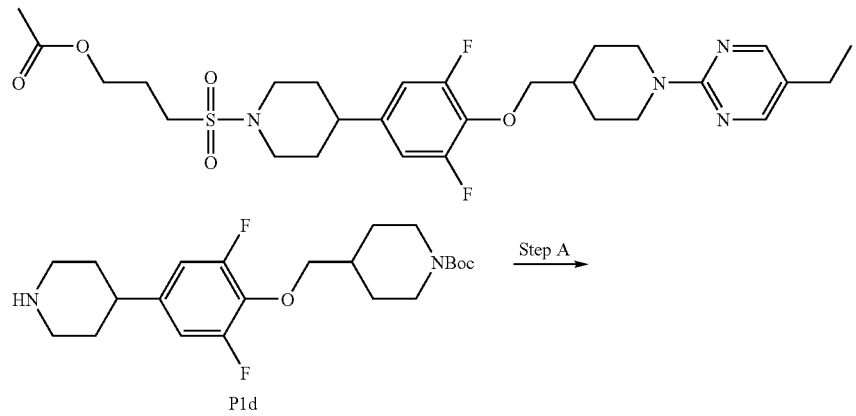

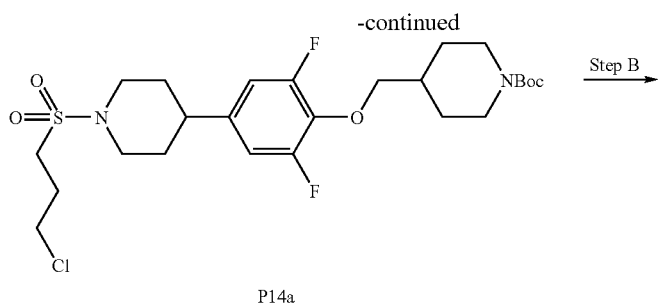

P14a

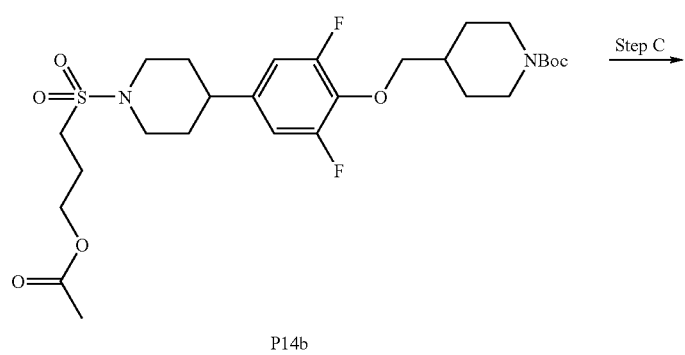

P14b

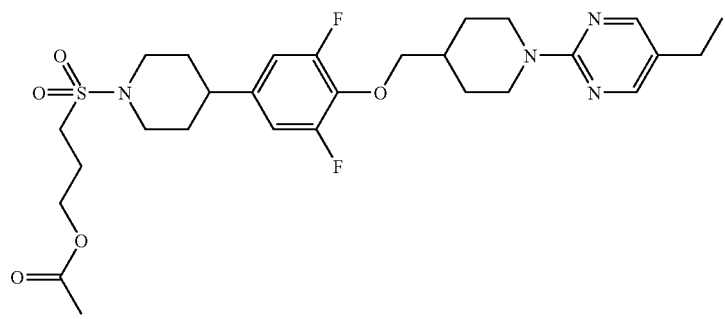

Example P14

Step A: A solution of P1d (200 mg, 0.49 mmol) and 3-chloropropanesulfonyl chloride (65 μL, 0.54 mmol) in dichloromethane (10 mL) is treated with triethylamine (75 μL, 0.54 mmol) and the mixture is stirred at room temperature for 1 hour. The mixture is diluted with water (10 mL), extracted with dichloromethane, dried over MgSO$_4$, filtered and concentrated. The residue is purified on silica gel using a linear gradient of 0 to 100% ethyl acetate in hexane to afford P14a: $^1$H-NMR (400 MHz, CDCl$_3$) δ 6.74 (d, J=9.2 Hz, 2H), 4.06 (m, 2H), 3.87 (m, 4H), 3.64 (t, J=6.0 Hz, 2H), 3.04 (t, J=6.0 Hz, 2H), 2.80 (dt, J=2.4, 12.4 Hz, 2H), 2.65 (m, 2H), 2.49 (tt, J=3.6, 12.4 Hz, 1H), 2.25 (m, 2H), 1.85 (m, 2H), 1.77 (m, 2H), 1.65, m, 2H), 1.39 (s, 9H), 1.18 (m, 2H); ESIMS calcd. for C$_{21}$H$_{30}$ClF$_2$N$_2$O$_5$S [M+H—C$_4$H$_8$]$^+$ 495.2. found 495.2.

Step B: A solution of P14a (138 mg, 0.25 mmol), NaOAc (62 mg, 0.75 mmol) and NaI (38 mg, 0.25 mmol) in N,N-dimethylformamide (1 mL) is heated at 120° C. for 2 hours. The mixture is cooled, diluted with water (10 mL) and extracted with ethyl acetate (10 mL). The organic layer is washed with water (10 mL) and brine (10 mL), dried (MgSO$_4$), filtered and concentrated to provide P14b which is used without further purification; ESIMS calcd. for C$_{23}$H$_{33}$F$_2$N$_2$O$_7$S [M+H—C$_4$H$_8$]$^+$ 519.2. found 519.2.

Step C: By following a procedure similar to the one used for preparing E1 from B2, except substituting P14b for B2, P14 is prepared; $^1$H-NMR (400 MHz, CDCl$_3$) δ 8.36 (s, 2H), 6.76 (m, 2H), 4.76 (m, 2H), 4.22 (t, J=6.4 Hz, 2H), 3.96 (m, 4H), 3.06 (m, 4H), 2.88 (dt, J=2.4, 12.0 Hz, 2H), 2.56 (m, 3H), 2.17 (m, 3H), 2.11 (s, 3H), 2.04 (m, 2H), 1.97 (m, 2H), 1.71 (m, 2H), 1.42 (m, 2H), 1.24 (t, J=7.6 Hz, 3H); ESIMS calcd. for C$_{28}$H$_{39}$F$_2$N$_4$O$_5$S [M+H]$^+$ 581.3. found 581.2.

Example P15

1-Methylcyclopropyl 4-((4-(1-(3-acetoxypropylsul-fonyl)piperidin-4-yl)-2,6-difluorophenoxy)methyl)piperidine-1-carboxylate

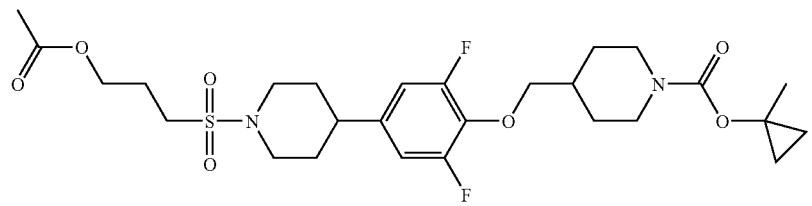

By following a procedure similar to the one used for preparing P14 from P1d, except substituting the procedure for preparing P13 from P1 for step C, P15 is prepared; $^1$H-NMR (400 MHz, CDCl$_3$) δ 6.75 (m, 2H), 4.22 (t, J=6.0 Hz, 2H), 3.95 (m, 4H), 3.03 (m, 2H), 2.88 (dt, J=2.4, 12.4 Hz, 2H), 2.76 (m, 2H), 2.57 (m, 1H), 2.17 (m, 2H), 2.09 (s, 3H), 1.92 (m, 2H), 1.88 (m, 2H), 1.72 (m, 2H), 1.56 (s, 3H), 1.25 (m, 2H), 0.87 (m, 2H), 0.63 (m, 2H); ESIMS calcd. for C$_{27}$H$_{39}$F$_2$N$_2$O$_7$S [M+H]$^+$ 573.2. found 573.2.

Example P16

3-(4-(4-((1-(5-Ethylpyrimidin-2-yl)piperidin-4-yl)methoxy)-3,5-difluorophenyl)piperidin-1-ylsulfonyl)propan-1-ol

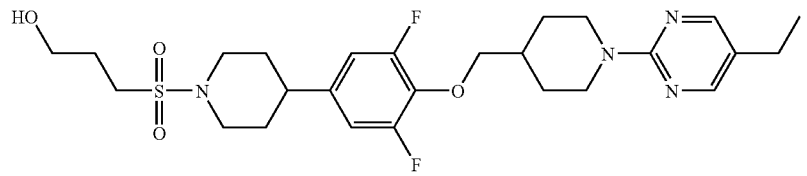

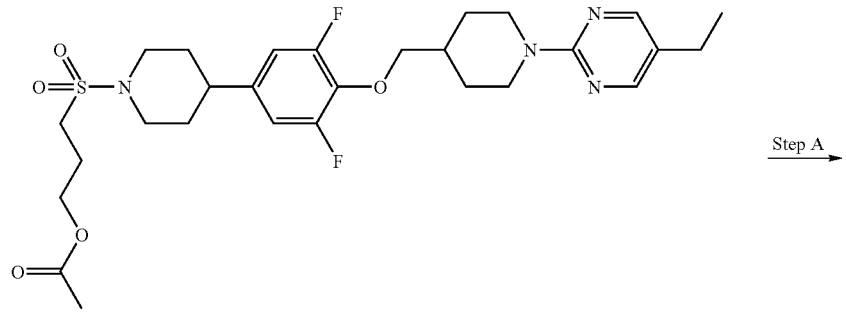

P14

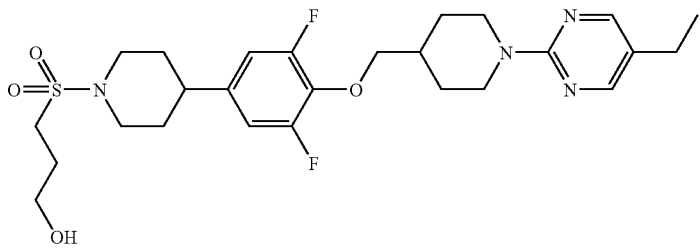

Example P16

A solution of P14 (30 mg, 0.05 mmol) in tetrahydrofuran (3 mL) is treated with LiOH hydrate (50 mg, 1.2 mmol) and the mixture is heated at 90° C. for 12 hours. The mixture is filtered, concentrated and purified by mass triggered reverse phase HPLC to afford P16; $^1$H-NMR (400 MHz, CDCl$_3$) δ 8.36 (s, 2H), 6.67 (m, 2H), 4.68 (m, 2H), 3.88 (m, 5H), 3.74 (t, J=5.6 Hz, 2H), 3.00 (m, 4H), 2.78 (dt, J=2.4, 12.0 Hz, 2H), 2.45 (m, 3H), 2.17 (m, 3H), 2.11 (s, 3H), 2.04 (m, 4H), 1.97 (m, 2H), 1.84 (m, 2H), 1.65 (m, 2H), 1.31 (m, 2H), 1.47 (t, J=7.6 Hz, 3H); ESIMS calcd. for C$_{26}$H$_{37}$F$_2$N$_4$O$_4$S [M+H]$^+$ 539.3. found 539.2.

Example P17

1-Methylcyclopropyl 4-((2,6-difluoro-4-(1-(3-hydroxypropylsulfonyl)piperidin-4-yl)phenoxy)methyl)piperidine-1-carboxylate

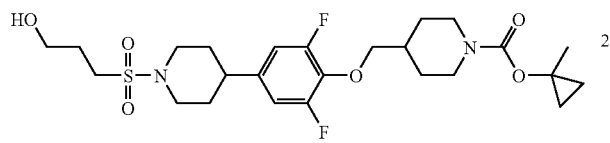

By following a procedure similar to the one used for preparing P16 from P14, except substituting P15 for P14, P17 is prepared; $^1$H-NMR (400 MHz, CDCl$_3$) δ 6.66 (m, 2H), 3.85 (m, 4H), 3.74 (t, J=6.0 Hz, 2H), 3.02 (m, 2H), 2.79 (dt, J=2.4, 12.0 Hz, 2H), 2.71 (m, 2H), 2.48 (m, 2H), 2.03 (m, 2H), 1.80 (m, 5H), 1.69 (m, 2H), 1.48 (s, 3H), 1.19 (m, 2H), 0.87 (m, 2H), 0.63 (m, 2H); ESIMS calcd. for C$_{25}$H$_{37}$F$_2$N$_2$O$_6$S [M+H]$^+$ 531.2. found 531.2.

Example Q1

Isopropyl 4-((5-(1,2,3,6-tetrahydro-1-methanesulfonylpyridin-4-yl)pyrazin-2-yloxy)methyl)piperidine-1-carboxylate

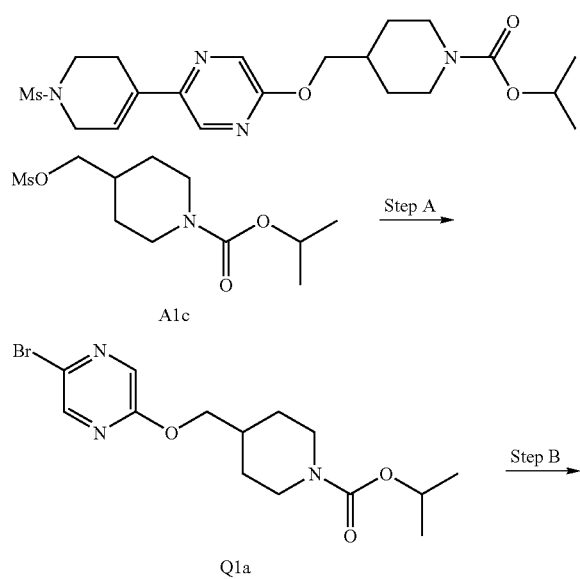

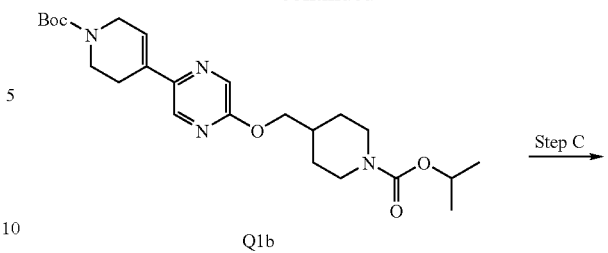

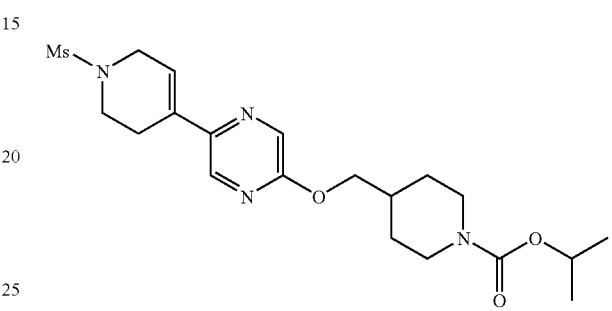

Step A: A solution of A1c (0.86 g, 3.1 mmol) and 2-bromo-5-hydroxypyrazine (0.52 g, 3.0 mmol) in dry acetonitrile (7 mL) is treated with powdered cesium carbonate (1.62 g, 5 mmol) and the mixture is stirred at 60° C. for 24 hours. Filtration, concentration, and purification on silica gel using a linear gradient of 0 to 100% ethyl acetate in hexane affords Q1a; ESIMS calcd. for C$_{14}$H$_{21}$BrN$_3$O$_3$ (M+H$^+$) 358.1. found 358.0.

Step B: To a solution of Q1a (83.5 mg, 0.2 mmol) in 1,2-dimethoxyethane (1.5 mL) are added tert-butyl 5,6-dihydro-4-(4,4,5,5-tetramethyl-1,3,2-dioxaborolan-2-yl)pyridine-1(2H)-carboxylate (66.7 mg, 0.2 mmol), powdered potassium carbonate (0.10 g, 0.7 mmol), and water (0.5 g). The mixture is degassed using argon, then tetrakis-(triphenylphosphino)palladium(0) (0.08 g, 0.07 mmol) is added and the mixture is heated to 180° C. for 5 min in a microwave reactor. Cooling, extraction with ethyl acetate, washing with water and brine, drying over Na$_2$SO$_4$ and concentration, followed by purification on silica gel using a linear gradient of 5 to 70% ethyl acetate in hexane affords Q1b; ESIMS calcd. for C$_{24}$H$_{37}$N$_4$O$_5$ (M+H$^+$) 461.3. found 461.1.

Step C: To a solution of Q1b (0.2 mmol) in dioxane (2 mL) is added hydrogen chloride in dioxane (4N, 1 mL), slowly, with stirring. The resulting solution is stirred at room temperature for 4 hours. After removing the solvent, the residue is dissolved in dichloromethane (3 mL) and treated with triethylamine (0.2 mL, 1.4 mmol). Then methanesulfonyl chloride (0.04 mL, 0.5 mmol) is added dropwise, with stirring, over 5 minutes. The resulting solution is stirred at room temperature for 2 hours. The solvent is removed and the residue is purified using mass-triggered reverse phase HPLC to yield Q1; ESIMS calcd. for $C_{20}H_{31}N_4O_5S$ (M+H$^+$) 439.2. found 439.1.

Example Q2

1-Methylcyclopropyl 4-((6-(1,2,3,6-tetrahydro-1-methanesulfonylpyridin-4-yl)pyridin-3-yloxy)methyl)piperidine-1-carboxylate

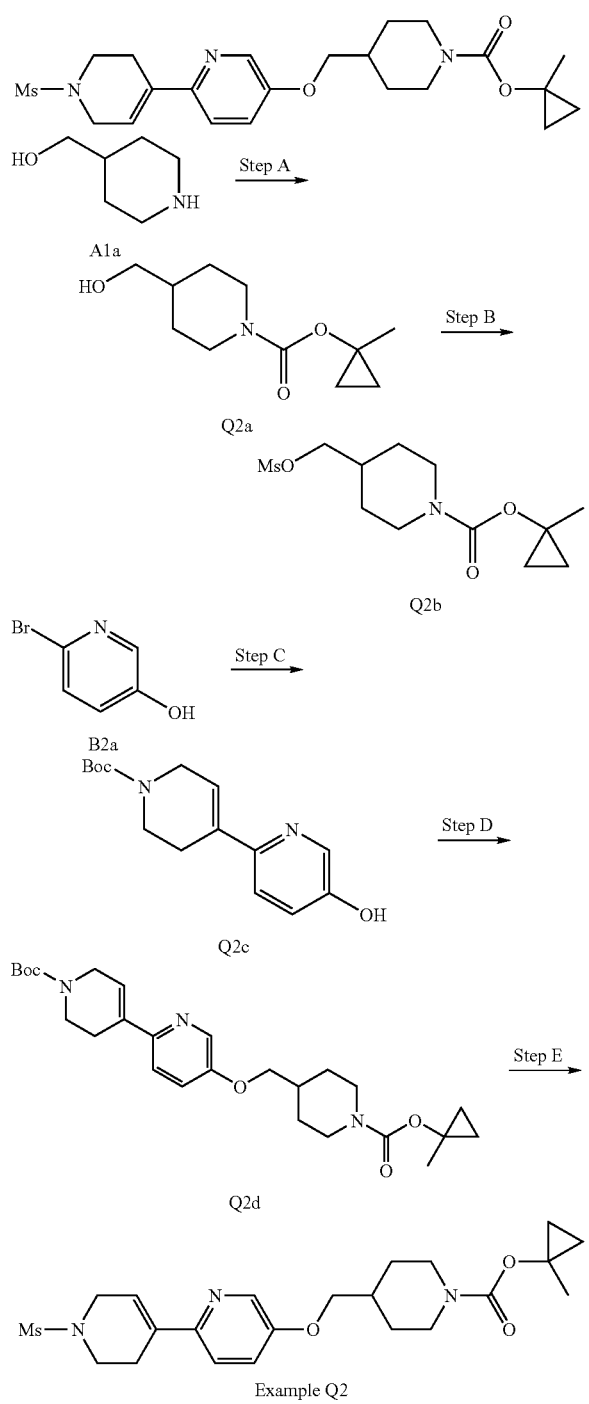

Step A: A solution of A1a (0.51 g, 4.4 mmol) in dichloromethane (7 mL) is treated with triethylamine (0.9 mL, 6.4 mmol) in one portion, followed by E3b (0.96 g, 4 mmol). The suspension is stirred at room temperature for 24 hours, diluted with more dichloromethane (25 mL), washed with water, saturated aqueous sodiumhydrogencarbonate (3×25 mL), and saturated aqueous ammonium chloride, dried over MgSO$_4$ and concentrated to yield Q2a; $^1$H NMR (CDCl$_3$, 400.13 MHz): δ 4.13 (br. s, 1H), 4.03 (br. s, 1H), 3.50 (m, 2H), 2.71 (t, J=12 Hz, 2H), 1.67 (m, 3H), 1.38 (br. s, 1H), 1.54 (s, 3H), 1.14 (br. s, 2H), 0.86 (m, 2H), 0.62 (m, 2H); ESIMS calcd. for $C_{11}H_{20}NO_3$ (M+H$^+$) 214.1. found 214.1.

Step B: To a solution of Q2a (0.71 g, 3.4 mmol) in dichloromethane (20 mL) is added triethylamine (0.9 mL, 6.4 mmol) in one portion. The resulting mixture is cooled in an ice/water bath and methanesulfonyl chloride (0.35 mL, 4.5 mmol) is added slowly, with stirring. The bath is removed and the resulting solution is stirred at room temperature for 2 hours. The reaction mixture is diluted with more dichloromethane (20 mL), washed with water and saturated aqueous ammonium chloride, dried over MgSO$_4$ and concentrated to yield Q2b; $^1$H NMR (CDCl$_3$, 400.13 MHz): δ 4.22 (br. s, 2H), 4.07 (s, 2H), 3.23 (m, 1H), 3.17 (s, 3H), 2.72 (m, 2H), 1.92 (m, 1H), 1.74 (m, 2H), 1.54 (s, 3H), 1.22 (br. s, 2H), 0.86 (m, 2H), 0.63 (m, 2H); ESIMS calcd. for $C_{12}H_{22}NO_5S$ (M+H$^+$) 292.1. found 292.0.

Step C: To a solution of B2a (0.1 g, 0.6 mmol) in 1,2-dimethoxyethane (1.5 mL) is added tert-butyl 5,6-dihydro-4-(4,4,5,5-tetramethyl-1,3,2-dioxaborolan-2-yl)pyridine-1(2H)-carboxylate (0.13 g, 0.4 mmol), powdered potassium carbonate (0.15 g, 1.1 mmol), and water (0.5 g). The mixture is degassed using argon, then tetrakis-(triphenylphosphino)palladium(0) (0.08 g, 0.07 mmol) is added and the mixture is heated to 180° C. for 5 min in a microwave reactor. Cooling, extraction with ethyl acetate, washing with water and brine, drying over Na$_2$SO$_4$ and concentration, followed by purification on silica gel using a linear gradient of 5 to 100% ethyl acetate in hexane affords Q2c. ESIMS calcd. for $C_{15}H_{21}N_2O_3$ (M+H$^+$) 277.2. found 277.0.

Step D: A solution of Q2b (0.05 g, 0.17 mmol) and Q2c (0.04 g, 0.15 mmol) in dry acetonitrile (2 mL) is treated with powdered cesium carbonate (0.1 g, 0.3 mmol) and the mixture is stirred at 60° C. for 24 hours. Filtration, concentration, and purification on silica gel using a linear gradient of 0 to 100% ethyl acetate in hexane affords Q2d; ESIMS calcd. for $C_{26}H_{38}N_3O_5$ (M+H$^+$) 472.3. found 472.0.

Step E: To a solution of Q2d (0.15 mmol) in dioxane (2 mL) is added hydrogen chloride in dioxane (4N, 0.5 mL), slowly, with stirring. The resulting solution is stirred at room temperature for 4 hours. The solvent is removed and the residue is dissolved in dichloromethane (3 mL) and treated with triethylamine (0.1 mL, 0.7 mmol) followed by methanesulfonyl chloride (0.025 mL, 0.3 mmol) dropwise, with stirring, over 5 minutes. The resulting solution is stirred at room temperature for 2 hours. The solvent is removed and the resulting residue is purified by mass triggered HPLC to afford Q2; ESIMS calcd. for $C_{22}H_{32}N_3O_5S$ (M+H$^+$) 450.2. found 450.1.

Example Q3

Isopropyl 4-(2-(6-(1,2,3,6-tetrahydro-1-methanesulfonylpyridin-4-yl)pyridin-3-yloxy)ethyl)piperidine-1-carboxylate

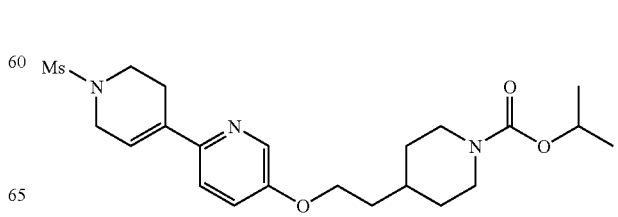

By following a procedure similar to the one used for preparing Q1 from A1c, except substituting isopropyl 4-(2-(methylsulfonyloxy)ethyl)piperidine-1-carboxylate for A1c, Q3 is prepared; ESIMS calcd. for $C_{22}H_{34}N_3O_5S$ (M+H$^+$) 452.2. found 452.1.

Example Q4

2-(4-((5-(1,2,3,6-Tetrahydro-1-methanesulfonylpyridin-4-yl)pyrazin-2-yloxy)methyl)piperidin-1-yl)-5-ethylpyrimidine

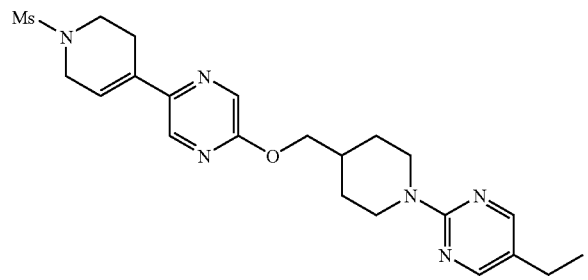

By following a procedure similar to the one used for preparing Q2 from A1a, except substituting B4a for B2a in Step A and Q4b (see scheme below) for Q2b in Step D, Q4 is prepared; ESIMS calcd. for $C_{22}H_{31}N_6O_3S$ (M+H$^+$) 459.2. found 459.1.

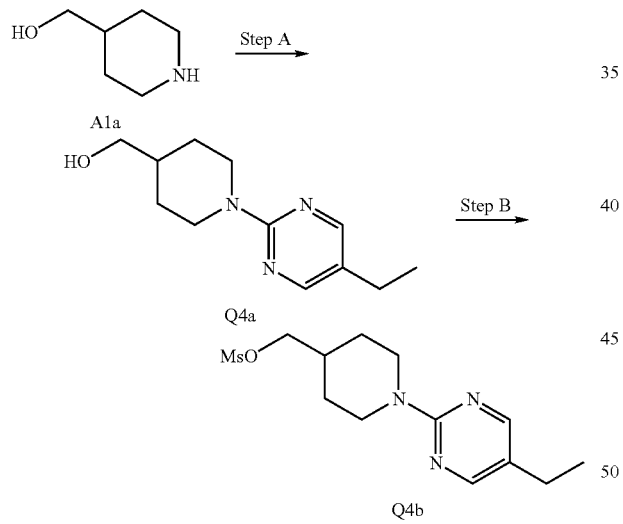

Step A: A solution of A1a (1.03 g, 9 mmol) and 2-chloro-5-ethylpyrimidine (1.1 mL, 9 mmol) in dimethylacetamide (7 mL) is treated with powdered cesium carbonate (4 g, 12.3 mmol) and the suspension is stirred at 75° C. for 48 hours. The reaction is then diluted with water (150 mL) and extracted with ethyl acetate/diethyl ether (1:1) (2×100 mL). The combined extracts are washed with water, saturated aqueous ammonium chloride, and brine, dried over $Na_2SO_4$ and concentrated to yield Q4a; $^1$H NMR (CDCl$_3$, 400.13 MHz): δ 8.16 (s, 2H), 4.74 (m, 2H), 3.53 (t, J=5.9 Hz, 2H), 2.87 (td, J=13.2, 2.4 Hz, 2H), 2.45 (q, J=7.6 Hz, 2H), 1.85 (m, 2H), 1.77 (m, 1H), 1.44 (t, J=5.5 Hz, 1H), 1.23 (m, 2H), 1.18 (t, J=7.6 Hz, 3H); ESIMS calcd. for $C_{12}H_{20}N_3O$ (M+H$^+$) 222.2. found 222.1.

Step B: To a solution of Q4a (0.92 g, 4.2 mmol) in dichloromethane (20 mL) is added triethylamine (1.0 mL, 7.1 mmol) in one portion. The resulting mixture is cooled in an ice/water bath and methanesulfonyl chloride (0.45 mL, 5.8 mmol) is added slowly, with stirring. The bath is removed and the resulting solution is stirred at room temperature for 2 hours. The reaction mixture is diluted with more dichloromethane (20 mL), washed with water and saturated aqueous ammonium chloride, dried over MgSO$_4$ and concentrated to yield Q4b; $^1$H NMR (CDCl$_3$, 400.13 MHz): $^1$H NMR (CDCl$_3$, 400.13 MHz): δ 8.17 (s, 2H), 4.78 (m, 2H), 4.09 (d, J=6.6 Hz, 2H), 3.02 (s, 3H), 2.88 (td, J=13.2, 2.6 Hz, 2H), 2.46 (q, J=7.6 Hz, 2H), 2.05 (m, 2H), 1.84 (m, 1H), 1.29 (ddd, J=4.4, 12.4, 12.7 Hz, 2H), 1.19 (t, J=7.6 Hz, 3H); ESIMS calcd. for $C_{13}H_{22}N_3O_3S$ (M+H$^+$) 300.1. found 300.0.

Example Q5

2-(4-((6-(1,2,3,6-Tetrahydro-1-methanesulfonylpyridin-4-yl)pyridin-3-yloxy)methyl)piperidin-1-yl)-5-ethylpyrimidine

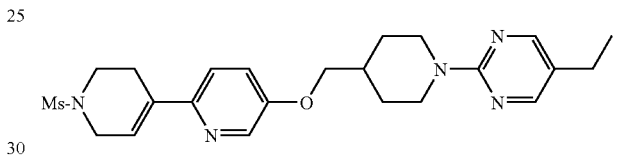

By following a procedure similar to the one used for preparing Q2 from Q2b, except substituting Q4b for Q2b, Q5 is prepared; ESIMS calcd. for $C_{23}H_{32}N_5O_3S$ (M+H$^+$) 458.2. found 458.1.

Example Q6

2-((1-(5-Ethylpyrimidin-2-yl)piperidin-4-yl)methoxy)-5-(1-methanesulfonylpiperidin-4-yl)pyrazine

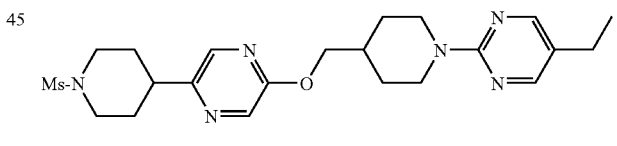

Example Q6 may be made from Q5 above, by hydrogenation with palladium on carbon. However, an alternate synthesis is as follows:

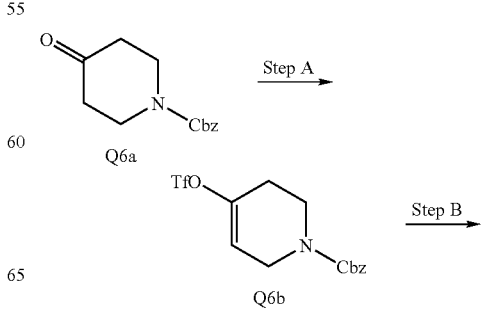

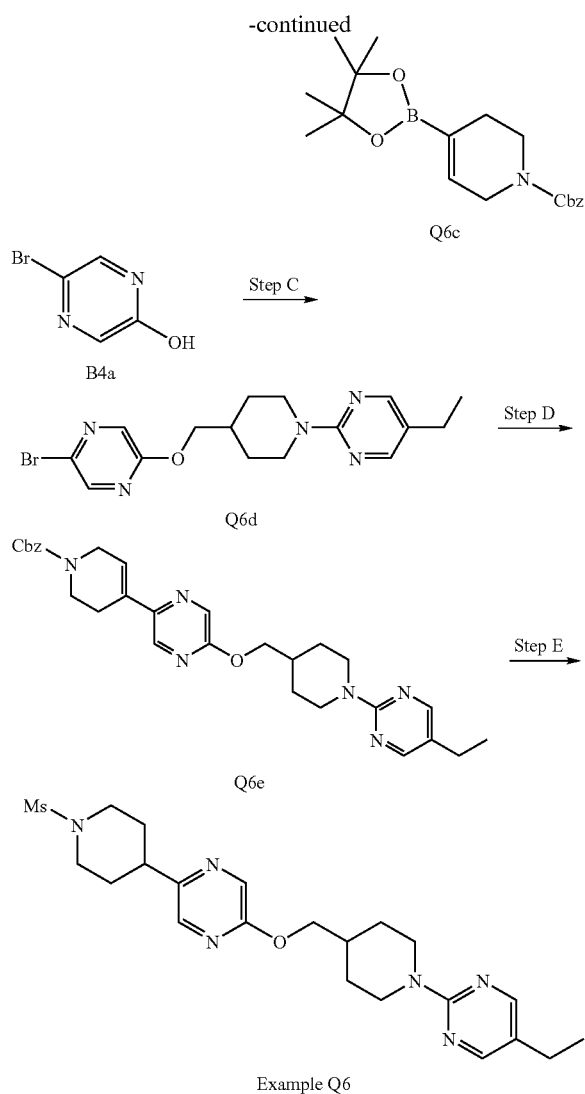

Step A: A solution of diisopropylamine (2 mL, 14.2 mmol) in dry tetrahydrofuran (10 mL) at −78° C. under nitrogen is treated with n-Butyllithium (2.46 M solution in hexanes; 5 mL, 12.25 mmol) and the mixture is stirred for 15 min at −78° C. A solution of Q6a (2.55 g, 10.9 mmol) in dry tetrahydrofuran (25 mL) is slowly added and stirring is continued at −78° C. for 2 hours. N-Phenyltriflimide (4.42 g, 12.4 mmol) in dry tetrahydrofuran (25 mL) is added dropwise at −78° C. The mixture is stirred at −78° C. for 2.5 hours and at room temperature for 30 minutes. Dilution with ethyl acetate (200 mL) and saturated aqueous ammonium chloride (50 mL), washing with water and brine, drying over $Na_2SO_4$ and concentration followed by purification on silica gel using a linear gradient of 0 to 40% ethyl acetate in hexane affords Q6b; $^1$H NMR ($CDCl_3$, 400.13 MHz): δ 7.3-7.4 (m, 5H), 5.78 (m, 1H), 5.16 (s, 2H), 4.13 (br. s, 2H), 3.72 (br. s, 2H), 2.47 (br. s, 2H); $^{19}$F NMR ($CDCl_3$, 376 MHz): 6-75.32; ESIMS calcd. for $C_{14}H_{15}F_3NO_5S$ (M+H$^+$) 366.1. found 366.1.

Step B: To a solution of Q6a (1.22 g, 3.3 mmol) in 1,4-dioxane (25 mL) is added 4,4,5,5-tetramethyl-2-(4,4,5,5-tetramethyl-1,3,2-dioxaborolan-2-yl)-1,3,2-dioxaborolane (1.02 g, 4 mmol), 1,1'-bis(diphenylphosphino)ferrocene (0.08 g, 0.14 mmol), [1,1'-bis(diphenylphosphino)ferrocene]dichloropalladium(II)dichloromethane complex (0.11 g, 0.13 mmol) and potassium acetate powder (1.26 g, 12.8 mmol). The mixture is degassed using argon and stirred at 80° C. for 18 hours. Cooling, diluting with water (50 mL), extraction with ethyl acetate, washing with water and brine, drying over $Na_2SO_4$ and concentration, followed by purification on silica gel using a linear gradient of 0 to 50% ethyl acetate in hexane affords Q6b; $^1$H NMR ($CDCl_3$, 400.13 MHz): δ 7.3-7.4 (m, 5H), 6.5 (m, 1H), 5.16 (s, 2H), 4.05 (m, 2H), 3.54 (m, 2H), 2.27 (br. s, 2H), 1.28 (s, 12H); ESIMS calcd. for $C_{19}H_{27}BNO_4$ (M+H$^+$) 344.2. found 344.1.

Step C: A solution of B4a (0.84 g, 4.8 mmol) and intermediate Q4b (1.28 g, 4.3 mmol) in dry dimethylacetamide (25 mL) is treated with powdered cesium carbonate (2.31 g, 7.1 mmol) and the mixture is stirred at 65° C. for 24 hours. Filtration, concentration, and by purification on silica gel using a linear gradient of 10 to 50% ethyl acetate in hexane affords Q4d; $^1$H NMR ($CDCl_3$, 400.13 MHz): δ 8.17 (s, 2H), 8.16 (d, J=1.4 Hz, 1H), 8.02 (d, J=1.4 Hz, 1H), 4.77 (m, 2H), 4.17 (d, J=6.6 Hz, 2H), 2.88 (td, J=13.1, 2.6 Hz, 2H), 2.46 (q, J=7.6 Hz, 2H), 2.10 (m, 2H), 1.89 (m, 1H), 1.34 (ddd, J=4.3, 12.4, 12.6 Hz, 2H), 1.19 (t, J=7.6 Hz, 3H); ESIMS calcd. for $C_{16}H_{21}BrN_5O$ (M+H$^+$) 378.1. found 378.1.

Step D: To a solution of Q6d (0.8 g, 2.1 mmol) in 1,2-dimethoxyethane (5 mL) is added intermediate Q6c (0.91 g, 2.7 mmol), powdered potassium carbonate (0.72 g, 5.2 mmol), and water (0.5 g). The mixture is degassed using argon, then tetrakis-(triphenylphosphino)palladium(0) (0.23 g, 0.2 mmol) is added and the mixture is heated to 180° C. for 20 min in a microwave reactor. Cooling, dilution with ethyl acetate, drying over $Na_2SO_4$ and concentration, followed by purification on silica gel using a linear gradient of 10 to 50% ethyl acetate in hexane affords Q6e; ESIMS calcd. for $C_{29}H_{35}N_6O_3$ (M+H$^+$) 515.3. found 515.1.

Step E: A solution of Q6e (0.6 g, 1.2 mmol) in ethyl acetate (100 mL) and ethanol (40 mL) is treated with palladium on carbon (5%; 0.85 g, 0.4 mmol) and the mixture is saturated with hydrogen gas and is then stirred at room temperature under 1 atmosphere of hydrogen for 3 hours. After filtration of the reaction through a pad of Celite® and concentration the residue is dissolved in dichloromethane (10 mL) and triethylamine (0.6 mL, 4.3 mmol). Methanesulfonyl chloride (0.15 mL, 1.9 mmol) is then slowly added, with stirring. After 2 hours, the mixture is concentrated and purified on silica gel using a linear gradient of 10 to 65% ethyl acetate in hexane to afford Q6. ESIMS calcd. for $C_{22}H_{33}N_6O_3S$ (M+H$^+$) 461.2. found 461.1.

Example Q7

2-(4-((6-(1-Methanesulfonylpiperidin-4-yl)pyridin-3-yloxy)methyl)piperidin-1-yl)-5-ethylpyrimidine

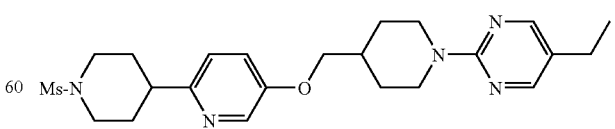

By following a procedure similar to the one used for preparing Q6 from B4a, except substituting B2a for B4a in Step C, Q7 is prepared; ESIMS calcd. for $C_{23}H_{34}N_5O_3S$ (M+H$^+$) 460.2. found 460.1.

Example Q8

3-((1-(5-Ethylpyrimidin-2-yl)piperidin-4-yl)methoxy)-6-(1-methanesulfonylpiperidin-4-yl)pyridazine

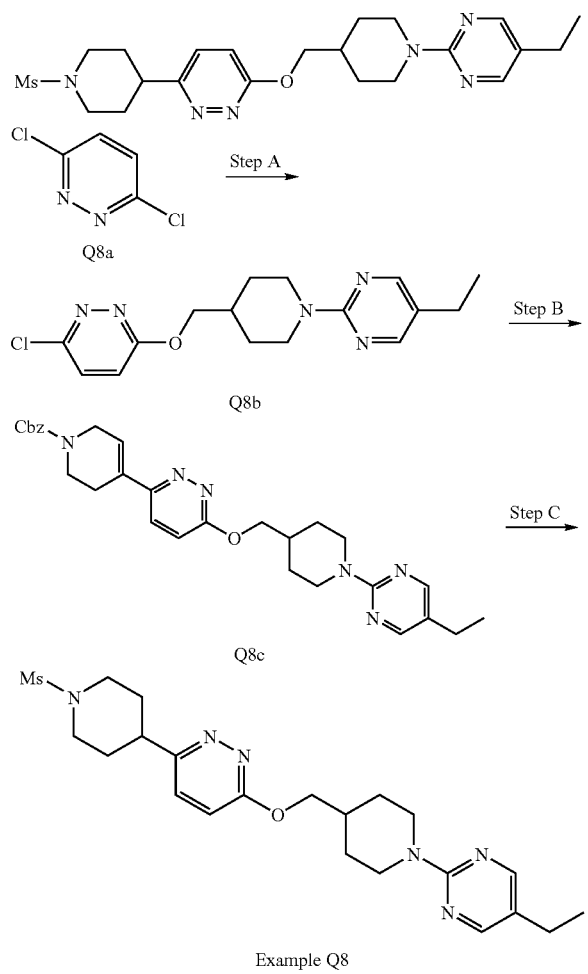

Example Q8

Step A: A solution of Q8a (0.64 g, 2.9 mmol) and Q4a (0.49 g, 3.3 mmol) in dry dimethylacetamide (6 mL) is treated with powdered potassium carbonate (0.7 g, 5.0 mmol) and the mixture is stirred at 150° C. for 2 days. Cooling, dilution with water (100 mL), extraction with ethyl acetate (2×100 mL), drying over $Na_2SO_4$, filtration, concentration, and purification on silica gel using a linear gradient of 10 to 100% ethyl acetate in hexane affords Q8b; $^1H$ NMR (CDCl$_3$, 400.13 MHz): δ 8.17 (s, 2H), 7.67 (d, J=9.2 Hz, 1H), 6.96 (d, J=9.2 Hz, 1H), 4.77 (m, 2H), 4.37 (d, J=6.6 Hz, 2H), 2.90 (td, J=13.1, 2.6 Hz, 2H), 2.46 (q, J=7.6 Hz, 2H), 2.15 (m, 2H), 1.89 (m, 1H), 1.36 (ddd, J=4.3, 12.4, 12.6 Hz, 2H), 1.19 (t, J=7.6 Hz, 3H); ESIMS calcd. for $C_{16}H_{21}ClN_5O$ (M+H$^+$) 334.1. found 334.1.

Step B: To a solution of Q8b (0.11 g, 0.3 mmol) in 1,2-dimethoxyethane (2 mL) is added intermediate Q6b (0.15 g, 0.4 mmol), powdered potassium carbonate (0.18 g, 1.3 mmol), and water (0.5 g). The mixture is degassed using argon, then tetrakis-(triphenylphosphino)palladium(0) (0.05 g, 0.04 mmol) is added and the mixture is heated to 180° C. for 20 min in a microwave reactor. Cooling, dilution with ethyl acetate, drying over $Na_2SO_4$ and concentration, followed by purification on silica gel using a linear gradient of 10 to 75% ethyl acetate in hexane affords Q8c; ESIMS calcd. for $C_{29}H_{35}N_6O_3$ (M+H$^+$) 515.3. found 515.1.

Step C: A solution of Q8c (0.15 g, 0.3 mmol) in ethyl acetate (20 mL) and ethanol (20 mL) is treated with palladium black on carbon (5%; 0.4 g, 0.2 mmol), saturated with hydrogen and then stirred at room temperature under 1 atmosphere of hydrogen for 6 hours. After exchanging the atmosphere for $N_2$, the reaction is filtered through a pad of Celite® and concentrated. The resulting oil is dissolved in dichloromethane (10 mL) and triethylamine (0.3 mL, 2.1 mmol). Methanesulfonyl chloride (0.05 mL, 0.6 mmol) is then slowly added, with stirring. After 2 hours, the mixture is concentrated and purified using mass-triggered reverse phase HPLC to afford Q8; ESIMS calcd. for $C_{22}H_{33}N_6O_3S$ (M+H$^+$) 461.2. found 461.1.

Example Q9

2-(4-((5-(1-Methanesulfonylpiperidin-4-yl)pyridin-2-yloxy)methyl)piperidin-1-yl)-5-ethylpyrimidine

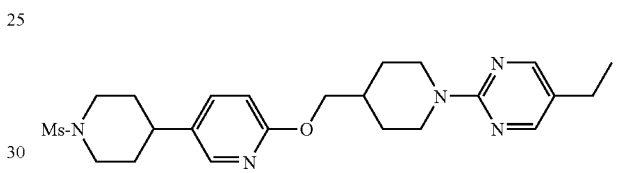

By following a procedure similar to the one used for preparing Q8 from Q8a, except substituting C1a for 8a, Q9 is prepared; ESIMS calcd. for $C_{23}H_{34}N_5O_3S$ (M+H$^+$) 460.2. found 460.2.

Example R1

1-tert-Butyl 4-(4-(1-(methylsulfonyl)piperidin-4-yl)phenyl)piperazine-1,4-dicarboxylate

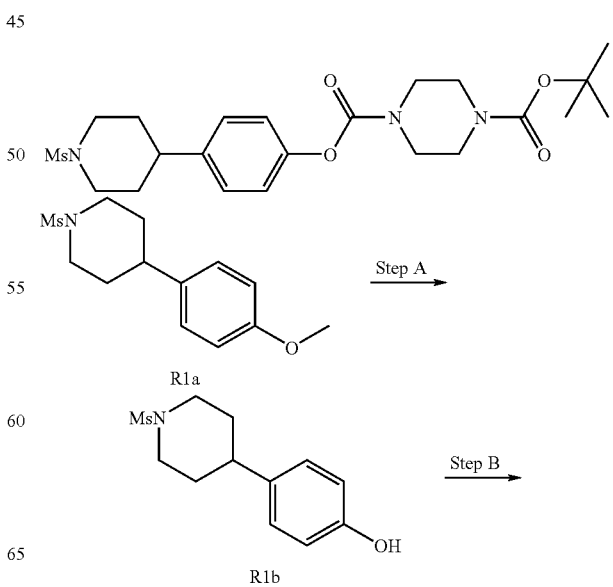

-continued

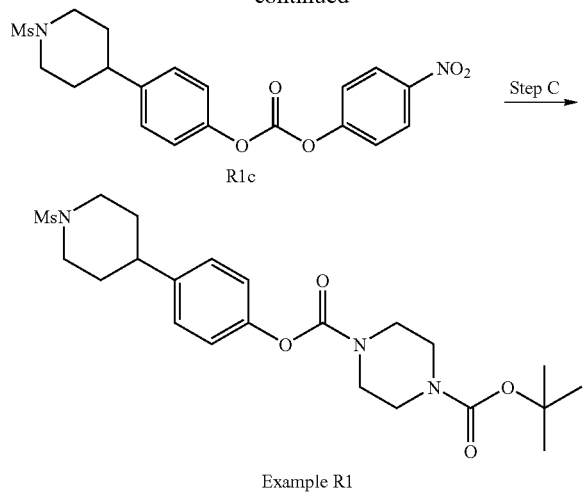

Example R1

Step A: A solution of R1a (2.2 g, 8.2 mmol) in dichloromethane (10 mL) is cooled in an ice/water bath and treated with neat $BBr_3$ (9.21 g, 37 mmol). The reaction is stirred at ice bath temperature for 10 minutes and at room temperature for 1 hour. The reaction is then poured on to crushed ice and allowed to quenchours. The resulting solid is collected and dried to afford R1b; ESIMS calcd. for $C_{12}H_{17}NO_3S$ $(M+H^+)$ 256.1. found 256.1.

Step B: A solution of R1b (100 mg, 0.39 mmol) and nitrophenyl chloroformate (87 mg, 0.43 mmol) in acetonitrile (5 mL) is treated with $K_2CO_3$ (108 mg, 0.78 mmol) and the mixture is stirred at room temperature for 2 hours, then is filtered, concentrated, and purified on silica gel using a linear gradient of 0 to 100% ethyl acetate in hexane to afford R1c; ESIMS calcd. for $C_{19}H_{21}N_2O_7S$ $[M+H]^+$ 421.1. found 421.1.

Step C: A solution of R1c (41 mg, 0.10 mmol), 1-Boc-piperazine (20 mg, 0.11 mmol) and triethylamine (68 μL, 0.50 mmol) in 1,2-dichloroethane (5 mL) is heated at 50° C. for 12 hours. The mixture is concentrated in vacuo and purified using mass-triggered reverse phase HPLC to afford R1; $^1$H-NMR (400 MHz, $CDCl_3$) δ 7.12 (d, J=8.4 Hz, 2H), 6.98 (d, J=8.8 Hz, 2H), 3.87 (m, 3H), 3.56 (m, 2H), 3.45 (m, 6H), 2.75 (s, 3H), 2.70 (m, 3H), 2.55 (m, 2H), 1.90 (m, 3H), 1.77 (m, 3H), 1.42 (s, 9H); ESIMS calcd. for $C_{22}H_{33}N_3NaO_6S$ $[M+Na]^+$ 490.2. found 490.1.

Example S1

N-((1-(5-Ethylpyrimidin-2-yl)piperidin-4-yl)methyl)-4-(1-(methylsulfonyl)piperidin-4-yl)aniline

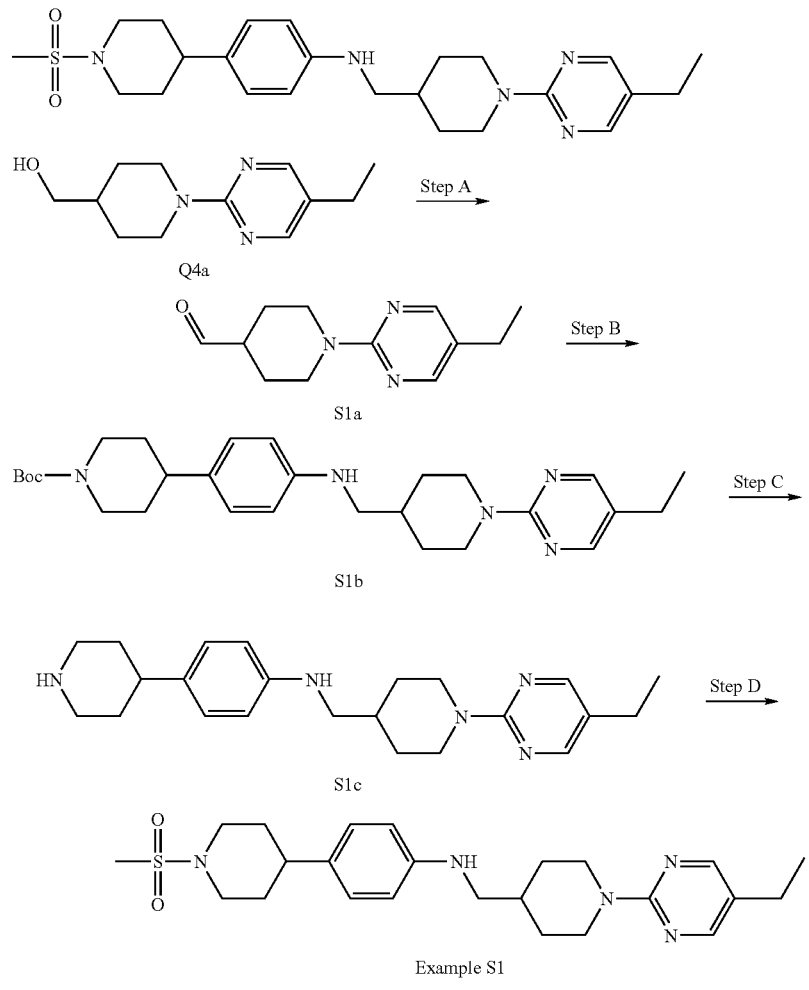

Step A: A solution of Q4a (444 mg, 2 mmol) in anhydrous dichloromethane (5 mL) is added to a solution of Dess-Martin periodinane (1.018 g, 2.4 mmol) in anhydrous dichloromethane (10 mL) and stirred overnight at room temperature. Additional dichloromethane (30 mL) is added and the reaction is filtered through Celite® and concentrated. Purification on silica gel using a linear gradient of 0 to 50% ethyl acetate in hexane to affords S1a; ESIMS calcd. for $C_{12}H_{18}N_3O$ (M+H$^+$) 220.1. found 220.1.

Step B: A mixture of S1a (318 mg, 1.5 mmol), tert-butyl 4-(4-aminophenyl)piperidine-1-carboxylate (482 mg, 1.74 mmol), and NaBH(OAc)$_3$ (636 mg, 3 mmol) in dichloromethane (7 mL) is stirred at room temperature for 5 hours. The reaction is quenched with water (20 mL) and extracted with dichloromethane (3×20 mL), washed with water (20 mL), dried (Na$_2$SO$_4$), and concentrated. Purification on silica gel using a linear gradient of 0 to 50% ethyl acetate in hexane to affords S1b; ESIMS calcd. for $C_{28}H_{42}N_5O_2$ (M+H$^+$) 480.3. found 480.4.

Step C: A solution of S1b (600 mg, 1.25 mmol) in MeOH (10 mL) is treated with a 4 M solution of HCl in dioxane (25 mL, 100 mmol) and stirred at room temperature overnight. The reaction mixture is concentrated, dioxane (20 mL) added and concentrated again to form the hydrochloride salt of S1c; ESIMS calcd. for $C_{23}H_{34}N_5$ (M+H$^+$) 380.3. found 380.3.

Step D: A cold (0° C.) mixture of S1c (810 mg, 1.25 mmol) and triethylamine (0.892 mL, 6.4 mmol) in dichloromethane (30 mL) is treated with methanesulfonyl chloride (0.152 mL, 1.96 mmol) dropwise and stirred at room temperature for 3 hours. Additional triethylamine (0.5 mL, 3.6 mmol) and methanesulfonyl chloride (0.076 mL, 0.98 mmol) are added and the reaction is stirred at room temperature for another 30 minutes. The reaction is quenched with water (20 mL), extracted with dichloromethane (3×20 mL), washed with water (20 mL), dried over Na$_2$SO$_4$, and concentrated. Purification using mass-triggered reverse phase HPLC affords SI; $^1$H NMR (CDCl$_3$, 400 MHz): δ 8.24 (s, 2H), 7.05 (m, 2H), 6.70 (m, 2H), 4.61 (m, 2H), 3.64 (m, 2H), 2.96 (m, 2H), 2.88 (s, 3H), 2.80 (m, 4H), 2.42 (q, J=7.6 Hz, 2H), 1.84 (m, 5H), 1.60 (m, 2H), 1.12 (m, 5H); ESIMS calcd. for $C_{24}H_{36}N_5O_2S$ (M+H$^+$) 458.3. found 458.3.

Example S2

N-((1-(5-Ethylpyrimidin-2-yl)piperidin-4-yl)methyl)-N-methyl-4-(1-(methylsulfonyl)piperidin-4-yl)aniline

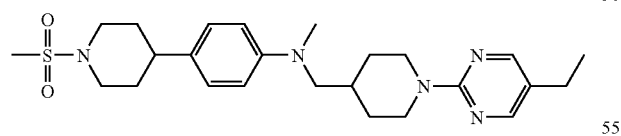

A solution of S1 (46 mg, 0.1 mmol) in tetrahydrofuran (1 mL) is added dropwise to an ice-cold solution of 10% aqueous H$_2$SO$_4$ (0.2 mL) and 37% aqueous formaldehyde (0.1 mL, 1.2 mmol) in tetrahydrofuran (0.5 mL). NaBH$_4$ (30 mg, 0.79 mmol) is added and the reaction mixture is warmed to room temperature. After stirring for 30 minutes the reaction is quenched with 0.2 M NaOH (10 mL) and extracted with ethyl acetate (3×15 mL), washed with brine (10 mL), dried over Na$_2$SO$_4$ and concentrated. The compound is purified using mass-triggered reverse phase HPLC to afford S2; $^1$H NMR (CDCl$_3$, 400 MHz): δ 8.23 (s, 2H), 7.08 (m, 2H), 6.68 (m, 2H), 4.60 (m, 2H), 3.64 (m, 2H), 3.19 (m, 2H), 2.92 (bs, 3H), 2.88 (s, 3H), 2.78 (m, 4H), 2.42 (q, J=7.6 Hz, 2H), 1.93 (m, 1H), 1.81 (m, 2H), 1.62 (m, 4H), 1.12 (m, 5H); ESIMS calcd. for $C_{25}H_{38}N_5O_2S$ (M+H$^+$) 472.3. found 472.3.

Examples T1f and T1

4-(4-((1-(5-fluoropyrimidin-2-yl)piperidin-4-yl)methoxy)phenyl)-1-(methylsulfonyl)piperidine-4-carbonitrile and 4-(4-((1-(5-fluoropyrimidin-2-yl)piperidin-4-yl)methoxy)phenyl)-1-(methylsulfonyl)piperidine-4-carboxylic acid

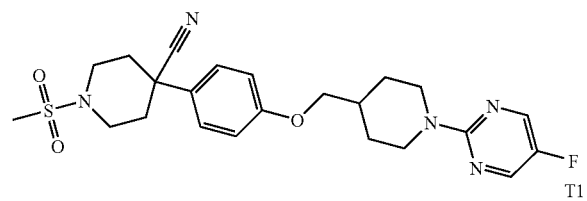

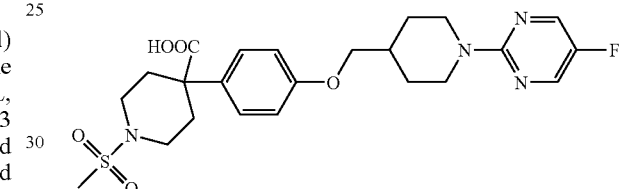

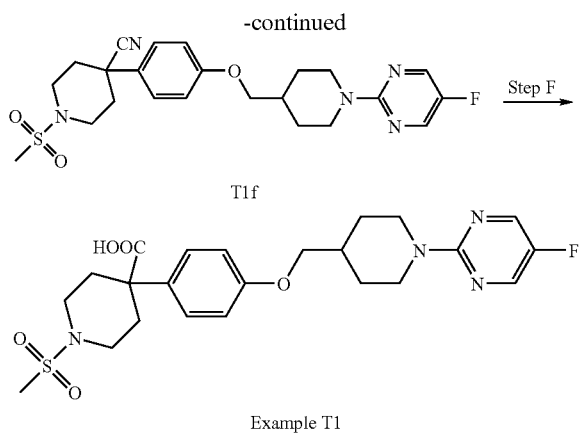

T1f

Example T1

Step A: To an ice-cold suspension of NaH (60% in oil, 120 mg, 3 mmol) in anhydrous N,N-dimethylformamide (2 mL) is added T1a (142 μL, 1.05 mmol) and stirred for 30 minutes under a nitrogen atmosphere. To the resulting brown solution is added tert-butyl bis(2-chloroethyl)carbamate (242 mg, 1 mmol) in N,N-dimethylformamide (0.2 mL) and the cooling bath is removed after 15 min. The reaction mixture is heated overnight at 75° C., cooled to room temperature and quenched with water (1 mL). More water is added (50 mL) and the reaction is extracted with dichlormethane (3×30 mL), dried over $Na_2SO_4$ and concentrated. Purification on silica gel using a linear gradient of 0 to 50% ethyl acetate in hexane to affords T1b; $^1$H-NMR (400 MHz, CDCl$_3$) δ 7.38 (m, 2H), 6.93 (m, 2H), 4.26 (m, 2H), 3.82 (s, 3H), 3.19 (m, 2H), 2.08 (d, J=12.9 Hz, 2H), 1.90 (td, J=13.0, 4.0 Hz, 2H), 1.48 (s, 9H); ESIMS calcd. for $C_{18}H_{24}N_2NaO_3$ (M+Na$^+$) 339.2. found 388.8.

Step B: To a solution of T1b (218 mg, 0.69 mmol) in dioxane (1 mL) is added 4 M solution of HCl in dioxane (2 mL, 8 mmol) and the reaction is stirred for 2 hours at room temperature. The solvent is removed and the residue is coevaporated with dioxane (10 mL) to afford T1c; ESIMS calcd. for $C_{13}H_{17}N_2O$ (M+H$^+$) 217.1. found 216.9.

Step C: A cold (ice/water bath) solution of T1c (0.69 mmol) and triethylamine (385 μL, 2.76 mmol) in dry dichloromethane (10 mL) is treated with methanesulfonyl chloride (64 μL, 0.83 mmol) dropwise. The resulting solution is stirred at room temperature overnight. The reaction mixture is added to water (40 mL) and extracted with dichloromethane (3×40 mL). The combined organic layers are dried over $Na_2SO_4$ and concentrated to yield T1d; ESIMS calcd. for $C_{14}H_{19}N_2O_3S$ (M+H$^+$) 295.1. found 295.0.

Step D: A solution of T1d (208 mg, 0.7 mmol) in anhydrous dichloromethane (3.5 mL) is cooled to −78° C. under nitrogen atmosphere and a 1M solution of BBr$_3$ (3.5 mL, 3.5 mmol) in dichloromethane is added dropwise. The reaction is stirred at room temperature overnight, then cooled to 0° C. and quenched with MeOH (2 mL). The reaction mixture is repeatedly concentrated with MeOH (3×20 mL) to afford T1e; ESIMS calcd. for $C_{13}H_{17}N_2O_3S$ (M+H$^+$) 281.1. found 281.0.

Step E: A mixture of T1e (196 mg, 0.7 mmol), (1-(5-fluoropyrimidin-2-yl)piperidin-4-yl)methyl methanesulfonate (202 mg, 0.7 mmol; prepared by following the procedure for Q4a except using 2-chloro-5-fluoropyrimidine as the electrophile), and Cs$_2$CO$_3$ (456 mg, 1.4 mmol) in acetonitrile (10 mL) is heated to 70° C. for 48 hours. The reaction mixture is concentrated and partitioned between water (20 mL) and ethyl acetate, the aqueous phase is extracted with ethyl acetate (2×20 mL). The combined organics are washed with water (2×10), dried over Na$_2$SO$_4$ and concentrated. Purification on silica gel using a linear gradient of 0 to 60% ethyl acetate in hexane to affords T1f; $^1$H-NMR (400 MHz, DMSO) δ 8.43 (d, J=0.8 Hz, 2H), 7.46 (m, 2H), 7.00 (m, 2H), 4.61 (m, 2H), 3.87 (d, J=6.4 Hz, 2H), 3.74 (m, 2H), 3.00 (m, 5H), 2.92 (m, 2H), 2.24 (m, 2H), 2.05 (m, 3H), 1.83 (m, 2H), 1.23 (m, 2H); ESIMS calcd. for $C_{23}H_{29}FN_5O_3S$ (M+H$^+$) 474.2. found 474.2.

Step F: A solution of T1f (30 mg, 0.063 mmol) and KOH (105 mg, 2.6 mmol) in 2-methoxyethanol (1 mL) and water (0.5 mL) is heated to 110° C. for 72 hours. The reaction mixture is acidified with 1N HCl to pH 2-3 and extracted with ethyl acetate (3×20 mL). The combined organics are dried over Na$_2$SO$_4$, and concentrated. The residue is purified using mass-triggered reverse phase HPLC to afford T1; $^1$H-NMR (400 MHz, DMSO-d$_6$) δ 8.42 (d, J=0.8 Hz, 2H), 7.30 (m, 2H), 6.92 (m, 2H), 4.60 (m, 2H), 3.83 (d, J=6.4 Hz, 2H), 2.88 (m, 7H), 2.48 (m, 2H), 2.04 (m, 1H), 1.83 (m, 4H), 1.22 (m, 2H). ESIMS calcd. for $C_{23}H_{30}FN_4O_5S$ (M+H$^+$) 493.2. found 493.1

Example U1

1-methylcyclopropyl 4-((2,6-difluoro-4-(3-(methylsulfonamido)azetidin-1-yl)phenoxy)methyl)piperidine-1-carboxylate

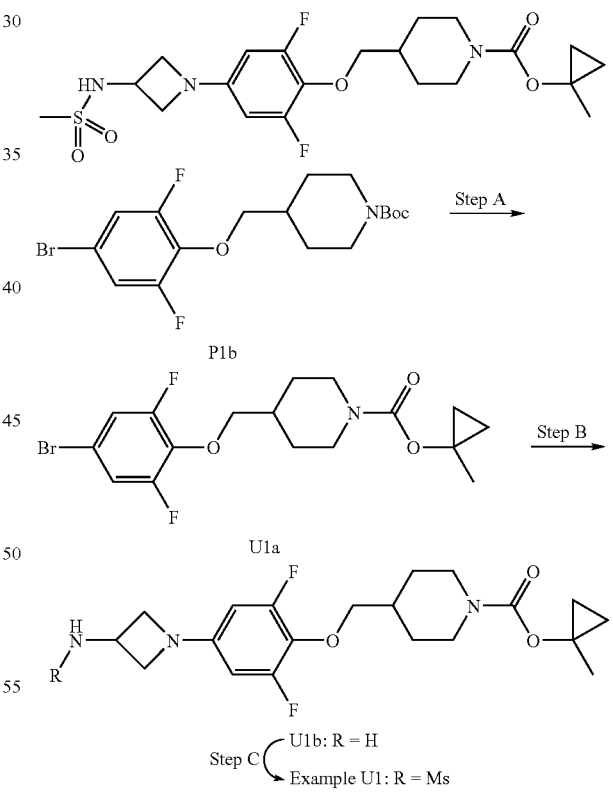

Step A: By following a similar procedure as that used to prepare E3 from E3a, except substituting P1b for E3a, U1a is prepared; ESIMS calcd. for $C_{17}H_{21}BrF_2NO_3$ [M+H]$^+$: 404.1. found: 404.0.

Step B: By following a similar procedure as that used to prepare B2 from B2b, except substituting benzyl azetidin-3-ylcarbamate for benzyl piperazine-1-carboxylate, U1b is prepared; It is observed that the Cbz group is removed under reaction conditions; ESIMS calcd. for $C_{20}H_{28}F_2N_3O_3$ [M+H$^+$] 396.2. found 369.3.

Step C: By following a similar procedure as that used to prepare G1 from G1a, except substituting U1b for G1a, U1 is prepared; $^1$H-NMR (400 MHz, CDCl$_3$) δ 5.95 (d, J=9.7 Hz, 2H), 4.85 (d, J=9.4 Hz, 1H), 4.40 (m, 1H), 4.20 (t, J=7.5 Hz, 2H), 4.29-3.94 (m, 2H), 3.80 (d, J=6.0 Hz, 2H), 3.65 (dd, J=5.3, 8.0 Hz, 2H), 3.00 (s, 3H), 2.74 (t, J=12.4 Hz, 2H), 1.9 (m, 1H), 1.82 (d, J=13.1 Hz, 2H), 1.54 (s, 3H), 1.22 (m, 2H), 0.86 (t, J=6.4 Hz, 2H), 0.62 (t, J=6.4 Hz, 2H). ESIMS calcd. for $C_{21}H_{30}F_2N_3O_5S$ [M+H$^+$] 474.2. found 474.1.

Example U2

1-methylcyclopropyl 4-((2,6-difluoro-4-(3-(2-methylpropylsulfonamido)azetidin-1-yl)phenoxy)methyl)piperidine-1-carboxylate

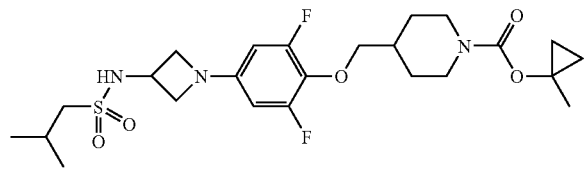

By following a similar procedure as that used to prepare U1 from U1c, except substituting isobutanesulfonyl chloride for methanesulfonyl chloride, U2 is prepared; $^1$H-NMR (400 MHz, CDCl$_3$) δ 5.96 (d, J=9.6 Hz, 2H), 4.87 (d, J=9.5 Hz, 1H), 4.40 (m, 1H), 4.20 (t, J=7.5 Hz, 2H), 4.29-3.94 (m, 2H), 3.82 (d, J=4.8 Hz, 2H), 3.65 (dd, J=7.9, 5.4 Hz, 2H), 2.93 (d, J=6.4 Hz, 2H), 2.75 (m, 2H), 2.28 (septet, J=6.7 Hz, 1H), 1.92 (m, 1H), 1.83 (d, J=12.6 Hz, 2H), 1.56 (s, 3H), 1.24 (m, 2H), 1.13 (d, J=6.7 Hz, 6H), 0.87 (t, J=6.3 Hz, 2H), 0.63 (t, J=6.3 Hz, 2H). ESIMS calcd. for $C_{24}H_{36}F_2N_3O_5S$ [M+H$^+$] 516.2. found 516.2.

Example U3

1-methylcyclopropyl 4-((2,6-difluoro-4-(3-(N-methylmethylsulfonamido)azetidin-1-yl)phenoxy)methyl)piperidine-1-carboxylate

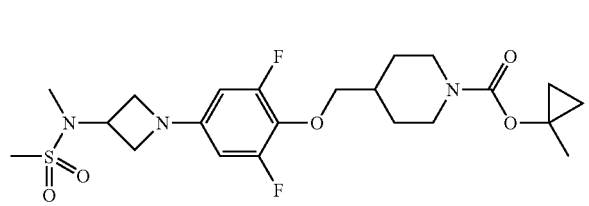

To a solution of U1 (25 mg, 0.05 mmol) and iodomethane (4 uL, 0.06 mmol) in dry N,N-dimethylformamide (1 mL) at 0° C. is added sodium hydride (5 mg, 0.2 mmol) in one portion. The mixture is allowed to warm slowly to room temperature and stirred an additional 1 hour. The mixture is partitioned between water and dichloromethane, and the organics washed with brine, dried over MgSO$_4$, filtered, evaporated and purified on silica gel using 0-50% ethyl acetate in dichloromethane to afford U3; $^1$H-NMR (400 MHz, CDCl$_3$) δ 5.97 (d, J=9.6 Hz, 2H), 4.71 (m, 1H), 4.06 (t, J=7.8 Hz, 2H), 4.29-3.95 (m, 2H), 3.88 (dd, J=8.0, 5.6 Hz, 2H), 3.81 (d, J=5.8 Hz, 2H), 2.97 (s, 3H), 2.83 (s, 3H), 2.74 (m, 2H), 1.91 (m, 1H), 1.83 (d, J=13.4 Hz, 2H), 1.54 (s, 3H), 1.24 (m, 2H), 0.86 (t, J=6.3 Hz, 2H), 0.62 (t, J=6.3 Hz, 2H). ESIMS calcd. for $C_{22}H_{32}F_2N_3O_5S$ [M+H$^+$] 488.2. found 488.2.

Example U4

1-methylcyclopropyl 4-((4-(3-(N,2-dimethylpropylsulfonamido)azetidin-1-yl)-2,6-difluorophenoxy)methyl)piperidine-1-carboxylate

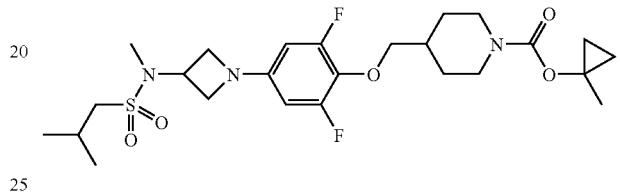

By following a similar procedure as that used to prepare U3 from U1, except substituting U2 for U1, U2 is prepared; $^1$H-NMR (400 MHz, CDCl$_3$) δ 5.96 (d, J=9.7 Hz, 2H), 4.77 (m, 1H), 4.04 (t, J=7.9 Hz, 2H), 4.25-3.96 (m, 2H), 3.87 (dd, J=5.6, 7.8 Hz, 2H), 3.81 (d, J=6.3 Hz, 2H), 2.97 (s, 3H), 2.77 (d, J=6.7 Hz, 2H), 2.74 (m, 2H), 2.24 (septet, J=6.6 Hz, 1H), 1.91 (m, 1H), 1.83 (d, J=13.3 Hz, 2H), 1.54 (s, 3H), 1.24 (m, 2H), 1.11 (d, J=6.5 Hz, 6H), 0.86 (t, J=6.3 Hz, 2H), 0.61 (t, J=6.3 Hz, 2H). ESIMS calcd. for $C_{25}H_{38}F_2N_3O_5S$ [M+H$^+$] 530.3. found 530.2.

Example U5

1-Methylcyclopropyl 4-((5-(3-(methylsulfonamido)azetidin-1-yl)pyrazin-2-yloxy)methyl)piperidine-1-carboxylate

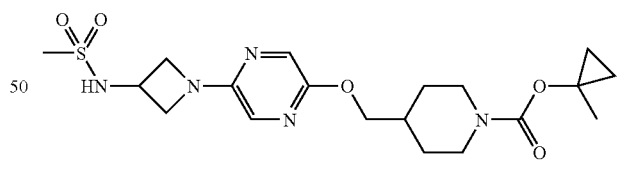

By following a similar procedure as that used to prepare M1 from M1a, except substituting benzyl azetidin-3-ylcarbamate for benzyl piperazine-1-carboxylate in step A and methanesulfonyl chloride for methyl 3-(chlorosulfonyl)propanoate in step d, U5 is prepared; $^1$H NMR (400 MHz, CDCl$_3$) δ 7.72 (d, J=1.4 Hz, 1H), 7.24 (d, J=1.4 Hz, 1H), 4.73 (d, J=9.2 Hz, 1H), 4.37 (m, 1H), 4.28 (m, 2H), 3.97 (d, J=6.4 Hz, 2H), 3.75 (m, 2H), 3.27 (s, 3H), 2.65 (m, 2H), 1.85 (m, 1H), 1.70 (m, 2H), 1.46 (s, 3H), 1.17 (m, 3H), 0.77 (m, 2H), 0.53 (m, 2H); ESIMS m/z for (M+H)$^+$ $C_{19}H_{30}N_5O_5S$ calcd: 440.2. found: 440.2.

Example U6

1-Methylcyclopropyl 4-((2,6-difluoro-4-(4-(methylsulfonyl)-2-oxopiperazin-1-yl)phenoxy)methyl)piperidine-1-carboxylate

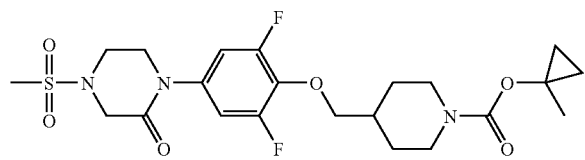

By following a similar procedure as that used to prepare O2 from B4b, except substituting P1b for B4b, U6 is prepared; $^1$H-NMR (400 MHz, DMSO-$d_6$) δ 7.28 (m, 2H), 3.94 (m, 6H), 3.77 (m, 2H), 3.53 (m, 2H), 3.05 (s, 3H), 2.75 (m, 2H), 1.88 (m, 2H), 1.74 (m, 2H), 1.46 (s, 3H), 1.14 (m, 2H), 0.76 (m, 2H), 0.59 (m, 2H); ESIMS calcd. for $C_{22}H_{30}F_2N_3O_6S$ [M+H]$^+$ 502.2. found 502.2.

Example V1

8-((1-(5-Ethylpyrimidin-2-yl)piperidin-4-yl)methoxy)-2-(methylsulfonyl)-1,2,3,4-tetrahydropyrazino[1,2-a]indole

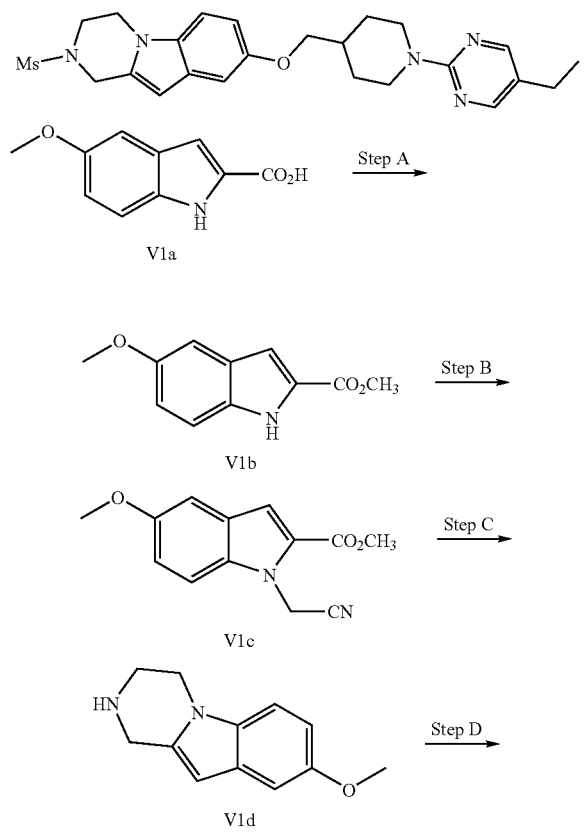

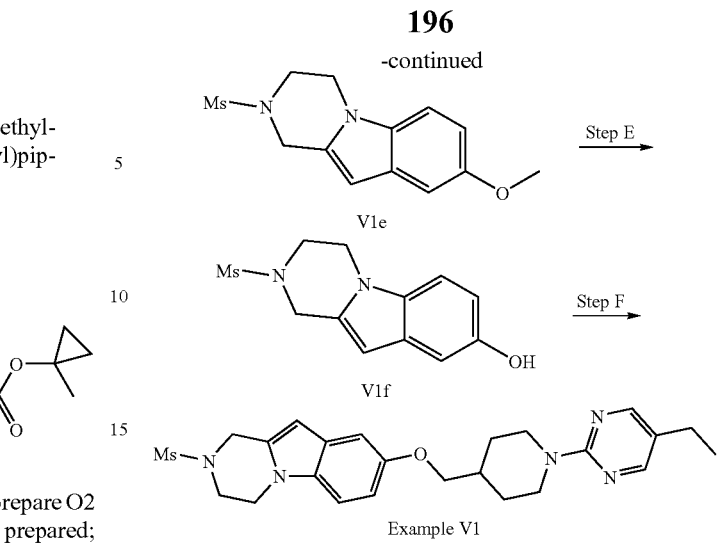

Step A: A suspension of V1a (2.26 g, 11.8 mmol) in methanol (20 mL) is treated with thionyl chloride (1.0 mL, 13.8 mmol) dropwise, with stirring. The resulting mixture is stirred at room temperature for 18 h, and then concentrated to dryness. The resulting solid is triturated with 1:1 water/aqueous saturated sodiumhydrogencarbonate, filtered, washed with water and dried to afford V1b; $^1$H NMR (DMSO-$d_6$, 400.13 MHz): δ 11.80 (s, 1H), 7.37 (d, J=8.9 Hz, 1H), 7.11 (d, J=2.2 Hz, 1H), 7.06 (d, J=2.2 Hz, 1H), 6.92 (dd, J=2.4, 8.9 Hz, 1H), 3.86 (s, 3H), 3.76 (s, 3H); ESIMS calcd. for $C_{11}H_{12}NO_3$ (M+H$^+$) 206.1. found 206.1.

Step B: A solution of V1b (1.86 g, 9.1 mmol) is in N,N-dimethylacetamide (25 mL) is treated with powdered cesium carbonate (5.31 g, 16.3 mmol) and chloroacetonitrile (0.90 mL, 14.3 mmol) and the mixture is stirred at 65° C. for 18 hours. Cooling to room temperature, dilution with ethyl acetate, washing with water (2×), saturated aqueous ammonium chloride and brine, drying over $Na_2SO_4$, filtration and concentration yields a solid. The residue is purified on silica gel using 5-30% ethyl acetate in hexanes to afford V1c; $^1$H NMR (CDCl$_3$, 400.13 MHz): δ 7.33 (d, J=8.9 Hz, 1H), 7.30 (d, J=1.0 Hz, 1H), 7.12 (m, 2H), 5.59 (s, 2H), 3.95 (s, 3H), 3.87 (s, 3H); ESIMS calcd. for $C_{13}H_{13}N_2O_3$ (M+H$^+$) 245.1. found 245.0.

Step C: V1d is prepared from V1c according to the literature procedure described in *Bioorg. Med. Chem. Lett.* 2002, 12, 155-158; ESIMS calcd. for $C_{12}H_{15}N_2O$ (M+H$^+$) 203.1. found 203.1.

Step D: To a solution of V1d (0.58 g, 2.5 mmol) in dichloromethane (15 mL) is added triethylamine (0.7 mL, 5 mmol) in one portion. The resulting mixture is cooled in an ice/water bathand methanesulfonyl chloride (0.25 mL, 3.2 mmol) is added dropwise, with stirring, over 5 minutes. The bath is removed and the resulting solution is stirred at room temperature for 30 minutes. The reaction mixture is added to water (40 mL) and extracted with dichloromethane (2×40 mL). The combined organic extracts are washed with saturated aqueous ammonium chloride solution, dried over MgSO$_4$, and concentrated to yield V1e; ESIMS calcd. for $C_{13}H_{17}N_2O_3S$ (M+H$^+$) 281.1. found 281.2.

Step E: A solution of V1e (0.60 g, 2.1 mmol) in dichloromethane (15 mL) is treated with neat boron tribromide (0.8 mL, 8.3 mmol) at room temperature. The resulting solution is stirred at room temperature for 30 minutes. The reaction mixture is carefully added to methanol (50 mL), treated with solid Na$_2$CO$_3$ (0.4 g), filtered and concentrated to dryness.

The crude V1f is used as such in the next step; ESIMS calcd. for $C_{12}H_{15}N_2O_3S$ (M+H$^+$) 267.1. found 267.1.

Step F: A solution of V1f and Q4b (0.03 g, 0.1 mmol) in dry acetonitrile (2 mL) is treated with powdered cesium carbonate (0.1 g, 0.3 mmol) and the mixture is stirred at 75° C. for 24 hours. Filtration and mass directed reverse phase HPLC purification yields V1; ESIMS calcd. for $C_{24}H_{32}N_5O_3S$ (M+H$^+$) 470.2. found 470.1.

By following a similar procedure as the one used for preparing V1 from V1f except substituting the appropriate mesylate for Q4b the following compounds are prepared;

-continued

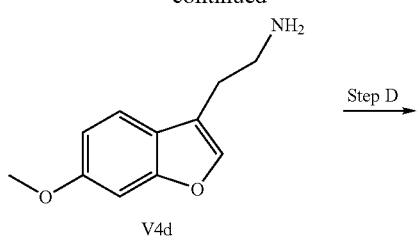

V4d

| Example | Structure | Analytical data |
|---------|-----------|-----------------|
| V2 | 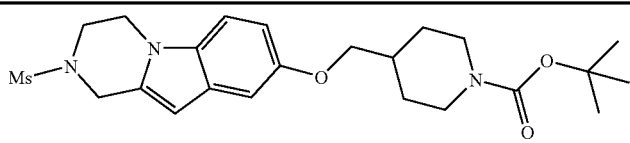 | $^1$H NMR (CDCl$_3$, 400.13 MHz): δ 7.17 (d, J = 8.8 Hz, 1 H), 7.03 (d, J = 2.3 Hz, 1 H), 6.85 (dd, J = 2.3, 8.8 Hz, 1 H), 6.24 (d, J = 0.7 Hz, 1 H), 4.67 (s, 2 H), 4.16 (br, 2 H), 4.15 (t, J = 5.4 Hz, 2 H), 3.84 (m, 4 H), 2.87 (s, 3 H), 2.76 (t, J = 12.2 Hz, 2 H), 1.98 (m, 1 H), 1.85 (t, J = 12.6 Hz, 2 H), 1.47 (s, 9 H), 1.28 (ddd, J = 4.7, 12.4, 12.4 Hz, 2 H); ESIMS calcd. for $C_{23}H_{34}N_3O_5S$ (M + H$^+$) 464.2, found 464.1. |
| V3 | 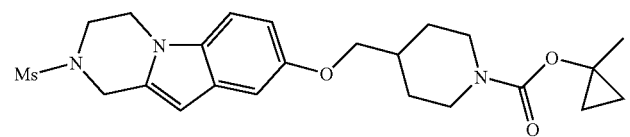 | ESIMS calcd. for $C_{23}H_{32}N_3O_5S$ (M + H$^+$) 462.2, found 462.2. |

Example V4

7-((1-(5-Ethylpyrimidin-2-yl)piperidin-4-yl)methoxy)-2-(methylsulfonyl)-1,2,3,4-tetrahydrobenzofuro[2,3-c]pyridine

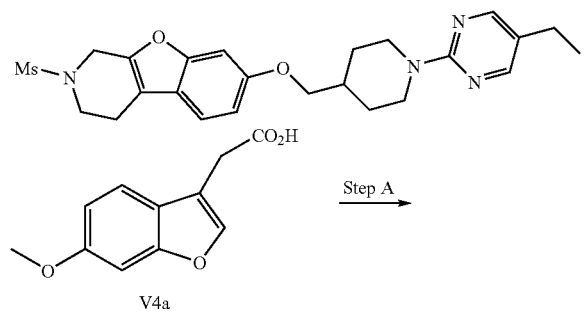

-continued

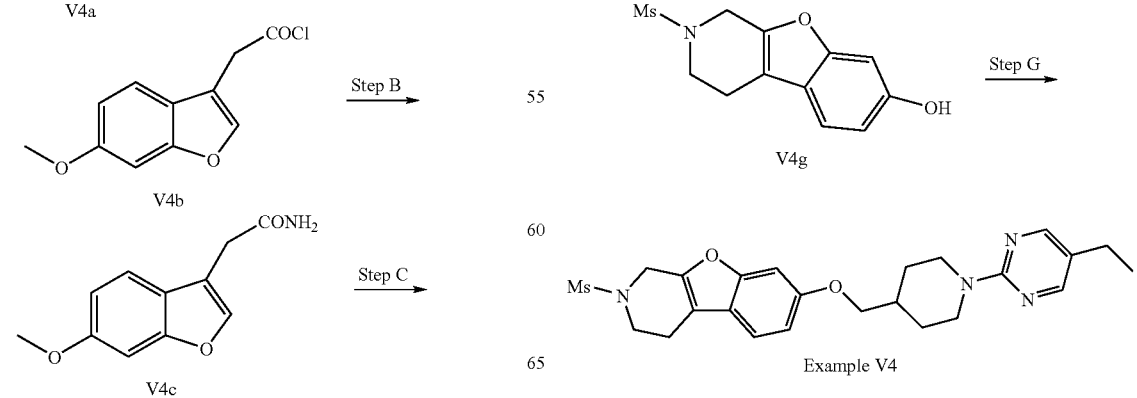

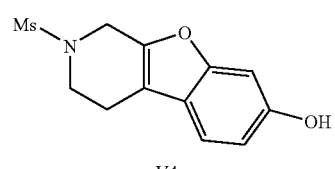

Step A: A suspension of V4a (3.99 g, 19.4 mmol) is in dichloromethane (50 mL) is treated with oxalyl chloride (1.8 mL, 21.3 mmol) slowly, with stirring, followed by dimethylformamide (0.01 mL). The resulting mixture is stirred at room temperature for 1 hour, and then concentrated to dryness to yield V4b; $^1$H NMR (CDCl$_3$, 400.13 MHz): δ 7.58 (t, J=1.0 Hz, 1H), 7.37 (d, J=8.6 Hz, 1H), 7.03 (d, J=2.2 Hz, 1H), 6.92 (dd, J=2.2, 8.6 Hz, 1H), 4.21 (d, J=1.0 Hz, 2H), 3.84 (s, 3H).

Step B: A solution of V4b (19.4 mmol) in dichloromethane (100 mL) is treated with ammonia gas by slow bubbling through the stirring solution for 5 minutes. The resulting suspension is stirred in a closed flask for 2 hours. The resulting suspension is filtered, the collected solids are washed with more dichloromethane and air dried to yield V4c; $^1$H NMR (CDCl$_3$, 400.13 MHz): δ 7.52 (t, J=0.7 Hz, 1H), 7.43 (d, J=8.6 Hz, 1H), 7.03 (d, J=2.2 Hz, 1H), 6.92 (dd, J=2.2, 8.6 Hz, 1H), 5.61 (s, 1H), 5.45 (s, 1H), 3.86 (s, 3H), 3.63 (d, J=0.7 Hz, 2H); ESIMS calcd. for C$_{11}$H$_{12}$NO$_3$ (M+H$^+$) 206.1. found 206.1.

Step C: A solution of V4c (2.79 g, 13.6 mmol) in dry tetrahydrofuran (100 mL) is treated with borane solution in tetrahydrofuran (1.0 N; 50 mL, 50 mmol) and the resulting solution is stirred in a closed flask overnight. The reaction mixture is carefully treated with methanol (50 mL) and concentrated to dryness. The residue is purified by silica gel chromatography using a linear gradient of 20 to 100% ethyl acetate in hexanes to afford V4d; $^1$H NMR (CDCl$_3$, 400.13 MHz): δ 7.46 (s, 1H), 7.38 (d, J=8.6 Hz, 1H), 7.02 (d, J=2.2 Hz, 1H), 6.90 (dd, J=2.2, 8.6 Hz, 1H), 3.85 (s, 3H), 3.63 (br. s, 2H), 3.14 (tt, J=6.4, 6.8 Hz, 2H), 3.02 (t, J=6.4 Hz, 2H); ESIMS calcd. for C$_{11}$H$_{14}$NO$_2$ (M+H$^+$) 192.1. found 192.1.

Step D: V4e acetic acid salt is prepared from V4d according to the procedure described in WO2000/020421, p. 15; $^1$H NMR (CDCl$_3$, 400.13 MHz): δ 7.30 (d, J=8.5 Hz, 1H), 6.99 (d, J=2.2 Hz, 1H), 6.86 (dd, J=2.2, 8.5 Hz, 1H), 3.88 (br. s, 2H), 3.85 (s, 3H), 3.06 (t, J=5.8 Hz, 2H), 2.85 (m, 2H), 2.72 (m, 1H); ESIMS calcd. for C$_{12}$H$_{14}$NO$_2$ (M+H$^+$) 204.1. found 204.1.

Step E: A solution of V4e acetic acid salt (0.18 g, 0.7 mmol) in dichloromethane (5 mL) is treated with triethylamine (0.2 mL, 1.4 mmol) and methanesulfonic anhydride (0.15 g, 0.86 mmol) and the mixture is stirred at room temperature for 1 hour. Washing with water, drying over MgSO$_4$ and concentration yields V4f; $^1$H NMR (CDCl$_3$, 400.13 MHz): δ 7.29 (d, J=8.5 Hz, 1H), 6.98 (d, J=2.2 Hz, 1H), 6.84 (dd, J=2.2, 8.5 Hz, 1H), 3.84 (s, 3H), 2.77 (m, 2H), 2.73 (m, 2H), 2.54 (s, 3H); ESIMS calcd. for C$_{13}$H$_{16}$NO$_4$S (M+H$^+$) 282.1. found 282.0.

Step F: A solution of V4f (0.15 g, 0.5 mmol) in dichloromethane (5 mL) is treated with neat boron tribromide (0.2 mL, 2.1 mmol) at room temperature. The resulting solution is stirred at room temperature for 30 minutes. The reaction mixture is carefully added to methanol (50 mL), treated with solid Na$_2$CO$_3$ (0.4 g), filtered and concentrated to dryness to afford V4g; ESIMS calcd. for C$_{12}$H$_{14}$NO$_4$S (M+H$^+$) 268.1. found 268.1.

Step G: A solution of V4g and Q4b (0.03 g, 0.1 mmol) in dry acetonitrile (2 mL) is treated with powdered cesium carbonate (0.08 g, 0.2 mmol) and the mixture is stirred at 75° C. for 24 hours. Filtration and mass directed HPLC purification yields V4; ESIMS calcd. for C$_{24}$H$_{31}$N$_4$O$_4$S (M+H$^+$) 471.2. found 471.2.

Example V5

7-(1-(5-Ethylpyrimidin-2-yl)piperidin-4-yloxy)-2-(methylsulfonyl)-1,2,3,4-tetrahydrobenzofuro[2,3-c]pyridine

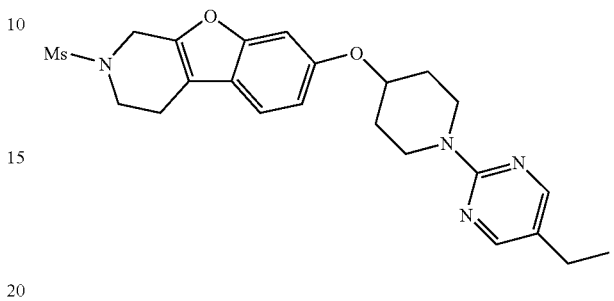

By following a similar procedure as the one used for preparing V4 from V4g except substituting 1-(5-ethylpyrimidin-2-yl)piperidin-4-yl methanesulfonate for Q4b the V5 is prepared; ESIMS calcd. for C$_{23}$H$_{29}$N$_4$O$_4$S (M+H$^+$) 457.2. found 457.1.

Biological Assays

Generation of Stable Cell Line

Flp-In-CHO cells (Invitrogen, Cat.# R758-07) are maintained in Ham's F12 medium supplemented with 10% fetal bovine serum, 1% antibiotic mixture and 2 mM L-glutamine. The cells are transfected with a DNA mixture containing human GPR119 (hGPR119) or mouse GPR119 (mGPR119) in the pcDNA5/FRT vector (Invitrogen) and the pOG44 vector (Invitrogen) in a 1:9 ratio using Fugene6 (Roche), according to the manufacturer's instructions. After 48 hours, the medium is changed to medium supplemented with 400 µg/mL hygromycin B to initiate the selection of stably transfected cells. The resultant cell lines are designated CHO-hGPR119 and CHO-mGPR119 respectively.

Cyclic AMP Assays

To test the activity of compounds of the invention on human GPR119, CHO-hGPR119 cells are harvested and resuspended at 300,000 cells/mL in assay media (Ham's F12 medium plus 3% lipid-depleted fetal bovine serum, 1 mM 3-isobutyl-1-methyl-xanthine (IBMX)). Cells (5 µl) are placed in each well of a white 1536-well plate. A compound of the invention (50 nL) diluted in 100% dimethyl sulfoxide (DMSO) is added to each well and the plates are incubated at 37° C. for 30 minutes. cAMP concentrations are then measured using the cAMP dynamic 2 kit (Cisbio Bioassays) according to the manufacturer's instructions. 2.5 µL of diluted cAMP-XL665 is added to each well, followed by 2.5 µL diluted anti-cAMP-Cryptate. The plate is covered and incubated for one hour at room temperature, then read on an Envision plate reader (Perkin Elmer) using the HTRF method with excitation at 337 nm, and emissions measured at 620 nm and 655 nm.

Activity of compounds of the invention on mouse GPR119 is measured by a similar method in 384-well plates. CHO-mGPR119 cells are harvested and resuspended in assay media at 500,000 cells/mL. 50 µl cells are placed in each well of a white 384-well plate. A compound of the invention (500 nL) diluted in 100% DMSO is added to each well and the plates are incubated at 37° C. for 30 minutes. cAMP concentrations are measured as above except that 20 μL of diluted cAMP-XL665 followed by 20 μL diluted anti-cAMP-Cryptate is added to each well.

Compounds of the invention, in free form or in pharmaceutically acceptable salt form, produced a concentration-dependent increase in intracellular cAMP level. Compounds of the invention show an $EC_{50}$ of between $1\times10^{-5}$ and $1\times10^{-10}$ M, preferably less than 500 nM, more preferably less than 100 nM. The following table shows a non-limiting sample of $EC_{50}$ measurements for compounds of the invention whereby +, ++ and +++ represent $EC_{50}$ ranges of >800 nM, 200-800 nM and <200 nM, respectively:

| Compound | Structure | $EC_{50}$ Activity |
|---|---|---|
| A3 | 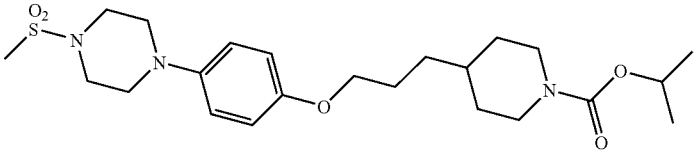 | + |
| C2 | 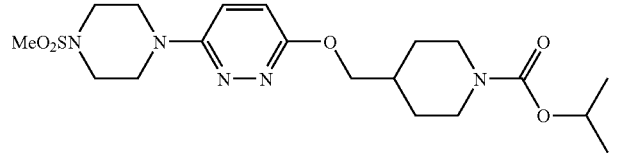 | + |
| D2 | 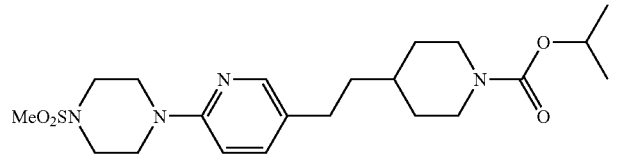 | ++ |
| E3 | 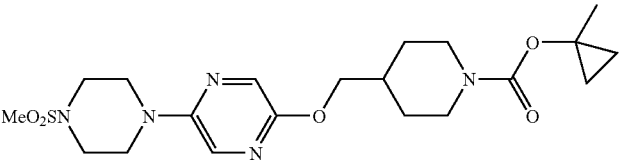 | +++ |
| E9 | 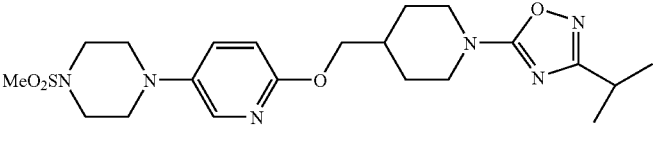 | ++ |
| G1 | 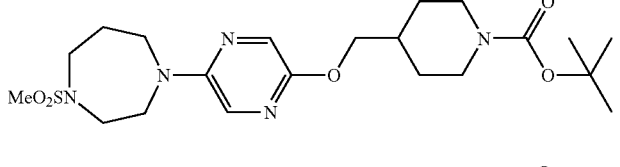 | + |
| G4 | 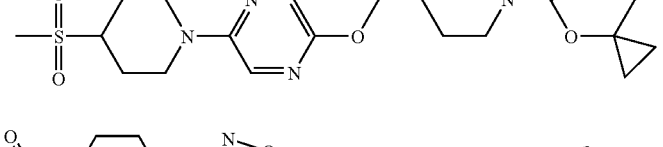 | +++ |
| H3 | 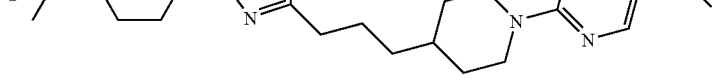 | +++ |

-continued

| Compound | Structure | EC$_{50}$ Activity |
|---|---|---|
| I1 | 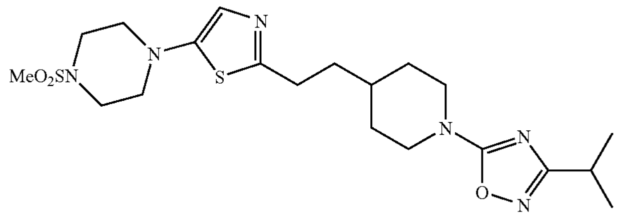 | +++ |
| J7 | 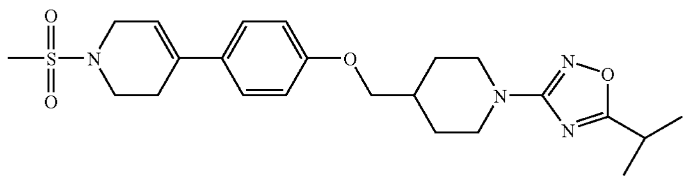 | +++ |
| J22 | 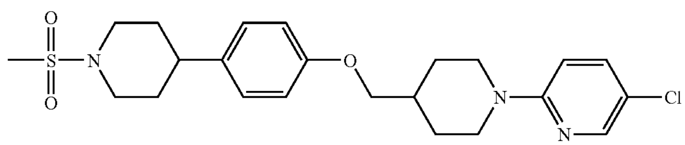 | +++ |
| K3 | 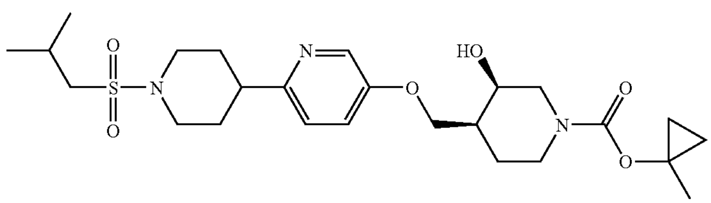 | +++ |
| O9 | 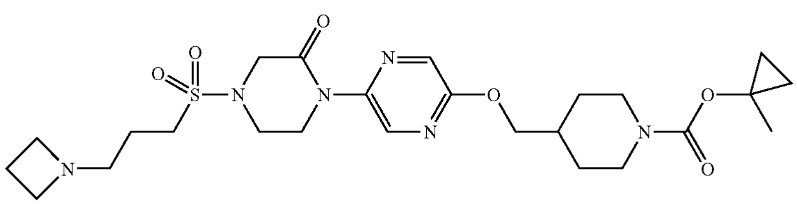 | +++ |
| O41 | 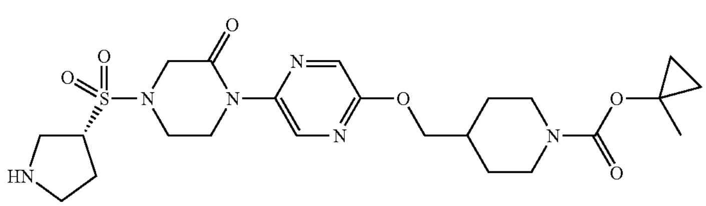 | +++ |
| P13 | 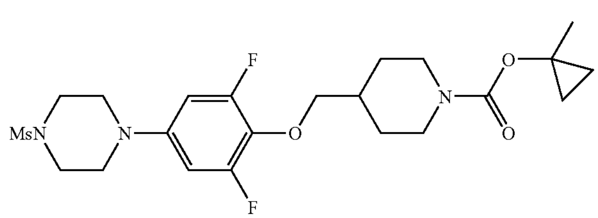 | +++ |

-continued

| Compound | Structure | EC$_{50}$ Activity |
|---|---|---|
| T1 | 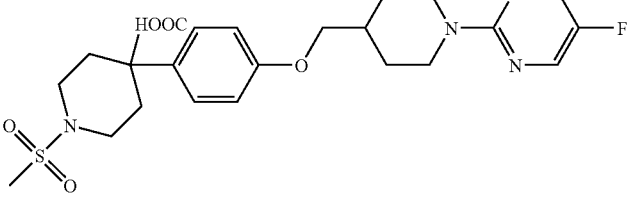 | ++ |
| U5 | 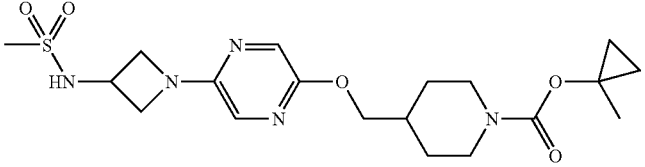 | +++ |
| V5 | 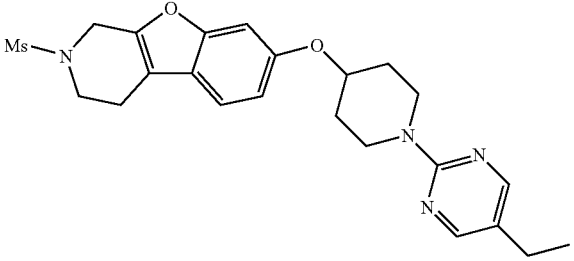 | +++ |

GLUTag GLP-1 Assay

The effect of compounds of the invention on GLP-1 secretion can be studied in GLUTag cells (a mouse entereoendocrine cell line that secretes GLP-1). GLUTag cells are plated in poly-D-lysine-coated 96-well plates on day one in complete medium (DMEM/10% FBS). On day two, the culture medium is replaced with a low glucose medium (DMEM/5.5 mM glucose/10% FBS). One day three, cells are washed twice and pre-incubated in glucose free EBSS buffer (100 mM NaCl, 5 mM KCl, 0.8 mM MgSO$_4$.7H$_2$O, 1.65 mM NaH$_2$PO$_4$.2H$_2$O, 26 mM NaHCO$_3$, 1.6 mM CaCl$_2$, 0.1% fatty acid-free bovine serum albumin, pH 7.35) for two hours at 37° C. with 5% CO$_2$. After this pre-incubation period, the cells are washed again with glucose free EBSS buffer, and then stimulated with a compound of the invention at various concentrations in EBSS buffer plus 10 mM glucose and a DPP-4 inhibitor at 37° C. in the presence of 5% CO$_2$. At the end of the incubation, the supernatants are then collected and transferred to a HEK293 cell line that over expresses human GLP-1 receptor and a CRE-luciferase reporter construct. The CRE-luciferase construct expresses luciferase gene under the control of a cAMP response element (CRE). GLP-1-stimulated GLP-1 receptor leads to cAMP production, which in turn, up regulates luciferase expression. The HEK293-GLP-1R reporter cells are plated the night before in white 384-well plates. After incubation with the supernatants from GLUTag cells treated with a compound of the invention, the HEK293-GLP-1R reporter cells are incubated at 37° C. in the presence of 5% CO$_2$ for 18 hours. Luciferase produced from the treatment is measured by the addition of Steady-Glo reagent (Promega, Cat. #E2550). The EC$_{50}$ values are calculated with nonlinear regression using Graphpad Prism.

HIT-T15 Insulin Assay

The effect of GPR119 agonist on insulin secretion is studied in HIT-T15 cells (a hamster beta cell line that secrets insulin). HIT-T15 cells are obtained from ATCC and are cultured in Ham's F12 Kaighn's medium plus 10% horse serum and 2.5% fetal bovine serum. On day one, HIT-T15 cells are plated in 96-well plates and cultured for 24 hours and then the medium is replaced with a low-glucose medium (RPMI 1640 medium supplemented with 10% horse serum, 2.5% fetal bovine serum and 3.0 mM D-(+)-glucose). On day three, the cells are washed twice and then pre-incubated with glucose-free Krebs-Ringer bicarbonate buffer (KRBB) that contains 119 mM NaCl, 4.74 mM KCl, 2.54 mM CaCl$_2$, 1.19 mM KH$_2$PO$_4$, 1.19 mM MgCl$_2$, 25 mM NaHCO$_3$, 10 mM HEPES and 0.1% fatty-acid-free bovine serum albumin at pH 7.4. One hour later, the cells are washed again for three times and incubated with a compound of the invention in KRBB plus 16.5 mM glucose for 3 hours at 37° C. After a 5 minute centrifugation at 1,000 rpm, supernatant is removed from each well and transferred into a separate plate for insulin measurement following the instructions for Cisbio insulin HTRF assay kit (Cisbio, Cat. #62INSPEC). The EC$_{50}$ values are calculated with nonlinear regression using Graphpad Prism.

GLP-1 Assay

Adult male wild-type C57BL/6J mice (age 9 weeks, JAX) are used as the experimental animals. In all experiments, mice are housed in a 12 hour light/dark cycle facility (light on from 5:00 a.m. to 5:00 p.m) and have access to food (Purina 5001) and water ad libitum. Mice (8 per group) are randomized into treatment groups based on their initial body weight. They are orally dosed with vehicle, DPP4 inhibitor alone, or DPP4 inhibitor and a compound of the invention, in a single dose. A glucose bolus (2 g/kg) is delivered sixty minutes post dosing. A sample is collected 2 minutes post glucose bolus.

Plasma active GLP-1 is measured in C57BL/6 mice following a single oral administration of increasing doses of a compound of the invention (3, 10 and 30 mg/kg). Animals are fasted for 16 hours prior to compound administration. Oral doses are administered at approximately 10:00 am in a 75% PEG300:25% D5W suspension. Blood is obtained (via retro-orbital bleeding) to measure plasma levels of active GLP-1. Approximately 200 μL samples of blood are removed for analysis at 62 minutes post dosing (2 minutes post glucose bolus). All data are expressed as the mean±SEM for each experimental group of mice. Statistical analysis of data is performed using a one-way ANOVA with a Bonferroni's Multiple Comparison Post Test (GraphPad Prism 4.02).

Treatment of mice with increasing doses of a compound of the invention (in combination with a DPP4 inhibitor) results in increasing levels of plasma active GLP-1. The magnitude of GLP-1 increase observed in the 10 mg/kg group demonstrate that some compounds of the invention can increase circulating levels of active GLP-1 by about 2.2× fold relative to the effect with a DPP4 inhibitor alone.

OGTT Assay

Adult male Zucker fa/fa rats (age 11 weeks, Charles River Labs) are used as the experimental animals. In all experiments, rats are housed in a 12 hour light/dark cycle facility (light on from 5:00 a.m. to 5:00 p.m) and have access to food (Purina 5001) and water ad libitum. Rats (6 per group) are randomized into treatment groups based on their initial body weight and are dosed (orally) with vehicle orally, a DPP4 inhibitor, or a compound of the invention. Sixty minutes after dosing, a 3 g/kg glucose bolus is administered.

A compound of the invention is dissolved in vehicle for dosing (orally using a gavage needle) at a final concentration of 0.2, 2 or 6 mg/mL. Oral doses are administered at approximately 7:30 am in a 75% PEG300:25% D5W.

OGTT evaluations are performed in conscious rats that are 11 weeks of age. The rats are fasted by removing food at 6 pm the day before. A baseline blood sample is taken at t=minus 60 minutes and the rats are then dosed orally with the a compound of the invention. A baseline blood sample is taken at t=zero minutes and the animals are then administered an oral glucose bolus (3 g/kg) immediately. Blood is obtained (via tail bleeding) to measure blood glucose (using a glucometer). A single drop of blood from the tail is measured for glucose using a glucometer at t=−60, 0, 10, 30, 60, 90, 120 and 180 minutes.

The area under the curve (AUC) is calculated using the trapezoidal rule. All data are expressed as the mean±sem for each experimental group of rats. Statistical analysis of data is performed using a one-way ANOVA with a Bonferroni's Multiple Comparison Post Test (GraphPad Prism 4.02).

Some compounds of the invention exhibit a clear dose-dependent effect on improved glucose clearance at 3, 10, and 30 mg/kg (about 31%, about 48%, and about 56% reduction in glucose AUC, respectively) when dosed in a 75% PEG300/25% D5W formulation. The results demonstrate that some compounds of the invention can lower blood glucose in response to glucose challenge.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

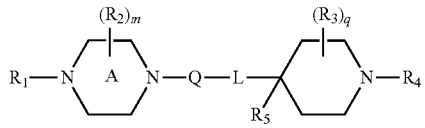

or a pharmaceutically acceptable salt thereof; in which:
Q is a divalent radical selected from $C_{6-10}$aryl, $C_{3-10}$heteroaryl, $C_{3-8}$cycloalkyl and $C_{3-8}$heterocycloalkyl; wherein said aryl, heteroaryl, cycloalkyl or heterocycloalkyl of Q is optionally substituted with up to 3 radicals independently selected from halo, $C_{1-6}$alkyl, halo-substituted-$C_{1-6}$alkyk $C_{1-6}$alkoxy, halo-substituted-$C_{1-6}$alkoxy, —C(O)$R_{20}$ and —C(O)O$R_{20}$;
wherein $R_{20}$ is selected from hydrogen and $C_{1-6}$alkyl;
ring A can have one ring carbon replaced by a —C(O)—;
L is selected from $C_{1-6}$alkylene, $C_{2-6}$alkenylene, —(CH$_2$)$_n$O—, —OC(O)(CH$_2$)$_n$—, —C(O)O(CH$_2$)$_n$—, —NR$_{26}$(CH$_2$)$_n$— and —O(CH$_2$)$_n$—; wherein $R_{26}$ is selected from hydrogen and $C_{1-6}$alkyl;
n is selected from 0, 1, 2, 3, 4 and 5;
any alkyl of L can be optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —C(O)$R_{22}$ and —C(O)O$R_{22}$; wherein $R_{22}$ is selected from hydrogen and $C_{1-6}$alkyl;
m is selected from 0, 1, 2, 3 and 4;
q is selected from 0, 1, 2, 3 and 4;
$R_1$ is selected from —$X_1$S(O)$_{0-2}$$X_2$$R_{6a}$, —$X_1$S(O)$_{0-2}$$X_2$O$R_{6a}$, —$X_1$S(O)$_{0-2}$$X_2$C(O)$R_{6a}$, —$X_1$S(O)$_{0-2}$$X_2$C(O)O$R_{6a}$, —$X_1$S(O)$_{0-2}$$X_2$OC(O)$R_{6a}$ and —$X_1$S(O)$_{0-2}$N$R_{6a}$$R_{6b}$; wherein
$X_1$ is selected from a bond, O, N$R_{7a}$ and $C_{1-4}$alkylene; wherein $R_{7a}$ is selected from hydrogen and $C_{1-6}$alkyl;
$X_2$ is selected from a bond and $C_{1-4}$alkylene;
$R_{6a}$ is selected from hydrogen, halo, $C_{1-6}$alkyl, $C_{2-6}$alkenyl, $C_{6-10}$aryl, $C_{3-10}$heteroaryl, $C_{3-8}$heterocycloalkyl and $C_{3-8}$cycloalkyl; wherein said aryl, heteroaryl, cycloalkyl and heterocycloalkyl of $R_{6a}$ is optionally substituted with 1 to 3 radicals independently selected from hydroxyl, halo, $C_{1-6}$alkyl, halo-substituted-$C_{1-6}$alkyl, hydroxyl-substituted-$C_{1-6}$alkyl, cyano-substituted-$C_{1-6}$alkyl, $C_{1-6}$alkoxy, halo-substituted-$C_{1-6}$alkoxy and $C_{6-10}$aryl-$C_{1-4}$alkoxy; and
$R_{6b}$ is selected from hydrogen and $C_{1-6}$alkyl;
$R_2$ and $R_3$ are independently selected from hydrogen, halo, hydroxyl, $C_{1-6}$alkyl, halo-substituted-$C_{1-6}$alkyl, hydroxyl-substituted-$C_{1-6}$alkyl, $C_{1-6}$alkoxy, halo-substituted-$C_{1-6}$alkoxy, —C(O)$R_{23}$, and —C(O)O$R_{23}$, wherein $R_{23}$ is selected from hydrogen and $C_{1-6}$alkyl;
$R_4$ is selected from $R_8$ and —C(O)O$R_8$; wherein $R_8$ is selected from $C_{1-6}$alkyl, $C_{6-10}$aryl, $C_{3-10}$heteroaryl, $C_{3-8}$cycloalkyl and $C_{3-8}$heterocycloalkyl; wherein said aryl, heteroaryl, cycloalkyl or heterocycloalkyl of $R_8$ is optionally substituted with 1 to 3 radicals independently selected from halo, $C_{1-6}$alkyl, $C_{3-8}$cycloalkyl, $C_{3-8}$heterocycloalkyl, halo-substituted-$C_{1-6}$alkyl, hydroxyl-substituted-$C_{1-6}$alkyl, $C_{1-6}$alkoxy and halo-substituted-$C_{1-6}$alkoxy; and
$R_5$ is selected from hydrogen, $C_{1-6}$alkyl, halo-substituted-$C_{1-6}$alkyl, hydroxyl-substituted-$C_{1-6}$alkyl, $C_{1-6}$alkoxy and halo-substituted-$C_{1-6}$alkoxy.

2. The compound of claim 1 of Formula Ia:

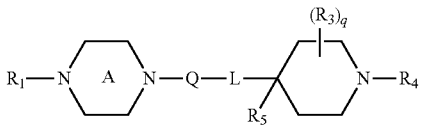

in which:
Q is a divalent radical selected from $C_{6-10}$aryl and $C_{3-10}$heteroaryl; wherein said aryl and heteroaryl of Q is optionally substituted with up to 3 radicals independently selected from halo, $C_{1-6}$alkyl, halo-substituted-$C_{1-6}$alkyl, $C_{1-6}$alkoxy, halo-substituted-$C_{1-6}$alkoxy, —C(O)R$_{20}$ and —C(O)OR$_{20}$; wherein R$_{20}$ is selected from hydrogen and $C_{1-6}$alkyl.

3. The compound of claim 2 in which Q is a divalent radical selected from phenyl, pyridinyl, pyrazinyl, pyridazinyl, pyrimidinyl, 1,2,4-oxadiazolyl, and thiazolyl; wherein said phenyl, pyridinyl, pyrazinyl, pyridazinyl, pyrimidinyl and thiazolyl of Q is optionally substituted with up to 3 radicals independently selected from halo, $C_{1-6}$alkyl, $C_{1-6}$alkoxy, halo-substituted-$C_{1-6}$alkyl, —C(O)OR$_{20}$ and —C(O)R$_{20}$; wherein R$_{20}$ is selected from hydrogen and $C_{1-6}$alkyl.

4. The compound of claim 3 in which:
L is selected from —O(CH$_2$)$_{0-4}$—, —(CH=CH)—, —OC(O)—, —NH(CH$_2$)$_{0-4}$—, —NCH$_3$(CH$_2$)$_{0-4}$— and —(CH$_2$)$_{1-4}$—.

5. The compound of claim 4 in which:
R$_1$ is selected from —S(O)$_{0-2}$X$_2$R$_{6a}$, —S(O)$_{0-2}$X$_2$OR$_{6a}$, —S(O)$_{0-2}$X$_2$C(O)OR$_{6a}$, —S(O)$_{0-2}$X$_2$OC(O)R$_{6a}$ and —S(O)$_{0-2}$NR$_{6a}$R$_{6b}$; wherein
X$_2$ is selected from a bond and $C_{1-4}$alkylene;
R$_{6a}$ is selected from hydrogen, halo, methyl, ethyl, propyl, isopropyl, ethenyl, pyridinyl, pyrrolidinyl, piperidinyl, morpholino, isoxazolyl, tetrazolyl, phenyl and imidazolyl; wherein said piperidinyl, pyridinyl, pyrrolidinyl, morpholino, isoxazolyl, tetrazolyl, phenyl or imidazolyl of R$_{6a}$ is optionally substituted with 1 to 3 radicals independently selected from hydroxy, halo, $C_{1-6}$alkyl and benzoxy; and
R$_{6b}$ is selected from hydrogen, methyl and ethyl.

6. The compound of claim 5 in which:
R$_4$ is selected from R$_8$ and —C(O)OR$_8$; wherein R$_8$ is selected from isopropyl, cyclopropyl, t-butyl, 1,2,4-oxadiazolyl, pyrimidinyl, pyridinyl, pyridazinyl, tetrahydro-2H-pyranyl, tetrahydrofuranyl, oxetanyl, 2H-tetrazolyl and thiazolyl; wherein said cyclopropyl, 1,2,4-oxadiazolyl, pyrimidinyl, pyridinyl, pyridazinyl, tetrahydro-2H-pyranyl, tetrahydrofuranyl, oxetanyl, 2H-tetrazolyl or thiazolyl of R$_8$ is optionally substituted with 1 to 3 radicals independently selected from halo, trifluoromethyl, isopropyl, t-butyl, methyl, ethyl and cyclopropyl; and
R$_5$ is selected from hydrogen and methoxy.

7. The compound of claim 1 selected from:
1-Methylcyclopropyl 4-((5-(4-(methylsulfonyl)piperazin-1-yl)pyrazin-2-yloxy)methyl)piperidine-1-carboxylate;
Isopropyl 4-((4-((4-methanesulfonylpiperazin)-1-yl)phenoxy)methyl)piperidine-1-carboxylate;
Isopropyl 4-(2-(4-(4-(methylsulfonyl)piperazin-1-yl)phenoxy)ethyl)piperidine-1-carboxylate;
Isopropyl 4-(3-(4-(4-(methylsulfonyl)piperazin-1-yl)phenoxy)propyl)piperidine-1-carboxylate;
Isopropyl 4-(4-(4-(4-(methylsulfonyl)piperazin-1-yl)phenoxy)butyl)piperidine-1-carboxylate;
Isopropyl 4-((6-(4-(methylsulfonyl)piperazin-1-yl)pyridin-3-yloxy)methyl)piperidine-1-carboxylate;
tert-Butyl 4-((6-(4-(methylsulfonyl)piperazin-1-yl)pyridin-3-yloxy)methyl)piperidine-1-carboxylate;
Isopropyl 4-((5-(4-(methylsulfonyl)piperazin-1-yl)pyrazin-2-yloxy)methyl)piperidine-1-carboxylate;
tert-Butyl 4-((5-(4-(methylsulfonyl)piperazin-1-yl)pyrazin-2-yloxy)methyl)piperidine-1-carboxylate;
3-Cyclopropyl-5-(4-((5-(4-(methylsulfonyl)piperazin-1-yl)pyrazin-2-yloxy)methyl)piperidin-1-yl)-1,2,4-oxadiazole;
5-Cyclopropyl-3-(4-((5-(4-(methylsulfonyl)piperazin-1-yl)pyrazin-2-yloxy)methyl)piperidin-1-yl)-1,2,4-oxadiazole;
2-(4-(Methylsulfonyl)piperazin-1-yl)-5-((1-(5-(trifluoromethyl)pyridin-2-yl)piperidin-4-yl)methoxy)pyrazine;
5-Isopropyl-3-(4-((5-(4-(methylsulfonyl)piperazin-1-yl)pyrazin-2-yloxy)methyl)piperidin-1-yl)-1,2,4-oxadiazole;
Tetrahydro-2H-pyran-4-yl 4-((5-(4-(methylsulfonyl)piperazin-1-yl)pyrazin-2-yloxy)methyl)piperidine-1-carboxylate;
(S)-Tetrahydrofuran-3-yl 4-((5-(4-(methylsulfonyl)piperazin-1-yl)pyrazin-2-yloxy)methyl)piperidine-1-carboxylate;
(R)-Tetrahydrofuran-3-yl 4-((5-(4-(methylsulfonyl)piperazin-1-yl)pyrazin-2-yloxy)methyl)piperidine-1-carboxylate;
2-Isopropyl-5-(4-((5-(4-(methylsulfonyl)piperazin-1-yl)pyrazin-2-yloxy)methyl)piperidin-1-yl)thiazole;
2-((1-(2-Methyl-2H-tetrazol-5-yl)piperidin-4-yl)methoxy)-5-(4-(methylsulfonyl)piperazin-1-yl)pyrazine;
Oxetan-3-yl 4-((5-(4-(methylsulfonyl)piperazin-1-yl)pyrazin-2-yloxy)methyl)piperidine-1-carboxylate;
Isopropyl 4-((5-(4-(methylsulfonyl)piperazin-1-yl)pyridin-2-yloxy)methyl)piperidine-1-carboxylate;
Isopropyl 4-((6-(4-(methyl sulfonyl)piperazin-1-yl)pyridazin-3-yloxy)methyl)piperidine-1-carboxylate;
Isopropyl 4-((5-(4-(methylsulfonyl)piperazin-1-yl)pyrimidin-2-yloxy)methyl)piperidine-1-carboxylate;
(E)-Isopropyl 4-(2-(6-(4-(methylsulfonyl)piperazin-1-yl)pyridin-3-yl)vinyl)piperidine-1-carboxylate;
Isopropyl 4-(2-(6-(4-(methylsulfonyl)piperazin-1-yl)pyridin-3-yl)ethyl)piperidine-1-carboxylate;
(E)-Isopropyl 4-(2-(2-(4-(methylsulfonyl)piperazin-1-yl)pyrimidin-5-yl)vinyl)piperidine-1-carboxylate;
5-Ethyl-2-(4-((6-(4-(methylsulfonyl)piperazin-1-yl)pyridin-3-yloxy)methyl)piperidin-1-yl)pyrimidine;
1-(Methylsulfonyl)-4-(5-((1-(5-(trifluoromethyl)pyridin-2-yl)piperidin-4-yl)methoxy)pyridin-2-yl)piperazine;
5-Ethyl-2-(4-((5-(4-(methylsulfonyl)piperazin-1-yl)pyrazin-2-yloxy)methyl)piperidin-1-yl)pyrimidine;
2-((1-(5-Methylpyridin-2-yl)piperidin-4-yl)methoxy)-5-(4-(methylsulfonyl)piperazin-1-yl)pyrazine;
1-Methylcyclopropyl 4-((5-(4-(methylsulfonyl)piperazin-1-yl)pyridin-2-yloxy)methyl)piperidine-1-carboxylate;
5-Ethyl-2-(4-((5-(4-(methylsulfonyl)piperazin-1-yl)pyridin-2-yloxy)methyl)piperidin-1-yl)pyrimidine;
3-Isopropyl-5-(4-((5-(4-(methylsulfonyl)piperazin-1-yl)pyrazin-2-yloxy)methyl)piperidin-1-yl)-1,2,4-oxadiazole;
3-Isopropyl-5-(4-((5-(4-(methylsulfonyl)piperazin-1-yl)pyridin-2-yloxy)methyl)piperidin-1-yl)-1,2,4-oxadiazole;

1-Methylcyclopropyl 4-((6-(4-(methylsulfonyl)piperazin-1-yl)pyridin-3-yloxy)methyl)piperidine-1-carboxylate;
5-Isopropyl-3-(4-((6-(4-(methylsulfonyl)piperazin-1-yl)pyridin-3-yloxy)methyl)piperidin-1-yl)-1,2,4-oxadiazole;
2-((1-(5-Fluoropyridin-2-yl)piperidin-4-yl)methoxy)-5-(4-(methylsulfonyl)piperazin-1-yl)pyrazine;
3-Isopropyl-5-(4-((6-(4-(methylsulfonyl)piperazin-1-yl)pyridin-3-yloxy)methyl)piperidin-1-yl)-1,2,4-oxadiazole;
tert-Butyl 4-(2-(3-(4-(methylsulfonyl)piperazin-1-yl)-1,2,4-oxadiazol-5-yl)ethyl)piperidine-1-carboxylate;
tert-Butyl 4-(3-(3-(4-(methylsulfonyl)piperazin-1-yl)-1,2,4-oxadiazol-5-yl)propyl)piperidine-1-carboxylate;
5-(3-(1-(5-Ethylpyrimidin-2-yl)piperidin-4-yl)propyl)-3-(4-(methylsulfonyl)piperazin-1-yl)-1,2,4-oxadiazole;
Isopropyl 4-(3-(3-(4-(methylsulfonyl)piperazin-1-yl)-1,2,4-oxadiazol-5-yl)propyl)piperidine-1-carboxylate;
3-Isopropyl-5-(4-(2-(5-(4-(methylsulfonyl)piperazin-1-yl)thiazol-2-yl)ethyl)piperidin-1-yl)-1,2,4-oxadiazole;
1-Methylcyclopropyl 4-methoxy-4-((5-(4-(methylsulfonyl)piperazin-1-yl)pyrazin-2-yloxy)methyl)piperidine-1-carboxylate;
1-Methylcyclopropyl 4-((6-formyl-5-(4-(methylsulfonyl)piperazin-1-yl)pyrazin-2-yloxy)methyl)piperidine-1-carboxylate;
1-Methylcyclopropyl 4-((6-chloro-5-(4-(methylsulfonyl)piperazin-1-yl)pyrazin-2-yloxy)methyl)piperidine-1-carboxylate;
1-Methylcyclopropyl 4-((5-(4-(3-methoxy-3-oxopropylsulfonyl)piperazin-1-yl)pyrazin-2-yloxy)methyl)piperidine-1-carboxylate;
3-(4-(5-((1-((1-Methylcyclopropoxy)carbonyl)-piperidin-4-yl)methoxy)pyrazin-2-yl)piperazin-1-ylsulfonyl)propanoic acid;
1-Methylcyclopropyl 4-((5-(4-(3-(1H-tetrazol-5-yl)propylsulfonyl)piperazin-1-yl)pyrazin-2-yloxy)methyl)piperidine-1-carboxylate;
1-Methylcyclopropyl 4-((5-(4-(vinylsulfonyl)piperazin-1-yl)pyrazin-2-yloxy)methyl)piperidine-1-carboxylate;
1-Methylcyclopropyl 4-((5-(4-(2-(piperidin-1-yl)ethylsulfonyl)piperazin-1-yl)pyrazin-2-yloxy)methyl)piperidine-1-carboxylate;
1-Methylcyclopropyl 4-((5-(4-(2-morpholinoethylsulfonyl)piperazin-1-yl)pyrazin-2-yloxy)methyl)piperidine-1-carboxylate;
tert-Butyl 4-((5-(4-(3-chloropropylsulfonyl)piperazin-1-yl)pyrazin-2-yloxy)methyl)piperidine-1-carboxylate;
tert-Butyl 4-((5-(4-(3-acetoxypropylsulfonyl)piperazin-1-yl)pyrazin-2-yloxy)methyl)piperidine-1-carboxylate;
1-Methylcyclopropyl 4-((5-(4-(2-ethoxyethylsulfonyl)piperazin-1-yl)pyrazin-2-yloxy)methyl)piperidine-1-carboxylate;
1-Methylcyclopropyl 4-((5-(4-(3-(pyrrolidin-1-yl)propylsulfonyl)piperazin-1-yl)pyrazin-2-yloxy)methyl)piperidine-1-carboxylate;
1-Methylcyclopropyl 4-((5-(4-(3-(2-methyl-1H-imidazol-1-yl)propylsulfonyl)piperazin-1-yl)pyrazin-2-yloxy)methyl)piperidine-1-carboxylate;
1-Methylcyclopropyl 4-((5-(4-(propylsulfonyl)piperazin-1-yl)pyrazin-2-yloxy)methyl)piperidine-1-carboxylate;
1-Methylcyclopropyl 4-((5-(4-(ethylsulfonyl)piperazin-1-yl)pyrazin-2-yloxy)methyl)piperidine-1-carboxylate;
1-Methylcyclopropyl 4-((5-(4-(isopropylsulfonyl)piperazin-1-yl)pyrazin-2-yloxy)methyl)piperidine-1-carboxylate;
1-Methylcyclopropyl 4-((5-(4-(isobutylsulfonyl)piperazin-1-yl)pyrazin-2-yloxy)methyl)piperidine-1-carboxylate;
1-Methylcyclopropyl 4-((5-(4-(sec-butylsulfonyl)piperazin-1-yl)pyrazin-2-yloxy)methyl)piperidine-1-carboxylate;
1-Methylcyclopropyl 4-((5-(4-(2-(pyridin-3-yl)ethylsulfonyl)piperazin-1-yl)pyrazin-2-yloxy)methyl)piperidine-1-carboxylate;
1-Methylcyclopropyl 4-((5-(4-(2-(pyridin-4-yl)ethylsulfonyl)piperazin-1-yl)pyrazin-2-yloxy)methyl)piperidine-1-carboxylate;
1-Methylcyclopropyl 4-((5-(4-sulfamoylpiperazin-1-yl)pyrazin-2-yloxy)methyl)piperidine-1-carboxylate;
tert-Butyl 4-((5-(4-(morpholinosulfonyl)piperazin-1-yl)pyrazin-2-yloxy)methyl)piperidine-1-carboxylate;
1-Methylcyclopropyl 4-((6-(4-(ethylsulfonyl)piperazin-1-yl)pyridin-3-yloxy)methyl)piperidine-1-carboxylate;
tert-Butyl 4-((5-(4-(methylsulfonyl)-2-oxopiperazin-1-yl)pyrazin-2-yloxy)methyl)piperidine-1-carboxylate;
1-Methylcyclopropyl 4-((5-(4-(methylsulfonyl)-2-oxopiperazin-1-yl)pyrazin-2-yloxy)methyl)piperidine-1-carboxylate;
1-Methylcyclopropyl 4-((5-(2-oxo-4-(propylsulfonyl)piperazin-1-yl)pyrazin-2-yloxy)methyl)piperidine-1-carboxylate;
1-Methylcyclopropyl 4-((5-(4-(isopropylsulfonyl)-2-oxopiperazin-1-yl)pyrazin-2-yloxy)methyl)piperidine-1-carboxylate;
1-Methylcyclopropyl 4-((6-(2-oxo-4-(propylsulfonyl)piperazin-1-yl)pyridin-3-yloxy)methyl)piperidine-1-carboxylate;
1-Methylcyclopropyl 4-((6-(4-(isopropylsulfonyl)-2-oxopiperazin-1-yl)pyridin-3-yloxy)methyl)piperidine-1-carboxylate;
1-(5-((1-(5-Ethylpyrimidin-2-yl)piperidin-4-yl)methoxy)pyrazin-2-yl)-4-(methylsulfonyl)piperazin-2-one;
1-(5-((1-(5-Ethylpyrimidin-2-yl)piperidin-4-yl)methoxy)pyridin-2-yl)-4-(methylsulfonyl)piperazin-2-one;
1-Methylcyclopropyl 4-({[5-(2-oxo-4-{[2-(pyrrolidin-1-yl)ethane]sulfonyl}piperazin-1-yl)pyrazin-2-yl]oxy}methyl)piperidine-1-carboxylate;
1-Methylcyclopropyl 4-({[5-(4-{[2-(morpholin-4-yl)ethane]sulfonyl}-2-oxopiperazin-1-yl)pyrazin-2-yl]oxy}methyl)piperidine-1-carboxylate;
1-Methylcyclopropyl 4-{[(5-{4-[1-(2-methylpropyl)pyrrolidine-3-sulfonyl]-2-oxopiperazin-1-yl}pyrazin-2-yl)oxy]methyl}piperidine-1-carboxylate;
1-Methylcyclopropyl 4-({[5-(2-oxo-4-{[3-(1H-pyrazol-1-yl)propane]sulfonyl}piperazin-1-yl)pyrazin-2-yl]oxy}methyl)piperidine-1-carboxylate;
1-Methylcyclopropyl 4-[({5-[2-oxo-4-(pyrrolidine-3-sulfonyl)piperazin-1-yl]pyrazin-2-yl}oxy)methyl]piperidine-1-carboxylate;
1-Methylcyclopropyl 4-({[5-(4-{[(1-methylpyrrolidin-3-yl)methane]sulfonyl}-2-oxopiperazin-1-yl)pyrazin-2-yl]oxy}methyl)piperidine-1-carboxylate;
1-Methylcyclopropyl 4-({[5-(4-{[2-(azetidin-1-yl)ethane]sulfonyl}-2-oxopiperazin-1-yl)pyrazin-2-yl]oxy}methyl)piperidine-1-carboxylate;
1-Methylcyclopropyl 4-({[5-(2-oxo-4-{[2-(1H-pyrazol-1-yl)ethane]sulfonyl}piperazin-1-yl)pyrazin-2-yl]oxy}methyl)piperidine-1-carboxylate;
1-Methylcyclopropyl 4-[({5-[4-(1-methylpyrrolidine-3-sulfonyl)-2-oxopiperazin-1-yl]pyrazin-2-yl}oxy)methyl]piperidine-1-carboxylate;

1-Methylcyclopropyl 4-({[5-(4-{[2-(3,3-difluoroazetidin-1-yl)ethane]sulfonyl}-2-oxopiperazin-1-yl)pyrazin-2-yl]oxy}methyl)piperidine-1-carboxylate;

1-Methylcyclopropyl 4-[({5-[4-(azetidine-3-sulfonyl)-2-oxopiperazin-1-yl]pyrazin-2-yl}oxy)methyl]piperidine-1-carboxylate;

1-Methylcyclopropyl 4-({[5-(4-{[3-(3,3-difluoroazetidin-1-yl)propane]sulfonyl}-2-oxopiperazin-1-yl)pyrazin-2-yl]oxy}methyl)piperidine-1-carboxylate;

1-Methylcyclopropyl 4-({[5-(4-{[3-(azetidin-1-yl)propane]sulfonyl}-2-oxopiperazin-1-yl)pyrazin-2-yl]oxy}methyl)piperidine-1-carboxylate;

1-Methylcyclopropyl 4-{[(5-{2-oxo-4-[(3S)-pyrrolidine-3-sulfonyl]piperazin-1-yl}pyrazin-2-yl)oxy]methyl}piperidine-1-carboxylate;

1-Methylcyclopropyl 4-{[(5-{4-[(3S)-1-methylpyrrolidine-3-sulfonyl]piperazin-1-yl}pyrazin-2-yl)oxy]methyl}piperidine-1-carboxylate;

1-Methylcyclopropyl 4-{[(5-{4-[(3R)-1-methylpyrrolidine-3-sulfonyl]piperazin-1-yl}pyrazin-2-yl)oxy]methyl}piperidine-1-carboxylate;

1-Methylcyclopropyl 4-{[(5-{4-[(3S)-pyrrolidine-3-sulfonyl]piperazin-1-yl}pyrazin-2-yl)oxy]methyl}piperidine-1-carboxylate;

1-Methylcyclopropyl 4-{[(5-{4-[(3R)-pyrrolidine-3-sulfonyl]piperazin-1-yl}pyrazin-2-yl)oxy]methyl}piperidine-1-carboxylate;

1-Methylcyclopropyl 4-{[(5-[4-(azetidine-3-sulfonyl)piperazin-1-yl]pyrazin-2-yl}oxy)methyl]piperidine-1-carboxylate;

1-Methylcyclopropyl 4-{[(5-{2-oxo-4-[(pyrrolidin-3-ylmethane)sulfonyl]piperazin-1-yl}pyrazin-2-yl)oxy]methyl}piperidine-1-carboxylate;

1-Methylcyclopropyl 4-[({5-[4-(1-hydroxy-2-methylpropane-2-sulfonyl)piperazin-1-yl]pyrazin-2-yl}oxy)methyl]piperidine-1-carboxylate;

1-Methylcyclopropyl 4-{[(5-{4-[(2-hydroxyethane)sulfonyl]piperazin-1-yl}pyrazin-2-yl)oxy]methyl}piperidine-1-carboxylate;

1-Methylcyclopropyl 4-{[(5-{4-[(azetidin-3-ylmethane)sulfonyl]piperazin-1-yl}pyrazin-2-yl)oxy]methyl}piperidine-1-carboxylate;

1-Methylcyclopropyl 4-({[5-(4-{[(1-methylpyrrolidin-2-yl)methane]sulfonyl}-2-oxopiperazin-1-yl)pyrazin-2-yl]oxy}methyl)piperidine-1-carboxylate;

1-Methylcyclopropyl 4-{[(5-{2-oxo-4-[(3R)-pyrrolidine-3-sulfonyl]piperazin-1-yl}pyrazin-2-yl)oxy]methyl}piperidine-1-carboxylate;

1-Methylcyclopropyl 4-[({5-[4-(1-methylazetidine-3-sulfonyl)piperazin-1-yl]pyrazin-2-yl}oxy)methyl]piperidine-1-carboxylate;

1-Methylcyclopropyl 4-[({5-[4-(1-methylazetidine-3-sulfonyl)-2-oxopiperazin-1-yl]pyrazin-2-yl}oxy)methyl]piperidine-1-carboxylate;

1-Methylcyclopropyl 4-({[5-(4-{[(1-methylazetidin-3-yl)methane]sulfonyl}-2-oxopiperazin-1-yl)pyrazin-2-yl]oxy}methyl)piperidine-1-carboxylate;

1-Methylcyclopropyl 4-({[5-(4-{[(1-methylazetidin-3-yl)methane]sulfonyl}piperazin-1-yl)pyrazin-2-yl]oxy}methyl)piperidine-1-carboxylate;

1-Methylcyclopropyl 4-[({5-[4-({3-[(3S,4S)-3,4-dihydroxypyrrolidin-1-yl]propane}sulfonyl)-2-oxopiperazin-1-yl]pyrazin-2-yl}oxy)methyl]piperidine-1-carboxylate;

1-Methylcyclopropyl 4-[({5-[4-({2-[(3S,4S)-3,4-dihydroxypyrrolidin-1-yl]ethane}sulfonyl)-2-oxopiperazin-1-yl]pyrazin-2-yl}oxy)methyl]piperidine-1-carboxylate;

1-Methylcyclopropyl 4-{[(5-{4-[(azetidin-3-ylmethane)sulfonyl]-2-oxopiperazin-1-yl}pyrazin-2-yl)oxy]methyl}piperidine-1-carboxylate;

1-Methylcyclopropyl 4-{[(5-{2-oxo-4-[(pyrrolidin-2-ylmethane)sulfonyl]piperazin-1-yl}pyrazin-2-yl)oxy]methyl}piperidine-1-carboxylate;

1-Methylcyclopropyl 4-({[5-(2-oxo-4-{[3-(pyrrolidin-1-yl)propane]sulfonyl}piperazin-1-yl)pyrazin-2-yl]oxy}methyl)piperidine-1-carboxylate;

1-Methylcyclopropyl 4-({[5-(4-{[3-(morpholin-4-yl)propane]sulfonyl}-2-oxopiperazin-1-yl)pyrazin-2-yl]oxy}methyl)piperidine-1-carboxylate;

1-Methylcyclopropyl 4-({[5-(4-{[(3-methyloxetan-3-yl)methane]sulfonyl}piperazin-1-yl)pyrazin-2-yl]oxy}methyl)piperidine-1-carboxylate;

1-Methylcyclopropyl 4-({[5-(4-{[3-(acetyloxy)propane]sulfonyl}-2-oxopiperazin-1-yl)pyrazin-2-yl]oxy}methyl)piperidine-1-carboxylate;

1-Methylcyclopropyl 4-{[(5-{4-[(3-chloropropane)sulfonyl]-2-oxopiperazin-1-yl}pyrazin-2-yl)oxy]methyl}piperidine-1-carboxylate;

1-Methylcyclopropyl 4-{[(5-{4-[(3-hydroxypropane)sulfonyl]-2-oxopiperazin-1-yl}pyrazin-2-yl)oxy]methyl}piperidine-1-carboxylate;

1-Methylcyclopropyl 4-{[(5-{2-oxo-4-[(3R)-oxolane-3-sulfonyl]piperazin-1-yl}pyrazin-2-yl)oxy]methyl}piperidine-1-carboxylate;

1-Methylcyclopropyl 4-{[(5-{2-oxo-4-[(3S)-oxolane-3-sulfonyl]piperazin-1-yl}pyrazin-2-yl)oxy]methyl}piperidine-1-carboxylate;

1-Methylcyclopropyl 4-({[5-(4-{[(1-hydroxycyclopropyl)methane]sulfonyl}piperazin-1-yl)pyrazin-2-yl]oxy}methyl)piperidine-1-carboxylate;

1-Methylcyclopropyl 4-({[5-(4-{[2-(1-hydroxycyclopropyl)ethane]sulfonyl}piperazin-1-yl)pyrazin-2-yl]oxy}methyl)piperidine-1-carboxylate;

1-Methylcyclopropyl 4-[({5-[4-({[1-(benzyloxy)cyclopropyl]methane}sulfonyl)piperazin-1-yl]pyrazin-2-yl}oxy)methyl]piperidine-1-carboxylate;

1-Methylcyclopropyl 4-({[5-(4-{[2-(1-hydroxycyclopropyl)ethane]sulfonyl}-2-oxopiperazin-1-yl)pyrazin-2-yl]oxy}methyl)piperidine-1-carboxylate;

1-Methylcyclopropyl (3S,4S)-3-hydroxy-4-{[(6-{4-[(2-methylpropane)sulfonyl]piperazin-1-yl}pyridin-3-yl)oxy]methyl}piperidine-1-carboxylate;

1-Methylcyclopropyl 4-{[(6-{4-[(2-hydroxy-2-methylpropane)sulfonyl]piperazin-1-yl}pyridin-3-yl)oxy]methyl}piperidine-1-carboxylate;

1-Methylcyclopropyl (3S,4R)-3-methoxy-4-{[(6-{4-[(2-methylpropane)sulfonyl]piperazin-1-yl}pyridin-3-yl)oxy]methyl}piperidine-1-carboxylate;

1-Methylcyclopropyl 4-({[5-(4-{[3-(3,3-difluoroazetidin-1-yl)propane]sulfonyl}piperazin-1-yl)pyrazin-2-yl]oxy}methyl)piperidine-1-carboxylate;

1-Methylcyclopropyl 4-({[5-(4-{[3-(azetidin-1-yl)propane]sulfonyl}piperazin-1-yl)pyrazin-2-yl]oxy}methyl)piperidine-1-carboxylate;

1-Methylcyclopropyl 4-{[(5-{4-[(3-methoxypropane)sulfonyl]piperazin-1-yl}pyrazin-2-yl)oxy]methyl}piperidine-1-carboxylate;

1-Methylcyclopropyl 4-{[(6-{4-[(3-chloropropane)sulfonyl]-2-oxopiperazin-1-yl}pyridin-3-yl)oxy]methyl}piperidine-1-carboxylate;

1-Methylcyclopropyl 4-({[5-(4-{[2-(azetidin-1-yl)ethane]sulfonyl}piperazin-1-yl)pyrazin-2-yl]oxy}methyl)piperidine-1-carboxylate;

1-Methylcyclopropyl 4-({[6-(4-{[3-(azetidin-1-yl)propane]sulfonyl}piperazin-1-yl)pyridin-3-yl]oxy}methyl)piperidine-1-carboxylate;

1-Methylcyclopropyl 4-[({5-[4-(pyrrolidine-3-sulfonyl)piperazin-1-yl]pyrazin-2-yl}oxy)methyl]piperidine-1-carboxylate;

1-Methylcyclopropyl 4-({[5-(4-{[2-(3,3-difluoroazetidin-1-yl)ethane]sulfonyl}piperazin-1-yl)pyrazin-2-yl]oxy}methyl)piperidine-1-carboxylate;

1-Methylcyclopropyl 4-{[6-{4-[(3-hydroxypropane)sulfonyl]-2-oxopiperazin-1-yl}pyridin-3-yl)oxy]methyl}piperidine-1-carboxylate;

1-Methylcyclopropyl 4-({[6-(4-{[3-(azetidin-1-yl)propane]sulfonyl}-2-oxopiperazin-1-yl)pyridin-3-yl]oxy}methyl)piperidine-1-carboxylate;

1-Methylcyclopropyl 4-[2,6-difluoro-4-(4-methanesulfonyl-2-oxopiperazin-1-yl)phenoxymethyl]piperidine-1-carboxylate; and 1-Methylcyclopropyl 4-[({5-[4-(oxetane-3-sulfonyl)-2-oxopiperazin-1-yl]pyrazin-2-yl}oxy)methyl]piperidine-1-carboxylate.

8. A pharmaceutical composition comprising a therapeutically effective amount of a compound of claim 1 in combination with a pharmaceutically acceptable excipient.

9. A compound of the formula:

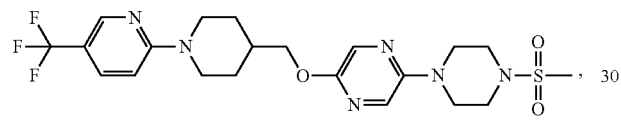

or a pharmaceutically acceptable salt thereof.

10. A compound of the formula:

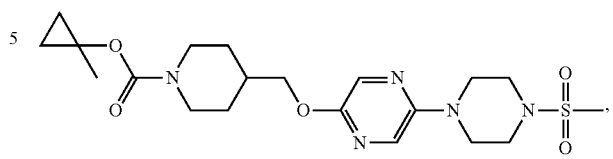

or a pharmaceutically acceptable salt thereof.

11. A compound of the formula:

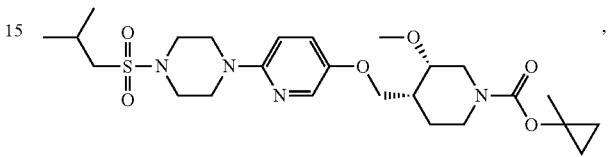

or a pharmaceutically acceptable salt thereof.

12. A compound of the formula:

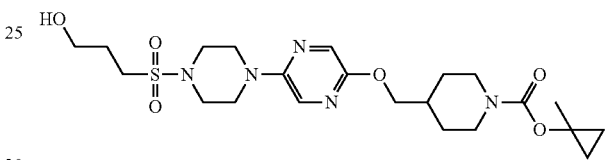

or a pharmaceutically acceptable salt thereof.

13. A compound of the formula:

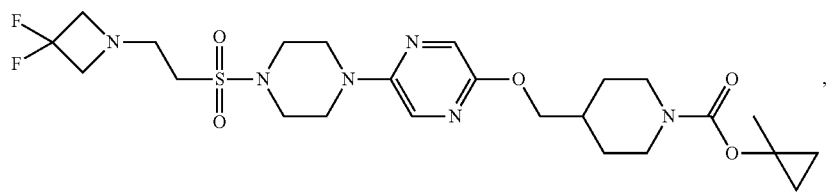

or a pharmaceutically acceptable salt thereof.

14. A compound of the formula:

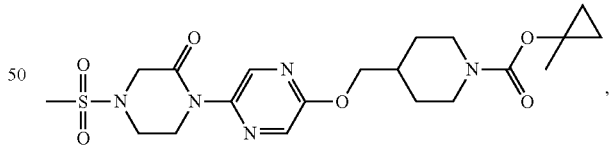

or a pharmaceutically acceptable salt thereof.

15. A compound of the formula:

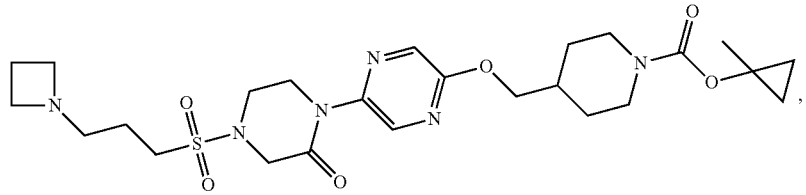

or a pharmaceutically acceptable salt thereof.

16. A compound of the formula:
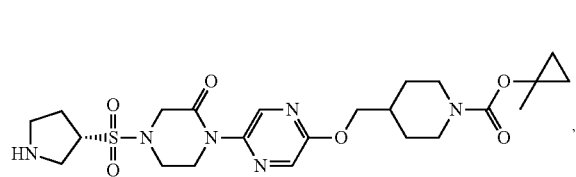
or a pharmaceutically acceptable salt thereof.
17. A compound of the formula:
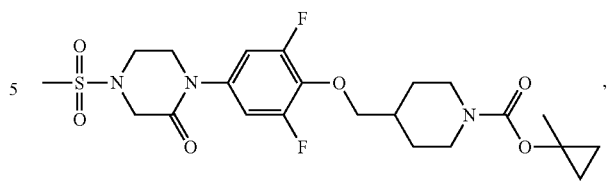
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 8,153,635 B2 | Page 1 of 1 |
| APPLICATION NO. | : 12/204600 | |
| DATED | : April 10, 2012 | |
| INVENTOR(S) | : Alper et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 76 days.

Signed and Sealed this
Eleventh Day of September, 2012

David J. Kappos
*Director of the United States Patent and Trademark Office*